US006943002B2

(12) United States Patent
Alibhai et al.

(10) Patent No.: US 6,943,002 B2
(45) Date of Patent: Sep. 13, 2005

(54) PREPARATION OF DEALLERGENIZED PROTEINS AND PERMUTEINS

(75) Inventors: Murtaza F. Alibhai, Chesterfield, MO (US); James D. Astwood, Eureka, MO (US); Charles A. McWherter, Chesterfield, MO (US); Hugh A. Sampson, Larchmont, NY (US)

(73) Assignee: Monsanto Technology LLC, St. Louis, MO (US)

( * ) Notice: Subject to any disclaimer, the term of this patent is extended or adjusted under 35 U.S.C. 154(b) by 163 days.

(21) Appl. No.: 10/658,180

(22) Filed: Sep. 9, 2003

(65) Prior Publication Data

US 2004/0216187 A1 Oct. 28, 2004

Related U.S. Application Data

(62) Division of application No. 09/755,630, filed on Jan. 5, 2001, now Pat. No. 6,639,054.
(60) Provisional application No. 60/174,669, filed on Jan. 6, 2000.

(51) Int. Cl.[7] ........................... C12N 9/18; C12N 1/20; C12N 15/00; C07H 21/04
(52) U.S. Cl. ................. 435/197; 435/252.3; 435/320.1; 536/23.2
(58) Field of Search ............................. 435/197, 252.3, 435/320.1; 536/23.2

(56) References Cited

U.S. PATENT DOCUMENTS 5,743,477 A 4/1998 Walsh et al. ............... 424/94.6
5,882,668 A 3/1999 Garnaat et al. ............. 424/405

FOREIGN PATENT DOCUMENTS

| | | |
|---|---|---|
| CA | 2090552 | 8/1994 |
| WO | WO 94/21805 | 9/1994 |
| WO | WO 96/37615 | 11/1996 |
| WO | WO 98/54327 | 12/1998 |
| WO | WO 99/38978 | 8/1999 |
| WO | WO 99/45961 | 9/1999 |

OTHER PUBLICATIONS

Gaillaird, T., The Enzymic Deacylation of Phospholipids and Galactolipids in Plants, *Biochem. J.,* 121: 379–390 (1971).

Racusen, D., Light acyl hydrolase of patatin, *Can. J. Bot.,* 62: 1640–1644 (1984).

Andrews, D.L., et al., Characterization of the lipid acyl hydrolase activity of the major potato (*Solanum tuberosum*) tuber protein, patatin, by cloning and abundant expression in a baculovirus vector, Biochem. J., 252: 199–206 (1988).

Strickland, J.A., et al., Inhibition of *Diabrotica* Larval Growth by Patatin, the Lipid Acyl Hydrolase from Potato Tubers, *Physiol.,* 109: 667–674 (1995).

Hofgen, R. and Willmitzer, L., Biochemical and Genetic Analysis of Different Patatin Isoforms Expressed in Various Organs of Potato (*Solanum Tuberosum*), *Plant Science,* 66: 221–230 (1990).

Mignery, G.A., Isolation and sequence analysis of cDNAs for the major potato tuber protein, patatin, *Nucleic Acids Research,* 12: 7987–8000 (1984).

Mignery, G.A., et al., Molecular characterization of the patatin multigene family of potato, *Gene,* 62: 27–44 (1988).

Stiekema, W.J., et al., Molecular cloning and analysis of four potato tuber mRNAs, *Plant Mol. Biol.,* 11: 255–269 (1988).

Ganal, M.W., et al., Genetic and physical mapping of the patatin genes in potato and tomato, *Mol. Gen. Genetics,* 225: 501–509 (1991).

Vancanneyt, G., et al., Expression of a Patatin–like Protein in the Anthers of Potato and Sweet Pepper Flowers, *Plant Cell,* 1: 533–540 (1989).

Rosahl, S., et al., Expression of a tuber–specific storage protein in transgenic tobacco plants: demonstration of an esterase activity, *EMBO J.,* 6: 1155–1159 (1987).

King, H.C., Exploring the Maze of Adverse Reactions to Foods, *Ear Nose Throat J.,* 73(4): 237–241 (1994).

Astwood, J.D., et al., Pollen allergen homologues in barley and other crop species, *Clin. Exp. Allergy,* 25: 66–72 (1995).

Astwood, J.D., and Fuchs, R.L., Allergenicity of Foods Derived from Transgenic Plants, *Monographs in allergy vol. 32: Highlights in food allergy,* pp. 105–120 (1996).

Metcalfe, D.D., et al., Assessment of the Allergenic Potential of Foods Derived from Genetically Engineered Crop Plants, *Critical Reviews in Food Science and Nutrition,* 36S: 165–186 (1996).

Elsayed, S. and Apold, J., Immunochemical Analysis of Cod Fish Allergen M: Locationsof the Immunoglobulin Binding Sites as Demonstrated by the Native and Synthetic Peptides, *Allergy,* 38(7): 449–459, 1983.

Elsayed, S., et al., The structural requirements of epitopes with IgE binding capacity demonstrated by three major allergens from fish, egg, and tree pollen, *Scand. J. Clin. Lab. Invest. Suppl.,* 204: 17–31 (1991).

Zhang, L., et al., Mapping of Antibody Binding Epitopes of a Recombinant Poa p IX Allergen, *Mol. Immunol.,* 29(11); 1383–1389 (1992).

Hefle, S., et al., Allergenic Foods, *Crit. Rev. in Food Sci. Nutr.,* 36S: 69–90 (1996).

(Continued)

*Primary Examiner*—Tekchand Saidha
(74) *Attorney, Agent, or Firm*—Timothy K. Ball, Esq.; Howery LLP

(57) ABSTRACT

Modified proteins are disclosed that maintain enzymatic and insecticidal activity while displaying reduced or eliminated allergenicity. Epitopes which bind to anti-patatin antibodies were identified, and removed via site directed mutagenesis. Tyrosines were observed to generally contribute to the allergenic properties of palatin proteins. Removal of glycosylation sites was observed to reduce or eliminate antibody binding. Permuteins are also disclosed which have a rearranged amino acid sequence while retaining enzymatic activity. Deallergenized proteins and permuteins can be used as insecticidal materials, as nutritional supplements, and as immunotherapeutic agents.

8 Claims, 12 Drawing Sheets

OTHER PUBLICATIONS

Church, et al., In: Kay, A.B. ed., *Allergy and Allergic Diseases*, Oxford, Blackwell Science, pp. 149–197 (1997).

Castells, M.C., Allergy to white potato, *Allergy Clin. Immunol.*, 8: 1110–1114 (1986).

Hannuksela, M., et al., Immediate reactions to fruits and vegetables, *Contact Dermatitis*, 3: 79–84 (1977).

Golbert, T.M., et al., Systematic allergic reactions to ingested antigens, *Journal of Allergy*, 44: 96–107 (1969).

Wahl, R., et al., IgE–Mediated Allergic Reactions to Potatoes, *Intl. Arch. Allergy Appl. Immunol.*, 92: 168–174 (1990).

Ebner, C., et al., Identification of Allergens in Apple, Pear, Celery, Carrot and Potato: Cross–Reactivity with Pollen Allergens, in: Wuthrich, B. & Ortolani, C. (eds)., *Highlights in Food Allergy. Monographs in Allergy*, vol. 32 Basil, Karger, pp. 73–77 (1996).

Seppala, U., et al., Identification of patatin as a novel allergen for children with positive skin prick test responses to raw potato, *J. Allergy Clin. Immunol.*, 103: 165–171 (1999).

Cunningham, B.A., et al., Favin versus concanavalin A: Circularly permuted amino acid sequences, *Proc. Natl. Sci., U.S.A.*, 76: 3218–3222 (1979).

Teather, R.M., et al., DNA Sequence of a *Fibrobacter succinogenes* Mixed–Linkage, β–Glucanase (1,3–1, 4–βD–Glucan 4–Glucanohydrolase) Gene, *J. Bacteriol.*, 172: 3837–3841 (1990).

Schimming, S., et al., Structure of the *Clostridium thermocellum* gene licB and the encoded β–1,3–1,4–glucanase, *Eur. J. Biochem.*, 204: 13–19 (1992).

Yamiuchi, D., et al., Structure of the gene encoding concanavalin A from *Canavalia gladiata* and its expression in *Escherichia coli* cells, *FEBS Lett.*, 260: 127–130 (1991).

MacGregor, E.A, et al., A circularly permuted α–amylase–type α/β–barrel structure in glucan–synthesizing glucosyltransferases, *FEBS Lett.*, 378: 263–266 (1996).

Goldenberg, D.P. and Creighton, T.E., Circular and Circularly Permuted Forms of Bovine Pancreatic Trypsin Inhibitor, *J. Mol. Biol.*, 165: 407–413 (1983).

Li, X. and Coffino, P., Degradation of Ornithin Decarboxylase: Exposure of the C–Terminal Target by a Polyamine–Inducible Inhibitory Protein, *Mol. Cell. Biol.*, 13: 2377–2383 (1993).

Zhang, T., et al., Entropic effects of disulphide bonds on protein stability, *Nature Struct. Biol.*, 1: 434–438 (1995).

Buchwalder, A., et al., A Fully Active Variant of Dihydrofolate Reductase with a Circularly Permuted Sequence, *Biochemistry*, 31: 1621–1630 (1994).

Protasova, N.Y., et al., Circularly permuted dihydrofolate reductase of *E. coli* has functional activity and a destabilized tertiary structure, *Prot. Eng.*, 7: 1373–1377 (1994).

Mullins, L.S., et al., Transposition of Protein Sequences; Circular Permutation of Ribonuclease T1, *J. Am. Chem. Soc.*, 116: 5529–5333 (1994).

Garrett, J.B., et al., Are turns required for the folding of ribonuclease T1, *Protein Science*, 5: 204–211 (1996).

Hahn, M., et al., Native–like in vivo folding of a circularly permuted jellyroll protein shown by crystal structure analysis, *Proc. Natl. Acad. Sci. U.S.A.*, 91: 10417–10421 (1994).

Yang, Y.R. and Schachman, H.K., Aspartate transcarbamoylase containing circularly permuted catalytic polypeptide chains, *Proc. Natl. Acad. Sci. U.S.A.*, 90: 11980–1194 (1993).

Luger, K., et al., An 8–fold βα barrel protein with redundant folding possibilities, *Prot. Eng.*, 3: 249–258 (1990).

Luger, K., et al., Correct Folding of Circularly Permuted Variants of a βα Barrel Enzyme in Vivo, *Science*, 243: 206–210 (1989).

Lin, X., et al., Rearranging the domains of pepsinogen, *Protein Science*, 4: 159–166 (1995).

Vignais, M.L., et al., Circular permutation within the coenzyme binding domain of the tetrameric glyceraldehyde–3–phosphate dehydrogenase from *Bacillus stearothermophilus*, *Protein Science*, 4: 994–1000 (1995).

Ritco–Vonsovici, M., et al., Is the Continuity of the Domains Required for the Correct Folding of a Two–Domain Protein, *Biochemistry*, 34: 16543–16551 (1995).

Horlick, R.A., et al., Permuteins of interleukin 1β–a simplified approach for the construction of permutated proteins having new termini, *Protein Eng.*, 5: 427–431 (1992).

Kreitman, R.J., et al., Circularly Permuted Interleukin 4 Retains Proliferative and Binding Activity, *Cytokine*, 7: 311–318 (1995).

Viguera, A.R., et al., The Order of Secondary Structure Elements does not Determine the Structure of a Protein but does Affect its Folding Kinetics, *J. Mol. Biol.*, 247: 670–681 (1995).

Koebnik, R. and Kramer, L., Membrane Assembly of Circularly Permuted Variants of the *E. coli* Outer Membrane Protein OmpA, *J. Mol. Biol.*, 250: 617–626 (1995).

Kreitman, R.J., et al., A ciruclarly permuted recombinant interleukin 4 toxin with increased activity, *Proc. Natl. Avad. Sci.*, 91: 6889–6893 (1994).

Stanley, J.S., et al., Identification and Mutational Analysis of the Immunodominant IgE Binding Epitopes of the Major Peanut Allergen Ara h 2, *Arch. Biochem. Biophys.*, 342(2): 244–253 (1997).

Hopp, T.P. and Woods, K.R., A Computer Program for Predicting Protein Antigenic Determinants, *Mol. Immunol.*, 20: 483–489 (1983).

Kyte, J. and Doolittle, R.F., A Simple Method for Displaying the Hydropathic Character of a Protein, *J. Mol. Biol.*, 157: 105–132 (1982).

Lee, B. and Richards, F.M., The Interpretation of Protein Structures: Estimation of Static Accessibility, *J. Mol. Biol.*, 55: 379–400 (1971).

Karplus, P.A. and Schulz, G.E., Prediction of Chain Flexibility in Proteins, *Naturwissenschaften*, 72: 212–213 (1985).

Sandhu, J., Protein Engineering of Antibodies, *Critical Rev. Biotech.*, 12: 437–467 (1992).

Fuchs, R.L. and Astwood, J.D., Allergenicity Assessment of Foods Derived from Gentically Modified Plants, *Food Technology*, 50: 83–88 (1996).

Kasturi, L., et al., Regulation of N–linked core glycosylation: use of a site–directed mutagenesis approach to identify Asn–Xaa–Ser/Thr sequons that are poor oligosaacharide acceptors, *Biochem. J.*, 323: 415–519 (1997).

Melquist, J.L., et al., The Amino Acid Following an ASN–X– Ser/Thr Sequon is an Important Determinant of N–Linked Core Glycosylation Efficiency, *Biochemistry*, 37: 6833–6837 (1998).

Alibhai, M., et al. Re–Engineering Patatin (Sol t 1) Protein to Eliminate IgE Binding, *J. Allergy Clin. Immunol.*, vol. 105, No. 1 (part 2): S79, paper 239 (2000).

Astwood, J.D., et al. Identification and Characterization of IgE Binding Epitopes of Patatin, a Major Food Allergen of Potato, *J. Allergy Clin. Immunol.,* vol. 105, No. 1 (part 2): S184, paper 555 (2000).

Rabjohn, P., et al. Molecular Cloning and Epitope Analysis of the Peanut Allergen Ara h 3, *J. Clin. Invest., NY,* 103: 535–542 (1999).

Rosahl, S.; Schmidt, R.; Schell, J.; Willmitzer, L. "Isolation and Characterization of a Gene from *Solanum tuberosum* Encoding Patatin, the Major Storage Protein of Potato Tubers." *Mol. Gen. Genet.* 1986, 203: 214–220.

Helm, R.M.; Cockrell, G.; Herman, E.; Burks, A.W.; Sampson, H.A.; Bannon, G.A. "Cellular and Molecular Characterization of a Major Soybean Allergan." *Int. Arch. Allergy Immunol.* 1998, 117: 29–37.

Shin, D.S., et al. "Biochemical and Structural Analysis of the IgE Binding Sites on Ara h1, and Abundant and Highly Allergenic Peanut Protein." *J. Biol. Chem.* 1998, 273 (22): 13753–13759.

| FIG. 1A |
|---|
| FIG. 1B |
| FIG. 1C |
| FIG. 1D |
| FIG. 1E |
| FIG. 1F |
| FIG. 1G |
| FIG. 1H |
| FIG. 1I |

FIG. 1

| | | |
|---|---|---|
| gi\|patatin_mtc | ----------------------------------MATTKSFLILIFMILA------TTSSTFAQLGEM | 28 |
| gi\|PatFm | --------------------------------------------------------MALEEM | 6 |
| gi\|PatIm | --------------------------------------------------------PWLEEM | 6 |
| gi\|PatL+ | ----------------------------------MATTKSFLILFFMILA------TTSSTCAKLEEM | 28 |
| gi\|PatA+ | ----------------------------------MATTKSFLILFFMILA------TTSSTCAKLEEM | 28 |
| gi\|PatB+ | ----------------------------------MATTKSVLVLFFMILA------TTSSTCATLGEM | 28 |
| gi\|pentin1_phb | -------------------------MKSKMAMLLLLFCVLSNQLVAAFSTQAKASKDGNL | 35 |
| gi\|5c9_phb | ----------------------------------------MGSIGRGTANCATVPQPPPSTGKL | 24 |
| gi\|corn3_pep | ----------------------------------------MGSIGRGTANCATVPQPPPSTGKL | 24 |
| gi\|corn2_pep | ----------------------------------------MGSIGRGTANCATVPQPPPSTGKL | 24 |
| gi\|corn4_pep | ----------------------------------------MGSIGRGTANCATVPQPPPSTGKL | 24 |
| gi\|corn1_pep | RPTRPRHPRNTQKRGALLVGWILFSLAASPVKFQTHMGSIGRGTANCATVPQPPPSTGKL | 60 |
| gi\|corn5_pep | ----------------------------------------MGSIGRGTANCATVPQPPPSTGKL | 24 |

FIG. 1A

| | | |
|---|---|---|
| gi\|patatin_mtc | VTVLSIDGGGIRGIIPATILEFLEGQLQEMDNNADARLADYFDVIGGTSTGGLLTAMIST | 88 |
| gi\|PatFm | VAVLSIDGGGIKGIIPGTILEFLEGQLQKMDNNADARLADYFDVIGGTSTGGLLTAMITT | 66 |
| gi\|PatIm | VTVLSIDGGGIKGIIPAIILEFLEGQLQEVDNNKDARLADYFDVIGGTSTGGLLTAMITT | 66 |
| gi\|PatL+ | VTVLSIDGGGIKGIIPAIILEFLEGQLQEVDNNKDARLADYFDVIGGTSTGGLLTAMITT | 88 |
| gi\|PatA+ | VTVLSIDGGGIKGIIPAIILEFLEGQLQEVDNNKDARLADYFDVIGGTSTGGLLTAMITT | 88 |
| gi\|PatB+ | VTVLSIDGGGIKGIIPATILEFLEGQLQEVDNNKDARLADYFDVIGGTSTGGLLTAMITT | 88 |
| gi\|pentin1_phb | VTVLAIDGGGIRGIIPGVILKQLEATLQRWDSS--ARLAEYFDVVAGTSTGGIITAILTA | 93 |
| gi\|5c9_phb | ITILSIDGGGIRGLIPATIIAYLEAKLQELDGP-DARIADYFDVIAGTSTGALLASMLAA | 83 |
| gi\|corn3_pep | ITILSIDGGGIRGLIPATIIAYLEAKLQELDGP-DARIADYFDVIAGTSTGALLASMLAA | 83 |
| gi\|corn2_pep | ITILSIDGGGIRGLIPATIIAYLEAKLQELDGP-DARIADYFDVIAGTSTGALLASMLAA | 83 |
| gi\|corn4_pep | ITILSIDGGGIRGLIPATIIAYLEAKLQELDGP-DARIADYFDVIAGTSTGALLASMLAA | 83 |
| gi\|corn1_pep | ITILSIDGGGIRGLIPATIIAYLEAKLQELDGP-DARIADYFDVIAGTSTGALLASMLAA | 119 |
| gi\|corn5_pep | ITILSIDGGGIRGLIPATIIAYLEAKLQELDGP-DARIADYFDVIAGTSTGALLASMLAA | 83 |

FIG. 1B

| | | | |
|---|---|---|---|
| gi\|patatin_mtc | PNENN--RPFAAAKEIVPFYFEHGPQIFNP------------SGQILGPKYDGKYLMQVL | 134 |
| gi\|PatFm | PNENN--RPFAAANEIVPFYFEHGPHIFNSR-----------YWPIFWPKYDGKYLMQVL | 113 |
| gi\|PatIm | PNENN--RPFAAAKDIVPFYFEHGPHIFNY------------SGSILGPMYDGKYLLQVL | 112 |
| gi\|PatL+ | PNENN--RPFAAAKDIVPFYFEHGPHIFNY------------SGSILGPMYDGKYLLQVL | 134 |
| gi\|PatA+ | PNENN--RPFAAAKDIVPFYFEHGPHIFNY------------SGSIIGPMYDGKYLLQVL | 134 |
| gi\|PatB+ | PNENN--RPFAAAKDIVPFYFEHGPHIFNS------------SGSIFGPMYDGKYFLQVL | 134 |
| gi\|pentin1_phb | PDPQNKDRPLYAAEEIIDFYIEHGPSIFNKSTA---------CSLPGIFCPKYDGKYLQEII | 146 |
| gi\|5c9_phb | PDENN--RPLFAAKDLTTFYLENGPKIFPQKKAGLLTPLRNLLGLVRGPKYDGVFLHDKI | 141 |
| gi\|corn3_pep | PDENN--RPLFAAKDLTTFYLENGPKIFPQKKAGLLTPLRNLLGLVRGPKYDGVFLHDKI | 141 |
| gi\|corn2_pep | PDENN--RPLFAAKDLTTFYLENGPKIFPQKKAGLLTPLRNLLGLVRGPKYDGVFLHDKI | 141 |
| gi\|corn4_pep | PDENN--RPLFAAKDLTTFYLENGPKIFPQKKAGLLTPLRNLLGLVRGPKYDGVFLHDKI | 141 |
| gi\|corn1_pep | PDENN--RPLFAAKDLTTFYLENGPKIFPQKKAGLLTPLRNLLGLVRGPKYDGVFLHDKI | 177 |
| gi\|corn5_pep | PDENN--RPLFAAKDLTTFYLENGPKIFPQKKAGLLTPLRNLLGLVRGPKYDGVFLHDKI | 141 |

FIG. 1C

| | | |
|---|---|---|
| gi\|patatin_mtc | QEKLGETRVHQALTEVVISSFDIKTNKPVIFTKSNLANSPELDAKMYDISYSTAAAPTYF | 194 |
| gi\|PatFm | QEKLGETRVHQALTEVAISSFDIKTNKPVIFTKSNLAKSPELDAKTYDICYSTAAAPTYF | 173 |
| gi\|PatIm | QEKLGETRVHQALTEVAISSFDIKTNKPVIFTKSNLAKSPELDAKMYDICYSTAAAPIYF | 172 |
| gi\|PatL+ | QEKLGETRVHQALTEVAISSFDIKTNKPVIFTKSNLAKSPELDAKMYDICYSTAAAPIYF | 194 |
| gi\|PatA+ | QEKLGETRVHQALTEVAISSFDIKTNKPVIFTKSNLAKSPELDAKMYDICYSTAAAPIYF | 194 |
| gi\|PatB+ | QEKLGETRVHQALTEVAISSFDIKTNKPVIFTKSNLAKSPELDAKMNDICYSTAAAPIYF | 194 |
| gi\|pentin1_phb | SQKLNETLLDQITTNVVIPSFDIKLLRPTIFSTFKLEEVPELNVKLSDVCMGTSAAPIVF | 206 |
| gi\|5c9_phb | KSLTHDVRVADTVTNVIVPAFDVKYLQPIIFSTYEAKTDTLKNAHLSDICISTSAAPTYF | 201 |
| gi\|corn3_pep | KSLTHDVRVADTVTNVIVPAFDVKYLQPIIFSTYEAKTDALKNAHLSDICISTSAAPTYF | 201 |
| gi\|corn2_pep | KSLTHDVRVADTVTNVIVPAFDVKSLQPIIFSTYEAKTDTLKNAHLSDICISTSAAPTYF | 201 |
| gi\|corn4_pep | KSLTHDVRVADTVTNVIVPAFDVKSLQPIIFSTYEAKTDTLKNAHLSDICISTSAAPTYF | 201 |
| gi\|corn1_pep | KSLTHDVRVADTVTNVIVPAFDVKYLQPIIFSTYEAKTDALKNAHLSDICISTSAAPTYF | 237 |
| gi\|corn5_pep | KSLTHDVRVADTVTNVIVPAFDVKYLQPIIFSTYEAKTDALKNAHLSDICISTSAAPTYF | 201 |

FIG. 1D

```
gi|patatin_mtc   PPHYFVTNTSNG-DEYEFNLVDGAVATVADPALLSISVATRLAQKDPAFASIRSLNYKKM  253
PatFm            PPHYFATNTING-DKYEFNLVDGAVATVADPALLSVSVATRRAQEDPAFASIRSLNYKKM  232
PatIm            PPHHFVTHTSNG-ARYEFNLVDGAVATVGDPALLSLSVATRLAQEDPAFSSIKSLDYKQM  231
PatL+            PPHHFVTHTSNG-ARYEFNLVDGAVATVGDPALLSLSVATRLAQEDPAFSSIKSLDYKQM  253
PatA+            PPHYFITHTSNG-DIYEFNLVDGGVATVGDPALLSLSVATRLAQEDPAFSSIKSLDYKQM  253
PatB+            PPHYFVTHTSNG-DKYEFNLVDGAVATVGDPALLSLSVRTKLAQVDPKFASIKSLNYNEM  253
gi|pentin1_phb   PPYYFKHG-----DTEFNLVDGAIIADIPAPVALSEVLQQEKYKN--KE-------I    249
gi|5c9_phb       PAHFFKTEATDGRPPREYHLVDGGVAANNPTMVAMSMLTKEVHRRNPNFNAGSPTEYTNY  261
gi|corn3_pep     PAHFFKTEATDGRPPREYHLVDGGVAANNPTMVAMSMLTKEVHRRNPNFNAGSPTEYTNY  261
gi|corn2_pep     PAHFFKTEATDGRPPREYHLVDGGVAANNPTMVAMSMLTKEVHRRNPNFNAGSPTEYTNY  261
gi|corn4_pep     PAHFFKIEATDGRPPREYHLVDGGVAANNPTMVAMSMLTKEVHRRNPNFNAGSPTEYTNY  261
gi|corn1_pep     PAHFFKTEATDGRPPREYHLVDGGVAANNPTMVAMSMLTKEVHRRNPNFNAGSPTEYTNY  297
gi|corn5_pep     PAHFFKTEATDGRPPREYHLVDGGVAANNPTMVAMSMLTKEVHRRNPNFNAGSPTEYTNY  261
```

FIG. 1E

```
gi|patatin_mtc   LLLSLGTGTGTTSEFDKTYTAKEAATWTAVHWMLVIQK--------MTDAASSYMTDYYLSTAFQ 308
gi|PatFm         LLLSLGTGTGTTSEFDKTYTAEETAKWGALQWMLVIQQ--------MTEAASSYMTDYYLSTVFQ 287
gi|PatIm         LLLSLGTGTNSEFDKTYTAEEAAKWGPLRWMLAIQQ--------MTNAASFYMTDYYISTVFQ 286
gi|PatL+         LLLSLGTGTNSEFDKTYTAEEAAKWGPLRWMLAIQQ--------MTNAASSYMTDYYISTVFQ 308
gi|PatA+         LLLSLGTGTNSEFDKTYTAQEAAKWGPLRWMLAIQQ--------MTNAASSYMTDYYISTVFQ 308
gi|PatB+         LLLSLGTGTNSEFDKTYTAEEAAKWGPLRWILAIQQ--------MTNAASSYMTDYYLSTVFQ 308
gi|pentin1_phb   LLLSIGTGVVKPGEGYSANRTWTIFDWSSETLIG--------LMGHGTRAMSDYYVGSHFK 302
gi|5c9_phb       LIISVGTGSAKQAEK-YTAEQCAKWGLIQWLYNGGFTPIIDIFSHASSDMVDIHASILFQ 320
gi|corn3_pep     LIISVGTGSAKQAEK-YTAEQCAKWGLIQWLYNGGFTPIIDIFSHASSDMVDIHASILFQ 320
gi|corn2_pep     LIISVGTGSAKQAEK-YTAEQCAKWGLIQWLYNGGFTPIIDIFSHASSDMVDIHASILFQ 320
gi|corn4_pep     LIISVGTGSAKQAEK-YTAEQCAKWGLIQWLYNGGFTPIIDIFSHASSDMVDIHASILFQ 320
gi|corn1_pep     LIISVGTGSAKQAEK-YTAEQCAKWGLIQWLYNGGFTPIIDIFSHASSDMVDIHASILFQ 356
gi|corn5_pep     LIISVGTGSAKQAEK-YTAEQCAKWGLIQWLYNGGFTPIIDIFSHASSDMVDIHASILFQ 320
```

FIG. 1F

```
gi|patatin_mtc    ALDSKNNYLRVQENALTGT----------------------------------TTEMDDASEANMELLVQ 344
gi|PatFm          DLHSQNNYLRVQENALTGT----------------------------------TTKADDASEANMELLAQ 323
gi|PatIm          ARHSQNNYLRVQENALNGT----------------------------------TTEMDDASEANMELLVQ 322
gi|PatL+          ARHSQNNYLRVQENALNGT----------------------------------TTEMDDASEANMELLVQ 344
gi|PatA+          ARHSQNNYLRVQENALTGT----------------------------------TTEMDDASEANMELLVQ 344
gi|PatB+          ARHSQNNYLRVQENALTGT----------------------------------TTEMDDASEANMELLVQ 344
gi|pentin1_phb    ALQPQNNYLRIQEYDLDPA----------------------------------LESIDDASTENMENLEK 338
gi|5c9_phb        ALHCEKKYLRIQDDTLTGN----------------------------------ASSVDIATKENMESLIS 356
gi|corn3_pep      ALHCEKKYLRIQDDTLTGN----------------------------------ASSVDIATKENMESLIS 356
gi|corn2_pep      ALHCEKKYLRIQDDTLTGN----------------------------------ASSVDIATKENMESLIS 356
gi|corn4_pep      ALHCEKKYLRIQDDTLTGN----------------------------------ASSVDIATKENMESLIS 356
gi|corn1_pep      ALHCEKKYLRIQLYYAGYFDWERIVRGHRHQGEHGVSDIDRPGAAQEASGESEHRHRAVR 416
gi|corn5_pep      ALHCEKKYLRIQLYYAG-------------------------------------------- 337
```

FIG. 1G

```
gi|patatin_mtc    VGENLLKKPVSEDNP----------------ETYEEALKRFAKLLSDRKKLRANKASY---------------- 386
gi|PatFm          VGENLLKKPVSKDNP----------------ETYEEALKRFAKLLSDRKKLRANKASY---------------- 365
gi|PatIm          VGETLLKKPVSRDSP----------------ETYEEALKRFAKLLSDRKKLRANKASY---------------- 364
gi|PatL+          VGATLLKKPVSKDSP----------------ETYEEALKRFAKLLSDRKKLRANKASY---------------- 386
gi|PatA+          VGETLLKKPVSKDSP----------------ETYEEALKRFAKLLSDRKKLRANKASY---------------- 386
gi|PatB+          VGEKLLKKPVSKDSP----------------ETYEEALKRFAKLLSDRKKLRANKASY---------------- 386
gi|pentin1_phb    VGQSLLNEPVKRMNLNT-FVVEETGEGTNAEALDRLAQILYEEKITRGLGKISLEVDNID------------- 397
gi|5c9_phb        IGQELLKKPVARVNIDTGVYESCDGEGTNAQSLADFAKQLSDERKLRKSNLNSN------------------- 410
gi|corn3_pep      IGQELLKKPVARVNIDTGLYESCDGEGTNAQSLADFAKQLSDERKLRKSNLNSN------------------- 410
gi|corn2_pep      IGQELLNKPVARVNIDTGLYESCEGEGTNAQSLADFAKQLSDERKLRKSNLNSN------------------- 410
gi|corn4_pep      IGQELLNKPVARVNIDTGLYESCEGEGTNAQSLADFAKQLSDERKLRKSNLNSN------------------- 410
gi|corn1_pep      IGQELLNKPVARVNIDTGLYESCEGEGTNAQSLADFAKQLSDERKLRKSNLNSN------------------- 410
gi|corn5_pep      VLRRGHKCTVASLRQATLRAQATQEQSQLQLINTSLSHSMCSFRRFTVSYFFNFNSVCVL------------- 476
```

FIG. 1H

| | | |
|---|---|---|
| gi\|patatin_mtc | -------------- | --- |
| gi\|PatFm | -------------- | --- |
| gi\|PatIm | -------------- | --- |
| gi\|PatL+ | -------------- | --- |
| gi\|PatA+ | -------------- | --- |
| gi\|PatB+ | PYTERVRKLLF--- | 408 |
| gi\|pentin1_phb | -------------- | --- |
| gi\|5c9_phb | -------------- | --- |
| gi\|corn3_pep | -------------- | --- |
| gi\|corn2_pep | -------------- | --- |
| gi\|corn4_pep | -------------- | --- |
| gi\|corn1_pep | CVLCVYQTFKFNQKKKKKKKKKKKKRAA | 508 |

FIG. 11

SEQUENCE LISTING

```
<160> NUMBER OF SEQ ID NOS: 295

<210> SEQ ID NO 1
<211> LENGTH: 1158
<212> TYPE: DNA
<213> ORGANISM: Solanum tuberosum

<400> SEQUENCE: 1
atggcaacta ctaaatcttt tttaatttta atatttatga tattagcaac tactagttca      60
acatttgctc agttgggaga atggtgact gttcttagta ttgatggagg tggaattaga     120
gggatcattc cggctaccat tctcgaattt cttgaaggac aacttcagga aatggacaat    180
aatgcagatg caagacttgc agattacttt gatgtaattg gaggaacaag tacaggaggt    240
ttattgactg ctatgataag tactccaaat gaaaacaatc gacctttgc tgctgccaaa     300 gaaattgtac cttttttactt cgaacatggc cctcagattt ttaatcctag tggtcaaatt    360
ttaggcccaa aatatgatgg aaaatatctt atgcaagttc ttcaagaaaa acttggagaa    420
actcgtgtgc atcaagcttt gacagaagtt gtcatctcaa gctttgacat caaaacaaat    480
aagccagtaa tattcactaa gtcaaattta gcaaactctc cagaattgga tgctaagatg    540
tatgacataa gttattccac agcagcagct ccaacatatt ttcctccgca ttactttgtt    600
actaatacta gtaatggaga tgaatatgag ttcaatcttg ttgatggtgc tgttgctact    660
gttgctgatc cggcgttatt atccattagc gttgcaacga gacttgcaca aaaggatcca    720
gcatttgctt caattaggtc attgaattac aaaaaaatgc tgttgctctc attaggcact    780
ggcactactt cagagtttga taaaacatat acagcaaaag aggcagctac ctggactgct    840
gtacattgga tgttagttat acagaaaatg actgatgcag caagttctta catgactgat    900
tattaccttt ctactgcttt tcaagctctt gattcaaaaa acaattacct cagggttcaa    960
gaaaatgcat taacaggcac aactactgaa atggatgatg cttctgaggc taatatggaa   1020
ttattagtac aagttggtga aaacttattg aagaaaccag tttccgaaga caatcctgaa   1080
acctatgagg aagctctaaa gaggtttgca aaattgctct ctgataggaa gaaactccga   1140
gcaaacaaag cttcttat                                                 1158

<210> SEQ ID NO 2
<211> LENGTH: 386
<212> TYPE: PRT
<213> ORGANISM: Solanum tuberosum

<400> SEQUENCE: 2

Met Ala Thr Thr Lys Ser Phe Leu Ile Leu Ile Phe Met Ile Leu Ala
1               5                  10                  15

Thr Thr Ser Ser Thr Phe Ala Gln Leu Gly Glu Met Val Thr Val Leu
                20                  25                  30

Ser Ile Asp Gly Gly Ile Arg Gly Ile Ile Pro Ala Thr Ile Leu
            35                  40                  45

Glu Phe Leu Glu Gly Gln Leu Gln Glu Met Asp Asn Asn Ala Asp Ala
```

```
                50                  55                  60
Arg Leu Ala Asp Tyr Phe Asp Val Ile Gly Gly Thr Ser Thr Gly Gly
65                  70                  75                  80

Leu Leu Thr Ala Met Ile Ser Thr Pro Asn Glu Asn Arg Pro Phe
                85                  90                  95

Ala Ala Ala Lys Glu Ile Val Pro Phe Tyr Phe Glu His Gly Pro Gln
                100                 105                 110

Ile Phe Asn Pro Ser Gly Gln Ile Leu Gly Pro Lys Tyr Asp Gly Lys
                115                 120                 125

Tyr Leu Met Gln Val Leu Gln Glu Lys Leu Gly Glu Thr Arg Val His
                130                 135                 140

Gln Ala Leu Thr Glu Val Val Ile Ser Ser Phe Asp Ile Lys Thr Asn
145                 150                 155                 160

Lys Pro Val Ile Phe Thr Lys Ser Asn Leu Ala Asn Ser Pro Glu Leu
                165                 170                 175

Asp Ala Lys Met Tyr Asp Ile Ser Tyr Ser Thr Ala Ala Pro Thr
                180                 185                 190

Tyr Phe Pro Pro His Tyr Phe Val Thr Asn Thr Ser Asn Gly Asp Glu
                195                 200                 205

Tyr Glu Phe Asn Leu Val Asp Gly Ala Val Ala Thr Val Ala Asp Pro
                210                 215                 220

Ala Leu Leu Ser Ile Ser Val Ala Thr Arg Leu Ala Gln Lys Asp Pro
225                 230                 235                 240

Ala Phe Ala Ser Ile Arg Ser Leu Asn Tyr Lys Lys Met Leu Leu Leu
                245                 250                 255

Ser Leu Gly Thr Gly Thr Thr Ser Glu Phe Asp Lys Thr Tyr Thr Ala
                260                 265                 270

Lys Glu Ala Ala Thr Trp Thr Ala Val His Trp Met Leu Val Ile Gln
                275                 280                 285

Lys Met Thr Asp Ala Ala Ser Ser Tyr Met Thr Asp Tyr Tyr Leu Ser
                290                 295                 300

Thr Ala Phe Gln Ala Leu Asp Ser Lys Asn Asn Tyr Leu Arg Val Gln
305                 310                 315                 320

Glu Asn Ala Leu Thr Gly Thr Thr Glu Met Asp Asp Ala Ser Glu
                325                 330                 335

Ala Asn Met Glu Leu Leu Val Gln Val Gly Glu Asn Leu Leu Lys Lys
                340                 345                 350

Pro Val Ser Glu Asp Asn Pro Glu Thr Tyr Glu Ala Leu Lys Arg
                355                 360                 365

Phe Ala Lys Leu Leu Ser Asp Arg Lys Lys Leu Arg Ala Asn Lys Ala
                370                 375                 380

Ser Tyr
385

<210> SEQ ID NO 3
<211> LENGTH: 54
<212> TYPE: DNA
<213> ORGANISM: Artificial
<220> FEATURE:
<223> OTHER INFORMATION: Synthetic construct

<400> SEQUENCE: 3
ggagctcgag aaaagagagg ctgaagctca gttgggagaa atggtgactg ttct        54

<210> SEQ ID NO 4
```

<211> LENGTH: 29
<212> TYPE: DNA
<213> ORGANISM: Artificial
<220> FEATURE:
<223> OTHER INFORMATION: Synthetic construct

<400> SEQUENCE: 4
ggtctagagg aattctcatt aataagaag                                          29

<210> SEQ ID NO 5
<211> LENGTH: 1138
<212> TYPE: DNA
<213> ORGANISM: Artificial
<220> FEATURE:
<223> OTHER INFORMATION: Synthetic construct

<400> SEQUENCE: 5

```
ggagctcgag aaaagagagg ctgaagctca gttgggagaa atggtgactg ttcttagtat      60
tgatggaggt ggaattagag ggatcattcc ggctaccatt ctcgaatttc ttgaaggaca     120
acttcaggaa atggacaata atgcagatgc aagacttgca gattactttg atgtaattgg     180
aggaacaagt acaggaggtt tattgactgc tatgataagt actccaaatg aaaacaatcg     240
acccttttgct gctgccaaag aaattgtacc tttttacttc gaacatggcc ctcagatttt     300
taatcctagt ggtcaaattt taggcccaaa atatgatgga aaatatctta tgcaagttct     360
tcaagaaaaa cttggagaaa ctcgtgtgca tcaagctttg acagaagttg tcatctcaag     420
ctttgacatc aaaacaaata agccagtaat attcactaag tcaaatttag caaactctcc     480
agaattggat gctaagatgt atgacataag ttattccaca gcagcagctc aacatatttt     540
tcctccgcat tactttgtta ctaatactag taatggagat gaatatgagt tcaatcttgt     600
tgatggtgct gttgctactg ttgctgatcc ggcgttatta tccattagcg ttgcaacgag     660
acttgcacaa aaggatccag catttgcttc aattaggtca ttgaattaca aaaaaatgct     720
gttgctctca ttaggcactg gcactacttc agagtttgat aaaacatata cagcaaaaga     780
ggcagctacc tggactgctg tacattggat gttagttata cagaaaatga ctgatgcagc     840
aagttcttac atgactgatt attaccttttc tactgctttt caagctcttg attcaaaaaa     900
caattacctc agggttcaag aaaatgcatt aacaggcaca actactgaaa tggatgatgc     960
ttctgaggct aatatggaat attagtaca agttggtgaa aacttattga agaaaccagt    1020
ttccgaagac aatcctgaaa cctatgagga agctctaaag aggtttgcaa aattgctctc    1080
tgataggaag aaactccgag caaacaaagc ttcttattaa tgagaattcc tctagacc     1138
```

<210> SEQ ID NO 6
<211> LENGTH: 452
<212> TYPE: PRT
<213> ORGANISM: Artificial
<220> FEATURE:
<223> OTHER INFORMATION: Synthetic polypeptide

<400> SEQUENCE: 6

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

-continued

```
Phe Ile Asn Thr Thr Ile Ala Ser Ile Ala Ala Lys Glu Glu Gly Val
 65                  70                  75                  80

Ser Leu Glu Lys Arg Glu Ala Glu Ala Gln Leu Gly Glu Met Val Thr
                 85                  90                  95

Val Leu Ser Ile Asp Gly Gly Ile Arg Gly Ile Ile Pro Ala Thr
            100                 105                 110

Ile Leu Glu Phe Leu Gly Gln Leu Gln Met Asp Asn Asn Ala
        115                 120                 125

Asp Ala Arg Leu Ala Asp Tyr Phe Asp Val Ile Gly Gly Thr Ser Thr
    130                 135                 140

Gly Gly Leu Leu Thr Ala Met Ile Ser Thr Pro Asn Glu Asn Asn Arg
145                 150                 155                 160

Pro Phe Ala Ala Ala Lys Glu Ile Val Pro Phe Tyr Phe Glu His Gly
                165                 170                 175

Pro Gln Ile Phe Asn Pro Ser Gly Gln Ile Leu Gly Pro Lys Tyr Asp
            180                 185                 190

Gly Lys Tyr Leu Met Gln Val Leu Gln Glu Lys Leu Gly Glu Thr Arg
        195                 200                 205

Val His Gln Ala Leu Thr Glu Val Val Ile Ser Ser Phe Asp Ile Lys
    210                 215                 220

Thr Asn Lys Pro Val Ile Phe Thr Lys Ser Asn Leu Ala Asn Ser Pro
225                 230                 235                 240

Glu Leu Asp Ala Lys Met Tyr Asp Ile Ser Tyr Ser Thr Ala Ala Ala
                245                 250                 255

Pro Thr Tyr Phe Pro Pro His Tyr Phe Val Thr Asn Thr Ser Asn Gly
            260                 265                 270

Asp Glu Tyr Glu Phe Asn Leu Val Asp Gly Ala Val Ala Thr Val Ala
        275                 280                 285

Asp Pro Ala Leu Leu Ser Ile Ser Val Ala Thr Arg Leu Ala Gln Lys
    290                 295                 300

Asp Pro Ala Phe Ala Ser Ile Arg Ser Leu Asn Tyr Lys Lys Met Leu
305                 310                 315                 320

Leu Leu Ser Leu Gly Thr Gly Thr Thr Ser Glu Phe Asp Lys Thr Tyr
                325                 330                 335

Thr Ala Lys Glu Ala Ala Thr Trp Thr Ala Val His Trp Met Leu Val
            340                 345                 350

Ile Gln Lys Met Thr Asp Ala Ala Ser Ser Tyr Met Thr Asp Tyr Tyr
        355                 360                 365

Leu Ser Thr Ala Phe Gln Ala Leu Asp Ser Lys Asn Asn Tyr Leu Arg
    370                 375                 380

Val Gln Glu Asn Ala Leu Thr Gly Thr Thr Thr Glu Met Asp Asp Ala
385                 390                 395                 400

Ser Glu Ala Asn Met Glu Leu Leu Val Gln Val Gly Glu Asn Leu Leu
                405                 410                 415

Lys Lys Pro Val Ser Glu Asp Asn Pro Glu Thr Tyr Glu Glu Ala Leu
            420                 425                 430

Lys Arg Phe Ala Lys Leu Leu Ser Asp Arg Lys Lys Leu Arg Ala Asn
        435                 440                 445

Lys Ala Ser Tyr
        450

<210> SEQ ID NO 7
<211> LENGTH: 367
```

<212> TYPE: PRT
<213> ORGANISM: Artificial
<220> FEATURE:
<223> OTHER INFORMATION: Synthetic polypeptide

<400> SEQUENCE: 7

```
Glu Ala Glu Ala Gln Leu Gly Glu Met Val Thr Val Leu Ser Ile Asp
1               5                   10                  15
Gly Gly Gly Ile Arg Gly Ile Ile Pro Ala Thr Ile Leu Glu Phe Leu
            20                  25                  30
Glu Gly Gln Leu Gln Glu Met Asp Asn Asn Ala Asp Ala Arg Leu Ala
        35                  40                  45
Asp Tyr Phe Asp Val Ile Gly Gly Thr Ser Thr Gly Gly Leu Leu Thr
    50                  55                  60
Ala Met Ile Ser Thr Pro Asn Glu Asn Asn Arg Pro Phe Ala Ala Ala
65                  70                  75                  80
Lys Glu Ile Val Pro Phe Tyr Phe Glu His Gly Pro Gln Ile Phe Asn
                85                  90                  95
Pro Ser Gly Gln Ile Leu Gly Pro Lys Tyr Asp Gly Lys Tyr Leu Met
            100                 105                 110
Gln Val Leu Gln Glu Lys Leu Gly Glu Thr Arg Val His Gln Ala Leu
        115                 120                 125
Thr Glu Val Val Ile Ser Ser Phe Asp Ile Lys Thr Asn Lys Pro Val
    130                 135                 140
Ile Phe Thr Lys Ser Asn Leu Ala Asn Ser Pro Glu Leu Asp Ala Lys
145                 150                 155                 160
Met Tyr Asp Ile Ser Tyr Ser Thr Ala Ala Pro Thr Tyr Phe Pro
                165                 170                 175
Pro His Tyr Phe Val Thr Asn Thr Ser Asn Gly Asp Glu Tyr Glu Phe
            180                 185                 190
Asn Leu Val Asp Gly Ala Val Ala Thr Val Ala Asp Pro Ala Leu Leu
        195                 200                 205
Ser Ile Ser Val Ala Thr Arg Leu Ala Gln Lys Asp Pro Ala Phe Ala
    210                 215                 220
Ser Ile Arg Ser Leu Asn Tyr Lys Lys Met Leu Leu Leu Ser Leu Gly
225                 230                 235                 240
Thr Gly Thr Thr Ser Glu Phe Asp Lys Thr Tyr Thr Ala Lys Glu Ala
                245                 250                 255
Ala Thr Trp Thr Ala Val His Trp Met Leu Val Ile Gln Lys Met Thr
            260                 265                 270
Asp Ala Ala Ser Ser Tyr Met Thr Asp Tyr Tyr Leu Ser Thr Ala Phe
        275                 280                 285
Gln Ala Leu Asp Ser Lys Asn Asn Tyr Leu Arg Val Gln Glu Asn Ala
    290                 295                 300
Leu Thr Gly Thr Thr Glu Met Asp Asp Ala Ser Glu Ala Asn Met
305                 310                 315                 320
Glu Leu Leu Val Gln Val Gly Glu Asn Leu Leu Lys Pro Val Ser
                325                 330                 335
Glu Asp Asn Pro Glu Thr Tyr Glu Glu Ala Leu Lys Arg Phe Ala Lys
            340                 345                 350
Leu Leu Ser Asp Arg Lys Lys Leu Arg Ala Asn Lys Ala Ser Tyr
        355                 360                 365
```

<210> SEQ ID NO 8
<211> LENGTH: 24

```
<212> TYPE: DNA
<213> ORGANISM: Artificial
<220> FEATURE:
<223> OTHER INFORMATION: Synthetic construct

<400> SEQUENCE: 8
atgttcgaag aaaaaaggta caat                                    24

<210> SEQ ID NO 9
<211> LENGTH: 24
<212> TYPE: DNA
<213> ORGANISM: Artificial
<220> FEATURE:
<223> OTHER INFORMATION: Synthetic construct

<400> SEQUENCE: 9
ttgcataaga aattttccat cata                                    24

<210> SEQ ID NO 10
<211> LENGTH: 24
<212> TYPE: DNA
<213> ORGANISM: Artificial
<220> FEATURE:
<223> OTHER INFORMATION: Synthetic construct

<400> SEQUENCE: 10
tgctgtggaa aaacttatgt cata                                    24

<210> SEQ ID NO 11
<211> LENGTH: 24
<212> TYPE: DNA
<213> ORGANISM: Artificial
<220> FEATURE:
<223> OTHER INFORMATION: Synthetic construct

<400> SEQUENCE: 11
cggaggaaaa aatgttggag ctgc                                    24

<210> SEQ ID NO 12
<211> LENGTH: 51
<212> TYPE: DNA
<213> ORGANISM: Artificial
<220> FEATURE:
<223> OTHER INFORMATION: Synthetic construct

<400> SEQUENCE: 12
atgcggagga aaaatgttg gagctgctgc tgtggaaaaa cttatgtcat a        51

<210> SEQ ID NO 13
<211> LENGTH: 24
<212> TYPE: DNA
<213> ORGANISM: Artificial
<220> FEATURE:
<223> OTHER INFORMATION: Synthetic construct

<400> SEQUENCE: 13
ttttgctgta aatgttttat caaa                                    24

<210> SEQ ID NO 14
<211> LENGTH: 24
<212> TYPE: DNA
<213> ORGANISM: Artificial
<220> FEATURE:
<223> OTHER INFORMATION: Synthetic construct

<400> SEQUENCE: 14
```

```
aaccctgagg aaattgtttt ttga                                                24
```

<210> SEQ ID NO 15
<211> LENGTH: 24
<212> TYPE: DNA
<213> ORGANISM: Artificial
<220> FEATURE:
<223> OTHER INFORMATION: Synthetic construct

<400> SEQUENCE: 15

```
agcttcctca aaggtttcag gatt                                                24
```

<210> SEQ ID NO 16
<211> LENGTH: 10
<212> TYPE: PRT
<213> ORGANISM: Artificial
<220> FEATURE:
<223> OTHER INFORMATION: Synthetic polypeptide

<400> SEQUENCE: 16

```
Gln Leu Gly Glu Met Val Thr Val Leu Ser
1               5                   10
```

<210> SEQ ID NO 17
<211> LENGTH: 10
<212> TYPE: PRT
<213> ORGANISM: Artificial
<220> FEATURE:
<223> OTHER INFORMATION: Synthetic polypeptide

<400> SEQUENCE: 17

```
Met Val Thr Val Leu Ser Ile Asp Gly Gly
1               5                   10
```

<210> SEQ ID NO 18
<211> LENGTH: 10
<212> TYPE: PRT
<213> ORGANISM: Artificial
<220> FEATURE:
<223> OTHER INFORMATION: Synthetic polypeptide

<400> SEQUENCE: 18

```
Leu Ser Ile Asp Gly Gly Gly Ile Arg Gly
1               5                   10
```

<210> SEQ ID NO 19
<211> LENGTH: 10
<212> TYPE: PRT
<213> ORGANISM: Artificial
<220> FEATURE:
<223> OTHER INFORMATION: Synthetic polypeptide

<400> SEQUENCE: 19

```
Gly Gly Gly Ile Arg Gly Ile Ile Pro Ala
1               5                   10
```

<210> SEQ ID NO 20
<211> LENGTH: 10
<212> TYPE: PRT
<213> ORGANISM: Artificial
<220> FEATURE:
<223> OTHER INFORMATION: Synthetic polypeptide

<400> SEQUENCE: 20

```
Arg Gly Ile Ile Pro Ala Thr Ile Leu Glu
1               5                   10
```

```
<210> SEQ ID NO 21
<211> LENGTH: 10
<212> TYPE: PRT
<213> ORGANISM: Artificial
<220> FEATURE:
<223> OTHER INFORMATION: Synthetic polypeptide

<400> SEQUENCE: 21

Pro Ala Thr Ile Leu Glu Phe Leu Glu Gly
1               5                   10

<210> SEQ ID NO 22
<211> LENGTH: 10
<212> TYPE: PRT
<213> ORGANISM: Artificial
<220> FEATURE:
<223> OTHER INFORMATION: Synthetic polypeptide

<400> SEQUENCE: 22

Leu Glu Phe Leu Glu Gly Gln Leu Gln Glu
1               5                   10

<210> SEQ ID NO 23
<211> LENGTH: 10
<212> TYPE: PRT
<213> ORGANISM: Artificial
<220> FEATURE:
<223> OTHER INFORMATION: Synthetic polypeptide

<400> SEQUENCE: 23

Glu Gly Gln Leu Gln Glu Met Asp Asn Asn
1               5                   10

<210> SEQ ID NO 24
<211> LENGTH: 10
<212> TYPE: PRT
<213> ORGANISM: Artificial
<220> FEATURE:
<223> OTHER INFORMATION: Synthetic polypeptide

<400> SEQUENCE: 24

Gln Glu Met Asp Asn Asn Ala Asp Ala Arg
1               5                   10

<210> SEQ ID NO 25
<211> LENGTH: 10
<212> TYPE: PRT
<213> ORGANISM: Artificial
<220> FEATURE:
<223> OTHER INFORMATION: Synthetic polypeptide

<400> SEQUENCE: 25

Asn Asn Ala Asp Ala Arg Leu Ala Asp Tyr
1               5                   10

<210> SEQ ID NO 26
<211> LENGTH: 10
<212> TYPE: PRT
<213> ORGANISM: Artificial
<220> FEATURE:
<223> OTHER INFORMATION: Synthetic polypeptide

<400> SEQUENCE: 26

Ala Arg Leu Ala Asp Tyr Phe Asp Val Ile
1               5                   10
```

```
<210> SEQ ID NO 27
<211> LENGTH: 10
<212> TYPE: PRT
<213> ORGANISM: Artificial
<220> FEATURE:
<223> OTHER INFORMATION: Synthetic polypeptide

<400> SEQUENCE: 27

Asp Tyr Phe Asp Val Ile Gly Gly Thr Ser
1               5                   10

<210> SEQ ID NO 28
<211> LENGTH: 10
<212> TYPE: PRT
<213> ORGANISM: Artificial
<220> FEATURE:
<223> OTHER INFORMATION: Synthetic polypeptide

<400> SEQUENCE: 28

Val Ile Gly Gly Thr Ser Thr Gly Gly Leu
1               5                   10

<210> SEQ ID NO 29
<211> LENGTH: 10
<212> TYPE: PRT
<213> ORGANISM: Artificial
<220> FEATURE:
<223> OTHER INFORMATION: Synthetic polypeptide

<400> SEQUENCE: 29

Thr Ser Thr Gly Gly Leu Leu Thr Ala Met
1               5                   10

<210> SEQ ID NO 30
<211> LENGTH: 10
<212> TYPE: PRT
<213> ORGANISM: Artificial
<220> FEATURE:
<223> OTHER INFORMATION: Synthetic polypeptide

<400> SEQUENCE: 30

Gly Leu Leu Thr Ala Met Ile Ser Thr Pro
1               5                   10

<210> SEQ ID NO 31
<211> LENGTH: 10
<212> TYPE: PRT
<213> ORGANISM: Artificial
<220> FEATURE:
<223> OTHER INFORMATION: Synthetic polypeptide

<400> SEQUENCE: 31

Ala Met Ile Ser Thr Pro Asn Glu Asn Asn
1               5                   10

<210> SEQ ID NO 32
<211> LENGTH: 10
<212> TYPE: PRT
<213> ORGANISM: Artificial
<220> FEATURE:
<223> OTHER INFORMATION: Synthetic polypeptide

<400> SEQUENCE: 32

Thr Pro Asn Glu Asn Asn Arg Pro Phe Ala
1               5                   10

<210> SEQ ID NO 33
```

```
<211> LENGTH: 10
<212> TYPE: PRT
<213> ORGANISM: Artificial
<220> FEATURE:
<223> OTHER INFORMATION: Synthetic polypeptide

<400> SEQUENCE: 33

Asn Asn Arg Pro Phe Ala Ala Ala Lys Glu
1               5                   10

<210> SEQ ID NO 34
<211> LENGTH: 10
<212> TYPE: PRT
<213> ORGANISM: Artificial
<220> FEATURE:
<223> OTHER INFORMATION: Synthetic polypeptide

<400> SEQUENCE: 34

Phe Ala Ala Ala Lys Glu Ile Val Pro Phe
1               5                   10

<210> SEQ ID NO 35
<211> LENGTH: 10
<212> TYPE: PRT
<213> ORGANISM: Artificial
<220> FEATURE:
<223> OTHER INFORMATION: Synthetic polypeptide

<400> SEQUENCE: 35

Lys Glu Ile Val Pro Phe Tyr Phe Glu His
1               5                   10

<210> SEQ ID NO 36
<211> LENGTH: 10
<212> TYPE: PRT
<213> ORGANISM: Artificial
<220> FEATURE:
<223> OTHER INFORMATION: Synthetic polypeptide

<400> SEQUENCE: 36

Pro Phe Tyr Phe Glu His Gly Pro Gln Ile
1               5                   10

<210> SEQ ID NO 37
<211> LENGTH: 10
<212> TYPE: PRT
<213> ORGANISM: Artificial
<220> FEATURE:
<223> OTHER INFORMATION: Synthetic polypeptide

<400> SEQUENCE: 37

Glu His Gly Pro Gln Ile Phe Asn Pro Ser
1               5                   10

<210> SEQ ID NO 38
<211> LENGTH: 10
<212> TYPE: PRT
<213> ORGANISM: Artificial
<220> FEATURE:
<223> OTHER INFORMATION: Synthetic polypeptide

<400> SEQUENCE: 38

Gln Ile Phe Asn Pro Ser Gly Gln Ile Leu
1               5                   10

<210> SEQ ID NO 39
<211> LENGTH: 10
```

```
<212> TYPE: PRT
<213> ORGANISM: Artificial
<220> FEATURE:
<223> OTHER INFORMATION: Synthetic polypeptide

<400> SEQUENCE: 39

Pro Ser Gly Gln Ile Leu Gly Pro Lys Tyr
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic polypeptide

<400> SEQUENCE: 40

Ile Leu Gly Pro Lys Tyr Asp Gly Lys Tyr
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic polypeptide

<400> SEQUENCE: 41

Lys Tyr Asp Gly Lys Tyr Leu Met Gln Val
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic polypeptide

<400> SEQUENCE: 42

Lys Tyr Leu Met Gln Val Leu Gln Glu Lys
1               5                   10

<210> SEQ ID NO 43
<211> LENGTH: 10
<212> TYPE: PRT
<213> ORGANISM: Artificial
<220> FEATURE:
<223> OTHER INFORMATION: Synthetic polypeptide

<400> SEQUENCE: 43

Gln Val Leu Gln Glu Lys Leu Gly Glu Thr
1               5                   10

<210> SEQ ID NO 44
<211> LENGTH: 10
<212> TYPE: PRT
<213> ORGANISM: Artificial
<220> FEATURE:
<223> OTHER INFORMATION: Synthetic polypeptide

<400> SEQUENCE: 44

Glu Lys Leu Gly Glu Thr Arg Val His Gln
1               5                   10

<210> SEQ ID NO 45
<211> LENGTH: 10
<212> TYPE: PRT
```

```
<213> ORGANISM: Artificial
<220> FEATURE:
<223> OTHER INFORMATION: Synthetic polypeptide

<400> SEQUENCE: 45

Glu Thr Arg Val His Gln Ala Leu Thr Glu
1               5                   10

<210> SEQ ID NO 46
<211> LENGTH: 10
<212> TYPE: PRT
<213> ORGANISM: Artificial
<220> FEATURE:
<223> OTHER INFORMATION: Synthetic polypeptide

<400> SEQUENCE: 46

His Gln Ala Leu Thr Glu Val Val Ile Ser
1               5                   10

<210> SEQ ID NO 47
<211> LENGTH: 10
<212> TYPE: PRT
<213> ORGANISM: Artificial
<220> FEATURE:
<223> OTHER INFORMATION: Synthetic polypeptide

<400> SEQUENCE: 47

Thr Glu Val Val Ile Ser Ser Phe Asp Ile
1               5                   10

<210> SEQ ID NO 48
<211> LENGTH: 10
<212> TYPE: PRT
<213> ORGANISM: Artificial
<220> FEATURE:
<223> OTHER INFORMATION: Synthetic polypeptide

<400> SEQUENCE: 48

Ile Ser Ser Phe Asp Ile Lys Thr Asn Lys
1               5                   10

<210> SEQ ID NO 49
<211> LENGTH: 10
<212> TYPE: PRT
<213> ORGANISM: Artificial
<220> FEATURE:
<223> OTHER INFORMATION: Synthetic polypeptide

<400> SEQUENCE: 49

Asp Ile Lys Thr Asn Lys Pro Val Ile Phe
1               5                   10

<210> SEQ ID NO 50
<211> LENGTH: 10
<212> TYPE: PRT
<213> ORGANISM: Artificial
<220> FEATURE:
<223> OTHER INFORMATION: Synthetic polypeptide

<400> SEQUENCE: 50

Asn Lys Pro Val Ile Phe Thr Lys Ser Asn
1               5                   10

<210> SEQ ID NO 51
<211> LENGTH: 10
<212> TYPE: PRT
<213> ORGANISM: Artificial
```

```
<220> FEATURE:
<223> OTHER INFORMATION: Synthetic polypeptide

<400> SEQUENCE: 51

Ile Phe Thr Lys Ser Asn Leu Ala Asn Ser
1               5                   10

<210> SEQ ID NO 52
<211> LENGTH: 10
<212> TYPE: PRT
<213> ORGANISM: Artificial
<220> FEATURE:
<223> OTHER INFORMATION: Synthetic polypeptide

<400> SEQUENCE: 52

Ser Asn Leu Ala Asn Ser Pro Glu Leu Asp
1               5                   10

<210> SEQ ID NO 53
<211> LENGTH: 10
<212> TYPE: PRT
<213> ORGANISM: Artificial
<220> FEATURE:
<223> OTHER INFORMATION: Synthetic polypeptide

<400> SEQUENCE: 53

Asn Ser Pro Glu Leu Asp Ala Lys Met Tyr
1               5                   10

<210> SEQ ID NO 54
<211> LENGTH: 10
<212> TYPE: PRT
<213> ORGANISM: Artificial
<220> FEATURE:
<223> OTHER INFORMATION: Synthetic polypeptide

<400> SEQUENCE: 54

Leu Asp Ala Lys Met Tyr Asp Ile Ser Tyr
1               5                   10

<210> SEQ ID NO 55
<211> LENGTH: 10
<212> TYPE: PRT
<213> ORGANISM: Artificial
<220> FEATURE:
<223> OTHER INFORMATION: Synthetic polypeptide

<400> SEQUENCE: 55

Met Tyr Asp Ile Ser Tyr Ser Thr Ala Ala
1               5                   10

<210> SEQ ID NO 56
<211> LENGTH: 10
<212> TYPE: PRT
<213> ORGANISM: Artificial
<220> FEATURE:
<223> OTHER INFORMATION: Synthetic polypeptide

<400> SEQUENCE: 56

Ser Tyr Ser Thr Ala Ala Ala Pro Thr Tyr
1               5                   10

<210> SEQ ID NO 57
<211> LENGTH: 10
<212> TYPE: PRT
<213> ORGANISM: Artificial
<220> FEATURE:
```

<223> OTHER INFORMATION: Synthetic polypeptide

<400> SEQUENCE: 57

Ala Ala Ala Pro Thr Tyr Phe Pro Pro His
1               5                   10

<210> SEQ ID NO 58
<211> LENGTH: 10
<212> TYPE: PRT
<213> ORGANISM: Artificial
<220> FEATURE:
<223> OTHER INFORMATION: Synthetic polypeptide

<400> SEQUENCE: 58

Thr Tyr Phe Pro Pro His Tyr Phe Val Thr
1               5                   10

<210> SEQ ID NO 59
<211> LENGTH: 10
<212> TYPE: PRT
<213> ORGANISM: Artificial
<220> FEATURE:
<223> OTHER INFORMATION: Synthetic polypeptide

<400> SEQUENCE: 59

Pro His Tyr Phe Val Thr Asn Thr Ser Asn
1               5                   10

<210> SEQ ID NO 60
<211> LENGTH: 10
<212> TYPE: PRT
<213> ORGANISM: Artificial
<220> FEATURE:
<223> OTHER INFORMATION: Synthetic polypeptide

<400> SEQUENCE: 60

Val Thr Asn Thr Ser Asn Gly Asp Glu Tyr
1               5                   10

<210> SEQ ID NO 61
<211> LENGTH: 10
<212> TYPE: PRT
<213> ORGANISM: Artificial
<220> FEATURE:
<223> OTHER INFORMATION: Synthetic polypeptide

<400> SEQUENCE: 61

Ser Asn Gly Asp Glu Tyr Glu Phe Asn Leu
1               5                   10

<210> SEQ ID NO 62
<211> LENGTH: 10
<212> TYPE: PRT
<213> ORGANISM: Artificial
<220> FEATURE:
<223> OTHER INFORMATION: Synthetic polypeptide

<400> SEQUENCE: 62

Glu Tyr Glu Phe Asn Leu Val Asp Gly Ala
1               5                   10

<210> SEQ ID NO 63
<211> LENGTH: 10
<212> TYPE: PRT
<213> ORGANISM: Artificial
<220> FEATURE:
<223> OTHER INFORMATION: Synthetic polypeptide

```
<400> SEQUENCE: 63

Asn Leu Val Asp Gly Ala Val Ala Thr Val
1               5                   10

<210> SEQ ID NO 64
<211> LENGTH: 10
<212> TYPE: PRT
<213> ORGANISM: Artificial
<220> FEATURE:
<223> OTHER INFORMATION: Synthetic polypeptide

<400> SEQUENCE: 64

Gly Ala Val Ala Thr Val Ala Asp Pro Ala
1               5                   10

<210> SEQ ID NO 65
<211> LENGTH: 10
<212> TYPE: PRT
<213> ORGANISM: Artificial
<220> FEATURE:
<223> OTHER INFORMATION: Synthetic polypeptide

<400> SEQUENCE: 65

Thr Val Ala Asp Pro Ala Leu Leu Ser Ile
1               5                   10

<210> SEQ ID NO 66
<211> LENGTH: 10
<212> TYPE: PRT
<213> ORGANISM: Artificial
<220> FEATURE:
<223> OTHER INFORMATION: Synthetic polypeptide

<400> SEQUENCE: 66

Pro Ala Leu Leu Ser Ile Ser Val Ala Thr
1               5                   10

<210> SEQ ID NO 67
<211> LENGTH: 10
<212> TYPE: PRT
<213> ORGANISM: Artificial
<220> FEATURE:
<223> OTHER INFORMATION: Synthetic polypeptide

<400> SEQUENCE: 67

Ser Ile Ser Val Ala Thr Arg Leu Ala Gln
1               5                   10

<210> SEQ ID NO 68
<211> LENGTH: 10
<212> TYPE: PRT
<213> ORGANISM: Artificial
<220> FEATURE:
<223> OTHER INFORMATION: Synthetic polypeptide

<400> SEQUENCE: 68

Ala Thr Arg Leu Ala Gln Lys Asp Pro Ala
1               5                   10

<210> SEQ ID NO 69
<211> LENGTH: 10
<212> TYPE: PRT
<213> ORGANISM: Artificial
<220> FEATURE:
<223> OTHER INFORMATION: Synthetic polypeptide
```

```
<400> SEQUENCE: 69

Ala Gln Lys Asp Pro Ala Phe Ala Ser Ile
1               5                   10

<210> SEQ ID NO 70
<211> LENGTH: 10
<212> TYPE: PRT
<213> ORGANISM: Artificial
<220> FEATURE:
<223> OTHER INFORMATION: Synthetic polypeptide

<400> SEQUENCE: 70

Pro Ala Phe Ala Ser Ile Arg Ser Leu Asn
1               5                   10

<210> SEQ ID NO 71
<211> LENGTH: 10
<212> TYPE: PRT
<213> ORGANISM: Artificial
<220> FEATURE:
<223> OTHER INFORMATION: Synthetic polypeptide

<400> SEQUENCE: 71

Ser Ile Arg Ser Leu Asn Tyr Lys Lys Met
1               5                   10

<210> SEQ ID NO 72
<211> LENGTH: 10
<212> TYPE: PRT
<213> ORGANISM: Artificial
<220> FEATURE:
<223> OTHER INFORMATION: Synthetic polypeptide

<400> SEQUENCE: 72

Leu Asn Tyr Lys Lys Met Leu Leu Leu Ser
1               5                   10

<210> SEQ ID NO 73
<211> LENGTH: 10
<212> TYPE: PRT
<213> ORGANISM: Artificial
<220> FEATURE:
<223> OTHER INFORMATION: Synthetic polypeptide

<400> SEQUENCE: 73

Lys Met Leu Leu Leu Ser Leu Gly Thr Gly
1               5                   10

<210> SEQ ID NO 74
<211> LENGTH: 10
<212> TYPE: PRT
<213> ORGANISM: Artificial
<220> FEATURE:
<223> OTHER INFORMATION: Synthetic polypeptide

<400> SEQUENCE: 74

Leu Ser Leu Gly Thr Gly Thr Thr Ser Glu
1               5                   10

<210> SEQ ID NO 75
<211> LENGTH: 10
<212> TYPE: PRT
<213> ORGANISM: Artificial
<220> FEATURE:
<223> OTHER INFORMATION: Synthetic polypeptide

<400> SEQUENCE: 75
```

```
Thr Gly Thr Thr Ser Glu Phe Asp Lys Thr
1               5                   10
```

<210> SEQ ID NO 76
<211> LENGTH: 10
<212> TYPE: PRT
<213> ORGANISM: Artificial
<220> FEATURE:
<223> OTHER INFORMATION: Synthetic polypeptide

<400> SEQUENCE: 76

```
Ser Glu Phe Asp Lys Thr Tyr Thr Ala Lys
1               5                   10
```

<210> SEQ ID NO 77
<211> LENGTH: 10
<212> TYPE: PRT
<213> ORGANISM: Artificial
<220> FEATURE:
<223> OTHER INFORMATION: Synthetic polypeptide

<400> SEQUENCE: 77

```
Lys Thr Tyr Thr Ala Lys Glu Ala Ala Thr
1               5                   10
```

<210> SEQ ID NO 78
<211> LENGTH: 10
<212> TYPE: PRT
<213> ORGANISM: Artificial
<220> FEATURE:
<223> OTHER INFORMATION: Synthetic polypeptide

<400> SEQUENCE: 78

```
Ala Lys Glu Ala Ala Thr Trp Thr Ala Val
1               5                   10
```

<210> SEQ ID NO 79
<211> LENGTH: 10
<212> TYPE: PRT
<213> ORGANISM: Artificial
<220> FEATURE:
<223> OTHER INFORMATION: Synthetic polypeptide

<400> SEQUENCE: 79

```
Ala Thr Trp Thr Ala Val His Trp Met Leu
1               5                   10
```

<210> SEQ ID NO 80
<211> LENGTH: 10
<212> TYPE: PRT
<213> ORGANISM: Artificial
<220> FEATURE:
<223> OTHER INFORMATION: Synthetic polypeptide

<400> SEQUENCE: 80

```
Ala Val His Trp Met Leu Val Ile Gln Lys
1               5                   10
```

<210> SEQ ID NO 81
<211> LENGTH: 10
<212> TYPE: PRT
<213> ORGANISM: Artificial
<220> FEATURE:
<223> OTHER INFORMATION: Synthetic polypeptide

<400> SEQUENCE: 81

```
Met Leu Val Ile Gln Lys Met Thr Asp Ala
1               5                   10
```

```
<210> SEQ ID NO 82
<211> LENGTH: 10
<212> TYPE: PRT
<213> ORGANISM: Artificial
<220> FEATURE:
<223> OTHER INFORMATION: Synthetic polypeptide

<400> SEQUENCE: 82

Gln Lys Met Thr Asp Tyr Tyr Leu Ser Thr
1               5                   10
```

```
<210> SEQ ID NO 83
<211> LENGTH: 10
<212> TYPE: PRT
<213> ORGANISM: Artificial
<220> FEATURE:
<223> OTHER INFORMATION: Synthetic polypeptide

<400> SEQUENCE: 83

Asp Ala Ala Ser Ser Tyr Met Thr Asp Tyr
1               5                   10
```

```
<210> SEQ ID NO 84
<211> LENGTH: 10
<212> TYPE: PRT
<213> ORGANISM: Artificial
<220> FEATURE:
<223> OTHER INFORMATION: Synthetic polypeptide

<400> SEQUENCE: 84

Ser Tyr Met Thr Asp Tyr Tyr Leu Ser Thr
1               5                   10
```

```
<210> SEQ ID NO 85
<211> LENGTH: 10
<212> TYPE: PRT
<213> ORGANISM: Artificial
<220> FEATURE:
<223> OTHER INFORMATION: Synthetic polypeptide

<400> SEQUENCE: 85

Asp Tyr Tyr Leu Ser Thr Ala Phe Gln Ala
1               5                   10
```

```
<210> SEQ ID NO 86
<211> LENGTH: 10
<212> TYPE: PRT
<213> ORGANISM: Artificial
<220> FEATURE:
<223> OTHER INFORMATION: Synthetic polypeptide

<400> SEQUENCE: 86

Ser Thr Ala Phe Gln Ala Leu Asp Ser Lys
1               5                   10
```

```
<210> SEQ ID NO 87
<211> LENGTH: 10
<212> TYPE: PRT
<213> ORGANISM: Artificial
<220> FEATURE:
<223> OTHER INFORMATION: Synthetic polypeptide

<400> SEQUENCE: 87

Gln Ala Leu Asp Ser Lys Asn Asn Tyr Leu
```

```
1               5                   10
```

<210> SEQ ID NO 88
<211> LENGTH: 10
<212> TYPE: PRT
<213> ORGANISM: Artificial
<220> FEATURE:
<223> OTHER INFORMATION: Synthetic polypeptide

<400> SEQUENCE: 88

```
Ser Lys Asn Asn Tyr Leu Arg Val Gln Glu
1               5                   10
```

<210> SEQ ID NO 89
<211> LENGTH: 10
<212> TYPE: PRT
<213> ORGANISM: Artificial
<220> FEATURE:
<223> OTHER INFORMATION: Synthetic polypeptide

<400> SEQUENCE: 89

```
Tyr Leu Arg Val Gln Glu Asn Ala Leu Thr
1               5                   10
```

<210> SEQ ID NO 90
<211> LENGTH: 10
<212> TYPE: PRT
<213> ORGANISM: Artificial
<220> FEATURE:
<223> OTHER INFORMATION: Synthetic polypeptide

<400> SEQUENCE: 90

```
Gln Glu Asn Ala Leu Thr Gly Thr Thr Thr
1               5                   10
```

<210> SEQ ID NO 91
<211> LENGTH: 10
<212> TYPE: PRT
<213> ORGANISM: Artificial
<220> FEATURE:
<223> OTHER INFORMATION: Synthetic polypeptide

<400> SEQUENCE: 91

```
Leu Thr Gly Thr Thr Thr Glu Met Asp Asp
1               5                   10
```

<210> SEQ ID NO 92
<211> LENGTH: 10
<212> TYPE: PRT
<213> ORGANISM: Artificial
<220> FEATURE:
<223> OTHER INFORMATION: Synthetic polypeptide

<400> SEQUENCE: 92

```
Thr Thr Glu Met Asp Asp Ala Ser Glu Ala
1               5                   10
```

<210> SEQ ID NO 93
<211> LENGTH: 10
<212> TYPE: PRT
<213> ORGANISM: Artificial
<220> FEATURE:
<223> OTHER INFORMATION: Synthetic polypeptide

<400> SEQUENCE: 93

```
Asp Asp Ala Ser Glu Ala Asn Met Glu Leu
1               5                   10
```

```
<210> SEQ ID NO 94
<211> LENGTH: 10
<212> TYPE: PRT
<213> ORGANISM: Artificial
<220> FEATURE:
<223> OTHER INFORMATION: Synthetic polypeptide

<400> SEQUENCE: 94

Glu Ala Asn Met Glu Leu Leu Val Gln Val
1               5                   10

<210> SEQ ID NO 95
<211> LENGTH: 10
<212> TYPE: PRT
<213> ORGANISM: Artificial
<220> FEATURE:
<223> OTHER INFORMATION: Synthetic polypeptide

<400> SEQUENCE: 95

Glu Leu Leu Val Gln Val Gly Glu Asn Leu
1               5                   10

<210> SEQ ID NO 96
<211> LENGTH: 10
<212> TYPE: PRT
<213> ORGANISM: Artificial
<220> FEATURE:
<223> OTHER INFORMATION: Synthetic polypeptide

<400> SEQUENCE: 96

Gln Val Gly Glu Asn Leu Leu Lys Lys Pro
1               5                   10

<210> SEQ ID NO 97
<211> LENGTH: 10
<212> TYPE: PRT
<213> ORGANISM: Artificial
<220> FEATURE:
<223> OTHER INFORMATION: Synthetic polypeptide

<400> SEQUENCE: 97

Asn Leu Leu Lys Lys Pro Val Ser Glu Asp
1               5                   10

<210> SEQ ID NO 98
<211> LENGTH: 10
<212> TYPE: PRT
<213> ORGANISM: Artificial
<220> FEATURE:
<223> OTHER INFORMATION: Synthetic polypeptide

<400> SEQUENCE: 98

Lys Pro Val Ser Glu Asp Asn Pro Glu Thr
1               5                   10

<210> SEQ ID NO 99
<211> LENGTH: 10
<212> TYPE: PRT
<213> ORGANISM: Artificial
<220> FEATURE:
<223> OTHER INFORMATION: Synthetic polypeptide

<400> SEQUENCE: 99

Glu Asp Asn Pro Glu Thr Tyr Glu Glu Ala
1               5                   10
```

```
<210> SEQ ID NO 100
<211> LENGTH: 10
<212> TYPE: PRT
<213> ORGANISM: Artificial
<220> FEATURE:
<223> OTHER INFORMATION: Synthetic polypeptide

<400> SEQUENCE: 100

Glu Thr Tyr Glu Glu Ala Leu Lys Arg Phe
1               5                   10

<210> SEQ ID NO 101
<211> LENGTH: 10
<212> TYPE: PRT
<213> ORGANISM: Artificial
<220> FEATURE:
<223> OTHER INFORMATION: Synthetic polypeptide

<400> SEQUENCE: 101

Glu Ala Leu Lys Arg Phe Ala Lys Leu Leu
1               5                   10

<210> SEQ ID NO 102
<211> LENGTH: 10
<212> TYPE: PRT
<213> ORGANISM: Artificial
<220> FEATURE:
<223> OTHER INFORMATION: Synthetic polypeptide

<400> SEQUENCE: 102

Arg Phe Ala Lys Leu Leu Ser Asp Arg Lys
1               5                   10

<210> SEQ ID NO 103
<211> LENGTH: 10
<212> TYPE: PRT
<213> ORGANISM: Artificial
<220> FEATURE:
<223> OTHER INFORMATION: Synthetic polypeptide

<400> SEQUENCE: 103

Leu Leu Ser Asp Arg Lys Lys Leu Arg Ala
1               5                   10

<210> SEQ ID NO 104
<211> LENGTH: 10
<212> TYPE: PRT
<213> ORGANISM: Artificial
<220> FEATURE:
<223> OTHER INFORMATION: Synthetic polypeptide

<400> SEQUENCE: 104

Arg Lys Lys Leu Arg Ala Asn Lys Ala Ser
1               5                   10

<210> SEQ ID NO 105
<211> LENGTH: 10
<212> TYPE: PRT
<213> ORGANISM: Artificial
<220> FEATURE:
<223> OTHER INFORMATION: Synthetic polypeptide

<400> SEQUENCE: 105

Asp Tyr Phe Asp Val Ile Gly Gly Thr Ser
1               5                   10
```

```
<210> SEQ ID NO 106
<211> LENGTH: 10
<212> TYPE: PRT
<213> ORGANISM: Artificial
<220> FEATURE:
<223> OTHER INFORMATION: Synthetic polypeptide

<400> SEQUENCE: 106

Asp Tyr Phe Asp Val Ile Ala Gly Thr Ser
1               5                   10

<210> SEQ ID NO 107
<211> LENGTH: 10
<212> TYPE: PRT
<213> ORGANISM: Artificial
<220> FEATURE:
<223> OTHER INFORMATION: Synthetic polypeptide

<400> SEQUENCE: 107

Val Ile Gly Gly Thr Ser Thr Gly Gly Leu
1               5                   10

<210> SEQ ID NO 108
<211> LENGTH: 10
<212> TYPE: PRT
<213> ORGANISM: Artificial
<220> FEATURE:
<223> OTHER INFORMATION: Synthetic polypeptide

<400> SEQUENCE: 108

Val Ile Ala Gly Thr Ser Thr Gly Ala Leu
1               5                   10

<210> SEQ ID NO 109
<211> LENGTH: 10
<212> TYPE: PRT
<213> ORGANISM: Artificial
<220> FEATURE:
<223> OTHER INFORMATION: Synthetic polypeptide

<400> SEQUENCE: 109

Ala Phe Tyr Phe Glu His Gly Pro Gln Ile
1               5                   10

<210> SEQ ID NO 110
<211> LENGTH: 10
<212> TYPE: PRT
<213> ORGANISM: Artificial
<220> FEATURE:
<223> OTHER INFORMATION: Synthetic polypeptide

<400> SEQUENCE: 110

Pro Ala Tyr Phe Glu His Gly Pro Gln Ile
1               5                   10

<210> SEQ ID NO 111
<211> LENGTH: 10
<212> TYPE: PRT
<213> ORGANISM: Artificial
<220> FEATURE:
<223> OTHER INFORMATION: Synthetic polypeptide

<400> SEQUENCE: 111

Pro Phe Ala Phe Glu His Gly Pro Gln Ile
1               5                   10

<210> SEQ ID NO 112
```

```
<211> LENGTH: 10
<212> TYPE: PRT
<213> ORGANISM: Artificial
<220> FEATURE:
<223> OTHER INFORMATION: Synthetic polypeptide

<400> SEQUENCE: 112

Pro Phe Tyr Ala Glu His Gly Pro Gln Ile
1               5                   10

<210> SEQ ID NO 113
<211> LENGTH: 10
<212> TYPE: PRT
<213> ORGANISM: Artificial
<220> FEATURE:
<223> OTHER INFORMATION: Synthetic polypeptide

<400> SEQUENCE: 113

Pro Phe Tyr Phe Ala His Gly Pro Gln Ile
1               5                   10

<210> SEQ ID NO 114
<211> LENGTH: 10
<212> TYPE: PRT
<213> ORGANISM: Artificial
<220> FEATURE:
<223> OTHER INFORMATION: Synthetic polypeptide

<400> SEQUENCE: 114

Pro Phe Tyr Phe Glu Ala Gly Pro Gln Ile
1               5                   10

<210> SEQ ID NO 115
<211> LENGTH: 10
<212> TYPE: PRT
<213> ORGANISM: Artificial
<220> FEATURE:
<223> OTHER INFORMATION: Synthetic polypeptide

<400> SEQUENCE: 115

Pro Phe Tyr Phe Glu His Ala Pro Gln Ile
1               5                   10

<210> SEQ ID NO 116
<211> LENGTH: 10
<212> TYPE: PRT
<213> ORGANISM: Artificial
<220> FEATURE:
<223> OTHER INFORMATION: Synthetic polypeptide

<400> SEQUENCE: 116

Pro Phe Tyr Phe Glu His Gly Ala Gln Ile
1               5                   10

<210> SEQ ID NO 117
<211> LENGTH: 10
<212> TYPE: PRT
<213> ORGANISM: Artificial
<220> FEATURE:
<223> OTHER INFORMATION: Synthetic polypeptide

<400> SEQUENCE: 117

Pro Phe Tyr Phe Glu His Gly Pro Ala Ile
1               5                   10

<210> SEQ ID NO 118
<211> LENGTH: 10
```

```
<212> TYPE: PRT
<213> ORGANISM: Artificial
<220> FEATURE:
<223> OTHER INFORMATION: Synthetic polypeptide

<400> SEQUENCE: 118

Pro Phe Tyr Phe Glu His Gly Pro Gln Ala
1               5                   10

<210> SEQ ID NO 119
<211> LENGTH: 10
<212> TYPE: PRT
<213> ORGANISM: Artificial
<220> FEATURE:
<223> OTHER INFORMATION: Synthetic polypeptide

<400> SEQUENCE: 119

Thr Phe Tyr Leu Glu Asn Gly Pro Lys Ile
1               5                   10

<210> SEQ ID NO 120
<211> LENGTH: 10
<212> TYPE: PRT
<213> ORGANISM: Artificial
<220> FEATURE:
<223> OTHER INFORMATION: Synthetic polypeptide

<400> SEQUENCE: 120

Pro Phe Phe Phe Glu His Gly Pro Gln Ile
1               5                   10

<210> SEQ ID NO 121
<211> LENGTH: 10
<212> TYPE: PRT
<213> ORGANISM: Artificial
<220> FEATURE:
<223> OTHER INFORMATION: Synthetic polypeptide

<400> SEQUENCE: 121

Ala Tyr Leu Met Gln Val Leu Gln Glu Lys
1               5                   10

<210> SEQ ID NO 122
<211> LENGTH: 10
<212> TYPE: PRT
<213> ORGANISM: Artificial
<220> FEATURE:
<223> OTHER INFORMATION: Synthetic polypeptide

<400> SEQUENCE: 122

Lys Ala Leu Met Gln Val Leu Gln Glu Lys
1               5                   10

<210> SEQ ID NO 123
<211> LENGTH: 10
<212> TYPE: PRT
<213> ORGANISM: Artificial
<220> FEATURE:
<223> OTHER INFORMATION: Synthetic polypeptide

<400> SEQUENCE: 123

Lys Tyr Ala Met Gln Val Leu Gln Glu Lys
1               5                   10

<210> SEQ ID NO 124
<211> LENGTH: 10
<212> TYPE: PRT
```

```
<213> ORGANISM: Artificial
<220> FEATURE:
<223> OTHER INFORMATION: Synthetic polypeptide

<400> SEQUENCE: 124

Lys Tyr Leu Ala Gln Val Leu Gln Glu Lys
1               5                   10

<210> SEQ ID NO 125
<211> LENGTH: 10
<212> TYPE: PRT
<213> ORGANISM: Artificial
<220> FEATURE:
<223> OTHER INFORMATION: Synthetic polypeptide

<400> SEQUENCE: 125

Lys Tyr Leu Met Ala Val Leu Gln Glu Lys
1               5                   10

<210> SEQ ID NO 126
<211> LENGTH: 10
<212> TYPE: PRT
<213> ORGANISM: Artificial
<220> FEATURE:
<223> OTHER INFORMATION: Synthetic polypeptide

<400> SEQUENCE: 126

Lys Tyr Leu Met Gln Ala Leu Gln Glu Lys
1               5                   10

<210> SEQ ID NO 127
<211> LENGTH: 10
<212> TYPE: PRT
<213> ORGANISM: Artificial
<220> FEATURE:
<223> OTHER INFORMATION: Synthetic polypeptide

<400> SEQUENCE: 127

Lys Tyr Leu Met Gln Val Ala Gln Glu Lys
1               5                   10

<210> SEQ ID NO 128
<211> LENGTH: 10
<212> TYPE: PRT
<213> ORGANISM: Artificial
<220> FEATURE:
<223> OTHER INFORMATION: Synthetic polypeptide

<400> SEQUENCE: 128

Lys Tyr Leu Met Gln Val Leu Ala Glu Lys
1               5                   10

<210> SEQ ID NO 129
<211> LENGTH: 10
<212> TYPE: PRT
<213> ORGANISM: Artificial
<220> FEATURE:
<223> OTHER INFORMATION: Synthetic polypeptide

<400> SEQUENCE: 129

Lys Tyr Leu Met Gln Val Leu Gln Ala Lys
1               5                   10

<210> SEQ ID NO 130
<211> LENGTH: 10
<212> TYPE: PRT
<213> ORGANISM: Artificial
```

```
<220> FEATURE:
<223> OTHER INFORMATION: Synthetic polypeptide

<400> SEQUENCE: 130

Lys Tyr Leu Met Gln Val Leu Gln Glu Ala
1               5                   10

<210> SEQ ID NO 131
<211> LENGTH: 10
<212> TYPE: PRT
<213> ORGANISM: Artificial
<220> FEATURE:
<223> OTHER INFORMATION: Synthetic polypeptide

<400> SEQUENCE: 131

Val Phe Leu His Asp Lys Ile Lys Ser Leu
1               5                   10

<210> SEQ ID NO 132
<211> LENGTH: 10
<212> TYPE: PRT
<213> ORGANISM: Artificial
<220> FEATURE:
<223> OTHER INFORMATION: Synthetic polypeptide

<400> SEQUENCE: 132

Ala Tyr Ser Thr Ala Ala Ala Pro Thr Tyr
1               5                   10

<210> SEQ ID NO 133
<211> LENGTH: 10
<212> TYPE: PRT
<213> ORGANISM: Artificial
<220> FEATURE:
<223> OTHER INFORMATION: Synthetic polypeptide

<400> SEQUENCE: 133

Ser Ala Ser Thr Ala Ala Ala Pro Thr Tyr
1               5                   10

<210> SEQ ID NO 134
<211> LENGTH: 10
<212> TYPE: PRT
<213> ORGANISM: Artificial
<220> FEATURE:
<223> OTHER INFORMATION: Synthetic polypeptide

<400> SEQUENCE: 134

Ser Tyr Ala Thr Ala Ala Ala Pro Thr Tyr
1               5                   10

<210> SEQ ID NO 135
<211> LENGTH: 10
<212> TYPE: PRT
<213> ORGANISM: Artificial
<220> FEATURE:
<223> OTHER INFORMATION: Synthetic polypeptide

<400> SEQUENCE: 135

Ser Tyr Ser Ala Ala Ala Ala Pro Thr Tyr
1               5                   10

<210> SEQ ID NO 136
<211> LENGTH: 10
<212> TYPE: PRT
<213> ORGANISM: Artificial
<220> FEATURE:
```

```
<223> OTHER INFORMATION: Synthetic polypeptide

<400> SEQUENCE: 136

Ser Tyr Ser Thr Ala Ala Ala Ala Thr Tyr
1               5                   10

<210> SEQ ID NO 137
<211> LENGTH: 10
<212> TYPE: PRT
<213> ORGANISM: Artificial
<220> FEATURE:
<223> OTHER INFORMATION: Synthetic polypeptide

<400> SEQUENCE: 137

Ser Tyr Ser Thr Ala Ala Ala Pro Ala Tyr
1               5                   10

<210> SEQ ID NO 138
<211> LENGTH: 10
<212> TYPE: PRT
<213> ORGANISM: Artificial
<220> FEATURE:
<223> OTHER INFORMATION: Synthetic polypeptide

<400> SEQUENCE: 138

Ser Tyr Ser Thr Ala Ala Ala Pro Thr Ala
1               5                   10

<210> SEQ ID NO 139
<211> LENGTH: 10
<212> TYPE: PRT
<213> ORGANISM: Artificial
<220> FEATURE:
<223> OTHER INFORMATION: Synthetic polypeptide

<400> SEQUENCE: 139

Cys Ile Ser Thr Ser Ala Ala Pro Thr Tyr
1               5                   10

<210> SEQ ID NO 140
<211> LENGTH: 10
<212> TYPE: PRT
<213> ORGANISM: Artificial
<220> FEATURE:
<223> OTHER INFORMATION: Synthetic polypeptide

<400> SEQUENCE: 140

Ser Tyr Ser Thr Ala Ala Ala Pro Ala Phe
1               5                   10

<210> SEQ ID NO 141
<211> LENGTH: 10
<212> TYPE: PRT
<213> ORGANISM: Artificial
<220> FEATURE:
<223> OTHER INFORMATION: Synthetic polypeptide

<400> SEQUENCE: 141

Ala Phe Ala Ala Ala Ala Ala Pro Thr Tyr
1               5                   10

<210> SEQ ID NO 142
<211> LENGTH: 10
<212> TYPE: PRT
<213> ORGANISM: Artificial
<220> FEATURE:
<223> OTHER INFORMATION: Synthetic polypeptide
```

<400> SEQUENCE: 142

Ser Tyr Ser Thr Ala Ala Ala Pro Thr Phe
1               5                   10

<210> SEQ ID NO 143
<211> LENGTH: 10
<212> TYPE: PRT
<213> ORGANISM: Artificial
<220> FEATURE:
<223> OTHER INFORMATION: Synthetic polypeptide

<400> SEQUENCE: 143

Ser Thr Ser Ala Ala Pro Thr Tyr Phe Pro
1               5                   10

<210> SEQ ID NO 144
<211> LENGTH: 10
<212> TYPE: PRT
<213> ORGANISM: Artificial
<220> FEATURE:
<223> OTHER INFORMATION: Synthetic polypeptide

<400> SEQUENCE: 144

Ser Thr Ser Ala Ala Pro Thr Phe Phe Pro
1               5                   10

<210> SEQ ID NO 145
<211> LENGTH: 10
<212> TYPE: PRT
<213> ORGANISM: Artificial
<220> FEATURE:
<223> OTHER INFORMATION: Synthetic polypeptide

<400> SEQUENCE: 145

Ser Thr Ser Ala Ala Pro Thr Ala Phe Pro
1               5                   10

<210> SEQ ID NO 146
<211> LENGTH: 10
<212> TYPE: PRT
<213> ORGANISM: Artificial
<220> FEATURE:
<223> OTHER INFORMATION: Synthetic polypeptide

<400> SEQUENCE: 146

Ser Thr Ala Ala Ala Pro Thr Phe Phe Pro
1               5                   10

<210> SEQ ID NO 147
<211> LENGTH: 10
<212> TYPE: PRT
<213> ORGANISM: Artificial
<220> FEATURE:
<223> OTHER INFORMATION: Synthetic polypeptide

<400> SEQUENCE: 147

Ala Ala Ala Ala Thr Tyr Phe Pro Pro His
1               5                   10

<210> SEQ ID NO 148
<211> LENGTH: 10
<212> TYPE: PRT
<213> ORGANISM: Artificial
<220> FEATURE:
<223> OTHER INFORMATION: Synthetic polypeptide

```
<400> SEQUENCE: 148

Ala Ala Ala Pro Ala Tyr Phe Pro Pro His
1               5                   10

<210> SEQ ID NO 149
<211> LENGTH: 10
<212> TYPE: PRT
<213> ORGANISM: Artificial
<220> FEATURE:
<223> OTHER INFORMATION: Synthetic polypeptide

<400> SEQUENCE: 149

Ala Ala Ala Pro Thr Ala Phe Pro Pro His
1               5                   10

<210> SEQ ID NO 150
<211> LENGTH: 10
<212> TYPE: PRT
<213> ORGANISM: Artificial
<220> FEATURE:
<223> OTHER INFORMATION: Synthetic polypeptide

<400> SEQUENCE: 150

Ala Ala Ala Pro Thr Tyr Ala Pro Pro His
1               5                   10

<210> SEQ ID NO 151
<211> LENGTH: 10
<212> TYPE: PRT
<213> ORGANISM: Artificial
<220> FEATURE:
<223> OTHER INFORMATION: Synthetic polypeptide

<400> SEQUENCE: 151

Ala Ala Ala Pro Thr Tyr Phe Ala Pro His
1               5                   10

<210> SEQ ID NO 152
<211> LENGTH: 10
<212> TYPE: PRT
<213> ORGANISM: Artificial
<220> FEATURE:
<223> OTHER INFORMATION: Synthetic polypeptide

<400> SEQUENCE: 152

Ala Ala Ala Pro Thr Tyr Phe Pro Ala His
1               5                   10

<210> SEQ ID NO 153
<211> LENGTH: 10
<212> TYPE: PRT
<213> ORGANISM: Artificial
<220> FEATURE:
<223> OTHER INFORMATION: Synthetic polypeptide

<400> SEQUENCE: 153

Ala Ala Ala Pro Thr Tyr Phe Pro Pro Ala
1               5                   10

<210> SEQ ID NO 154
<211> LENGTH: 10
<212> TYPE: PRT
<213> ORGANISM: Artificial
<220> FEATURE:
<223> OTHER INFORMATION: Synthetic polypeptide

<400> SEQUENCE: 154
```

```
Ser Ala Ala Pro Thr Tyr Phe Pro Ala His
1               5                   10
```

<210> SEQ ID NO 155
<211> LENGTH: 10
<212> TYPE: PRT
<213> ORGANISM: Artificial
<220> FEATURE:
<223> OTHER INFORMATION: Synthetic polypeptide

<400> SEQUENCE: 155

```
Ala Ala Ala Pro Ala Phe Phe Pro Pro His
1               5                   10
```

<210> SEQ ID NO 156
<211> LENGTH: 10
<212> TYPE: PRT
<213> ORGANISM: Artificial
<220> FEATURE:
<223> OTHER INFORMATION: Synthetic polypeptide

<400> SEQUENCE: 156

```
Ala Ala Ala Pro Pro Phe Phe Pro Pro His
1               5                   10
```

<210> SEQ ID NO 157
<211> LENGTH: 10
<212> TYPE: PRT
<213> ORGANISM: Artificial
<220> FEATURE:
<223> OTHER INFORMATION: Synthetic polypeptide

<400> SEQUENCE: 157

```
Ala Ala Ala Pro Thr Phe Phe Pro Pro His
1               5                   10
```

<210> SEQ ID NO 158
<211> LENGTH: 10
<212> TYPE: PRT
<213> ORGANISM: Artificial
<220> FEATURE:
<223> OTHER INFORMATION: Synthetic polypeptide

<400> SEQUENCE: 158

```
Ser Ile Ser Val Ala Thr Arg Leu Ala Gln
1               5                   10
```

<210> SEQ ID NO 159
<211> LENGTH: 10
<212> TYPE: PRT
<213> ORGANISM: Artificial
<220> FEATURE:
<223> OTHER INFORMATION: Synthetic polypeptide

<400> SEQUENCE: 159

```
Ala Met Ser Met Leu Thr Lys Glu Val His
1               5                   10
```

<210> SEQ ID NO 160
<211> LENGTH: 10
<212> TYPE: PRT
<213> ORGANISM: Artificial
<220> FEATURE:
<223> OTHER INFORMATION: Synthetic polypeptide

<400> SEQUENCE: 160

```
Pro Ala Phe Ala Ser Ile Arg Ser Leu Asn
1               5                   10
```

<210> SEQ ID NO 161
<211> LENGTH: 10
<212> TYPE: PRT
<213> ORGANISM: Artificial
<220> FEATURE:
<223> OTHER INFORMATION: Synthetic polypeptide

<400> SEQUENCE: 161

```
Pro Asn Phe Asn Ala Gly Ser Pro Thr Glu
1               5                   10
```

<210> SEQ ID NO 162
<211> LENGTH: 10
<212> TYPE: PRT
<213> ORGANISM: Artificial
<220> FEATURE:
<223> OTHER INFORMATION: Synthetic polypeptide

<400> SEQUENCE: 162

```
Lys Met Leu Leu Leu Ser Leu Gly Thr Gly
1               5                   10
```

<210> SEQ ID NO 163
<211> LENGTH: 10
<212> TYPE: PRT
<213> ORGANISM: Artificial
<220> FEATURE:
<223> OTHER INFORMATION: Synthetic polypeptide

<400> SEQUENCE: 163

```
Asn Tyr Leu Ile Ile Ser Val Gly Thr Gly
1               5                   10
```

<210> SEQ ID NO 164
<211> LENGTH: 10
<212> TYPE: PRT
<213> ORGANISM: Artificial
<220> FEATURE:
<223> OTHER INFORMATION: Synthetic polypeptide

<400> SEQUENCE: 164

```
Lys Met Leu Leu Leu Ser Leu Gly Ala Gly
1               5                   10
```

<210> SEQ ID NO 165
<211> LENGTH: 10
<212> TYPE: PRT
<213> ORGANISM: Artificial
<220> FEATURE:
<223> OTHER INFORMATION: Synthetic polypeptide

<400> SEQUENCE: 165

```
Ala Glu Phe Asp Lys Thr Tyr Thr Ala Lys
1               5                   10
```

<210> SEQ ID NO 166
<211> LENGTH: 10
<212> TYPE: PRT
<213> ORGANISM: Artificial
<220> FEATURE:
<223> OTHER INFORMATION: Synthetic polypeptide

<400> SEQUENCE: 166

```
Ser Ala Phe Asp Lys Thr Tyr Thr Ala Lys
```

```
1               5                   10
```

<210> SEQ ID NO 167
<211> LENGTH: 10
<212> TYPE: PRT
<213> ORGANISM: Artificial
<220> FEATURE:
<223> OTHER INFORMATION: Synthetic polypeptide

<400> SEQUENCE: 167

```
Ser Glu Ala Asp Lys Thr Tyr Thr Ala Lys
1               5                   10
```

<210> SEQ ID NO 168
<211> LENGTH: 10
<212> TYPE: PRT
<213> ORGANISM: Artificial
<220> FEATURE:
<223> OTHER INFORMATION: Synthetic polypeptide

<400> SEQUENCE: 168

```
Ser Glu Phe Ala Lys Thr Tyr Thr Ala Lys
1               5                   10
```

<210> SEQ ID NO 169
<211> LENGTH: 10
<212> TYPE: PRT
<213> ORGANISM: Artificial
<220> FEATURE:
<223> OTHER INFORMATION: Synthetic polypeptide

<400> SEQUENCE: 169

```
Ser Glu Phe Asp Ala Thr Tyr Thr Ala Lys
1               5                   10
```

<210> SEQ ID NO 170
<211> LENGTH: 10
<212> TYPE: PRT
<213> ORGANISM: Artificial
<220> FEATURE:
<223> OTHER INFORMATION: Synthetic polypeptide

<400> SEQUENCE: 170

```
Ser Glu Phe Asp Lys Ala Tyr Thr Ala Lys
1               5                   10
```

<210> SEQ ID NO 171
<211> LENGTH: 10
<212> TYPE: PRT
<213> ORGANISM: Artificial
<220> FEATURE:
<223> OTHER INFORMATION: Synthetic polypeptide

<400> SEQUENCE: 171

```
Ser Glu Phe Asp Lys Thr Ala Thr Ala Lys
1               5                   10
```

<210> SEQ ID NO 172
<211> LENGTH: 10
<212> TYPE: PRT
<213> ORGANISM: Artificial
<220> FEATURE:
<223> OTHER INFORMATION: Synthetic polypeptide

<400> SEQUENCE: 172

```
Ser Glu Phe Asp Lys Thr Tyr Ala Ala Lys
1               5                   10
```

```
<210> SEQ ID NO 173
<211> LENGTH: 10
<212> TYPE: PRT
<213> ORGANISM: Artificial
<220> FEATURE:
<223> OTHER INFORMATION: Synthetic polypeptide

<400> SEQUENCE: 173

Ser Glu Phe Asp Lys Thr Tyr Thr Ala Ala
1               5                   10

<210> SEQ ID NO 174
<211> LENGTH: 10
<212> TYPE: PRT
<213> ORGANISM: Artificial
<220> FEATURE:
<223> OTHER INFORMATION: Synthetic polypeptide

<400> SEQUENCE: 174

Lys Gln Ala Glu Lys Tyr Thr Ala Glu Gln
1               5                   10

<210> SEQ ID NO 175
<211> LENGTH: 10
<212> TYPE: PRT
<213> ORGANISM: Artificial
<220> FEATURE:
<223> OTHER INFORMATION: Synthetic polypeptide

<400> SEQUENCE: 175

Ser Glu Phe Asp Ala Ala Phe Ala Ala Ala
1               5                   10

<210> SEQ ID NO 176
<211> LENGTH: 10
<212> TYPE: PRT
<213> ORGANISM: Artificial
<220> FEATURE:
<223> OTHER INFORMATION: Synthetic polypeptide

<400> SEQUENCE: 176

Ser Glu Phe Asp Lys Thr Phe Thr Ala Lys
1               5                   10

<210> SEQ ID NO 177
<211> LENGTH: 10
<212> TYPE: PRT
<213> ORGANISM: Artificial
<220> FEATURE:
<223> OTHER INFORMATION: Synthetic polypeptide

<400> SEQUENCE: 177

Ala Glu Lys Tyr Thr Ala Glu Gln Cys Ala
1               5                   10

<210> SEQ ID NO 178
<211> LENGTH: 10
<212> TYPE: PRT
<213> ORGANISM: Artificial
<220> FEATURE:
<223> OTHER INFORMATION: Synthetic polypeptide

<400> SEQUENCE: 178

Ala Thr Tyr Thr Ala Lys Glu Ala Ala Thr
1               5                   10
```

```
<210> SEQ ID NO 179
<211> LENGTH: 10
<212> TYPE: PRT
<213> ORGANISM: Artificial
<220> FEATURE:
<223> OTHER INFORMATION: Synthetic polypeptide

<400> SEQUENCE: 179

Lys Ala Tyr Thr Ala Lys Glu Ala Ala Thr
1               5                   10

<210> SEQ ID NO 180
<211> LENGTH: 10
<212> TYPE: PRT
<213> ORGANISM: Artificial
<220> FEATURE:
<223> OTHER INFORMATION: Synthetic polypeptide

<400> SEQUENCE: 180

Lys Thr Ala Thr Ala Lys Glu Ala Ala Thr
1               5                   10

<210> SEQ ID NO 181
<211> LENGTH: 10
<212> TYPE: PRT
<213> ORGANISM: Artificial
<220> FEATURE:
<223> OTHER INFORMATION: Synthetic polypeptide

<400> SEQUENCE: 181

Lys Thr Tyr Ala Ala Lys Glu Ala Ala Thr
1               5                   10

<210> SEQ ID NO 182
<211> LENGTH: 10
<212> TYPE: PRT
<213> ORGANISM: Artificial
<220> FEATURE:
<223> OTHER INFORMATION: Synthetic polypeptide

<400> SEQUENCE: 182

Lys Thr Tyr Thr Ala Ala Glu Ala Ala Thr
1               5                   10

<210> SEQ ID NO 183
<211> LENGTH: 10
<212> TYPE: PRT
<213> ORGANISM: Artificial
<220> FEATURE:
<223> OTHER INFORMATION: Synthetic polypeptide

<400> SEQUENCE: 183

Lys Thr Tyr Thr Ala Lys Ala Ala Ala Thr
1               5                   10

<210> SEQ ID NO 184
<211> LENGTH: 10
<212> TYPE: PRT
<213> ORGANISM: Artificial
<220> FEATURE:
<223> OTHER INFORMATION: Synthetic polypeptide

<400> SEQUENCE: 184

Lys Thr Tyr Thr Ala Lys Glu Ala Ala Ala
1               5                   10
```

```
<210> SEQ ID NO 185
<211> LENGTH: 10
<212> TYPE: PRT
<213> ORGANISM: Artificial
<220> FEATURE:
<223> OTHER INFORMATION: Synthetic polypeptide

<400> SEQUENCE: 185

Glu Lys Tyr Thr Ala Glu Gln Cys Ala Lys
1               5                   10

<210> SEQ ID NO 186
<211> LENGTH: 10
<212> TYPE: PRT
<213> ORGANISM: Artificial
<220> FEATURE:
<223> OTHER INFORMATION: Synthetic polypeptide

<400> SEQUENCE: 186

Ala Ala Phe Ala Ala Ala Glu Ala Ala Thr
1               5                   10

<210> SEQ ID NO 187
<211> LENGTH: 10
<212> TYPE: PRT
<213> ORGANISM: Artificial
<220> FEATURE:
<223> OTHER INFORMATION: Synthetic polypeptide

<400> SEQUENCE: 187

Lys Thr Phe Thr Ala Lys Glu Ala Ala Thr
1               5                   10

<210> SEQ ID NO 188
<211> LENGTH: 10
<212> TYPE: PRT
<213> ORGANISM: Artificial
<220> FEATURE:
<223> OTHER INFORMATION: Synthetic polypeptide

<400> SEQUENCE: 188

Gln Ala Leu His Cys Glu Lys Lys Tyr Leu
1               5                   10

<210> SEQ ID NO 189
<211> LENGTH: 10
<212> TYPE: PRT
<213> ORGANISM: Artificial
<220> FEATURE:
<223> OTHER INFORMATION: Synthetic polypeptide

<400> SEQUENCE: 189

Gln Ala Leu Asp Ser Lys Ala Ala Tyr Leu
1               5                   10

<210> SEQ ID NO 190
<211> LENGTH: 10
<212> TYPE: PRT
<213> ORGANISM: Artificial
<220> FEATURE:
<223> OTHER INFORMATION: Synthetic polypeptide

<400> SEQUENCE: 190

Gln Ala Leu Asp Ser Lys Asn Asn Phe Leu
1               5                   10

<210> SEQ ID NO 191
```

```
<211> LENGTH: 10
<212> TYPE: PRT
<213> ORGANISM: Artificial
<220> FEATURE:
<223> OTHER INFORMATION: Synthetic polypeptide

<400> SEQUENCE: 191

Gln Ala Leu His Cys Glu Asn Asn Phe Leu
1               5                   10

<210> SEQ ID NO 192
<211> LENGTH: 10
<212> TYPE: PRT
<213> ORGANISM: Artificial
<220> FEATURE:
<223> OTHER INFORMATION: Synthetic polypeptide

<400> SEQUENCE: 192

Cys Glu Lys Lys Tyr Leu Arg Ile Gln Asp
1               5                   10

<210> SEQ ID NO 193
<211> LENGTH: 10
<212> TYPE: PRT
<213> ORGANISM: Artificial
<220> FEATURE:
<223> OTHER INFORMATION: Synthetic polypeptide

<400> SEQUENCE: 193

Ser Lys Asn Asn Phe Leu Arg Val Gln Glu
1               5                   10

<210> SEQ ID NO 194
<211> LENGTH: 10
<212> TYPE: PRT
<213> ORGANISM: Artificial
<220> FEATURE:
<223> OTHER INFORMATION: Synthetic polypeptide

<400> SEQUENCE: 194

Ser Glu Asn Asn Tyr Leu Arg Val Gln Glu
1               5                   10

<210> SEQ ID NO 195
<211> LENGTH: 10
<212> TYPE: PRT
<213> ORGANISM: Artificial
<220> FEATURE:
<223> OTHER INFORMATION: Synthetic polypeptide

<400> SEQUENCE: 195

Ala Leu Arg Val Gln Glu Asn Ala Leu Thr
1               5                   10

<210> SEQ ID NO 196
<211> LENGTH: 10
<212> TYPE: PRT
<213> ORGANISM: Artificial
<220> FEATURE:
<223> OTHER INFORMATION: Synthetic polypeptide

<400> SEQUENCE: 196

Tyr Ala Arg Val Gln Glu Asn Ala Leu Thr
1               5                   10

<210> SEQ ID NO 197
<211> LENGTH: 10
```

```
<212> TYPE: PRT
<213> ORGANISM: Artificial
<220> FEATURE:
<223> OTHER INFORMATION: Synthetic polypeptide

<400> SEQUENCE: 197

Tyr Leu Ala Val Gln Glu Asn Ala Leu Thr
1               5                   10

<210> SEQ ID NO 198
<211> LENGTH: 10
<212> TYPE: PRT
<213> ORGANISM: Artificial
<220> FEATURE:
<223> OTHER INFORMATION: Synthetic polypeptide

<400> SEQUENCE: 198

Tyr Leu Arg Ala Gln Glu Asn Ala Leu Thr
1               5                   10

<210> SEQ ID NO 199
<211> LENGTH: 10
<212> TYPE: PRT
<213> ORGANISM: Artificial
<220> FEATURE:
<223> OTHER INFORMATION: Synthetic polypeptide

<400> SEQUENCE: 199

Tyr Leu Arg Val Ala Glu Asn Ala Leu Thr
1               5                   10

<210> SEQ ID NO 200
<211> LENGTH: 10
<212> TYPE: PRT
<213> ORGANISM: Artificial
<220> FEATURE:
<223> OTHER INFORMATION: Synthetic polypeptide

<400> SEQUENCE: 200

Tyr Leu Arg Val Gln Ala Asn Ala Leu Thr
1               5                   10

<210> SEQ ID NO 201
<211> LENGTH: 10
<212> TYPE: PRT
<213> ORGANISM: Artificial
<220> FEATURE:
<223> OTHER INFORMATION: Synthetic polypeptide

<400> SEQUENCE: 201

Tyr Leu Arg Val Gln Glu Ala Ala Leu Thr
1               5                   10

<210> SEQ ID NO 202
<211> LENGTH: 10
<212> TYPE: PRT
<213> ORGANISM: Artificial
<220> FEATURE:
<223> OTHER INFORMATION: Synthetic polypeptide

<400> SEQUENCE: 202

Tyr Leu Arg Val Gln Glu Asn Ala Ala Thr
1               5                   10

<210> SEQ ID NO 203
<211> LENGTH: 10
<212> TYPE: PRT
```

```
<213> ORGANISM: Artificial
<220> FEATURE:
<223> OTHER INFORMATION: Synthetic polypeptide

<400> SEQUENCE: 203

Tyr Leu Arg Val Gln Glu Asn Ala Leu Ala
1               5                   10

<210> SEQ ID NO 204
<211> LENGTH: 10
<212> TYPE: PRT
<213> ORGANISM: Artificial
<220> FEATURE:
<223> OTHER INFORMATION: Synthetic polypeptide

<400> SEQUENCE: 204

Tyr Leu Arg Ile Gln Asp Asp Thr Leu Thr
1               5                   10

<210> SEQ ID NO 205
<211> LENGTH: 10
<212> TYPE: PRT
<213> ORGANISM: Artificial
<220> FEATURE:
<223> OTHER INFORMATION: Synthetic polypeptide

<400> SEQUENCE: 205

Tyr Leu Thr Val Ala Ala Ala Ala Leu Thr
1               5                   10

<210> SEQ ID NO 206
<211> LENGTH: 10
<212> TYPE: PRT
<213> ORGANISM: Artificial
<220> FEATURE:
<223> OTHER INFORMATION: Synthetic polypeptide

<400> SEQUENCE: 206

Phe Leu Arg Val Gln Glu Asn Ala Leu Thr
1               5                   10

<210> SEQ ID NO 207
<211> LENGTH: 10
<212> TYPE: PRT
<213> ORGANISM: Artificial
<220> FEATURE:
<223> OTHER INFORMATION: Synthetic polypeptide

<400> SEQUENCE: 207

Asn Asn Tyr Leu Arg Val Gln Glu Asn Ala
1               5                   10

<210> SEQ ID NO 208
<211> LENGTH: 10
<212> TYPE: PRT
<213> ORGANISM: Artificial
<220> FEATURE:
<223> OTHER INFORMATION: Synthetic polypeptide

<400> SEQUENCE: 208

Lys Lys Tyr Leu Arg Ile Gln Asp Asp Thr
1               5                   10

<210> SEQ ID NO 209
<211> LENGTH: 10
<212> TYPE: PRT
<213> ORGANISM: Artificial
```

```
<220> FEATURE:
<223> OTHER INFORMATION: Synthetic polypeptide

<400> SEQUENCE: 209

Asn Asn Phe Leu Arg Val Gln Glu Asn Ala
1               5                   10

<210> SEQ ID NO 210
<211> LENGTH: 10
<212> TYPE: PRT
<213> ORGANISM: Artificial
<220> FEATURE:
<223> OTHER INFORMATION: Synthetic polypeptide

<400> SEQUENCE: 210

Asn Ala Tyr Leu Arg Val Gln Glu Asn Ala
1               5                   10

<210> SEQ ID NO 211
<211> LENGTH: 10
<212> TYPE: PRT
<213> ORGANISM: Artificial
<220> FEATURE:
<223> OTHER INFORMATION: Synthetic polypeptide

<400> SEQUENCE: 211

Ala Thr Tyr Glu Glu Ala Lys Leu Arg Phe
1               5                   10

<210> SEQ ID NO 212
<211> LENGTH: 10
<212> TYPE: PRT
<213> ORGANISM: Artificial
<220> FEATURE:
<223> OTHER INFORMATION: Synthetic polypeptide

<400> SEQUENCE: 212

Glu Ala Tyr Glu Glu Ala Leu Lys Arg Phe
1               5                   10

<210> SEQ ID NO 213
<211> LENGTH: 10
<212> TYPE: PRT
<213> ORGANISM: Artificial
<220> FEATURE:
<223> OTHER INFORMATION: Synthetic polypeptide

<400> SEQUENCE: 213

Glu Thr Ala Glu Glu Ala Leu Lys Arg Phe
1               5                   10

<210> SEQ ID NO 214
<211> LENGTH: 10
<212> TYPE: PRT
<213> ORGANISM: Artificial
<220> FEATURE:
<223> OTHER INFORMATION: Synthetic polypeptide

<400> SEQUENCE: 214

Glu Thr Tyr Ala Glu Ala Leu Lys Arg Phe
1               5                   10

<210> SEQ ID NO 215
<211> LENGTH: 10
<212> TYPE: PRT
<213> ORGANISM: Artificial
<220> FEATURE:
```

<223> OTHER INFORMATION: Synthetic polypeptide

<400> SEQUENCE: 215

Glu Thr Tyr Glu Ala Ala Leu Lys Arg Phe
1               5                   10

<210> SEQ ID NO 216
<211> LENGTH: 10
<212> TYPE: PRT
<213> ORGANISM: Artificial
<220> FEATURE:
<223> OTHER INFORMATION: Synthetic polypeptide

<400> SEQUENCE: 216

Glu Thr Tyr Glu Glu Ala Ala Lys Arg Phe
1               5                   10

<210> SEQ ID NO 217
<211> LENGTH: 10
<212> TYPE: PRT
<213> ORGANISM: Artificial
<220> FEATURE:
<223> OTHER INFORMATION: Synthetic polypeptide

<400> SEQUENCE: 217

Glu Thr Tyr Glu Glu Ala Leu Ala Arg Phe
1               5                   10

<210> SEQ ID NO 218
<211> LENGTH: 10
<212> TYPE: PRT
<213> ORGANISM: Artificial
<220> FEATURE:
<223> OTHER INFORMATION: Synthetic polypeptide

<400> SEQUENCE: 218

Glu Thr Tyr Glu Glu Ala Leu Lys Ala Phe
1               5                   10

<210> SEQ ID NO 219
<211> LENGTH: 10
<212> TYPE: PRT
<213> ORGANISM: Artificial
<220> FEATURE:
<223> OTHER INFORMATION: Synthetic polypeptide

<400> SEQUENCE: 219

Glu Thr Tyr Glu Glu Ala Leu Lys Arg Ala
1               5                   10

<210> SEQ ID NO 220
<211> LENGTH: 10
<212> TYPE: PRT
<213> ORGANISM: Artificial
<220> FEATURE:
<223> OTHER INFORMATION: Synthetic polypeptide

<400> SEQUENCE: 220

Gly Thr Asn Ala Gln Ser Leu Ala Asp Phe
1               5                   10

<210> SEQ ID NO 221
<211> LENGTH: 10
<212> TYPE: PRT
<213> ORGANISM: Artificial
<220> FEATURE:
<223> OTHER INFORMATION: Synthetic polypeptide

```
<400> SEQUENCE: 221

Glu Thr Tyr Glu Ala Ala Leu Ala Ala Phe
1               5                   10

<210> SEQ ID NO 222
<211> LENGTH: 10
<212> TYPE: PRT
<213> ORGANISM: Artificial
<220> FEATURE:
<223> OTHER INFORMATION: Synthetic polypeptide

<400> SEQUENCE: 222

Glu Thr Phe Glu Glu Ala Leu Lys Arg Phe
1               5                   10

<210> SEQ ID NO 223
<211> LENGTH: 10
<212> TYPE: PRT
<213> ORGANISM: Artificial
<220> FEATURE:
<223> OTHER INFORMATION: Synthetic polypeptide

<400> SEQUENCE: 223

Tyr Glu Glu Ala Leu Lys Thr Phe Ala Lys
1               5                   10

<210> SEQ ID NO 224
<211> LENGTH: 10
<212> TYPE: PRT
<213> ORGANISM: Artificial
<220> FEATURE:
<223> OTHER INFORMATION: Synthetic polypeptide

<400> SEQUENCE: 224

Phe Glu Glu Ala Leu Lys Arg Phe Ala Lys
1               5                   10

<210> SEQ ID NO 225
<211> LENGTH: 10
<212> TYPE: PRT
<213> ORGANISM: Artificial
<220> FEATURE:
<223> OTHER INFORMATION: Synthetic polypeptide

<400> SEQUENCE: 225

Ala Ala Leu Lys Arg Phe Ala Lys Leu Leu
1               5                   10

<210> SEQ ID NO 226
<211> LENGTH: 10
<212> TYPE: PRT
<213> ORGANISM: Artificial
<220> FEATURE:
<223> OTHER INFORMATION: Synthetic polypeptide

<400> SEQUENCE: 226

Glu Ala Ala Lys Arg Phe Ala Lys Leu Leu
1               5                   10

<210> SEQ ID NO 227
<211> LENGTH: 10
<212> TYPE: PRT
<213> ORGANISM: Artificial
<220> FEATURE:
<223> OTHER INFORMATION: Synthetic polypeptide
```

```
<400> SEQUENCE: 227

Glu Ala Leu Ala Arg Phe Ala Lys Leu Leu
1               5                   10

<210> SEQ ID NO 228
<211> LENGTH: 10
<212> TYPE: PRT
<213> ORGANISM: Artificial
<220> FEATURE:
<223> OTHER INFORMATION: Synthetic polypeptide

<400> SEQUENCE: 228

Glu Ala Leu Lys Ala Phe Ala Lys Leu Leu
1               5                   10

<210> SEQ ID NO 229
<211> LENGTH: 10
<212> TYPE: PRT
<213> ORGANISM: Artificial
<220> FEATURE:
<223> OTHER INFORMATION: Synthetic polypeptide

<400> SEQUENCE: 229

Glu Ala Leu Lys Arg Ala Ala Lys Leu Leu
1               5                   10

<210> SEQ ID NO 230
<211> LENGTH: 10
<212> TYPE: PRT
<213> ORGANISM: Artificial
<220> FEATURE:
<223> OTHER INFORMATION: Synthetic polypeptide

<400> SEQUENCE: 230

Glu Ala Leu Lys Arg Phe Ala Ala Leu Leu
1               5                   10

<210> SEQ ID NO 231
<211> LENGTH: 10
<212> TYPE: PRT
<213> ORGANISM: Artificial
<220> FEATURE:
<223> OTHER INFORMATION: Synthetic polypeptide

<400> SEQUENCE: 231

Glu Ala Leu Lys Arg Phe Ala Lys Ala Leu
1               5                   10

<210> SEQ ID NO 232
<211> LENGTH: 10
<212> TYPE: PRT
<213> ORGANISM: Artificial
<220> FEATURE:
<223> OTHER INFORMATION: Synthetic polypeptide

<400> SEQUENCE: 232

Glu Ala Leu Lys Arg Phe Ala Lys Leu Ala
1               5                   10

<210> SEQ ID NO 233
<211> LENGTH: 10
<212> TYPE: PRT
<213> ORGANISM: Artificial
<220> FEATURE:
<223> OTHER INFORMATION: Synthetic polypeptide

<400> SEQUENCE: 233
```

Gln Ser Leu Ala Asp Phe Ala Lys Gln Leu
1               5                   10

<210> SEQ ID NO 234
<211> LENGTH: 10
<212> TYPE: PRT
<213> ORGANISM: Artificial
<220> FEATURE:
<223> OTHER INFORMATION: Synthetic polypeptide

<400> SEQUENCE: 234

Ala Ala Leu Ala Ala Phe Ala Lys Leu Leu
1               5                   10

<210> SEQ ID NO 235
<211> LENGTH: 10
<212> TYPE: PRT
<213> ORGANISM: Artificial
<220> FEATURE:
<223> OTHER INFORMATION: Synthetic polypeptide

<400> SEQUENCE: 235

Leu Ala Asp Phe Ala Lys Gln Leu Ser Asp
1               5                   10

<210> SEQ ID NO 236
<211> LENGTH: 10
<212> TYPE: PRT
<213> ORGANISM: Artificial
<220> FEATURE:
<223> OTHER INFORMATION: Synthetic polypeptide

<400> SEQUENCE: 236

Asp Phe Ala Lys Gln Leu Ser Asp Glu Arg
1               5                   10

<210> SEQ ID NO 237
<211> LENGTH: 10
<212> TYPE: PRT
<213> ORGANISM: Artificial
<220> FEATURE:
<223> OTHER INFORMATION: Synthetic polypeptide

<400> SEQUENCE: 237

Ala Phe Ala Ala Leu Leu Ser Asp Arg Lys
1               5                   10

<210> SEQ ID NO 238
<211> LENGTH: 10
<212> TYPE: PRT
<213> ORGANISM: Artificial
<220> FEATURE:
<223> OTHER INFORMATION: Synthetic polypeptide

<400> SEQUENCE: 238

Ser Thr Ala Ala Ala Pro Thr Tyr Phe Pro
1               5                   10

<210> SEQ ID NO 239
<211> LENGTH: 10
<212> TYPE: PRT
<213> ORGANISM: Artificial
<220> FEATURE:
<223> OTHER INFORMATION: Synthetic polypeptide

<400> SEQUENCE: 239

```
Leu Lys Arg Phe Ala Lys Leu Leu Ser Asp
1               5                   10
```

<210> SEQ ID NO 240
<211> LENGTH: 10
<212> TYPE: PRT
<213> ORGANISM: Artificial
<220> FEATURE:
<223> OTHER INFORMATION: Synthetic polypeptide

<400> SEQUENCE: 240

```
Gln Ala Leu Asp Ser Glu Asn Asn Phe Leu
1               5                   10
```

<210> SEQ ID NO 241
<211> LENGTH: 10
<212> TYPE: PRT
<213> ORGANISM: Artificial
<220> FEATURE:
<223> OTHER INFORMATION: Synthetic polypeptide

<400> SEQUENCE: 241

```
Ser Asp Leu Ala Asp Phe Ala Lys Gln Leu
1               5                   10
```

<210> SEQ ID NO 242
<211> LENGTH: 55
<212> TYPE: DNA
<213> ORGANISM: Artificial
<220> FEATURE:
<223> OTHER INFORMATION: Synthetic construct

<400> SEQUENCE: 242
ggagctcgag aaaagagagg ctgaagcttc attgaattac aaaaaaatgc tgttg        55

<210> SEQ ID NO 243
<211> LENGTH: 42
<212> TYPE: DNA
<213> ORGANISM: Artificial
<220> FEATURE:
<223> OTHER INFORMATION: Synthetic construct

<400> SEQUENCE: 243
tcccaactgt cctggtccat aagaagcttt gtttgctcgg ag                      42

<210> SEQ ID NO 244
<211> LENGTH: 36
<212> TYPE: DNA
<213> ORGANISM: Artificial
<220> FEATURE:
<223> OTHER INFORMATION: Synthetic construct

<400> SEQUENCE: 244
gcttcttatg gaccaggaca gttgggagaa atggtg                             36

<210> SEQ ID NO 245
<211> LENGTH: 39
<212> TYPE: DNA
<213> ORGANISM: Artificial
<220> FEATURE:
<223> OTHER INFORMATION: Synthetic construct

<400> SEQUENCE: 245
ggtctagagg aattctcatt acctaattga agcaaatgc                          39

<210> SEQ ID NO 246

-continued

<211> LENGTH: 1128
<212> TYPE: DNA
<213> ORGANISM: Artificial
<220> FEATURE:
<223> OTHER INFORMATION: Synthetic construct

<400> SEQUENCE: 246

| | | |
|---|---|---|
| tcgagaaaag agaggctgaa gcttcattga attacaaaaa aatgctgttg ctctcattag | 60 |
| gcactggcac tacttcagag tttgataaaa catatacagc aaaagaggca gctacctgga | 120 |
| ctgctgtaca ttggatgtta gttatacaga aaatgactga tgcagcaagt tcttacatga | 180 |
| ctgattatta cctttctact gcttttcaag ctcttgattc aaaaaacaat tacctcaggg | 240 |
| ttcaagaaaa tgcattaaca ggcacaacta ctgaaatgga tgatgcttct gaggctaata | 300 |
| tggaattatt agtacaagtt ggtgaaaact tattgaagaa accagtttcc gaagacaatc | 360 |
| ctgaaaccta tgaggaagct ctaaagaggt ttgcaaaatt gctctctgat aggaagaaac | 420 |
| tccgagcaaa caaagcttct tatgaccag gacagtggg agaaatggtg actgttctta | 480 |
| gtattgatgg aggtggaatt agagggatca ttccggctac cattctcgaa tttcttgaag | 540 |
| gacaacttca ggaaatggac aataatgcag atgcaagact tgcagattac tttgatgtaa | 600 |
| ttggaggaac aagtacagga ggtttattga ctgctatgat aagtactcca aatgaaaaca | 660 |
| atcgacccct tgctgctgcc aaagaaattg tacctttta cttcgaacat ggccctcaga | 720 |
| tttttaatcc tagtggtcaa attttaggcc caaaatatga tggaaaatat cttatgcaag | 780 |
| ttcttcaaga aaaacttgga gaaactcgtg tgcatcaagc tttgacagaa gttgtcatct | 840 |
| caagctttga catcaaaaca aataagccag taatattcac taagtcaaat ttagcaaact | 900 |
| ctccagaatt ggatgctaag atgtatgaca taagttattc cacagcagca gctccaacat | 960 |
| attttcctcc gcattacttt gttactaata ctagtaatgg agatgaatat gagttcaatc | 1020 |
| ttgttgatgg tgctgttgct actgttgctg atccggcgtt attatccatt agcgttgcaa | 1080 |
| cgagacttgc acaaaaggat ccagcatttg cttcaattag gtaatgag | 1128 |

<210> SEQ ID NO 247
<211> LENGTH: 366
<212> TYPE: PRT
<213> ORGANISM: Artificial
<220> FEATURE:
<223> OTHER INFORMATION: Synthetic polypeptide

<400> SEQUENCE: 247

Ser Leu Asn Tyr Lys Lys Met Leu Leu Ser Leu Gly Thr Gly Thr
1               5                   10                  15

Thr Ser Glu Phe Asp Lys Thr Tyr Thr Ala Lys Glu Ala Thr Trp
            20                  25                  30

Thr Ala Val His Trp Met Leu Val Ile Gln Lys Met Thr Asp Ala Ala
        35                  40                  45

Ser Ser Tyr Met Thr Asp Tyr Tyr Leu Ser Thr Ala Phe Gln Ala Leu
    50                  55                  60

Asp Ser Lys Asn Asn Tyr Leu Arg Val Gln Glu Asn Ala Leu Thr Gly
65                  70                  75                  80

Thr Thr Thr Glu Met Asp Asp Ala Ser Glu Ala Asn Met Glu Leu Leu
                85                  90                  95

Val Gln Val Gly Glu Asn Leu Leu Lys Lys Pro Val Ser Glu Asp Asn
            100                 105                 110

Pro Glu Thr Tyr Glu Glu Ala Leu Lys Arg Phe Ala Lys Leu Leu Ser
        115                 120                 125

```
Asp Arg Lys Lys Leu Arg Ala Asn Lys Ala Ser Tyr Gly Pro Gly Gln
    130                 135                 140

Leu Gly Glu Met Val Thr Val Leu Ser Ile Asp Gly Gly Ile Arg
145                 150                 155                 160

Gly Ile Ile Pro Ala Thr Ile Leu Glu Phe Leu Glu Gly Gln Leu Gln
                165                 170                 175

Glu Met Asp Asn Asn Ala Asp Ala Arg Leu Ala Asp Tyr Phe Asp Val
            180                 185                 190

Ile Gly Gly Thr Ser Thr Gly Gly Leu Leu Thr Ala Met Ile Ser Thr
        195                 200                 205

Pro Asn Glu Asn Asn Arg Pro Phe Ala Ala Lys Glu Ile Val Pro
    210                 215                 220

Phe Tyr Phe Glu His Gly Pro Gln Ile Phe Asn Pro Ser Gly Gln Ile
225                 230                 235                 240

Leu Gly Pro Lys Tyr Asp Gly Lys Tyr Leu Met Gln Val Leu Gln Glu
                245                 250                 255

Lys Leu Gly Glu Thr Arg Val His Gln Ala Leu Thr Glu Val Val Ile
            260                 265                 270

Ser Ser Phe Asp Ile Lys Thr Asn Lys Pro Val Ile Phe Thr Lys Ser
        275                 280                 285

Asn Leu Ala Asn Ser Pro Glu Leu Asp Ala Lys Met Tyr Asp Ile Ser
    290                 295                 300

Tyr Ser Thr Ala Ala Pro Thr Tyr Phe Pro Pro His Tyr Phe Val
305                 310                 315                 320

Thr Asn Thr Ser Asn Gly Asp Glu Tyr Glu Phe Asn Leu Val Asp Gly
                325                 330                 335

Ala Val Ala Thr Val Ala Asp Pro Ala Leu Leu Ser Ile Ser Val Ala
            340                 345                 350

Thr Arg Leu Ala Gln Lys Asp Pro Ala Phe Ala Ser Ile Arg
        355                 360                 365

<210> SEQ ID NO 248
<211> LENGTH: 55
<212> TYPE: DNA
<213> ORGANISM: Artificial
<220> FEATURE:
<223> OTHER INFORMATION: Synthetic construct

<400> SEQUENCE: 248
ggagctcgag aaaagagagg ctgaagctaa tactagtaat ggagatgaat atgag      55

<210> SEQ ID NO 249
<211> LENGTH: 39
<212> TYPE: DNA
<213> ORGANISM: Artificial
<220> FEATURE:
<223> OTHER INFORMATION: Synthetic construct

<400> SEQUENCE: 249
ggtctagagg aattctcatt aagtaacaaa gtaatgcgg                         39

<210> SEQ ID NO 250
<211> LENGTH: 1128
<212> TYPE: DNA
<213> ORGANISM: Artificial
<220> FEATURE:
<223> OTHER INFORMATION: Synthetic construct

<400> SEQUENCE: 250
```

-continued

```
tcgagaaaag agaggctgaa gctaatacta gtaatggaga tgaatatgag ttcaatcttg      60
ttgatggtgc tgttgctact gttgctgatc cggcgttatt atccattagc gttgcaacga     120
gacttgcaca aaaggatcca gcatttgctt caattaggtc attgaattac aaaaaaatgc     180
tgttgctctc attaggcact ggcactactt cagagtttga taaaacatat acagcaaaag     240
aggcagctac ctggactgct gtacattgga tgttagttat acagaaaatg actgatgcag     300
caagttctta catgactgat tattaccttt ctactgcttt tcaagctctt gattcaaaaa     360
acaattacct cagggttcaa gaaaatgcat taacaggcac aactactgaa atggatgatg     420
cttctgaggc taatatggaa ttattagtac aagttggtga aaacttattg aagaaaccag     480
tttccgaaga caatcctgaa acctatgagg aagctctaaa gaggtttgca aaattgctct     540
ctgataggaa gaaactccga gcaaacaaag cttcttatgg accaggacag ttgggagaaa     600
tggtgactgt tcttagtatt gatggaggtg gaattagagg gatcattccg gctaccattc     660
tcgaatttct tgaaggacaa cttcaggaaa tggacaataa tgcagatgca agacttgcag     720
attactttga tgtaattgga ggaacaagta caggaggttt attgactgct atgataagta     780
ctccaaatga aaacaatcga ccctttgctg ctgccaaaga aattgtacct ttttacttcg     840
aacatggccc tcagattttt aatcctagtg gtcaaatttt aggcccaaaa tatgatggaa     900
aatatcttat gcaagttctt caagaaaaac ttggagaaac tcgtgtgcat caagctttga     960
cagaagttgt catctcaagc tttgacatca aacaaataa gccagtaata ttcactaagt    1020
caaatttagc aaaactctcca gaattggatg ctaagatgta tgcataagt tattccacag    1080 cagcagctcc aacatatttt cctccgcatt actttgttac ttaatgag                 1128
```

<210> SEQ ID NO 251
<211> LENGTH: 366
<212> TYPE: PRT
<213> ORGANISM: Artificial
<220> FEATURE:
<223> OTHER INFORMATION: Synthetic polypeptide

<400> SEQUENCE: 251

```
Asn Thr Ser Asn Gly Asp Glu Tyr Glu Phe Asn Leu Val Asp Gly Ala
1               5                   10                  15

Val Ala Thr Val Ala Asp Pro Ala Leu Leu Ser Ile Ser Val Ala Thr
            20                  25                  30

Arg Leu Ala Gln Lys Asp Pro Ala Phe Ala Ser Ile Arg Ser Leu Asn
        35                  40                  45

Tyr Lys Lys Met Leu Leu Ser Leu Gly Thr Gly Thr Thr Ser Glu
    50                  55                  60

Phe Asp Lys Thr Tyr Thr Ala Lys Glu Ala Ala Thr Trp Thr Ala Val
65                  70                  75                  80

His Trp Met Leu Val Ile Gln Lys Met Thr Asp Ala Ala Ser Ser Tyr
                85                  90                  95

Met Thr Asp Tyr Tyr Leu Ser Thr Ala Phe Gln Ala Leu Asp Ser Lys
            100                 105                 110

Asn Asn Tyr Leu Arg Val Gln Glu Asn Ala Leu Thr Gly Thr Thr Thr
        115                 120                 125

Glu Met Asp Asp Ala Ser Glu Ala Asn Met Glu Leu Leu Val Gln Val
    130                 135                 140

Gly Glu Asn Leu Leu Lys Lys Pro Val Ser Glu Asp Asn Pro Glu Thr
145                 150                 155                 160
```

-continued

```
Tyr Glu Glu Ala Leu Lys Arg Phe Ala Lys Leu Leu Ser Asp Arg Lys
                165                 170                 175
Lys Leu Arg Ala Asn Lys Ala Ser Tyr Gly Pro Gly Gln Leu Gly Glu
            180                 185                 190
Met Val Thr Val Leu Ser Ile Asp Gly Gly Ile Arg Gly Ile Ile
        195                 200                 205
Pro Ala Thr Ile Leu Glu Phe Leu Glu Gly Gln Leu Gln Met Asp
    210                 215                 220
Asn Asn Ala Asp Ala Arg Leu Ala Asp Tyr Phe Asp Val Ile Gly Gly
225                 230                 235                 240
Thr Ser Thr Gly Gly Leu Leu Thr Ala Met Ile Ser Thr Pro Asn Glu
                245                 250                 255
Asn Asn Arg Pro Phe Ala Ala Lys Glu Ile Val Pro Phe Tyr Phe
            260                 265                 270
Glu His Gly Pro Gln Ile Phe Asn Pro Ser Gly Gln Ile Leu Gly Pro
        275                 280                 285
Lys Tyr Asp Gly Lys Tyr Leu Met Gln Val Leu Gln Glu Lys Leu Gly
    290                 295                 300
Glu Thr Arg Val His Gln Ala Leu Thr Glu Val Val Ile Ser Ser Phe
305                 310                 315                 320
Asp Ile Lys Thr Asn Lys Pro Val Ile Phe Thr Lys Ser Asn Leu Ala
                325                 330                 335
Asn Ser Pro Glu Leu Asp Ala Lys Met Tyr Asp Ile Ser Tyr Ser Thr
            340                 345                 350
Ala Ala Ala Pro Thr Tyr Phe Pro Pro His Tyr Phe Val Thr
        355                 360                 365

<210> SEQ ID NO 252
<211> LENGTH: 55
<212> TYPE: DNA
<213> ORGANISM: Artificial
<220> FEATURE:
<223> OTHER INFORMATION: Synthetic construct

<400> SEQUENCE: 252
ggagctcgag aaaagagagg ctgaagctag ttattccaca gcagcagctc caaca        55

<210> SEQ ID NO 253
<211> LENGTH: 39
<212> TYPE: DNA
<213> ORGANISM: Artificial
<220> FEATURE:
<223> OTHER INFORMATION: Synthetic construct

<400> SEQUENCE: 253
ggtctagagg aattctcatt atatgtcata catcttagc                          39

<210> SEQ ID NO 254
<211> LENGTH: 1128
<212> TYPE: DNA
<213> ORGANISM: Artificial
<220> FEATURE:
<223> OTHER INFORMATION: Synthetic construct

<400> SEQUENCE: 254
tcgagaaaag agaggctgaa gctagttatt ccacagcagc agctccaaca tattttcctc   60
cgcattactt tgttactaat actagtaatg gagatgaata tgagttcat cttgttgatg   120 gtgctgttgc tactgttgct gatccggcgt tattatccat tagcgttgca acgagacttg  180
```

```
cacaaaagga tccagcattt gcttcaatta ggtcattgaa ttacaaaaaa atgctgttgc     240
tctcattagg cactggcact acttcagagt ttgataaaac atatacagca aaagaggcag     300
ctacctggac tgctgtacat tggatgttag ttatacagaa aatgactgat gcagcaagtt     360
cttacatgac tgattattac ctttctactg cttttcaagc tcttgattca aaaaacaatt     420
acctcagggt tcaagaaaat gcattaacag gcacaactac tgaaatggat gatgcttctg     480
aggctaatat ggaattatta gtacaagttg gtgaaaactt attgaagaaa ccagtttccg     540
aagacaatcc tgaaacctat gaggaagctc taaagaggtt tgcaaaattg ctctctgata     600
ggaagaaact ccgagcaaac aaagcttctt atggaccagg acagttggga gaaatggtga     660
ctgttcttag tattgatgga ggtggaatta gagggatcat tccggctacc attctcgaat     720
ttcttgaagg acaacttcag gaaatggaca ataatgcaga tgcaagactt gcagattact     780
ttgatgtaat tggaggaaca agtacaggag gtttattgac tgctatgata agtactccaa     840
atgaaaacaa tcgacccttt gctgctgcca agaaaattgt acctttttac ttcgaacatg     900
gccctcagat ttttaatcct agtggtcaaa tttttaggccc aaaatatgat ggaaaatatc     960
ttatgcaagt tcttcaagaa aaacttggag aaactcgtgt gcatcaagct ttgacagaag    1020
ttgtcatctc aagctttgac atcaaaacaa ataagccagt aatattcact aagtcaaatt    1080
tagcaaactc tccagaattg gatgctaaga tgtatgacat ataatgag                  1128
```

<210> SEQ ID NO 255
<211> LENGTH: 366
<212> TYPE: PRT
<213> ORGANISM: Artificial
<220> FEATURE:
<223> OTHER INFORMATION: Synthetic polypeptide

<400> SEQUENCE: 255

```
Ser Tyr Ser Thr Ala Ala Pro Thr Tyr Phe Pro Pro His Tyr Phe
1               5                  10                  15

Val Thr Asn Thr Ser Asn Gly Asp Glu Tyr Glu Phe Asn Leu Val Asp
            20                  25                  30

Gly Ala Val Ala Thr Val Ala Asp Pro Ala Leu Leu Ser Ile Ser Val
        35                  40                  45

Ala Thr Arg Leu Ala Gln Lys Asp Pro Ala Phe Ala Ser Ile Arg Ser
    50                  55                  60

Leu Asn Tyr Lys Lys Met Leu Leu Ser Leu Gly Thr Gly Thr Thr
65                  70                  75                  80

Ser Glu Phe Asp Lys Thr Tyr Thr Ala Lys Glu Ala Ala Thr Trp Thr
                85                  90                  95

Ala Val His Trp Met Leu Val Ile Gln Lys Met Thr Asp Ala Ala Ser
            100                 105                 110

Ser Tyr Met Thr Asp Tyr Tyr Leu Ser Thr Ala Phe Gln Ala Leu Asp
        115                 120                 125

Ser Lys Asn Asn Tyr Leu Arg Val Gln Glu Asn Ala Leu Thr Gly Thr
    130                 135                 140

Thr Thr Glu Met Asp Asp Ala Ser Glu Ala Asn Met Glu Leu Leu Val
145                 150                 155                 160

Gln Val Gly Glu Asn Leu Leu Lys Lys Pro Val Ser Glu Asp Asn Pro
                165                 170                 175

Glu Thr Tyr Glu Glu Ala Leu Lys Arg Phe Ala Lys Leu Leu Ser Asp
            180                 185                 190

Arg Lys Lys Leu Arg Ala Asn Lys Ala Ser Tyr Gly Pro Gly Gln Leu
```

```
                195                 200                 205
Gly Glu Met Val Thr Val Leu Ser Ile Asp Gly Gly Ile Arg Gly
    210                 215                 220
Ile Ile Pro Ala Thr Ile Leu Glu Phe Leu Glu Gly Gln Leu Gln Glu
225                 230                 235                 240
Met Asp Asn Asn Ala Asp Ala Arg Leu Ala Asp Tyr Phe Asp Val Ile
                245                 250                 255
Gly Gly Thr Ser Thr Gly Gly Leu Leu Thr Ala Met Ile Ser Thr Pro
            260                 265                 270
Asn Glu Asn Asn Arg Pro Phe Ala Ala Lys Glu Ile Val Pro Phe
    275                 280                 285
Tyr Phe Glu His Gly Pro Gln Ile Phe Asn Pro Ser Gly Gln Ile Leu
    290                 295                 300
Gly Pro Lys Tyr Asp Gly Lys Tyr Leu Met Gln Val Leu Gln Glu Lys
305                 310                 315                 320
Leu Gly Glu Thr Arg Val His Gln Ala Leu Thr Glu Val Val Ile Ser
                325                 330                 335
Ser Phe Asp Ile Lys Thr Asn Lys Pro Val Ile Phe Thr Lys Ser Asn
                340                 345                 350
Leu Ala Asn Ser Pro Glu Leu Asp Ala Lys Met Tyr Asp Ile
            355                 360                 365

<210> SEQ ID NO 256
<211> LENGTH: 55
<212> TYPE: DNA
<213> ORGANISM: Artificial
<220> FEATURE:
<223> OTHER INFORMATION: Synthetic construct

<400> SEQUENCE: 256
ggagctcgag aaaagagagg ctgaagctac atatacagca aagaggcag ctacc        55

<210> SEQ ID NO 257
<211> LENGTH: 39
<212> TYPE: DNA
<213> ORGANISM: Artificial
<220> FEATURE:
<223> OTHER INFORMATION: Synthetic construct

<400> SEQUENCE: 257
ggtctagagg aattctcatt atttatcaaa ctctgaagt                         39

<210> SEQ ID NO 258
<211> LENGTH: 1128
<212> TYPE: DNA
<213> ORGANISM: Artificial
<220> FEATURE:
<223> OTHER INFORMATION: Synthetic construct

<400> SEQUENCE: 258
tcgagaaaag agaggctgaa gctacatata cagcaaaaga ggcagctacc tggactgctg    60
tacattggat gttagttata cagaaaatga ctgatgcagc aagttcttac atgactgatt   120
attacctttc tactgctttt caagctcttg attcaaaaaa caattacctc agggttcaag   180
aaaatgcatt aacaggcaca actactgaaa tggatgatgc ttctgaggct aatatggaat   240
tattagtaca agttggtgaa aacttattga agaaaccagt ttccgaagac aatcctgaaa   300
cctatgagga agctctaaag aggttttgcaa aattgctctc tgataggaag aaactccgat   360
caaacaaagc ttcttatgga ccaggacagt tgggagaaat ggtgactgtt cttagtattg   420
```

```
atggaggtgg aattagaggg atcattccgg ctaccattct cgaatttctt gaaggacaac    480
ttcaggaaat ggacaataat gcagatgcaa gacttgcaga ttactttgat gtaattggag    540
gaacaagtac aggaggttta ttgactgcta tgataagtac tccaaatgaa acaatcgac     600 cctttgctgc tgccaaagaa attgtacctt tttacttcga acatggccct cagatttta    660 atcctagtgg tcaaatttta ggcccaaaat atgatggaaa atatcttatg caagttcttc    720
aagaaaaact tggagaaact cgtgtgcatc aagctttgac agaagttgtc atctcaagct    780
ttgacatcaa aacaaataag ccagtaatat tcactaagtc aaatttagca aactctccag    840
aattggatgc taagatgtat gacataagtt attccacagc agcagctcca acatattttc    900
ctccgcatta ctttgttact aatactagta atggagatga atatgagttc aatcttgttg    960
atggtgctgt tgctactgtt gctgatccgg cgttattatc cattagcgtt gcaacgagac   1020
ttgcacaaaa ggatccagca tttgcttcaa ttaggtcatt gaattacaaa aaaatgctgt   1080
tgctctcatt aggcactggc actacttcag agtttgataa ataatgag                1128
```

<210> SEQ ID NO 259
<211> LENGTH: 366
<212> TYPE: PRT
<213> ORGANISM: Artificial
<220> FEATURE:
<223> OTHER INFORMATION: Synthetic polypeptide

<400> SEQUENCE: 259

```
Thr Tyr Thr Ala Lys Glu Ala Ala Thr Trp Thr Ala Val His Trp Met
1               5                   10                  15

Leu Val Ile Gln Lys Met Thr Asp Ala Ala Ser Ser Tyr Met Thr Asp
            20                  25                  30

Tyr Tyr Leu Ser Thr Ala Phe Gln Ala Leu Asp Ser Lys Asn Asn Tyr
        35                  40                  45

Leu Arg Val Gln Glu Asn Ala Leu Thr Gly Thr Thr Thr Glu Met Asp
    50                  55                  60

Asp Ala Ser Glu Ala Asn Met Glu Leu Leu Val Gln Val Gly Glu Asn
65                  70                  75                  80

Leu Leu Lys Lys Pro Val Ser Glu Asp Asn Pro Glu Thr Tyr Glu Glu
                85                  90                  95

Ala Leu Lys Arg Phe Ala Lys Leu Leu Ser Asp Arg Lys Lys Leu Arg
            100                 105                 110

Ser Asn Lys Ala Ser Tyr Gly Pro Gly Gln Leu Gly Glu Met Val Thr
        115                 120                 125

Val Leu Ser Ile Asp Gly Gly Gly Ile Arg Gly Ile Ile Pro Ala Thr
    130                 135                 140

Ile Leu Glu Phe Leu Glu Gly Gln Leu Gln Glu Met Asp Asn Asn Ala
145                 150                 155                 160

Asp Ala Arg Leu Ala Asp Tyr Phe Asp Val Ile Gly Gly Thr Ser Thr
                165                 170                 175

Gly Gly Leu Leu Thr Ala Met Ile Ser Thr Pro Asn Glu Asn Asn Arg
            180                 185                 190

Pro Phe Ala Ala Ala Lys Glu Ile Val Pro Phe Tyr Phe Glu His Gly
        195                 200                 205

Pro Gln Ile Phe Asn Pro Ser Gly Gln Ile Leu Gly Pro Lys Tyr Asp
    210                 215                 220

Gly Lys Tyr Leu Met Gln Val Leu Gln Glu Lys Leu Gly Glu Thr Arg
225                 230                 235                 240
```

```
Val His Gln Ala Leu Thr Glu Val Val Ile Ser Ser Phe Asp Ile Lys
            245                 250                 255

Thr Asn Lys Pro Val Ile Phe Thr Lys Ser Asn Leu Ala Asn Ser Pro
        260                 265                 270

Glu Leu Asp Ala Lys Met Tyr Asp Ile Ser Tyr Ser Thr Ala Ala Ala
    275                 280                 285

Pro Thr Tyr Phe Pro Pro His Tyr Phe Val Thr Asn Thr Ser Asn Gly
290                 295                 300

Asp Glu Tyr Glu Phe Asn Leu Val Asp Gly Ala Val Ala Thr Val Ala
305                 310                 315                 320

Asp Pro Ala Leu Leu Ser Ile Ser Val Ala Thr Arg Leu Ala Gln Lys
            325                 330                 335

Asp Pro Ala Phe Ala Ser Ile Arg Ser Leu Asn Tyr Lys Lys Met Leu
        340                 345                 350

Leu Leu Ser Leu Gly Thr Gly Thr Thr Ser Glu Phe Asp Lys
    355                 360                 365

<210> SEQ ID NO 260
<211> LENGTH: 55
<212> TYPE: DNA
<213> ORGANISM: Artificial
<220> FEATURE:
<223> OTHER INFORMATION: Synthetic construct

<400> SEQUENCE: 260
ggagctcgag aaaagagagg ctgaagctaa tgcattaaca ggcacaacta ctgaa        55

<210> SEQ ID NO 261
<211> LENGTH: 39
<212> TYPE: DNA
<213> ORGANISM: Artificial
<220> FEATURE:
<223> OTHER INFORMATION: Synthetic construct

<400> SEQUENCE: 261
ggtctagagg aattctcatt attcttgaac cctgaggta                          39

<210> SEQ ID NO 262
<211> LENGTH: 1128
<212> TYPE: DNA
<213> ORGANISM: Artificial
<220> FEATURE:
<223> OTHER INFORMATION: Synthetic construct

<400> SEQUENCE: 262
tcgagaaaag agaggctgaa gctaatgcat aacaggcac aactactgaa atggatgatg    60
cttctgaggc taatatggaa ttattagtac aagttggtga aaacttattg aagaaaccag   120
tttccgaaga caatcctgaa acctatgagg aagctctaaa gaggtttgca aaattgctct   180
ctgataggaa gaaactccga gcaaacaaag cttcttatgg accaggacag ttgggagaaa   240
tggtgactgt tcttagtatt gatggaggtg gaattagagg gatcattccg gctaccattc   300
tcgaatttct tgaaggacaa cttcaggaaa tggacaataa tgcagatgca agacttgcag   360
attactttga tgtaattgga ggaacaagta caggaggttt attgactgct atgataagta   420
ctccaaatga aacaatcga ccctttgctg ctgccaaaga aattgtacct ttttacttcg    480
aacatggccc tcagattttt aatcctagtg gtcaaatttt aggcccaaaa tatgatggaa   540 atatcttat gcaagttctt caagaaaaac ttggagaaac tcgtgtgcat caagctttga   600
```

```
cagaagttgt catctcaagc tttgacatca aaacaaataa gccagtaata ttcactaagt   660
caaatttagc aaactctcca gaattggatg ctaagatgta tgacataagt tattccacag   720
cagcagctcc aacatatttt cctccgcatt actttgttac taatactagt aatggagatg   780
aatatgagtt caatcttgtt gatggtgctg ttgctactgt tgctgatccg gcgttattat   840
ccattagcgt tgcaacgaga cttgcacaaa aggatccagc atttgcttca attaggtcat   900
tgaattacaa aaaaatgctg ttgctctcat taggcactgg cactacttca gagtttgata   960
aaacatatac agcaaagag gcagctacct ggactgctgt acattggatg ttagttatac  1020
agaaaatgac tgatgcagca agttcttaca tgactgatta ttacctttct actgcttttc  1080
aagctcttga ttcaaaaaac aattacctca gggttcaaga ataatgag                1128
```

<210> SEQ ID NO 263
<211> LENGTH: 366
<212> TYPE: PRT
<213> ORGANISM: Artificial
<220> FEATURE:
<223> OTHER INFORMATION: Synthetic polypeptide

<400> SEQUENCE: 263

```
Asn Ala Leu Thr Gly Thr Thr Thr Glu Met Asp Asp Ala Ser Glu Ala
1               5                   10                  15

Asn Met Glu Leu Leu Val Gln Val Gly Glu Asn Leu Leu Lys Lys Pro
            20                  25                  30

Val Ser Glu Asp Asn Pro Glu Thr Tyr Glu Glu Ala Leu Lys Arg Phe
        35                  40                  45

Ala Lys Leu Leu Ser Asp Arg Lys Lys Leu Arg Ala Asn Lys Ala Ser
    50                  55                  60

Tyr Gly Pro Gly Gln Leu Gly Glu Met Val Thr Val Leu Ser Ile Asp
65                  70                  75                  80

Gly Gly Gly Ile Arg Gly Ile Ile Pro Ala Thr Ile Leu Glu Phe Leu
                85                  90                  95

Glu Gly Gln Leu Gln Glu Met Asp Asn Asn Ala Asp Ala Arg Leu Ala
            100                 105                 110

Asp Tyr Phe Asp Val Ile Gly Gly Thr Ser Thr Gly Gly Leu Leu Thr
        115                 120                 125

Ala Met Ile Ser Thr Pro Asn Glu Asn Asn Arg Pro Phe Ala Ala Ala
    130                 135                 140

Lys Glu Ile Val Pro Phe Tyr Phe Glu His Gly Pro Gln Ile Phe Asn
145                 150                 155                 160

Pro Ser Gly Gln Ile Leu Gly Pro Lys Tyr Asp Gly Lys Tyr Leu Met
                165                 170                 175

Gln Val Leu Gln Glu Lys Leu Gly Glu Thr Arg Val His Gln Ala Leu
            180                 185                 190

Thr Glu Val Val Ile Ser Ser Phe Asp Ile Lys Thr Asn Lys Pro Val
        195                 200                 205

Ile Phe Thr Lys Ser Asn Leu Ala Asn Ser Pro Glu Leu Asp Ala Lys
    210                 215                 220

Met Tyr Asp Ile Ser Tyr Ser Thr Ala Ala Pro Thr Tyr Phe Pro
225                 230                 235                 240

Pro His Tyr Phe Val Thr Asn Thr Ser Asn Gly Asp Glu Tyr Glu Phe
                245                 250                 255

Asn Leu Val Asp Gly Ala Val Ala Thr Val Ala Asp Pro Ala Leu Leu
            260                 265                 270
```

```
Ser Ile Ser Val Ala Thr Arg Leu Ala Gln Lys Asp Pro Ala Phe Ala
        275                 280                 285

Ser Ile Arg Ser Leu Asn Tyr Lys Lys Met Leu Leu Leu Ser Leu Gly
        290                 295                 300

Thr Gly Thr Thr Ser Glu Phe Asp Lys Thr Tyr Thr Ala Lys Glu Ala
305                 310                 315                 320

Ala Thr Trp Thr Ala Val His Trp Met Leu Val Ile Gln Lys Met Thr
                325                 330                 335

Asp Ala Ala Ser Ser Tyr Met Thr Asp Tyr Tyr Leu Ser Thr Ala Phe
                340                 345                 350

Gln Ala Leu Asp Ser Lys Asn Asn Tyr Leu Arg Val Gln Glu
        355                 360                 365

<210> SEQ ID NO 264
<211> LENGTH: 1158
<212> TYPE: DNA
<213> ORGANISM: Artificial
<220> FEATURE:
<223> OTHER INFORMATION: Synthetic construct

<400> SEQUENCE: 264
atggccacca ccaagagctt cctcatcctg atcttcatga tcctggccac caccagcagc      60
accttcgccc agctcggcga gatggtgacc gtgctctcca tcgacggcgg tggcatcagg     120
ggcatcatcc cggccaccat cctggagttc ctggagggcc aactccagga gatggacaac     180
aacgccgacg cccgcctggc cgactacttc gacgtgatcg gtggcaccag caccggcggt     240
ctcctgaccg ccatgatctc cactccgaac gagaacaacc gcccttcgc cgctgcgaag     300
gagatcgtcc cgttctactt cgaacacggc cctcagattt tcaaccctc gggtcaaatc     360
ctgggcccca gtacgacgg caagtacctt atgcaagtgc ttcaggagaa gctgggcgag     420
actaggtgc accaggcgct gaccgaggtc gtcatctcca gcttcgacat caagaccaac     480
aagccagtca tcttccacca gtccaacctg gccaacagcc cggagctgga cgctaagatg     540
tacgacatct cctactccac tgctgccgct cccacgtact ccctccgca ctacttcgtc     600
accaacacca gcaacggcga cgagtacgag ttcaaccttg ttgacggtgc ggtggctacg     660
gtggcggacc cggcgctcct gtccatcagc gtcgccacgc gcctggccca gaaggatcca     720
gccttcgcta gcattaggag cctcaactac aagaagatgc tgctgctcag cctgggcact     780
ggcacgacct ccgagttcga caagacctac actgccaagg aggccgctac ctggaccgcc     840
gtccattgga tgctggtcat ccagaagatg acggacgccg cttccagcta catgaccgac     900
tactacctct ccactgcgtt ccaggcgctt gactccaaga acaactacct ccgtgttcag     960
gagaatgccc tcactggcac cacgaccgag atggacgatg cctccgaggc caacatggag    1020
ctgctcgtcc aggtgggtga aacctcctg aagaagcccg tctccgaaga caatcccgag    1080
acctatgagg aagcgctcaa gcgctttgcc aagctgctct ctgataggaa gaaactccgc    1140
gctaacaagg ccagctac                                                 1158

<210> SEQ ID NO 265
<211> LENGTH: 386
<212> TYPE: PRT
<213> ORGANISM: Artificial
<220> FEATURE:
<223> OTHER INFORMATION: Synthetic polypeptide

<400> SEQUENCE: 265

Met Ala Thr Thr Lys Ser Phe Leu Ile Leu Ile Phe Met Ile Leu Ala
```

```
  1               5                   10                  15
Thr Thr Ser Ser Thr Phe Ala Gln Leu Gly Glu Met Val Thr Val Leu
                20                  25                  30

Ser Ile Asp Gly Gly Gly Ile Arg Gly Ile Ile Pro Ala Thr Ile Leu
                35                  40                  45

Glu Phe Leu Glu Gly Gln Leu Gln Glu Met Asp Asn Asn Ala Asp Ala
                50                  55                  60

Arg Leu Ala Asp Tyr Phe Asp Val Ile Gly Thr Ser Thr Gly Gly
65                  70                  75                  80

Leu Leu Thr Ala Met Ile Ser Thr Pro Asn Glu Asn Asn Arg Pro Phe
                    85                  90                  95

Ala Ala Ala Lys Glu Ile Val Pro Phe Tyr Phe Glu His Gly Pro Gln
                100                 105                 110

Ile Phe Asn Pro Ser Gly Gln Ile Leu Gly Pro Lys Tyr Asp Gly Lys
                115                 120                 125

Tyr Leu Met Gln Val Leu Gln Glu Lys Leu Gly Glu Thr Arg Val His
                130                 135                 140

Gln Ala Leu Thr Glu Val Val Ile Ser Ser Phe Asp Ile Lys Thr Asn
145                 150                 155                 160

Lys Pro Val Ile Phe Thr Lys Ser Asn Leu Ala Asn Ser Pro Glu Leu
                165                 170                 175

Asp Ala Lys Met Tyr Asp Ile Ser Tyr Ser Thr Ala Ala Pro Thr
                180                 185                 190

Tyr Phe Pro Pro His Tyr Phe Val Thr Asn Thr Ser Asn Gly Asp Glu
                195                 200                 205

Tyr Glu Phe Asn Leu Val Asp Gly Ala Val Ala Thr Val Ala Asp Pro
                210                 215                 220

Ala Leu Leu Ser Ile Ser Val Ala Thr Arg Leu Ala Gln Lys Asp Pro
225                 230                 235                 240

Ala Phe Ala Ser Ile Arg Ser Leu Asn Tyr Lys Lys Met Leu Leu Leu
                245                 250                 255

Ser Leu Gly Thr Gly Thr Thr Ser Glu Phe Asp Lys Thr Tyr Thr Ala
                260                 265                 270

Lys Glu Ala Ala Thr Trp Thr Ala Val His Trp Met Leu Val Ile Gln
                275                 280                 285

Lys Met Thr Asp Ala Ala Ser Ser Tyr Met Thr Asp Tyr Tyr Leu Ser
                290                 295                 300

Thr Ala Phe Gln Ala Leu Asp Ser Lys Asn Asn Tyr Leu Arg Val Gln
305                 310                 315                 320

Glu Asn Ala Leu Thr Gly Thr Thr Thr Glu Met Asp Asp Ala Ser Glu
                325                 330                 335

Ala Asn Met Glu Leu Leu Val Gln Val Gly Glu Asn Leu Leu Lys Lys
                340                 345                 350

Pro Val Ser Glu Asp Asn Pro Glu Thr Tyr Glu Glu Ala Leu Lys Arg
                355                 360                 365

Phe Ala Lys Leu Leu Ser Asp Arg Lys Lys Leu Arg Ala Asn Lys Ala
                370                 375                 380

Ser Tyr
385

<210> SEQ ID NO 266
<211> LENGTH: 55
<212> TYPE: DNA
<213> ORGANISM: Artificial
```

```
<220> FEATURE:
<223> OTHER INFORMATION: Synthetic construct

<400> SEQUENCE: 266
ggagctcgag aaaagagagg ctgaagctag cctcaactac aagaagatgc tgctg        55

<210> SEQ ID NO 267
<211> LENGTH: 42
<212> TYPE: DNA
<213> ORGANISM: Artificial
<220> FEATURE:
<223> OTHER INFORMATION: Synthetic construct

<400> SEQUENCE: 267
gccgagctgt cctggtccgt agctggcctt gttagcgcgg ag                     42

<210> SEQ ID NO 268
<211> LENGTH: 36
<212> TYPE: DNA
<213> ORGANISM: Artificial
<220> FEATURE:
<223> OTHER INFORMATION: Synthetic construct

<400> SEQUENCE: 268
gccagctacg gaccaggaca gctcggcgag atggtg                            36

<210> SEQ ID NO 269
<211> LENGTH: 39
<212> TYPE: DNA
<213> ORGANISM: Artificial
<220> FEATURE:
<223> OTHER INFORMATION: Synthetic construct

<400> SEQUENCE: 269
ggtctagagg aattctcatt acctaatgct agcgaaggc                         39

<210> SEQ ID NO 270
<211> LENGTH: 1167
<212> TYPE: DNA
<213> ORGANISM: Artificial
<220> FEATURE:
<223> OTHER INFORMATION: Synthetic construct

<400> SEQUENCE: 270
atggccacca ccaagagctt cctcatcctg atcttcatga tcctggccac caccagcagc    60
accttcgcca gcctcaacta caagaagatg ctgctgctca gcctgggcac tggcacgacc   120
tccgagttcg acaagaccta cactgccaag gaggccgcta cctggaccgc cgtccattgg   180
atgctggtca tccagaagat gacggacgcc gcttccagct acatgaccga ctactacctc   240
tccactgcgt tccaggcgct tgactccaag aacaactacc tccgtgttca ggagaatgcc   300
ctcactggca ccacgaccga gatggacgat gcctccgagg ccaacatgga gctgctcgtc   360
caggtgggtg agaacctcct gaagaagccc gtctccgaag acaatcccga gacctatgag   420
gaagcgctca gcgctttgc caagctgctc tctgatagga gaaaactccg cgctaacaag   480
gccagctacg gaccaggaca gctcggcgag atggtgaccg tgctctccat cgacggcggt   540
ggcatcaggg gcatcatccc ggccaccatc ctggagttcc tgagggcca actccaggag   600 atggacaaca acgccgacgc ccgcctggcc gactacttcg acgtgatcgg tgcaccagc    660 accggcggtc tcctgaccgc catgatctcc actccgaacg agaacaaccg ccccttcgcc   720
gctgcgaagg agatcgtccc gttctacttc gaacacggcc ctcagatttt caaccccctcg   780
```

-continued

```
ggtcaaatcc tgggccccaa gtacgacggc aagtacctta tgcaagtgct tcaggagaag    840
ctgggcgaga ctagggtgca ccaggcgctg accgaggtcg tcatctccag cttcgacatc    900
aagaccaaca agccagtcat cttcaccaag tccaacctgg ccaacagccc ggagctggac    960
gctaagatgt acgacatctc ctactccact gctgccgctc ccacgtactt ccctccgcac   1020
tacttcgtca ccaacaccag caacggcgac gagtacgagt tcaaccttgt tgacggtgcg   1080
gtggctacgg tggcggaccc ggcgctcctg tccatcagcg tcgccacgcg cctggcccag   1140
aaggatccag ccttcgctag cattagg                                       1167
```

<210> SEQ ID NO 271
<211> LENGTH: 389
<212> TYPE: PRT
<213> ORGANISM: Artificial
<220> FEATURE:
<223> OTHER INFORMATION: Synthetic polypeptide

<400> SEQUENCE: 271

```
Met Ala Thr Thr Lys Ser Phe Leu Ile Leu Ile Phe Met Ile Leu Ala
1               5                   10                  15

Thr Thr Ser Ser Thr Phe Ala Ser Leu Asn Tyr Lys Lys Met Leu Leu
            20                  25                  30

Leu Ser Leu Gly Thr Gly Thr Thr Ser Glu Phe Asp Lys Thr Tyr Thr
        35                  40                  45

Ala Lys Glu Ala Ala Thr Trp Thr Ala Val His Trp Met Leu Val Ile
    50                  55                  60

Gln Lys Met Thr Asp Ala Ala Ser Ser Tyr Met Thr Asp Tyr Tyr Leu
65                  70                  75                  80

Ser Thr Ala Phe Gln Ala Leu Asp Ser Lys Asn Asn Tyr Leu Arg Val
                85                  90                  95

Gln Glu Asn Ala Leu Thr Gly Thr Thr Thr Glu Met Asp Asp Ala Ser
            100                 105                 110

Glu Ala Asn Met Glu Leu Leu Val Gln Val Gly Glu Asn Leu Leu Lys
        115                 120                 125

Lys Pro Val Ser Glu Asp Asn Pro Glu Thr Tyr Glu Glu Ala Leu Lys
    130                 135                 140

Arg Phe Ala Lys Leu Leu Ser Asp Arg Lys Lys Leu Arg Ala Asn Lys
145                 150                 155                 160

Ala Ser Tyr Gly Pro Gly Gln Leu Gly Glu Met Val Thr Val Leu Ser
                165                 170                 175

Ile Asp Gly Gly Gly Ile Arg Gly Ile Ile Pro Ala Thr Ile Leu Glu
            180                 185                 190

Phe Leu Glu Gly Gln Leu Gln Glu Met Asp Asn Asn Ala Asp Ala Arg
        195                 200                 205

Leu Ala Asp Tyr Phe Asp Val Ile Gly Gly Thr Ser Thr Gly Gly Leu
    210                 215                 220

Leu Thr Ala Met Ile Ser Thr Pro Asn Glu Asn Asn Arg Pro Phe Ala
225                 230                 235                 240

Ala Ala Lys Glu Ile Val Pro Phe Tyr Phe Glu His Gly Pro Gln Ile
                245                 250                 255

Phe Asn Pro Ser Gly Gln Ile Leu Gly Pro Lys Tyr Asp Gly Lys Tyr
            260                 265                 270

Leu Met Gln Val Leu Gln Glu Lys Leu Gly Glu Thr Arg Val His Gln
        275                 280                 285

Ala Leu Thr Glu Val Val Ile Ser Ser Phe Asp Ile Lys Thr Asn Lys
```

-continued

```
                290                 295                 300
Pro Val Ile Phe Thr Lys Ser Asn Leu Ala Asn Ser Pro Glu Leu Asp
305                 310                 315                 320

Ala Lys Met Tyr Asp Ile Ser Tyr Ser Thr Ala Ala Pro Thr Tyr
                325                 330                 335

Phe Pro Pro His Tyr Phe Val Thr Asn Thr Ser Asn Gly Asp Glu Tyr
                340                 345                 350

Glu Phe Asn Leu Val Asp Gly Ala Val Ala Thr Val Ala Asp Pro Ala
            355                 360                 365

Leu Leu Ser Ile Ser Val Ala Thr Arg Leu Ala Gln Lys Asp Pro Ala
    370                 375                 380

Phe Ala Ser Ile Arg
385

<210> SEQ ID NO 272
<211> LENGTH: 55
<212> TYPE: DNA
<213> ORGANISM: Artificial
<220> FEATURE:
<223> OTHER INFORMATION: Synthetic construct

<400> SEQUENCE: 272
ggagctcgag aaaagagagg ctgaagctac tgccaaggag ccgctacct ggacc          55

<210> SEQ ID NO 273
<211> LENGTH: 39
<212> TYPE: DNA
<213> ORGANISM: Artificial
<220> FEATURE:
<223> OTHER INFORMATION: Synthetic construct

<400> SEQUENCE: 273
ggtctagagg aattctcatt acttgtcgaa ctcggaggt                           39

<210> SEQ ID NO 274
<211> LENGTH: 1167
<212> TYPE: DNA
<213> ORGANISM: Artificial
<220> FEATURE:
<223> OTHER INFORMATION: Synthetic construct

<400> SEQUENCE: 274
atggccacca ccaagagctt cctcatcctg atcttcatga tcctggccac caccagcagc    60
accttcgcca cctacactgc caaggaggcc gctacctgga ccgccgtcca ttggatgctg   120
gtcatccaga agatgacgga cgccgcttcc agctacatga ccgactacta cctctccact   180
gcgttccagg cgcttgactc caagaacaac tacctccgtg ttcaggagaa tgccctcact   240
ggcaccacga ccgagatgga cgatgcctcc gaggccaaca tggagctgct cgtccaggtg   300
ggtgagaacc tcctgaagaa gcccgtctcc gaagacaatc ccgagaccta tgaggaagcg   360
ctcaagcgct tgccaagct gctctctgat aggaagaaac tccgcgctaa caaggccagc   420 tacgaccag acagctcgg cgagatggtg accgtgctct ccatcgacgg cggtggcatc   480 agggcatca tcccggccac catcctggag ttcctggagg ccaactcca ggagatggac   540 aacaacgccg acgccgcct ggccgactac ttcgacgtga tcgtggcac cagcaccggc   600 ggtctcctga ccgccatgat ctccactccg aacgagaaca accgcccctt cgccgctgcg   660
aaggagatcg tccgttcta cttcgaacac ggccctcaga ttttcaaccc ctcgggtcaa   720
atcctgggcc ccaagtacga cggcaagtac cttatgcaag tgcttcagga gaagctgggc   780
```

```
gagactaggg tgcaccaggc gctgaccgag gtcgtcatct ccagcttcga catcaagacc    840
aacaagccag tcatcttcac caagtccaac ctggccaaca gcccggagct ggacgctaag    900
atgtacgaca tctcctactc cactgctgcc gctcccacgt acttccctcc gcactacttc    960
gtcaccaaca ccagcaacgg cgacgagtac gagttcaacc ttgttgacgg tgcggtggct   1020
acggtggcgg acccggcgct cctgtccatc agcgtcgcca cgcgcctggc ccagaaggat   1080
ccagccttcg ctagcattag gagcctcaac tacaagaaga tgctgctgct cagcctgggc   1140
actggcacga cctccgagtt cgacaag                                      1167
```

<210> SEQ ID NO 275
<211> LENGTH: 389
<212> TYPE: PRT
<213> ORGANISM: Artificial
<220> FEATURE:
<223> OTHER INFORMATION: Synthetic polypeptide

<400> SEQUENCE: 275

```
Met Ala Thr Thr Lys Ser Phe Leu Ile Leu Ile Phe Met Ile Leu Ala
1               5                   10                  15

Thr Thr Ser Ser Thr Phe Ala Thr Tyr Thr Ala Lys Glu Ala Ala Thr
            20                  25                  30

Trp Thr Ala Val His Trp Met Leu Val Ile Gln Lys Met Thr Asp Ala
        35                  40                  45

Ala Ser Ser Tyr Met Thr Asp Tyr Tyr Leu Ser Thr Ala Phe Gln Ala
    50                  55                  60

Leu Asp Ser Lys Asn Asn Tyr Leu Arg Val Gln Glu Asn Ala Leu Thr
65                  70                  75                  80

Gly Thr Thr Thr Glu Met Asp Asp Ala Ser Glu Ala Asn Met Glu Leu
                85                  90                  95

Leu Val Gln Val Gly Glu Asn Leu Leu Lys Lys Pro Val Ser Glu Asp
            100                 105                 110

Asn Pro Glu Thr Tyr Glu Glu Ala Leu Lys Arg Phe Ala Lys Leu Leu
        115                 120                 125

Ser Asp Arg Lys Lys Leu Arg Ala Asn Lys Ala Ser Tyr Gly Pro Gly
    130                 135                 140

Gln Leu Gly Glu Met Val Thr Val Leu Ser Ile Asp Gly Gly Gly Ile
145                 150                 155                 160

Arg Gly Ile Ile Pro Ala Thr Ile Leu Glu Phe Leu Glu Gly Gln Leu
                165                 170                 175

Gln Glu Met Asp Asn Asn Ala Asp Ala Arg Leu Ala Asp Tyr Phe Asp
            180                 185                 190

Val Ile Gly Gly Thr Ser Thr Gly Gly Leu Leu Thr Ala Met Ile Ser
        195                 200                 205

Thr Pro Asn Glu Asn Asn Arg Pro Phe Ala Ala Ala Lys Glu Ile Val
    210                 215                 220

Pro Phe Tyr Phe Glu His Gly Pro Gln Ile Phe Asn Pro Ser Gly Gln
225                 230                 235                 240

Ile Leu Gly Pro Lys Tyr Asp Gly Lys Tyr Leu Met Gln Val Leu Gln
                245                 250                 255

Glu Lys Leu Gly Glu Thr Arg Val His Gln Ala Leu Thr Glu Val Val
            260                 265                 270

Ile Ser Ser Phe Asp Ile Lys Thr Asn Lys Pro Val Ile Phe Thr Lys
        275                 280                 285
```

```
Ser Asn Leu Ala Asn Ser Pro Glu Leu Asp Ala Lys Met Tyr Asp Ile
    290                 295                 300

Ser Tyr Ser Thr Ala Ala Pro Thr Tyr Phe Pro Pro His Tyr Phe
305                 310                 315                 320

Val Thr Asn Thr Ser Asn Gly Asp Glu Tyr Glu Phe Asn Leu Val Asp
                325                 330                 335

Gly Ala Val Ala Thr Val Ala Asp Pro Ala Leu Leu Ser Ile Ser Val
            340                 345                 350

Ala Thr Arg Leu Ala Gln Lys Asp Pro Ala Phe Ala Ser Ile Arg Ser
            355                 360                 365

Leu Asn Tyr Lys Lys Met Leu Leu Ser Leu Gly Thr Gly Thr Thr
    370                 375                 380

Ser Glu Phe Asp Lys
385

<210> SEQ ID NO 276
<211> LENGTH: 7
<212> TYPE: PRT
<213> ORGANISM: Artificial
<220> FEATURE:
<223> OTHER INFORMATION: Synthetic polypeptide

<400> SEQUENCE: 276

Gly Gly Gly Ser Gly Gly Gly
1               5

<210> SEQ ID NO 277
<211> LENGTH: 3
<212> TYPE: PRT
<213> ORGANISM: Artificial
<220> FEATURE:
<223> OTHER INFORMATION: Synthetic polypeptide

<400> SEQUENCE: 277

Gly Pro Gly
1

<210> SEQ ID NO 278
<211> LENGTH: 386
<212> TYPE: PRT
<213> ORGANISM: Solanum tuberosum

<400> SEQUENCE: 278

Met Ala Thr Thr Lys Ser Phe Leu Ile Leu Phe Phe Met Ile Leu Ala
1               5                   10                  15

Thr Thr Ser Ser Thr Cys Ala Lys Leu Glu Glu Met Val Thr Val Leu
                20                  25                  30

Ser Ile Asp Gly Gly Ile Lys Gly Ile Pro Ala Ile Ile Leu
            35                  40                  45

Glu Phe Leu Glu Gly Gln Leu Gln Glu Val Asp Asn Asn Lys Asp Ala
    50                  55                  60

Arg Leu Ala Asp Tyr Phe Asp Val Ile Gly Gly Thr Ser Thr Gly Gly
65                  70                  75                  80

Leu Leu Thr Ala Met Ile Thr Thr Pro Asn Glu Asn Asn Arg Pro Phe
                85                  90                  95

Ala Ala Ala Lys Asp Ile Val Pro Phe Tyr Phe Glu His Gly Pro His
            100                 105                 110

Ile Phe Asn Tyr Ser Gly Ser Ile Ile Gly Pro Met Tyr Asp Gly Lys
            115                 120                 125
```

```
Tyr Leu Leu Gln Val Leu Gln Glu Lys Leu Gly Glu Thr Arg Val His
        130                 135                 140
Gln Ala Leu Thr Glu Val Ala Ile Ser Ser Phe Asp Ile Lys Thr Asn
145                 150                 155                 160
Lys Pro Val Ile Phe Thr Lys Ser Asn Leu Ala Lys Ser Pro Glu Leu
                165                 170                 175
Asp Ala Lys Met Tyr Asp Ile Cys Tyr Ser Thr Ala Ala Pro Ile
                180                 185                 190
Tyr Phe Pro Pro His Tyr Phe Ile Thr His Thr Ser Asn Gly Asp Ile
                195                 200                 205
Tyr Glu Phe Asn Leu Val Asp Gly Val Ala Thr Val Gly Asp Pro
    210                 215                 220
Ala Leu Leu Ser Leu Ser Val Ala Thr Arg Leu Ala Gln Glu Asp Pro
225                 230                 235                 240
Ala Phe Ser Ser Ile Lys Ser Leu Asp Tyr Lys Gln Met Leu Leu Leu
                245                 250                 255
Ser Leu Gly Thr Gly Thr Asn Ser Glu Phe Asp Lys Thr Tyr Thr Ala
                260                 265                 270
Gln Glu Ala Ala Lys Trp Gly Pro Leu Arg Trp Met Leu Ala Ile Gln
                275                 280                 285
Gln Met Thr Asn Ala Ala Ser Ser Tyr Met Thr Asp Tyr Tyr Ile Ser
    290                 295                 300
Thr Val Phe Gln Ala Arg His Ser Gln Asn Asn Tyr Leu Arg Val Gln
305                 310                 315                 320
Glu Asn Ala Leu Thr Gly Thr Thr Thr Glu Met Asp Asp Ala Ser Glu
                325                 330                 335
Ala Asn Met Glu Leu Leu Val Gln Val Gly Glu Thr Leu Leu Lys Lys
                340                 345                 350
Pro Val Ser Lys Asp Ser Pro Glu Thr Tyr Glu Glu Ala Leu Lys Arg
                355                 360                 365
Phe Ala Lys Leu Leu Ser Asp Arg Lys Lys Leu Arg Ala Asn Lys Ala
                370                 375                 380
Ser Tyr
385

<210> SEQ ID NO 279
<211> LENGTH: 386
<212> TYPE: PRT
<213> ORGANISM: Solanum tuberosum

<400> SEQUENCE: 279

Met Ala Thr Thr Lys Ser Val Leu Val Leu Phe Phe Met Ile Leu Ala
1               5                   10                  15
Thr Thr Ser Ser Thr Cys Ala Thr Leu Gly Glu Met Val Thr Val Leu
                20                  25                  30
Ser Ile Asp Gly Gly Ile Lys Gly Ile Pro Ala Thr Ile Leu
            35                  40                  45
Glu Phe Leu Glu Gly Gln Leu Gln Glu Val Asp Asn Asn Lys Asp Ala
    50                  55                  60
Arg Leu Ala Asp Tyr Phe Asp Val Ile Gly Thr Ser Thr Gly Gly
65                  70                  75                  80
Leu Leu Thr Ala Met Ile Thr Thr Pro Asn Glu Asn Asn Arg Pro Phe
                85                  90                  95
Ala Ala Ala Lys Asp Ile Val Pro Phe Tyr Phe Glu His Gly Pro His
                100                 105                 110
```

-continued

```
Ile Phe Asn Ser Ser Gly Ser Ile Phe Gly Pro Met Tyr Asp Gly Lys
            115                 120                 125

Tyr Phe Leu Gln Val Leu Gln Glu Lys Leu Gly Glu Thr Arg Val His
    130                 135                 140

Gln Ala Leu Thr Glu Val Ala Ile Ser Ser Phe Asp Ile Lys Thr Asn
145                 150                 155                 160

Lys Pro Val Ile Phe Thr Lys Ser Asn Leu Ala Lys Ser Pro Glu Leu
                165                 170                 175

Asp Ala Lys Met Asn Asp Ile Cys Tyr Ser Thr Ala Ala Pro Thr
            180                 185                 190

Tyr Phe Pro Pro His Tyr Phe Val Thr His Thr Ser Asn Gly Asp Lys
    195                 200                 205

Tyr Glu Phe Asn Leu Val Asp Gly Ala Val Ala Thr Val Gly Asp Pro
    210                 215                 220

Ala Leu Leu Ser Leu Ser Val Arg Thr Lys Leu Ala Gln Val Asp Pro
225                 230                 235                 240

Lys Phe Ala Ser Ile Lys Ser Leu Asn Tyr Asn Glu Met Leu Leu Leu
                245                 250                 255

Ser Leu Gly Thr Gly Thr Asn Ser Glu Phe Asp Lys Thr Tyr Thr Ala
            260                 265                 270

Glu Glu Ala Ala Lys Trp Gly Pro Leu Arg Trp Ile Leu Ala Ile Gln
            275                 280                 285

Gln Met Thr Asn Ala Ala Ser Ser Tyr Met Thr Asp Tyr Tyr Leu Ser
    290                 295                 300

Thr Val Phe Gln Ala Arg His Ser Gln Asn Asn Tyr Leu Arg Val Gln
305                 310                 315                 320

Glu Asn Ala Leu Thr Gly Thr Thr Thr Glu Met Asp Asp Ala Ser Glu
                325                 330                 335

Ala Asn Met Glu Leu Leu Val Gln Val Gly Glu Lys Leu Leu Lys Lys
            340                 345                 350

Pro Val Ser Lys Asp Ser Pro Glu Thr Tyr Glu Glu Ala Leu Lys Arg
    355                 360                 365

Phe Ala Lys Leu Leu Ser Asp Arg Lys Lys Leu Arg Ala Asn Lys Ala
    370                 375                 380

Ser Tyr
385

<210> SEQ ID NO 280
<211> LENGTH: 365
<212> TYPE: PRT
<213> ORGANISM: Solanum tuberosum

<400> SEQUENCE: 280

Met Ala Leu Glu Glu Met Val Ala Val Leu Ser Ile Asp Gly Gly Gly
1               5                   10                  15

Ile Lys Gly Ile Ile Pro Gly Thr Ile Leu Glu Phe Leu Glu Gly Gln
            20                  25                  30

Leu Gln Lys Met Asp Asn Asn Ala Asp Ala Arg Leu Ala Asp Tyr Phe
        35                  40                  45

Asp Val Ile Gly Gly Thr Ser Thr Gly Gly Leu Leu Thr Ala Met Ile
    50                  55                  60

Thr Thr Pro Asn Glu Asn Asn Arg Pro Phe Ala Ala Ala Asn Glu Ile
65                  70                  75                  80

Val Pro Phe Tyr Phe Glu His Gly Pro His Ile Phe Asn Ser Arg Tyr
```

```
                    85                  90                  95
Trp Pro Ile Phe Trp Pro Lys Tyr Asp Gly Lys Tyr Leu Met Gln Val
                100                 105                 110

Leu Gln Glu Lys Leu Gly Glu Thr Arg Val His Gln Ala Leu Thr Glu
            115                 120                 125

Val Ala Ile Ser Ser Phe Asp Ile Lys Thr Asn Lys Pro Val Ile Phe
        130                 135                 140

Thr Lys Ser Asn Leu Ala Lys Ser Pro Glu Leu Asp Ala Lys Thr Tyr
145                 150                 155                 160

Asp Ile Cys Tyr Ser Thr Ala Ala Pro Thr Tyr Phe Pro Pro His
                165                 170                 175

Tyr Phe Ala Thr Asn Thr Ile Asn Gly Asp Lys Tyr Glu Phe Asn Leu
                180                 185                 190

Val Asp Gly Ala Val Ala Thr Val Ala Asp Pro Ala Leu Leu Ser Val
            195                 200                 205

Ser Val Ala Thr Arg Arg Ala Gln Glu Asp Pro Ala Phe Ala Ser Ile
        210                 215                 220

Arg Ser Leu Asn Tyr Lys Lys Met Leu Leu Leu Ser Leu Gly Thr Gly
225                 230                 235                 240

Thr Thr Ser Glu Phe Asp Lys Thr His Thr Ala Glu Glu Thr Ala Lys
                245                 250                 255

Trp Gly Ala Leu Gln Trp Met Leu Val Ile Gln Gln Met Thr Glu Ala
                260                 265                 270

Ala Ser Ser Tyr Met Thr Asp Tyr Tyr Leu Ser Thr Val Phe Gln Asp
            275                 280                 285

Leu His Ser Gln Asn Asn Tyr Leu Arg Val Gln Glu Asn Ala Leu Thr
        290                 295                 300

Gly Thr Thr Thr Lys Ala Asp Asp Ala Ser Glu Ala Asn Met Glu Leu
305                 310                 315                 320

Leu Ala Gln Val Gly Glu Asn Leu Leu Lys Lys Pro Val Ser Lys Asp
                325                 330                 335

Asn Pro Glu Thr Tyr Glu Glu Ala Leu Lys Arg Phe Ala Lys Leu Leu
                340                 345                 350

Ser Asp Arg Lys Lys Leu Arg Ala Asn Lys Ala Ser Tyr
            355                 360                 365

<210> SEQ ID NO 281
<211> LENGTH: 364
<212> TYPE: PRT
<213> ORGANISM: Solanum tuberosum

<400> SEQUENCE: 281

Pro Trp Leu Glu Glu Met Val Thr Val Leu Ser Ile Asp Gly Gly Gly
1               5                   10                  15

Ile Lys Gly Ile Ile Pro Ala Ile Ile Leu Glu Phe Leu Glu Gly Gln
            20                  25                  30

Leu Gln Glu Val Asp Asn Asn Lys Asp Ala Arg Leu Ala Asp Tyr Phe
        35                  40                  45

Asp Val Ile Gly Gly Thr Ser Thr Gly Gly Leu Leu Thr Ala Met Ile
    50                  55                  60

Thr Thr Pro Asn Glu Asn Arg Pro Phe Ala Ala Lys Asp Ile
65                  70                  75                  80

Val Pro Phe Tyr Phe Glu His Gly Pro His Ile Phe Asn Tyr Ser Gly
                85                  90                  95
```

```
Ser Ile Leu Gly Pro Met Tyr Asp Gly Lys Tyr Leu Gln Val Leu
            100                 105                 110

Gln Glu Lys Leu Gly Glu Thr Arg Val His Gln Ala Leu Thr Glu Val
        115                 120                 125

Ala Ile Ser Ser Phe Asp Ile Lys Thr Asn Lys Pro Val Ile Phe Thr
    130                 135                 140

Lys Ser Asn Leu Ala Lys Ser Pro Glu Leu Asp Ala Lys Met Tyr Asp
145                 150                 155                 160

Ile Cys Tyr Ser Thr Ala Ala Pro Ile Tyr Phe Pro His His
                165                 170                 175

Phe Val Thr His Thr Ser Asn Gly Ala Arg Tyr Glu Phe Asn Leu Val
            180                 185                 190

Asp Gly Ala Val Ala Thr Val Gly Asp Pro Ala Leu Leu Ser Leu Ser
            195                 200                 205

Val Ala Thr Arg Leu Ala Gln Glu Asp Pro Ala Phe Ser Ser Ile Lys
        210                 215                 220

Ser Leu Asp Tyr Lys Gln Met Leu Leu Leu Ser Leu Gly Thr Gly Thr
225                 230                 235                 240

Asn Ser Glu Phe Asp Lys Thr Tyr Thr Ala Glu Ala Ala Lys Trp
                245                 250                 255

Gly Pro Leu Arg Trp Met Leu Ala Ile Gln Gln Met Thr Asn Ala Ala
            260                 265                 270

Ser Phe Tyr Met Thr Asp Tyr Tyr Ile Ser Thr Val Phe Gln Ala Arg
        275                 280                 285

His Ser Gln Asn Asn Tyr Leu Arg Val Gln Glu Asn Ala Leu Asn Gly
    290                 295                 300

Thr Thr Thr Glu Met Asp Asp Ala Ser Glu Ala Asn Met Glu Leu Leu
305                 310                 315                 320

Val Gln Val Gly Glu Thr Leu Leu Lys Lys Pro Val Ser Arg Asp Ser
                325                 330                 335

Pro Glu Thr Tyr Glu Glu Ala Leu Lys Arg Phe Ala Lys Leu Leu Ser
            340                 345                 350

Asp Arg Lys Lys Leu Arg Ala Asn Lys Ala Ser Tyr
        355                 360

<210> SEQ ID NO 282
<211> LENGTH: 386
<212> TYPE: PRT
<213> ORGANISM: Solanum tuberosum

<400> SEQUENCE: 282

Met Ala Thr Thr Lys Ser Phe Leu Ile Leu Phe Phe Met Ile Leu Ala
1               5                   10                  15

Thr Thr Ser Ser Thr Cys Ala Lys Leu Glu Glu Met Val Thr Val Leu
            20                  25                  30

Ser Ile Asp Gly Gly Ile Lys Gly Ile Pro Ala Ile Ile Leu
        35                  40                  45

Glu Phe Leu Glu Gly Gln Leu Gln Glu Val Asp Asn Asn Lys Asp Ala
    50                  55                  60

Arg Leu Ala Asp Tyr Phe Asp Val Ile Gly Thr Ser Thr Gly Gly
65                  70                  75                  80

Leu Leu Thr Ala Met Ile Thr Thr Pro Asn Glu Asn Asn Arg Pro Phe
                85                  90                  95

Ala Ala Ala Lys Asp Ile Val Pro Phe Tyr Phe Glu His Gly Pro His
            100                 105                 110
```

```
Ile Phe Asn Tyr Ser Gly Ser Ile Leu Gly Pro Met Tyr Asp Gly Lys
        115                 120                 125

Tyr Leu Leu Gln Val Leu Gln Glu Lys Leu Gly Glu Thr Arg Val His
    130                 135                 140

Gln Ala Leu Thr Glu Val Ala Ile Ser Ser Phe Asp Ile Lys Thr Asn
145                 150                 155                 160

Lys Pro Val Ile Phe Thr Lys Ser Asn Leu Ala Lys Ser Pro Glu Leu
                165                 170                 175

Asp Ala Lys Met Tyr Asp Ile Cys Tyr Ser Thr Ala Ala Pro Ile
            180                 185                 190

Tyr Phe Pro Pro His His Phe Val Thr His Thr Ser Asn Gly Ala Arg
        195                 200                 205

Tyr Glu Phe Asn Leu Val Asp Gly Ala Val Ala Thr Val Gly Asp Pro
        210                 215                 220

Ala Leu Leu Ser Leu Ser Val Ala Thr Arg Leu Ala Gln Glu Asp Pro
225                 230                 235                 240

Ala Phe Ser Ser Ile Lys Ser Leu Asp Tyr Lys Gln Met Leu Leu Leu
                245                 250                 255

Ser Leu Gly Thr Gly Thr Asn Ser Glu Phe Asp Lys Thr Tyr Thr Ala
            260                 265                 270

Glu Glu Ala Ala Lys Trp Gly Pro Leu Arg Trp Met Leu Ala Ile Gln
        275                 280                 285

Gln Met Thr Asn Ala Ala Ser Ser Tyr Met Thr Asp Tyr Tyr Ile Ser
        290                 295                 300

Thr Val Phe Gln Ala Arg His Ser Gln Asn Asn Tyr Leu Arg Val Gln
305                 310                 315                 320

Glu Asn Ala Leu Asn Gly Thr Thr Thr Glu Met Asp Ala Ser Glu
                325                 330                 335

Ala Asn Met Glu Leu Leu Val Gln Val Gly Ala Thr Leu Leu Lys Lys
            340                 345                 350

Pro Val Ser Lys Asp Ser Pro Glu Thr Tyr Glu Glu Ala Leu Lys Arg
        355                 360                 365

Phe Ala Lys Leu Leu Ser Asp Arg Lys Lys Leu Arg Ala Asn Lys Ala
        370                 375                 380

Ser Tyr
385

<210> SEQ ID NO 283
<211> LENGTH: 10
<212> TYPE: PRT
<213> ORGANISM: Artificial
<220> FEATURE:
<223> OTHER INFORMATION: Synthetic polypeptide

<400> SEQUENCE: 283

Ala Phe Phe Asp Lys Thr Tyr Thr Ala Lys
1               5                   10

<210> SEQ ID NO 284
<211> LENGTH: 10
<212> TYPE: PRT
<213> ORGANISM: Artificial
<220> FEATURE:
<223> OTHER INFORMATION: Synthetic polypeptide

<400> SEQUENCE: 284

Cys Ile Phe Asp Ser Thr Tyr Thr Ala Lys
```

-continued

<210> SEQ ID NO 285
<211> LENGTH: 1161
<212> TYPE: DNA
<213> ORGANISM: Solanum tuberosum

<400> SEQUENCE: 285

| | | | | | |
|---|---|---|---|---|---|
| atggcaacta | ctaaatcttt | tttaatttta | atatttatga | tattagcaac | tactagttca | 60 |
| acatttgctc | agttgggaga | atggtgact | gttcttagta | ttgatggagg | tggaattaga | 120 |
| gggatcattc | cggctaccat | tctcgaattt | cttgaaggac | aacttcagga | aatggacaat | 180 |
| aatgcagatg | caagacttgc | agattacttt | gatgtaattg | gaggaacaag | tacaggaggt | 240 |
| ttattgactg | ctatgataag | tactccaaat | gaaacaatc | gacccttgc | tgctgccaaa | 300 |
| gaaattgtac | cttttactt | cgaacatggc | cctcagattt | ttaatcctag | tggtcaaatt | 360 |
| ttaggcccaa | aatatgatgg | aaaatatctt | atgcaagttc | ttcaagaaaa | acttggagaa | 420 |
| actcgtgtgc | atcaagcttt | gacagaagtt | gtcatctcaa | gctttgacat | caaaacaaat | 480 |
| aagccagtaa | tattcactaa | gtcaaattta | gcaaactctc | cagaattgga | tgctaagatg | 540 |
| tatgacataa | gttattccac | agcagcagct | ccaacatatt | ttcctccgca | ttactttgtt | 600 |
| actaatacta | gtaatggaga | tgaatatgag | ttcaatcttg | ttgatggtgc | tgttgctact | 660 |
| gttgctgatc | cggcgttatt | atccattagc | gttgcaacga | gcttgcaca | aaaggatcca | 720 |
| gcatttgctt | caattaggtc | attgaattac | aaaaaaatgc | tgttgctctc | attaggcact | 780 |
| ggcactactt | cagagtttga | taaaacatat | acagcaaaag | aggcagctac | ctggactgct | 840 |
| gtacattgga | tgttagttat | acagaaaatg | actgatgcag | caagttctta | catgactgat | 900 |
| tattaccttt | ctactgcttt | tcaagctctt | gattcaaaaa | acaattacct | cagggttcaa | 960 |
| gaaaatgcat | taacaggcac | aactactgaa | atggatgatg | cttctgaggc | taatatggaa | 1020 |
| ttattagtac | aagttggtga | aaacttattg | aagaaaccag | tttccgaaga | caatcctgaa | 1080 |
| acctatgagg | aagctctaaa | gaggtttgca | aaattgctct | ctgataggaa | gaaactccga | 1140 |
| gcaaacaaag | cttcttatta | a | | | | 1161 |

<210> SEQ ID NO 286
<211> LENGTH: 386
<212> TYPE: PRT
<213> ORGANISM: Solanum tuberosum

<400> SEQUENCE: 286

Met Ala Thr Thr Lys Ser Phe Leu Ile Leu Ile Phe Met Ile Leu Ala
1               5                   10                  15

Thr Thr Ser Ser Thr Phe Ala Gln Leu Gly Glu Met Val Thr Val Leu
                20                  25                  30

Ser Ile Asp Gly Gly Gly Ile Arg Gly Ile Ile Pro Ala Thr Ile Leu
            35                  40                  45

Glu Phe Leu Glu Gly Gln Leu Gln Glu Met Asp Asn Asn Ala Asp Ala
        50                  55                  60

Arg Leu Ala Asp Tyr Phe Asp Val Ile Gly Gly Thr Ser Thr Gly Gly
65                  70                  75                  80

Leu Leu Thr Ala Met Ile Ser Thr Pro Asn Glu Asn Asn Arg Pro Phe
                85                  90                  95

Ala Ala Ala Lys Glu Ile Val Pro Phe Tyr Phe Glu His Gly Pro Gln
            100                 105                 110

```
Ile Phe Asn Pro Ser Gly Gln Ile Leu Gly Pro Lys Tyr Asp Gly Lys
        115                 120                 125

Tyr Leu Met Gln Val Leu Gln Glu Lys Leu Gly Glu Thr Arg Val His
    130                 135                 140

Gln Ala Leu Thr Glu Val Ile Ser Ser Phe Asp Ile Lys Thr Asn
145                 150                 155                 160

Lys Pro Val Ile Phe Thr Lys Ser Asn Leu Ala Asn Ser Pro Glu Leu
                165                 170                 175

Asp Ala Lys Met Tyr Asp Ile Ser Tyr Ser Thr Ala Ala Pro Thr
            180                 185                 190

Tyr Phe Pro Pro His Tyr Phe Val Thr Asn Thr Ser Asn Gly Asp Glu
        195                 200                 205

Tyr Glu Phe Asn Leu Val Asp Gly Ala Val Ala Thr Val Ala Asp Pro
    210                 215                 220

Ala Leu Leu Ser Ile Ser Val Ala Thr Arg Leu Ala Gln Lys Asp Pro
225                 230                 235                 240

Ala Phe Ala Ser Ile Arg Ser Leu Asn Tyr Lys Lys Met Leu Leu Leu
                245                 250                 255

Ser Leu Gly Thr Gly Thr Thr Ser Glu Phe Asp Lys Thr Tyr Thr Ala
            260                 265                 270

Lys Glu Ala Ala Thr Trp Thr Ala Val His Trp Met Leu Val Ile Gln
        275                 280                 285

Lys Met Thr Asp Ala Ala Ser Ser Tyr Met Thr Asp Tyr Tyr Leu Ser
        290                 295                 300

Thr Ala Phe Gln Ala Leu Asp Ser Lys Asn Asn Tyr Leu Arg Val Gln
305                 310                 315                 320

Glu Asn Ala Leu Thr Gly Thr Thr Glu Met Asp Asp Ala Ser Glu
                325                 330                 335

Ala Asn Met Glu Leu Leu Val Gln Val Gly Glu Asn Leu Leu Lys Lys
            340                 345                 350

Pro Val Ser Glu Asp Asn Pro Glu Thr Tyr Glu Glu Ala Leu Lys Arg
        355                 360                 365

Phe Ala Lys Leu Leu Ser Asp Arg Lys Lys Leu Arg Ala Asn Lys Ala
        370                 375                 380

Ser Tyr
385

<210> SEQ ID NO 287
<211> LENGTH: 408
<212> TYPE: PRT
<213> ORGANISM: Artificial
<220> FEATURE:
<223> OTHER INFORMATION: Synthetic polypeptide

<400> SEQUENCE: 287

Met Lys Ser Lys Met Ala Met Leu Leu Leu Phe Cys Val Leu Ser
1               5                   10                  15

Asn Gln Leu Val Ala Ala Phe Ser Thr Gln Ala Lys Ala Ser Lys Asp
            20                  25                  30

Gly Asn Leu Val Thr Val Leu Ala Ile Asp Gly Gly Ile Arg Gly
        35                  40                  45

Ile Ile Pro Gly Val Ile Lys Gln Leu Glu Ala Thr Leu Gln Arg
    50                  55                  60

Trp Asp Ser Ser Ala Arg Leu Ala Glu Tyr Phe Asp Val Val Ala Gly
65                  70                  75                  80
```

```
Thr Ser Thr Gly Gly Ile Ile Thr Ala Ile Leu Thr Ala Pro Asp Pro
                85                  90                  95

Gln Asn Lys Asp Arg Pro Leu Tyr Ala Ala Glu Glu Ile Ile Asp Phe
            100                 105                 110

Tyr Ile Glu His Gly Pro Ser Ile Phe Asn Lys Ser Thr Ala Cys Ser
        115                 120                 125

Leu Pro Gly Ile Phe Cys Pro Lys Tyr Asp Gly Lys Tyr Leu Gln Glu
    130                 135                 140

Ile Ile Ser Gln Lys Leu Asn Glu Thr Leu Leu Asp Gln Thr Thr Thr
145                 150                 155                 160

Asn Val Val Ile Pro Ser Phe Asp Ile Lys Leu Leu Arg Pro Thr Ile
                165                 170                 175

Phe Ser Thr Phe Lys Leu Glu Glu Val Pro Glu Leu Asn Val Lys Leu
            180                 185                 190

Ser Asp Val Cys Met Gly Thr Ser Ala Ala Pro Ile Val Phe Pro Pro
        195                 200                 205

Tyr Tyr Phe Lys His Gly Asp Thr Glu Phe Asn Leu Val Asp Gly Ala
    210                 215                 220

Ile Ile Ala Asp Ile Pro Ala Pro Val Ala Leu Ser Glu Val Leu Gln
225                 230                 235                 240

Gln Glu Lys Tyr Lys Asn Lys Glu Ile Leu Leu Ser Ile Gly Thr
                245                 250                 255

Gly Val Val Lys Pro Gly Glu Gly Tyr Ser Ala Asn Arg Thr Trp Thr
            260                 265                 270

Ile Phe Asp Trp Ser Ser Glu Thr Leu Ile Gly Leu Met Gly His Gly
        275                 280                 285

Thr Arg Ala Met Ser Asp Tyr Tyr Val Gly Ser His Phe Lys Ala Leu
    290                 295                 300

Gln Pro Gln Asn Asn Tyr Leu Arg Ile Gln Glu Tyr Asp Leu Asp Pro
305                 310                 315                 320

Ala Leu Glu Ser Ile Asp Asp Ala Ser Thr Glu Asn Met Glu Asn Leu
                325                 330                 335

Glu Lys Val Gly Gln Ser Leu Leu Asn Glu Pro Val Lys Arg Met Asn
            340                 345                 350

Leu Asn Thr Phe Val Val Glu Glu Thr Gly Glu Gly Thr Asn Ala Glu
        355                 360                 365

Ala Leu Asp Arg Leu Ala Gln Ile Leu Tyr Glu Glu Lys Ile Thr Arg
    370                 375                 380

Gly Leu Gly Lys Ile Ser Leu Glu Val Asp Asn Ile Asp Pro Tyr Thr
385                 390                 395                 400

Glu Arg Val Arg Lys Leu Leu Phe
                405

<210> SEQ ID NO 288
<211> LENGTH: 410
<212> TYPE: PRT
<213> ORGANISM: Zea mays

<400> SEQUENCE: 288

Met Gly Ser Ile Gly Arg Gly Thr Ala Asn Cys Ala Thr Val Pro Gln
1               5                   10                  15

Pro Pro Pro Ser Thr Gly Lys Leu Ile Thr Ile Leu Ser Ile Asp Gly
            20                  25                  30

Gly Gly Ile Arg Gly Leu Ile Pro Ala Thr Ile Ile Ala Tyr Leu Glu
        35                  40                  45
```

```
Ala Lys Leu Gln Glu Leu Asp Gly Pro Asp Ala Arg Ile Ala Asp Tyr
         50                  55                  60

Phe Asp Val Ile Ala Gly Thr Ser Thr Gly Ala Leu Leu Ala Ser Met
 65                  70                  75                  80

Leu Ala Ala Pro Asp Glu Asn Asn Arg Pro Leu Phe Ala Ala Lys Asp
                 85                  90                  95

Leu Thr Thr Phe Tyr Leu Glu Asn Gly Pro Lys Ile Phe Pro Gln Lys
                100                 105                 110

Lys Ala Gly Leu Leu Thr Pro Leu Arg Asn Leu Leu Gly Leu Val Arg
            115                 120                 125

Gly Pro Lys Tyr Asp Gly Val Phe Leu His Asp Lys Ile Lys Ser Leu
        130                 135                 140

Thr His Asp Val Arg Val Ala Asp Thr Val Thr Asn Val Ile Val Pro
145                 150                 155                 160

Ala Phe Asp Val Lys Tyr Leu Gln Pro Ile Ile Phe Ser Thr Tyr Glu
                165                 170                 175

Ala Lys Thr Asp Thr Leu Lys Asn Ala His Leu Ser Asp Ile Cys Ile
            180                 185                 190

Ser Thr Ser Ala Ala Pro Thr Tyr Phe Pro Ala His Phe Lys Thr
        195                 200                 205

Glu Ala Thr Asp Gly Arg Pro Pro Arg Glu Tyr His Leu Val Asp Gly
    210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
                245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
        275                 280                 285

Gln Trp Leu Tyr Asn Gly Gly Phe Thr Pro Ile Ile Asp Ile Phe Ser
    290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Asp Asp Thr Leu
                325                 330                 335

Thr Gly Asn Ala Ser Ser Val Asp Ile Ala Thr Lys Glu Asn Met Glu
            340                 345                 350

Ser Leu Ile Ser Ile Gly Gln Glu Leu Leu Lys Lys Pro Val Ala Arg
        355                 360                 365

Val Asn Ile Asp Thr Gly Val Tyr Glu Ser Cys Asp Gly Glu Gly Thr
    370                 375                 380

Asn Ala Gln Ser Leu Ala Asp Phe Ala Lys Gln Leu Ser Asp Glu Arg
385                 390                 395                 400

Lys Leu Arg Lys Ser Asn Leu Asn Ser Asn
                405                 410

<210> SEQ ID NO 289
<211> LENGTH: 508
<212> TYPE: PRT
<213> ORGANISM: Zea mays

<400> SEQUENCE: 289

Arg Pro Thr Arg Pro Arg His Pro Arg Asn Thr Gln Lys Arg Gly Ala
```

```
              1               5                   10                  15
            Leu Leu Val Gly Trp Ile Leu Phe Ser Leu Ala Ala Ser Pro Val Lys
                        20                  25                  30

Phe Gln Thr His Met Gly Ser Ile Gly Arg Gly Thr Ala Asn Cys Ala
                        35                  40                  45

Thr Val Pro Gln Pro Pro Ser Thr Gly Lys Leu Ile Thr Ile Leu
                        50                  55                  60

Ser Ile Asp Gly Gly Ile Arg Gly Leu Ile Pro Ala Thr Ile Ile
            65                      70                  75                  80

Ala Tyr Leu Glu Ala Lys Leu Gln Glu Leu Asp Gly Pro Asp Ala Arg
                        85                  90                  95

Ile Ala Asp Tyr Phe Asp Val Ile Ala Gly Thr Ser Thr Gly Ala Leu
                        100                 105                 110

Leu Ala Ser Met Leu Ala Ala Pro Asp Glu Asn Asn Arg Pro Leu Phe
                        115                 120                 125

Ala Ala Lys Asp Leu Thr Thr Phe Tyr Leu Glu Asn Gly Pro Lys Ile
                        130                 135                 140

Phe Pro Gln Lys Lys Ala Gly Leu Leu Thr Pro Leu Arg Asn Leu Leu
            145                     150                 155                 160

Gly Leu Val Arg Gly Pro Lys Tyr Asp Gly Val Phe Leu His Asp Lys
                        165                 170                 175

Ile Lys Ser Leu Thr His Asp Val Arg Val Ala Asp Thr Val Thr Asn
                        180                 185                 190

Val Ile Val Pro Ala Phe Asp Val Lys Tyr Leu Gln Pro Ile Ile Phe
                        195                 200                 205

Ser Thr Tyr Glu Ala Lys Thr Asp Ala Leu Lys Asn Ala His Leu Ser
                        210                 215                 220

Asp Ile Cys Ile Ser Thr Ser Ala Ala Pro Thr Tyr Phe Pro Ala His
            225                     230                 235                 240

Phe Phe Lys Thr Glu Ala Thr Asp Gly Arg Pro Pro Arg Glu Tyr His
                        245                 250                 255

Leu Val Asp Gly Gly Val Ala Ala Asn Asn Pro Thr Met Val Ala Met
                        260                 265                 270

Ser Met Leu Thr Lys Glu Val His Arg Arg Asn Pro Asn Phe Asn Ala
                        275                 280                 285

Gly Ser Pro Thr Glu Tyr Thr Asn Tyr Leu Ile Ile Ser Val Gly Thr
                        290                 295                 300

Gly Ser Ala Lys Gln Ala Glu Lys Tyr Thr Ala Glu Gln Cys Ala Lys
            305                     310                 315                 320

Trp Gly Leu Ile Gln Trp Leu Tyr Asn Gly Gly Phe Thr Pro Ile Ile
                        325                 330                 335

Asp Ile Phe Ser His Ala Ser Ser Asp Met Val Asp Ile His Ala Ser
                        340                 345                 350

Ile Leu Phe Gln Ala Leu His Cys Glu Lys Lys Tyr Leu Arg Ile Gln
                        355                 360                 365

Leu Tyr Tyr Ala Gly Tyr Phe Asp Trp Glu Arg Ile Val Arg Gly His
                        370                 375                 380

Arg His Gln Gly Glu His Gly Val Ser Asp Ile Asp Arg Pro Gly Ala
            385                     390                 395                 400

Ala Gln Glu Ala Ser Gly Glu Ser Glu His Arg His Arg Ala Val Arg
                        405                 410                 415

Val Leu Arg Arg Gly His Lys Cys Thr Val Ala Ser Leu Arg Gln Ala
                        420                 425                 430
```

```
Thr Leu Arg Ala Gln Ala Thr Gln Glu Gln Ser Gln Leu Gln Leu Ile
        435                 440                 445

Asn Thr Ser Leu Ser His Ser Met Cys Ser Phe Arg Arg Phe Thr Val
        450                 455                 460

Ser Tyr Phe Phe Asn Phe Asn Ser Val Cys Val Leu Cys Val Leu Cys
465                 470                 475                 480

Val Tyr Gln Thr Phe Lys Phe Asn Gln Lys Lys Lys Lys Lys Lys Lys
                485                 490                 495

Lys Lys Lys Lys Lys Lys Lys Lys Arg Ala Ala
            500                 505

<210> SEQ ID NO 290
<211> LENGTH: 410
<212> TYPE: PRT
<213> ORGANISM: Zea mays

<400> SEQUENCE: 290

Met Gly Ser Ile Gly Arg Gly Thr Ala Asn Cys Ala Thr Val Pro Gln
1               5                   10                  15

Pro Pro Pro Ser Thr Gly Lys Leu Ile Thr Ile Leu Ser Ile Asp Gly
                20                  25                  30

Gly Gly Ile Arg Gly Leu Ile Pro Ala Thr Ile Ala Tyr Leu Glu
            35                  40                  45

Ala Lys Leu Gln Glu Leu Asp Gly Pro Asp Ala Arg Ile Ala Asp Tyr
        50                  55                  60

Phe Asp Val Ile Ala Gly Thr Ser Thr Gly Ala Leu Leu Ala Ser Met
65                  70                  75                  80

Leu Ala Ala Pro Asp Glu Asn Asn Arg Pro Leu Phe Ala Ala Lys Asp
                85                  90                  95

Leu Thr Thr Phe Tyr Leu Glu Asn Gly Pro Lys Ile Phe Pro Gln Lys
                100                 105                 110

Lys Ala Gly Leu Leu Thr Pro Leu Arg Asn Leu Leu Gly Leu Val Arg
            115                 120                 125

Gly Pro Lys Tyr Asp Gly Val Phe Leu His Asp Lys Ile Lys Ser Leu
        130                 135                 140

Thr His Asp Val Arg Val Ala Asp Thr Val Thr Asn Val Ile Val Pro
145                 150                 155                 160

Ala Phe Asp Val Lys Ser Leu Gln Pro Ile Ile Phe Ser Thr Tyr Glu
                165                 170                 175

Ala Lys Thr Asp Thr Leu Lys Asn Ala His Leu Ser Asp Ile Cys Ile
            180                 185                 190

Ser Thr Ser Ala Ala Pro Thr Tyr Phe Pro Ala His Phe Phe Lys Thr
        195                 200                 205

Glu Ala Thr Asp Gly Arg Pro Pro Arg Glu Tyr His Leu Val Asp Gly
    210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
                245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
        275                 280                 285

Gln Trp Leu Tyr Asn Gly Gly Phe Thr Pro Ile Ile Asp Ile Phe Ser
```

```
                    290                 295                 300
His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Asp Asp Thr Leu
                325                 330                 335

Thr Gly Asn Ala Ser Val Asp Ile Ala Thr Lys Glu Asn Met Glu
                340                 345                 350

Ser Leu Ile Ser Ile Gly Gln Glu Leu Leu Asn Lys Pro Val Ala Arg
                355                 360                 365

Val Asn Ile Asp Thr Gly Leu Tyr Glu Ser Cys Glu Gly Gly Thr
                370                 375                 380

Asn Ala Gln Ser Leu Ala Asp Phe Ala Lys Gln Leu Ser Asp Glu Arg
385                 390                 395                 400

Lys Leu Arg Lys Ser Asn Leu Asn Ser Asn
                405                 410

<210> SEQ ID NO 291
<211> LENGTH: 410
<212> TYPE: PRT
<213> ORGANISM: Zea mays

<400> SEQUENCE: 291

Met Gly Ser Ile Gly Arg Gly Thr Ala Asn Cys Ala Thr Val Pro Gln
1               5                   10                  15

Pro Pro Pro Ser Thr Gly Lys Leu Ile Thr Ile Leu Ser Ile Asp Gly
                20                  25                  30

Gly Gly Ile Arg Gly Leu Ile Pro Ala Thr Ile Ile Ala Tyr Leu Glu
            35                  40                  45

Ala Lys Leu Gln Glu Leu Asp Gly Pro Asp Ala Arg Ile Ala Asp Tyr
        50                  55                  60

Phe Asp Val Ile Ala Gly Thr Ser Thr Gly Ala Leu Leu Ala Ser Met
65                  70                  75                  80

Leu Ala Ala Pro Asp Glu Asn Asn Arg Pro Leu Phe Ala Ala Lys Asp
                85                  90                  95

Leu Thr Thr Phe Tyr Leu Glu Asn Gly Pro Lys Ile Phe Pro Gln Lys
                100                 105                 110

Lys Ala Gly Leu Leu Thr Pro Leu Arg Asn Leu Gly Leu Val Arg
            115                 120                 125

Gly Pro Lys Tyr Asp Gly Val Phe Leu His Asp Lys Ile Lys Ser Leu
        130                 135                 140

Thr His Asp Val Arg Val Ala Asp Thr Val Thr Asn Val Ile Val Pro
145                 150                 155                 160

Ala Phe Asp Val Lys Tyr Leu Gln Pro Ile Ile Phe Ser Thr Tyr Glu
                165                 170                 175

Ala Lys Thr Asp Ala Leu Lys Asn Ala His Leu Ser Asp Ile Cys Ile
                180                 185                 190

Ser Thr Ser Ala Ala Pro Thr Tyr Phe Pro Ala His Phe Lys Thr
            195                 200                 205

Glu Ala Thr Asp Gly Arg Pro Pro Arg Glu Tyr His Leu Val Asp Gly
        210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
                245                 250                 255
```

-continued

```
Glu Tyr Thr Asn Tyr Leu Ile Ile Ser Val Gly Thr Gly Ser Ala Lys
                260                 265                 270

Gln Ala Glu Lys Tyr Thr Ala Glu Gln Cys Ala Lys Trp Gly Leu Ile
            275                 280                 285

Gln Trp Leu Tyr Asn Gly Gly Phe Thr Pro Ile Ile Asp Ile Phe Ser
290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Asp Asp Thr Leu
                325                 330                 335

Thr Gly Asn Ala Ser Ser Val Asp Ile Ala Thr Lys Glu Asn Met Glu
            340                 345                 350

Ser Leu Ile Ser Ile Gly Gln Glu Leu Leu Lys Lys Pro Val Ala Arg
        355                 360                 365

Val Asn Ile Asp Thr Gly Leu Tyr Glu Ser Cys Asp Gly Glu Gly Thr
    370                 375                 380

Asn Ala Gln Ser Leu Ala Asp Phe Ala Lys Gln Leu Ser Asp Glu Arg
385                 390                 395                 400

Lys Leu Arg Lys Ser Asn Leu Asn Ser Asn
                405                 410

<210> SEQ ID NO 292
<211> LENGTH: 410
<212> TYPE: PRT
<213> ORGANISM: Zea mays

<400> SEQUENCE: 292

Met Gly Ser Ile Gly Arg Gly Thr Ala Asn Cys Ala Thr Val Pro Gln
1               5                   10                  15

Pro Pro Pro Ser Thr Gly Lys Leu Ile Thr Ile Leu Ser Ile Asp Gly
            20                  25                  30

Gly Gly Ile Arg Gly Leu Ile Pro Ala Thr Ile Ile Ala Tyr Leu Glu
        35                  40                  45

Ala Lys Leu Gln Glu Leu Asp Gly Pro Asp Ala Arg Ile Ala Asp Tyr
    50                  55                  60

Phe Asp Val Ile Ala Gly Thr Ser Thr Gly Ala Leu Leu Ala Ser Met
65                  70                  75                  80

Leu Ala Ala Pro Asp Glu Asn Arg Pro Leu Phe Ala Ala Lys Asp
                85                  90                  95

Leu Thr Thr Phe Tyr Leu Glu Asn Gly Pro Lys Ile Phe Pro Gln Lys
                100                 105                 110

Lys Ala Gly Leu Leu Thr Pro Leu Arg Asn Leu Leu Gly Leu Val Arg
            115                 120                 125

Gly Pro Lys Tyr Asp Gly Val Phe Leu His Asp Lys Ile Lys Ser Leu
        130                 135                 140

Thr His Asp Val Arg Val Ala Asp Thr Val Thr Asn Val Ile Val Pro
145                 150                 155                 160

Ala Phe Asp Val Lys Ser Leu Gln Pro Ile Ile Phe Ser Thr Tyr Glu
                165                 170                 175

Ala Lys Thr Asp Thr Leu Lys Asn Ala His Leu Ser Asp Ile Cys Ile
                180                 185                 190

Ser Thr Ser Ala Ala Pro Thr Tyr Phe Pro Ala His Phe Lys Ile
            195                 200                 205

Glu Ala Thr Asp Gly Arg Pro Arg Glu Tyr His Leu Val Asp Gly
    210                 215                 220
```

-continued

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
            245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
        275                 280                 285

Gln Trp Leu Tyr Asn Gly Gly Phe Thr Pro Ile Ile Asp Ile Phe Ser
290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Asp Asp Thr Leu
            325                 330                 335

Thr Gly Asn Ala Ser Ser Val Asp Ile Ala Thr Lys Glu Asn Met Glu
            340                 345                 350

Ser Leu Ile Ser Ile Gly Gln Glu Leu Leu Asn Lys Pro Val Ala Arg
        355                 360                 365

Val Asn Ile Asp Thr Gly Leu Tyr Glu Ser Cys Glu Gly Glu Gly Thr
    370                 375                 380

Asn Ala Gln Ser Leu Ala Asp Phe Ala Lys Gln Leu Ser Asp Glu Arg
385                 390                 395                 400

Lys Leu Arg Lys Ser Asn Leu Asn Ser Asn
            405                 410

<210> SEQ ID NO 293
<211> LENGTH: 337
<212> TYPE: PRT
<213> ORGANISM: Zea mays

<400> SEQUENCE: 293

Met Gly Ser Ile Gly Arg Gly Thr Ala Asn Cys Ala Thr Val Pro Gln
1               5                   10                  15

Pro Pro Pro Ser Thr Gly Lys Leu Ile Thr Ile Leu Ser Ile Asp Gly
            20                  25                  30

Gly Gly Ile Arg Gly Leu Ile Pro Ala Thr Ile Ala Tyr Leu Glu
        35                  40                  45

Ala Lys Leu Gln Glu Leu Asp Gly Pro Asp Ala Arg Ile Ala Asp Tyr
    50                  55                  60

Phe Asp Val Ile Ala Gly Thr Ser Thr Gly Ala Leu Leu Ala Ser Met
65                  70                  75                  80

Leu Ala Ala Pro Asp Glu Asn Asn Arg Pro Leu Phe Ala Ala Lys Asp
                85                  90                  95

Leu Thr Thr Phe Tyr Leu Glu Asn Gly Pro Lys Ile Phe Pro Gln Lys
            100                 105                 110

Lys Ala Gly Leu Leu Thr Pro Leu Arg Asn Leu Leu Gly Leu Val Arg
        115                 120                 125

Gly Pro Lys Tyr Asp Gly Val Phe Leu His Asp Lys Ile Lys Ser Leu
    130                 135                 140

Thr His Asp Val Arg Val Ala Asp Thr Val Thr Asn Val Ile Val Pro
145                 150                 155                 160

Ala Phe Asp Val Lys Tyr Leu Gln Pro Ile Ile Phe Ser Thr Tyr Glu
                165                 170                 175

Ala Lys Thr Asp Ala Leu Lys Asn Ala His Leu Ser Asp Ile Cys Ile

-continued

```
                180                 185                 190
Ser Thr Ser Ala Ala Pro Thr Tyr Phe Pro Ala His Phe Phe Lys Thr
            195                 200                 205

Glu Ala Thr Asp Gly Arg Pro Pro Arg Glu Tyr His Leu Val Asp Gly
        210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
                245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
        275                 280                 285

Gln Trp Leu Tyr Asn Gly Gly Phe Thr Pro Ile Ile Asp Ile Phe Ser
    290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Leu Tyr Tyr Ala
                325                 330                 335

Gly

<210> SEQ ID NO 294
<211> LENGTH: 29
<212> TYPE: DNA
<213> ORGANISM: Artificial
<220> FEATURE:
<223> OTHER INFORMATION: Synthetic construct

<400> SEQUENCE: 294
gggccatggc gcagttggga gaaatggtg                                        29

<210> SEQ ID NO 295
<211> LENGTH: 37
<212> TYPE: DNA
<213> ORGANISM: Artificial
<220> FEATURE:
<223> OTHER INFORMATION: Synthetic construct

<400> SEQUENCE: 295
aacaaagctt cttattgagg tgcggccgct tgcatgc                               37
```

PREPARATION OF DEALLERGENIZED PROTEINS AND PERMUTEINS

CROSS REFERENCE TO RELATED APPLICATIONS

This application is a divisional of co-pending U.S. patent application Ser. No. 09/755,630 filed Jan. 5, 2001 now U.S. Pat. No. 6,639,054, which claims the benefit of U.S. Provisional Application Ser. No. 60/174,669 filed on Jan. 6, 2000.

FIELD OF THE INVENTION

The invention relates generally to non-naturally occurring novel proteins which have insecticidal properties, and more specifically to the design, preparation, and use of proteins that have been deallergenized while maintaining their insecticidal properties. Deallergenized patatin proteins include variants that have had allergenic sequences modified, and permuteins that have had their amino acid sequences rearranged at one or more breakpoints.

BACKGROUND OF THE INVENTION

Insecticidal Proteins

The use of natural products, including proteins, is a well known method of controlling many insect, fungal, viral, bacterial, and nematode pathogens. For example, endotoxins of *Bacillus thuringiensis* (*B.t.*) are used to control both lepidopteran and coleopteran insect pests. Genes producing these endotoxins have been introduced into and expressed by various plants, including cotton, tobacco, and tomato. There are, however, several economically important insect pests such as boll weevil (BWV), *Anthonomus grandis*, and corn rootworm (CRW), *Diabrotica* spp. that are not as susceptible to *B.t.* endotoxins as are insects such as lepidopterans. In addition, having other, different gene products for control of insects which are susceptible to *B.t.* endotoxins is important, if not vital, for resistance management.

It has been recently discovered that the major storage protein of potato tubers, patatins (Gaillaird, T., *Biochem. J.* 121: 379–390, 1971; Racusen, D., *Can. J. Bot.*, 62: 1640–1644, 1984; Andrews, D. L., et al., *Biochem. J.*, 252: 199–206, 1988), will control various insects, including western rootworm (WCRW, *Diabrotica virigifera*), southern corn rootworm (SCRW, *Diabrotica undecimpunctata*), and boll weevil (BWV, *Anthonomus grandis*) (U.S. Pat. No. 5,743,477). Patatins are lethal to some larvae and will stunt the growth of survivors so that maturation is prevented or severely delayed, resulting in no reproduction. These proteins, have nonspecific lipid acyl hydrolase activity and studies have shown that the enzyme activity is essential for its insecticidal activity (Strickland, J. A., et al., *Plant Physiol.*, 109: 667–674, 1995; U.S. Pat. No. 5,743,477). Patatins can be applied directly to the plants or introduced in other ways well known in the art, such as through the application of plant-colonizing microorganisms, which have been transformed to produce the enzymes, or by the plants themselves after similar transformation.

In potato, the patatins are found predominantly in tubers, but also at much lower levels in other plant organs (Hofgen, R. and Willmitzer, L., *Plant Science*, 66: 221–230, 1990). Genes that encode patatins have been previously isolated by Mignery, G. A., et al. (*Nucleic Acids Research*, 12: 7987–8000, 1984; Mignery, G. A., et al., *Gene*, 62: 27–44, 1988; Stiekema, et al., *Plant Mol. Biol.*, 11: 255–269, 1988) and others. Patatins are found in other plants, particularly solanaceous species (Ganal, et al., *Mol. Gen. Genetics*, 225: 501–509, 1991; Vancanneyt, et al., *Plant Cell*, 1: 533–540, 1989) and recently *Zea mays* (WO 96/37615). Rosahl, et al. (*EMBO J.*, 6: 1155–1159, 1987) transferred it to tobacco plants, and observed expression of patatin, demonstrating that the patatin genes can be heterologously expressed by plants.

Patatin is an attractive for use in planta as an insect control agent, but unfortunately a small segment of the population displays allergic reactions to patatin proteins, and in particular to potato patatin, as described below.

Food Allergens

There are a variety of proteins that cause allergic reactions. Proteins that have been identified as causing an allergic reaction in hypersensitive patients occur in many plant and animal derived foods, pollens, fungal spores, insect venoms, insect feces, and animal dander and urine (King, H. C., *Ear Nose Throat J.*, 73(4): 237–241, 1994; Astwood, J. D., et al., *Clin. Exp. Allergy*, 25: 66–72, 1995; Astwood, J. D. and Fuchs R. L., *Monographs in allergy Vol. 32: Highlights in food allergy*, pp. 105–120, 1996; Metcalfe, D. D., et al., *Critical Reviews in Food Science and Nutrition*, 36S: 165–186, 1996). The offending proteins of many major sources of allergens have been characterized by clinical and molecular methods. The functions of allergenic proteins in vivo are diverse, ranging from enzymes to regulators of the cell cytoskeleton.

To understand the molecular basis of allergic disease, the important IgE binding epitopes of many allergen proteins have been mapped (Elsayed, S. and Apold, J., *Allergy* 38(7): 449–459, 1983; Elsayed, S. et al., *Scand J. Clin. Lab. Invest. Suppl.* 204: 17–31 1991; Zhang, L., et al., *Mol. Immunol.* 29(11): 1383–1389, 1992). The optimal peptide length for IgE binding has been reported to be between 8 and 12 amino acids. Conservation of epitope sequences is observed in homologous allergens of disparate species (Astwood, J. D., et al., *Clin. Exp. Allergy*, 25: 66–72, 1995). Indeed, conservative substitutions introduced by site-directed mutagenesis reduce IgE binding of known epitopes when presented as peptides.

Food allergy occurs in 2–6% of the population. Eight foods or food groups (milk, eggs, fish, crustacea, wheat, peanuts, soybeans, and tree nuts) account for 90% of allergies to foods. Nevertheless, over 160 different foods have been reported to cause adverse reactions, including potato (Hefle, S., et al., *Crit. Rev. in Food Sci. Nutr.*, 36S: 69–90, 1996).

Mode of Action of Allergens

Regardless of the identity of the allergen, it is theorized that the underlying mechanism of allergen response is the same. Immediate hypersensitivity (or anaphylactic response) is a form of allergic reaction which develops very quickly, i.e., within seconds or minutes of exposure of the patient to the causative allergen, and is mediated by B lymphocyte IgE antibody produciton. Allergic patients exhibit elevated levels of IgE, mediating hypersensitivity by priming mast cells which are abundant in the skin, lymphoid organs, in the membranes of the eye, nose and mouth, and in the respiratory tree and intestines. The IgE in allergy-suffering patients becomes bound to the IgE receptors of mast cells. When this bound IgE is subsequently contacted by the appropriate allergen, the mast cell is caused to degranulate and release various substances such as histamine into the surrounding tissue (Church et al. In: Kay, A. B. ed., *Allergy and Allergic Diseases*, Oxford, Blackwell Science, pp. 149–197, 1997).

It is the release of these substances which is responsible for the clinical symptoms typical of immediate hypersensitivity, namely contraction of smooth muscle in the airways or in the intestine, the dilation of small blood vessels, and the increase in their permeability to water and plasma proteins, the secretion of thick sticky mucus, and (in the skin) the stimulation of nerve endings that result in itching or pain. Immediate hypersensitivity is, at best, a nuisance to the suffer; at worst it can present very serious problems and can in rare cases even result in death.

Allergic Reactions to Potato

Food allergy to potato is considered rare in the general population (Castells, M. C., et al., *Allergy Clin. Immunol.*, 8: 1110–1114, 1986; Hannuksela, M., et al., *Contact Dermatitis*, 3: 79–84, 1977; Golbert, T. M., et al., *Journal of Allergy*, 44: 96–107, 1969). Approximately 200 individuals have participated in published clinical accounts of potato allergy (Hefle, S. et al., *Critical Reviews in Food Science and Nutrition*, 36S: 69–90, 1996). A number of IgE binding proteins have been identified in potato tuber extracts (see Table 1), however the amino acid sequence and function of these proteins has not been determined (Wahl, R., et al., *Intl. Arch. Allergy Appl. Immunol.*, 92: 168–174, 1990).

TABLE 1

Studies of potato tuber IgE-binding proteins (allergens)

| Study | Protein Characteristics |
|---|---|
| (Castells, M. C. et al. J. Allergy Clin. Immunol. 78, 1110–1114, 1986) | Unknown 14 to 40 kDa |
| (Wahl, R. et al. Int. Arch. Allergy Appl. Immunol. 92: 168–174, 1990) | Unknown 42/43 kDa |
| | Unknown 65 kDa |
| | Unknown 26 kDa |
| | Unknown 20 kDa |
| | Unknown 14 kDa |
| | Unknown <14 kDa (~5 kDa) |
| (Ebner, C. et al. in: Wuthrich, B. & Ortolani, C. (eds.), Highlights in food allergy. Monographs in Allergy, Volume 32 Basil, Karger, pp. 73–77, 1996) | Unknown 42/43 kDa |
| | Unknown 23 kDa |
| | Unknown ~16 kDa |
| | Unknown <14 kDa (~5 kDa) |

Improved Safety from the use of Hypoallergenic Proteins

Patatin has been identified as an allergenic protein (Seppala, U. et al., *J. Allergy Clin. Immunol.* 103:165–171, 1999). Accordingly, potato allergic subjects may not be able to safely consume products containing unmodified patatin protein, such as crops to which foliar applications of patatins have been applied, or crops which have been engineered to express patatin. In addition, proliferation of food allergens in the food supply is considered hazardous (Metcalfe, D. D., et al., *Critical Reviews and Food Science and Nutrition*, 36S: 165–186, 1996). There are additional concerns regarding the use of potentially allergenic food proteins where workers might be exposed to airborne particulates, initiating a new allergic response (Moneret-Vautrin, D. A., et al., *Rev. Med. Interne.*, 17(7): 551–557, 1996).

Permuteins

Novel proteins generated by the method of sequence transposition resembles that of naturally occurring pairs of proteins that are related by linear reorganization of their amino acid sequences (Cunningham, et al. *Proc. Natl. Sci., U.S.A.*, 76: 3218–3222, 1979; Teather, et al., *J. Bacteriol.*, 172: 3837–3841, 1990; Schimming, et al., *Eur. J. Biochem.*, 204: 13–19, 1992; Yamiuchi, et al., *FEBS Lett.*, 260: 127–130, 1991; MacGregor, et al., *FEBS Lett.*, 378: 263–266, 1996). The first in vitro application of sequence rearrangement to proteins was described by Goldenberg and Creighton (Goldenberg and Creighton, *J. Mol. Biol.*, 165: 407–413, 1983). A new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion or sequence (linker), to an amino acid that is at or near the original N-terminus, and the new sequence continues with the same sequence as the original until it reaches a point that is at or near the amino acid that was N-terminal to the breakpoint site of the original sequence, this residue forming the new C-terminus of the chain. This approach has been applied to proteins which range in size from 58 to 462 amino acids and represent a broad range of structural classes (Goldenberg and Creighton, *J. Mol. Biol.*, 165: 407–413, 1983; Li and Coffino, *Mol. Cell. Biol.*, 13: 2377–2383, 1993; Zhang, et al., *Nature Struct. Biol.*, 1: 434–438, 1995; Buchwalder, et al., *Biochemistry*, 31: 1621–1630, 1994; Protasova, et al., *Prot. Eng.*, 7: 1373–1377, 1995; Mullins, et al., *J. Am. Chem. Soc.*, 116: 5529–5533, 1994; Garrett, et al., *Protein Science*, 5: 204–211, 1996; Hahn, et al., *Proc. Natl. Acad. Sci. USA.*, 91: 10417–10421, 1994; Yang and Schachman, *Proc. Natl. Acad. Sci. U.S.A.*, 90: 11980–11984, 1993; Luger, et al., *Science*, 243: 206–210, 1989; Luger, et al., *Prot. Eng.*, 3: 249–258, 1990; Lin, et al., *Protein Science*, 4: 159–166, 1995; Vignais, et al., *Protein Science*, 4: 994–1000, 1995; Ritco-Vonsovici, et al., *Biochemistry*, 34: 16543–16551, 1995; Horlick, et al., *Protein Eng.*, 5: 427–431, 1992; Kreitman, et al., *Cytokine*, 7: 311–318, 1995; Viguera, et al., *Mol. Biol.*, 247: 670–681, 1995; Koebnik and Kramer, *J. Mol. Biol.*, 250: 617–626, 1995; Kreitman, et al., *Proc. Natl. Acad. Sci.*, 91: 6889–6893, 1994).

There exists a need for the development of plant expressible insecticidal proteins which possess minimal or no allergenic properties.

SUMMARY OF THE INVENTION

Novel protein sequences, and nucleic acid sequences encoding them are disclosed. The proteins maintain desirable enzymatic and insecticidal properties while displaying reduced or eliminated allergenicity.

Allergenic epitopes are identified by scanning overlapping peptide sequences with an immunoreactivity assay. Alanine scanning and 'rational substitution' is performed on identified peptide sequences to determine specific amino acids which contribute to antibody binding, and presumably, to the allergenic properties of the whole protein. Individual mutations are introduced into the whole protein sequence by methods such as site directed mutagenesis of the encoding nucleic acid sequence to delete or modify the allergenic sequences.

Glycosylation target residues are identified within amino acid sequences of proteins which have demonstrated allergy eliciting properties. Glycosylation target amino acid residues are rationally substutited with other amino acid residues to eliminate glycosylation and to provide a variant deglycosylated protein. The variant protein may then exhibit reduced allergen eliciting properties and may also exhibit reduced binding to IgE within serum of patients observed to be allergic to said glycosylated protein.

Permuteins of the deallergenized protein sequences can be constructed to further reduce or eliminate allergic reactions.

The encoding nucleic acid sequence is modified to produce a non-naturally occurring protein having a linear amino acid sequence different from the naturally occurring protein sequence, while maintaining enzymatic and insecticidal properties. The permutein is preferably produced in plant cells, and more preferably produced at a concentration which is toxic to insects ingesting the plant cells.

Methods for reducing, eliminating, or decreasing allergen eliciting properties of a protein are specifically contemplated herein. Such methods comprise steps including identifying one or more patients exhibiting an allergic sensitivity to an allergen eliciting protein and obtaining a sample of serum from the patient; exposing the patient serum to a first set of synthetic overlapping peptides which represent the allergen eliciting protein in order to identify such peptides which exhibit epitopes which bind to IgE present within the allergic patients' serum and wherein the IgE present in the serum has a specific affinity for the said allergen eliciting protein; producing a second set of peptides which are variant peptides based on the first set of peptides which were identified to bind specifically to IgE present in patient serum, wherein the second set variant peptides exhibit alanine scanning or rational scanning amino acid substitutions which exhibit reduced, decreased, or eliminated IgE binding when compared to the first set non-variant peptides, and wherein such substitutions which reduce, eliminate or decrease IgE binding are identified as result effective substitutions; and modifying the amino acid sequence of the allergen eliciting protein to contain one or more of said result effective substitutions, wherein the modified protein is a variant of the allergen eliciting protein which lacks allergen eliciting protein or exhibits reduced allergen eliciting properties, and wherein the variant of the allergen eliciting protein comprising one or more result effective substitutions exhibits reduced, decreased, or totally eliminated binding of IgE present within said patients' serum.

The novel proteins can be used in controlling insects, as nutritional supplements, in immunotherapy protocols, and in other potential applications. Transgenic plant cells and plants containing the encoding nucleic acid sequence can be particularly beneficial in the control of insects, and as a nutritional/immunotherapy material.

DESCRIPTION OF THE FIGURES

The following figures form part of the present specification and are included to further demonstrate certain aspects of the present invention. The invention can be better understood by reference to one or more of these drawings in combination with the detailed description of specific embodiments presented herein.

FIG. 1 illustrates the alignment of potato patatin PatA (acyl lipid hydrolase) with patatin (acyl lipid hydrolase) homologs and related amino acid sequences, the homologs and related sequences being from both dicot and monocot plant species.

DESCRIPTION OF THE SEQUENCE LISTINGS

Figure 2:
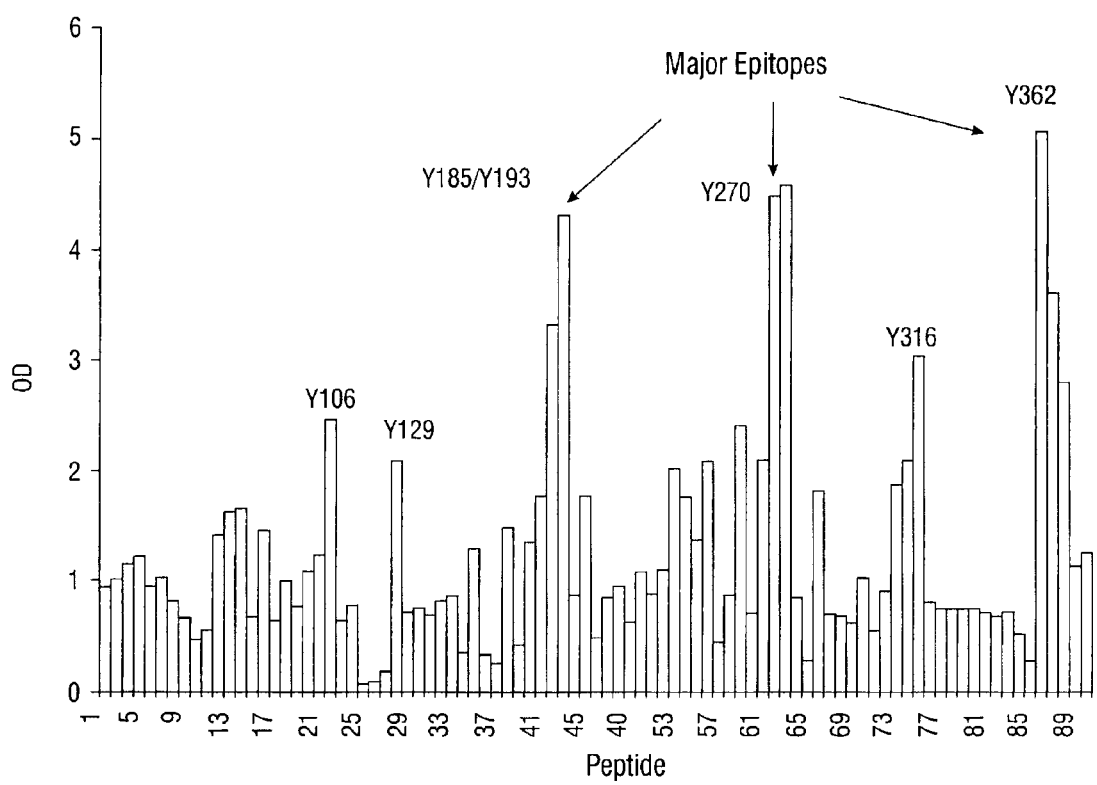
FIG. 2 illustrates IgE binding to overlapping peptide sequences.

The following description of the sequence listing forms part of the present specification and is included to further demonstrate certain aspects of the present invention. The invention can be better understood by reference to one or more of these sequences in combination with the detailed description of specific embodiments presented herein.

| | |
|---|---|
| SEQ ID NO: 1 | DNA sequence encoding a patatin (acyl lipid hydrolase) protein |
| SEQ ID NO: 2 | potato patatin protein sequence |
| SEQ ID NO: 3 | thermal amplification primer |
| SEQ ID NO: 4 | thermal amplification primer |
| SEQ ID NO: 5 | thermal amplification product |
| SEQ ID NO: 6 | Pre-cleavage patatin protein produced in *Pichia pastoris* |
| SEQ ID NO: 7 | Post-cleavage patatin protein produced in *Pichia pastoris* |
| SEQ ID NO: 8 | Y106F mutagenic primer |
| SEQ ID NO: 9 | Y129F mutagenic primer |
| SEQ ID NO: 10 | Y185F mutagenic primer |
| SEQ ID NO: 11 | Y193F mutagenic primer |
| SEQ ID NO: 12 | Y185F and Y193F mutagenic primer |
| SEQ ID NO: 13 | Y270F mutagenic primer |
| SEQ ID NO: 14 | Y316F mutagenic primer |
| SEQ ID NO: 15 | Y362F mutagenic primer |
| SEQ ID NO: 16–104 | Peptide scan sequences of a patatin protein |
| SEQ ID NO: 105–241 | Alanine and rational scan sequences of selected patatin peptides |
| SEQ ID NO: 242 | thermal amplification primer 27 |
| SEQ ID NO: 243 | thermal amplification primer 48 |
| SEQ ID NO: 244 | thermal amplification primer 47 |
| SEQ ID NO: 245 | thermal amplification primer 36 |
| SEQ ID NO: 246 | pMON37402 sequence encoding permutein protein |
| SEQ ID NO: 247 | Permutein protein encoded from pMON37402 sequence |
| SEQ ID NO: 248 | thermal amplification primer 58 |
| SEQ ID NO: 249 | thermal amplification primer 59 |
| SEQ ID NO: 250 | pMON37405 sequence encoding permutein protein |
| SEQ ID NO: 251 | Permutein protein encoded by pMON37405 sequence |
| SEQ ID NO: 252 | thermal amplification primer 60 |
| SEQ ID NO: 253 | thermal amplification primer 61 |
| SEQ ID NO: 254 | pMON37406 sequence encoding permutein protein |
| SEQ ID NO: 255 | Permutein protein encoded by pMON37406 sequence |
| SEQ ID NO: 256 | thermal amplification primer 62 |
| SEQ ID NO: 257 | thermal amplification primer 63 |
| SEQ ID NO: 258 | pMON37407 sequence encoding permutein protein |
| SEQ ID NO: 259 | Permutein protein encoded by pMON37407 sequence |
| SEQ ID NO: 260 | thermal amplification primer 60 |
| SEQ ID NO: 261 | thermal amplification primer 65 |
| SEQ ID NO: 262 | pMON37408 sequence encoding permutein protein |
| SEQ ID NO: 263 | Permutein protein encoded by pMON37408 sequence |
| SEQ ID NO: 264 | pMON40701 sequence encoding permutein protein |
| SEQ ID NO: 265 | Permutein protein encoded by pMON40701 sequence |
| SEQ ID NO: 266 | thermal amplification primer Syn1 |
| SEQ ID NO: 267 | thermal amplification primer Syn2 |
| SEQ ID NO: 268 | thermal amplification primer Syn3 |
| SEQ ID NO: 269 | thermal amplification primer Syn4 |
| SEQ ID NO: 270 | pMON40703 sequence encoding permutein protein |
| SEQ ID NO: 271 | Permutein protein encoded by pMON40703 sequence |
| SEQ ID NO: 272 | thermal amplification primer Syn10 |
| SEQ ID NO: 273 | thermal amplification primer Syn11 |
| SEQ ID NO: 274 | pMON40705 sequence encoding permutein protein |
| SEQ ID NO: 275 | Permutein protein encoded by pMON40705 sequence |
| SEQ ID NO: 276–277 | Permutein linker sequences |
| SEQ ID NO: 278 | Patatin isozyme PatA+ (including signal peptide) |
| SEQ ID NO: 279 | Patatin isozyme PatB+ (including signal peptide) |

-continued

| | |
|---|---|
| SEQ ID NO: 280 | Patatin isozyme PatFm (mature protein lacking signal peptide) |
| SEQ ID NO: 281 | Patatin isozyme PatIm (mature protein lacking signal peptide) |
| SEQ ID NO: 282 | Patatin isozyme PatL+ (including signal peptide) |
| SEQ ID NO: 283 | Rational substitution peptide |
| SEQ ID NO: 284 | Corn homolog peptide |
| SEQ ID NO: 285 | patatin homolog Pat17 DNA coding sequence and amino acid translation |
| SEQ ID NO: 286 | patatin homolog Pat17 amino acid sequence |
| SEQ ID NO: 287 | dicot patatin homolog amino acid sequence pentin1_phb |
| SEQ ID NO: 288 | dicot patatin homolog amino acid sequence 5c9_phb |
| SEQ ID NO: 289 | maize patatin homolog amino acid sequence corn1_pep |
| SEQ ID NO: 290 | maize patatin homolog amino acid sequence corn2_pep |
| SEQ ID NO: 291 | maize patatin homolog amino acid sequence corn3_pep |
| SEQ ID NO: 292 | maize patatin homolog amino acid sequence corn4_pep |
| SEQ ID NO: 293 | maize patatin homolog amino acid sequence corn5_pep |

Definitions

The following definitions are provided in order to aid those skilled in the art in understanding the detailed description of the present invention. Some words and phrases may also be defined in other sections of the specification. No limitation should be placed on the definitions presented for the terms below, where other meanings are evidenced elseqhere in the specification in addition to those specified below.

"Allergen" refers to a biological or chemical substance that induces an allergic reaction or response. An allergic response can be an immunoglobulin E-mediated response.

Amino acid codes: A (Ala)=alanine; C (Cys)=cysteine; D (Asp)=aspartic acid; E (Glu)=glutamic acid; F (Phe)=phenylalanine; G (Gly)=glycine; H (His)=histidine; I (Ile)=isoleucine; K (Lys)=lysine; L (Leu)=leucine; M (Met)=methionine; N (Asn)=asparagine; P (Pro)=proline; Q (Gln)=glutamine; R (Arg)=arginine; S (Ser)=serine; T (Thr)=threonine; V=(Val) valine; W (Trp)=tryptophan; Y (Tyr)=tyrosine.

"Amplification: refers to increasing the number of copies of a desired molecule.

"Coding sequence", "open reading frame", and "structural sequence" refer to the region of continuous sequential nucleic acid base pair triplets encoding a protein, polypeptide, or peptide sequence.

"Codon" refers to a sequence of three nucleotides that specify a particular amino acid.

"Complementarity" refers to the specific binding of adenine to thymine (or uracil in RNA) and cytosine to guanine on opposite strands of DNA or RNA.

"Deallergenize" (render hypoallergenic) refers to the method of engineering or modifying a protein or the encoding DNA such that the protein has a reduced or eliminated ability to induce an allergic response with respect to the ability of the unmodified protein. A deallergenized protein can be referred to as being hypoallergenic. The degree of deallergenization of a protein can be measured in vitro by the reduced binding of IgE antibodies.

"DNA segment heterologous to the promoter region" means that the coding DNA segment does not exist in nature in the same gene with the promoter to which it is now attached.

"DNA segment" refers to a DNA molecule that has been isolated free of total genomic DNA of a particular species.

"Electroporation" refers to a method of introducing foreign DNA into cells that uses a brief, high voltage DC (direct current) charge to permeabilize the host cells, causing them to take up extra-chromosomal DNA.

"Encoding DNA" refers to chromosomal DNA, plasmid DNA, cDNA, or synthetic DNA which encodes any of the enzymes discussed herein.

"Endogenous" refers to materials originating from within an organism or cell.

"Endonuclease" refers to an enzyme that hydrolyzes double stranded DNA at internal locations.

"Epitope" refers to a region on an allergen that interacts with the cells of the immune system. Epitopes are often further defined by the type of antibody or cell with which they interact, e.g. if the region reacts with B-cells or antibodies (IgE), it is called a B-cell epitope.

"Exogenous" refers to materials originating from outside of an organism or cell. This typically applies to nucleic acid molecules used in producing transformed or transgenic host cells and plants.

"Expressibly coupled" and "expressibly linked" refer to a promoter or promoter region and a coding or structural sequence in such an orientation and distance that transcription of the coding or structural sequence can be directed by the promoter or promoter region.

"Expression" refers to the transcription of a gene to produce the corresponding mRNA and translation of this mRNA to produce the corresponding gene product, i.e., a peptide, polypeptide, or protein.

"Heterologous DNA" refers to DNA from a source different than that of the recipient cell.

"Homologous DNA" refers to DNA from the same source as that of the recipient cell.

"Identity" refers to the degree of similarity between two nucleic acid or protein sequences. An alignment of the two sequences is performed by a suitable computer program. A widely used and accepted computer program for performing sequence alignments is CLUSTALW v1.6 (Thompson, et al. *Nucl. Acids Res.*, 22: 4673–4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

"IgE" (Immunoglobulin E) refers to a specific class of immunoglobulin secreted by B cells. IgE binds to specific receptors on Mast cells. Interaction of an allergen with mast cell-bound IgE may trigger allergic symptoms.

"Immunotherapy" refers to any type of treatment that targets the immune system. Allergy immunotherapy is a treatment in which a progressively increasing dose of an allergen is given in order to induce an immune response characterized by tolerance to the antigen/allergen, also known as desensitization.

"In vitro" refers to "in the laboratory" and/or "outside of a living organism".

"In vivo" refers to "in a living organism".

"Insecticidal polypeptide" refers to a polypeptide having insecticidal properties that adversely affects the growth and development of insect pests.

"Monocot" refers to plants having a single cotyledon (the first leaf of the embryo of seed plants); examples include cereals such as maize, rice, wheat, oats, and barley.

"Multiple cloning site" refers to an artificially constructed collection of restriction enzyme sites in a vector that facilitates insertion of foreign DNA into the vector.

"Mutation" refers to any change or alteration in a nucleic acid sequence. Several types exist, including point, frame shift, splicing, and insertion/deletions.

"Native" refers to "naturally occurring in the same organism". For example, a native promoter is the promoter naturally found operatively linked to a given coding sequence in an organism. A native protein is one naturally found in nature and untouched or not otherwise manipulated by the hand of man.

"Nucleic acid segment" is a nucleic acid molecule that has been isolated free of total genomic DNA of a particular species, or that has been synthesized. Included with the term "nucleic acid segment" are DNA segments, recombinant vectors, plasmids, cosmids, phagemids, phage, viruses, etcetera.

"Nucleic acid" refers to deoxyribonucleic acid (DNA) and ribonucleic acid (RNA).

Nucleic acid codes: A=adenosine; C=cytosine; G=guanosine; T=thymidine; N=equimolar A, C, G, and T; I=deoxyinosine; K=equimolar G and T; R=equimolar A and G; S=equimolar C and G; W=equimolar A and T; Y=equimolar C and T.

"Open reading frame (ORF)" refers to a region of DNA or RNA encoding a peptide, polypeptide, or protein or capable of being translated to protein, or a regioiu of DNA capable of being transcribed into an RNA product.

"Plasmid" refers to a circular, extrachromosomal, self-replicating piece of DNA.

"Point mutation" refers to an alteration of a single nucleotide in a nucleic acid sequence.

"Polymerase chain reaction (PCR)" refers to an enzymatic technique to create multiple copies of one sequence of nucleic acid. Copies of DNA sequence are prepared by shuttling a DNA polymerase between two oligonucleotides. The basis of this amplification method is multiple cycles of temperature changes to denature, then re-anneal amplimers, followed by extension to synthesize new DNA strands in the region located between the flanking amplimers. Also known as thermal amplification.

"Probe" refers to a polynucleotide sequence which is complementary to a target polynucleotide sequence in the analyte. An antibody can also be used as a probe to detect the presence of an antigen. In that sense, the antigen binding domain of the antibody has some detectable affinity for the antigen and binds thereto. The binding of the antibody to the antigen can be measured by means known in the art, such as by chemiluminescence, phosphorescence, flourescence, colorimetric chemical deposition at the site of binding, or otherwise.

"Promoter" or "promoter region" refers to a DNA sequence, usually found upstream (5') to a coding sequence, that controls expression of the coding sequence by controlling production of messenger RNA (mRNA) by providing the recognition site for RNA polymerase and/or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

"Recombinant DNA construct" or "recombinant vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA which is translated and therefore expressed. Recombinant DNA constructs or recombinant vectors can be constructed to be capable of expressing antisense RNAs, in order to inhibit translation of a specific RNA of interest.

"Recombinant proteins", also referred to as "heterologous proteins", are proteins which are normally not produced by the host cell.

"Regeneration" refers to the process of growing a plant from a plant cell (e.g., plant protoplast or explant).

"Regeneration" refers to the process of growing a plant from a plant cell (e.g., plant protoplast or explant).

"Regulatory sequence" refers to a nucleotide sequence located upstream (5'), within, and/or downstream (3') to a DNA sequence encoding a selected gene product whose transcription and expression is controlled by the regulatory sequence in conjunction with the protein synthetic apparatus of the cell.

"Restriction enzyme" refers to an enzyme that recognizes a specific palindromic sequence of nucleotides in double stranded DNA and cleaves both strands; also called a restriction endonuclease. Cleavage typically occurs within the restriction site.

"Result-effective substitution" (RES) refers to an amino acid substitution within an IgE-binding region (epitope) of a target protein which reduces or eliminates the IgE binding by that epitope. Examples herein are directed to patatin protein and homologues, however, as will be readily recognized by those skilled in the art, the method is more broadly applicable to proteins other than patatins, and in particular is applicable to any protein exhibiting allergen eliciting properties.

"Selectable marker" refers to a nucleic acid sequence whose expression confers a phenotype facilitating identification of cells containing the nucleic acid sequence. Selectable markers include those which confer resistance to toxic chemicals (e.g. ampicillin resistance, kanamycin resistance), complement a nutritional deficiency (e.g. uracil, histidine, leucine), or impart a visually distinguishing characteristic (e.g. color changes or fluorescence).

"Transcription" refers to the process of producing an RNA copy from a DNA template.

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

"Transformed cell" is a cell whose DNA has been altered by the introduction of an exogenous nucleic acid molecule into that cell.

"Transgenic cell" refers to any cell derived from or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

"Transgenic plant" refers to a plant or progeny thereof derived from a transformed plant cell or protoplast, wherein the plant DNA contains an introduced exogenous nucleic acid sequence not originally present in a native, non-transgenic plant of the same species. Alternatively, the plant DNA can contain the introduced nucleic acid sequence in a higher copy number than in the native, non-transgenic plant of the same species.

"Translation" refers to the production of protein from messenger RNA.

"Vector" refers to a plasmid, cosmid, bacteriophage, or virus that carries foreign DNA into a host organism.

"Western blot" refers to protein or proteins that have been separated by electrophoresis, transferred and immobilized onto a solid support, then probed with an antibody.

DETAILED DESCRIPTION OF THE INVENTION

Design of Deallergenized Patatin Proteins

Deallergenizing a protein can be accomplished by the identification of allergenic sites, followed by modification of the sites to reduce or eliminate the binding of antibodies to the sites. The IgE-binding regions of patatin were previously unreported. Mapping of the IgE epitopes was accomplished by synthesizing 10-mer peptides based on the patatin 17 protein sequence (SEQ ID NO: 2) which overlap by six amino acids. As potato proteins are denatured upon cooking potato products, it is expected that the 10-mer peptides sufficiently mimic the unfolded full length protein for antibody binding purposes. Peptides were identified based upon their ability to bind to IgE antibodies. Individual amino acids within the identified peptides were changed to reduce or eliminate binding to IgE present in sera from potato sensitive patients. These changes are termed result-effective amino acid substitutions (RES). The RES can be subsequently introduced into the full length protein by site directed mutagenesis of the encoding nucleic acid sequence or other means known in the art. Similar strategies have been employed elsewhere to determine the dominant IgE epitopes in a major peanut allergen (Stanley, J. S., et al., Arch. Biochem. Biophys., 342(2): 244–253, 1997).

Certain amino acid residues important for allergenicity of patatin are identified. Some of the designed patatin peptides wherein single amino acid residues were replaced with alanine or phenylalanine, showed significantly reduced or no binding to sera from potato sensitive patients.

A "deallergenized patatin" refers to a patatin protein differing in at least one of the amino acid residues as defined by the result effective substitutions resulting in the patatin protein having reduced reactivity towards sera from potato sensitive patients. The deallergenized patatin preferably maintains insecticidal properties, and preferably maintains its characteristic enzymatic profile.

Summary of Method to Deallergenize a Patatin Protein

Mapping of IgE epitopes by immunoassay of synthetic overlapping peptides using sera from potato sensitive patients;

Identification of result-effective substitutions by alanine scanning and/or rational scanning;

Modification of the amino acid sequence of patatin by site-directed mutagenesis of the encoding nucleic acid sequence;

Evaluation of enzyme activity (esterase) and/or insecticidal activity of the modified protein(s); and Evaluation of the new protein(s) for allergenicity by IgE immunoassay.

Nucleic acid sequences encoding patatin have been cloned by several investigators (e.g. Mignery, et al., Nucleic Acids Research, 12: 7987–8000, 1984; Mignery, et al., Gene, 62: 27–44, 1988; WO 94/21805; Canadian Patent Application No. 2090552). These nucleic acid sequences can then be manipulated using site directed mutagenesis to encode a hypoallergenic patatin. These nucleic acid sequences can than be used to transform bacterial, yeast or plant cells, resulting in the production of hypoallergenic patatin protein.

Deallergenized Patatin Proteins

For simplicity, individual amino acids are referred to by their single letter codes. Correlation between the single letter codes, three letter codes, and full amino acid names is presented in the definitions section above.

One embodiment of the invention is an isolated deallergenized patatin protein. The protein is modified relative to the wild-type protein sequence such that they exhibit reduced binding to anti-patatin antibodies such as those obtained from humans or animals allergic to potatoes. The reduced binding is measured relative to the binding of the unmodified patatin protein to the anti-patatin antibodies.

The deallergenized patatin protein can comprise SEQ ID NO:2 modified in one or more of the following regions, or SEQ ID NO:7 modified in one or more of the following regions. The single or multiple amino acid modifications reduce the binding of the modified protein relative to the binding of the corresponding unmodified protein. The regions for modification include amino acid positions 104–113 of SEQ ID NO:2 (85–94 of SEQ ID NO:7), 128–137 of SEQ ID NO:2 (109–118 of SEQ ID NO:7), 184–197 of SEQ ID NO:2 (165–178 of SEQ ID NO:7), 264–277 of SEQ ID NO:2 (245–258 of SEQ ID NO:7), 316–325 of SEQ ID NO:2 (297–306 of SEQ ID NO:7), and 360–377 of SEQ ID NO:2 (341–358 of SEQ ID NO:7). The possible amino acid modifications include replacing an amino acid with A, E, F, P, or S. The modifications replace one or more amino acids in the identified regions, without increasing or decreasing the total number of amino acids in the protein.

Preferably, the deallergenized patatin protein comprises SEQ ID NO:2 modified by one or more changes, or SEQ ID NO:7 modified by one or more changes. SEQ ID NO:7 differs from wild type SEQ ID NO:2 in that the first 22 amino acids of SEQ ID NO:2 are replaced with EAE (Glu-Ala-Glu). For example, the changes to SEQ ID NO:2 or SEQ ID NO:7 can be: the Y corresponding to position 106 of SEQ ID NO:2 or position 87 of SEQ ID NO:7 is replaced with F or A; the I corresponding to position 113 of SEQ ID NO:2 or position 94 of SEQ ID NO:7 is replaced with A; the Y corresponding to position 129 of SEQ ID NO:2 or position 110 of SEQ ID NO:7 is replaced with F or A; the K corresponding to position 137 of SEQ ID NO:2 or position 118 of SEQ ID NO:7 is replaced with A; the S corresponding to position 184 of SEQ ID NO:2 or position 165 of SEQ ID NO:7 is replaced with A; the Y corresponding to position 185 of SEQ ID NO:2 or position 166 of SEQ ID NO:7 is replaced with F or A; the A corresponding to position 188 of SEQ ID NO:2 or position 169 of SEQ ID NO:7 is replaced with S; the T corresponding to position 192 of SEQ ID NO:2 or position 173 of SEQ ID NO:7 is replaced with A or P; the Y corresponding to position 193 of SEQ ID NO:2 or position 174 of SEQ ID NO:7 is replaced with F or A; the K corresponding to position 268 of SEQ ID NO:2 or position 249 of SEQ ID NO:7 is replaced with A or E; the T corresponding to position 269 of SEQ ID NO:2 or position 250 of SEQ ID NO:7 is replaced with A; the Y corresponding to position 270 of SEQ ID NO:2 or position 251 of SEQ ID NO:7 is replaced with F or A; the K corresponding to position 273 of SEQ ID NO:2 or position 254 of SEQ ID NO:7 is replaced with A; the K corresponding to position 313 of SEQ ID NO:2 or position 294 of SEQ ID NO:7 is replaced with E; the N corresponding to position 314 of SEQ ID NO:2 or position 295 of SEQ ID NO:7 is replaced with A; the N corresponding to position 315 of SEQ ID NO:2 or position 296 of SEQ ID NO:7 is replaced with A; the Y corresponding to position 316 of SEQ ID NO:2 or position 297 of SEQ ID NO:7 is replaced with F or A; the Y corresponding to position 362 of SEQ ID NO:2 or position 343 of SEQ ID NO:7 is replaced with F; the K corresponding to position 367 of SEQ ID NO:2 or position 348 of SEQ ID NO:7 is replaced with A; the R corresponding to position 368 of SEQ ID NO:2 or position 349 of SEQ ID NO:7 is replaced with A; the F corresponding to position 369 of SEQ ID NO:2 or position 350 of SEQ ID NO:7 is replaced with A; the K corresponding to position 371 of SEQ ID NO:2 or position 352 of SEQ ID NO:7 is replaced with A; the L corresponding to position 372 of SEQ ID NO:2 or position 353 of SEQ ID NO:7 is replaced with A; and the L corresponding to position 373 of SEQ ID NO:2 or position 354 of SEQ ID NO:7 is replaced with A.

More preferably, SEQ ID NO:2 is modified by the following changes or SEQ ID NO:7 is modified by the following changes: the Y corresponding to position 106 of SEQ ID NO:2 or position 87 of SEQ ID NO:7 is replaced with F; the Y corresponding to position 129 of SEQ ID NO:2 or position 110 of SEQ ID NO:7 is replaced with F; the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Most preferably, SEQ ID NO:2 is modified by the following changes or SEQ ID NO:7 is modified by the following changes: the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Nucleic Acids

An additional embodiment of the invention is an isolated nucleic acid molecule segment comprising a structural nucleic acid sequence which encodes a deallergenized patatin protein.

The structural nucleic acid sequence can generally encode any deallergenized patatin protein. The structural nucleic acid sequence preferably encodes a deallergenized patatin protein comprising SEQ ID NO:2 modified in one or more of the following regions, or SEQ ID NO:7 modified in one or more of the following regions. The single or multiple amino acid modifications reduce the binding of the modified protein relative to the binding of the corresponding unmodified protein. The regions for modification include amino acid positions 104–113 of SEQ ID NO:2 (85–94 of SEQ ID NO:7), 128–137 of SEQ ID NO:2 (109–118 of SEQ ID NO:7), 184–197 of SEQ ID NO:2 (165–178 of SEQ ID NO:7), 264–277 of SEQ ID NO:2 (245–258 of SEQ ID NO:7), 316–325 of SEQ ID NO:2 (297–306 of SEQ ID NO:7), and 360–377 of SEQ ID NO:2 (341–358 of SEQ ID NO:7). The possible amino acid modifications include replacing an amino acid with A, E, F, P, or S. The modifications replace one or more amino acids in the identified regions, without increasing or decreasing the total number of amino acids in the protein.

Alternatively, the structural nucleic acid sequence encodes SEQ ID NO:2 modified by one or more of the following changes or encoding SEQ ID NO:7 modified by one or more of the following changes: the Y corresponding to position 106 of SEQ ID NO:2 or position 87 of SEQ ID NO:7 is replaced with F or A; the I corresponding to position 113 of SEQ ID NO:2 or position 94 of SEQ ID NO:7 is replaced with A; the Y corresponding to position 129 of SEQ ID NO:2 or position 110 of SEQ ID NO:7 is replaced with F or A; the K corresponding to position 137 of SEQ ID NO:2 or position 118 of SEQ ID NO:7 is replaced with A; the S corresponding to position 184 of SEQ ID NO:2 or position 165 of SEQ ID NO:7 is replaced with A; the Y corresponding to position 185 of SEQ ID NO:2 or position 166 of SEQ ID NO:7 is replaced with F or A; the A corresponding to position 188 of SEQ ID NO:2 or position 169 of SEQ ID NO:7 is replaced with S; the T corresponding to position 192 of SEQ ID NO:2 or position 173 of SEQ ID NO:7 is replaced with A or P; the Y corresponding to position 193 of SEQ ID NO:2 or position 174 of SEQ ID NO:7 is replaced with F or A; the K corresponding to position 268 of SEQ ID NO:2 or position 249 of SEQ ID NO:7 is replaced with A or E; the T corresponding to position 269 of SEQ ID NO:2 or position 250 of SEQ ID NO:7 is replaced with A; the Y corresponding to position 270 of SEQ ID NO:2 or position 251 of SEQ ID NO:7 is replaced with F or A; the K corresponding to position 273 of SEQ ID NO:2 or position 254 of SEQ ID NO:7 is replaced with A; the K corresponding to position 313 of SEQ ID NO:2 or position 294 of SEQ ID NO:7 is replaced with E; the N corresponding to position 314 of SEQ ID NO:2 or position 295 of SEQ ID NO:7 is replaced with A; the N corresponding to position 315 of SEQ ID NO:2 or position 296 of SEQ ID NO:7 is replaced with A; the Y corresponding to position 316 of SEQ ID NO:2 or position 297 of SEQ ID NO:7 is replaced with F or A; the Y corresponding to position 362 of SEQ ID NO:2 or position 343 of SEQ ID NO:7 is replaced with F; the K corresponding to position 367 of SEQ ID NO:2 or position 348 of SEQ ID NO:7 is replaced with A; the R corresponding to position 368 of SEQ ID NO:2 or position 349 of SEQ ID NO:7 is replaced with A; the F corresponding to position 369 of SEQ ID NO:2 or position 350 of SEQ ID NO:7 is replaced with A; the K corresponding to position 371 of SEQ ID NO:2 or position 352 of SEQ ID NO:7 is replaced with A; the L corresponding to position 372 of SEQ ID NO:2 or position 353 of SEQ ID NO:7 is replaced with A; and the L corresponding to position 373 of SEQ ID NO:2 or position 354 of SEQ ID NO:7 is replaced with A.

More preferably, the structural nucleic acid sequence encodes SEQ ID NO:2 modified by the following changes or SEQ ID NO:7 modified by the following changes: the Y corresponding to position 106 of SEQ ID NO:2 or position 87 of SEQ ID NO:7 is replaced with F; the Y corresponding to position 129 of SEQ ID NO:2 or position 110 of SEQ ID NO:7 is replaced with F; the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Most preferably, the structural nucleic acid sequence encodes SEQ ID NO:2 modified by the following changes or SEQ ID NO:7 modified by the following changes: the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Recombinant Vectors

An additional embodiment is directed towards recombinant vectors comprising a structural nucleic acid sequence which encodes a deallergenized patatin protein. The recombinant vector comprises operatively linked in the 5' to 3' orientation: a promoter that directs transcription of a structural nucleic acid sequence; a structural nucleic acid sequence, and a 3' transcription terminator.

The structural nucleic acid sequence can encode SEQ ID NO:2 modified in one or more of the following regions, or SEQ ID NO:7 modified in one or more of the following regions. The single or multiple amino acid modifications reduce the binding of the modified protein relative to the binding of the corresponding unmodified protein. The regions for modification include amino acid positions 104–113 of SEQ ID NO:2 (85–94 of SEQ ID NO:7), 128–137 of SEQ ID NO:2 (109–118 of SEQ ID NO:7), 184–197 of SEQ ID NO:2 (165–178 of SEQ ID NO:7), 264–277 of SEQ ID NO:2 (245–258 of SEQ ID NO:7), 316–325 of SEQ ID NO:2 (297–306 of SEQ ID NO:7), and 360–377 of SEQ ID NO:2 (341–358 of SEQ ID NO:7). The possible amino acid modifications include replacing an amino acid with A, E, F, P, or S. The modifications replace one or more amino acids in the identified regions, without increasing or decreasing the total number of amino acids in the protein.

Alternatively, the recombinant vector comprises operatively linked in the 5' to 3' orientation: a promoter that directs transcription of a structural nucleic acid sequence; a structural nucleic acid sequence encoding SEQ ID NO:2 modified by one or more of the following changes or encoding SEQ ID NO:7 modified by one or more of the following changes: the Y corresponding to position 106 of SEQ ID NO:2 or position 87 of SEQ ID NO:7 is replaced with F or A; the I corresponding to position 113 of SEQ ID NO:2 or position 94 of SEQ ID NO:7 is replaced with A; the Y corresponding to position 129 of SEQ ID NO:2 or position 110 of SEQ ID NO:7 is replaced with F or A; the K corresponding to position 137 of SEQ ID NO:2 or position 118 of SEQ ID NO:7 is replaced with A; the S corresponding to position 184 of SEQ ID NO:2 or position 165 of SEQ ID NO:7 is replaced with A; the Y corresponding to position 185 of SEQ ID NO:2 or position 166 of SEQ ID NO:7 is replaced with F or A; the A corresponding to position 188 of SEQ ID NO:2 or position 169 of SEQ ID NO:7 is replaced with S; the T corresponding to position 192 of SEQ ID NO:2 or position 173 of SEQ ID NO:7 is replaced with A or P; the Y corresponding to position 193 of SEQ ID NO:2 or position 174 of SEQ ID NO:7 is replaced with F or A; the K corresponding to position 268 of SEQ ID NO:2 or position 249 of SEQ ID NO:7 is replaced with A or E; the T corresponding to position 269 of SEQ ID NO:2 or position 250 of SEQ ID NO:7 is replaced with A; the Y corresponding to position 270 of SEQ ID NO:2 or position 251 of SEQ ID NO:7 is replaced with F or A; the K corresponding to position 273 of SEQ ID NO:2 or position 254 of SEQ ID NO:7 is replaced with A; the K corresponding to position 313 of SEQ ID NO:2 or position 294 of SEQ ID NO:7 is replaced with E; the N corresponding to position 314 of SEQ ID NO:2 or position 295 of SEQ ID NO:7 is replaced with A; the N corresponding to position 315 of SEQ ID NO:2 or position 296 of SEQ ID NO:7 is replaced with A; the Y corresponding to position 316 of SEQ ID NO:2 or position 297 of SEQ ID NO:7 is replaced with F or A; the Y corresponding to position 362 of SEQ ID NO:2 or position 343 of SEQ ID NO:7 is replaced with F; the K corresponding to position 367 of SEQ ID NO:2 or position 348 of SEQ ID NO:7 is replaced with A; the R corresponding to position 368 of SEQ ID NO:2 or position 349 of SEQ ID NO:7 is replaced with A; the F corresponding to position 369 of SEQ ID NO:2 or position 350 of SEQ ID NO:7 is replaced with A; the K corresponding to position 371 of SEQ ID NO:2 or position 352 of SEQ ID NO:7 is replaced with A; the L corresponding to position 372 of SEQ ID NO:2 or position 353 of SEQ ID NO:7 is replaced with A; and the L corresponding to position 373 of SEQ ID NO:2 or position 354 of SEQ ID NO:7 is replaced with A; and a 3' transcription terminator.

More preferably, the vector comprises a structural nucleic acid sequence encoding SEQ ID NO:2 modified by the following changes or SEQ ID NO:7 modified by the following changes: the Y corresponding to position 106 of SEQ ID NO:2 or position 87 of SEQ ID NO:7 is replaced with F; the Y corresponding to position 129 of SEQ ID NO:2 or position 110 of SEQ ID NO:7 is replaced with F; the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Most preferably, the vector comprises a structural nucleic acid sequence encoding SEQ ID NO:2 modified by the following changes or SEQ ID NO:7 modified by the following changes: the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Recombinant Host Cells A further embodiment of the invention is directed towards recombinant host cells comprising a structural nucleic acid sequence encoding a deallergenized patatin protein. The recombinant host cell preferably produces a deallergenized patatin protein. More preferably, the recombinant host cell produces a deallergenized patatin protein in a concentration sufficient to inhibit growth or to kill an insect which ingests the recombinant host cell. The recombinant host cell can generally comprise any structural nucleic acid sequence encoding a deallergenized patatin protein.

The recombinant host cell can comprise a structural nucleic acid sequence encoding SEQ ID NO:2 modified in one or more of the following regions, or SEQ ID NO:7 modified in one or more of the following regions. The single or multiple amino acid modifications reduce the binding of the modified protein relative to the binding of the corresponding unmodified protein. The regions for modification include amino acid positions 104–113 of SEQ ID NO:2 (85–94 of SEQ ID NO:7), 128–137 of SEQ ID NO:2 (109–118 of SEQ ID NO:7), 184–197 of SEQ ID NO:2 (165–178 of SEQ ID NO:7), 264–277 of SEQ ID NO:2 (245–258 of SEQ ID NO:7), 316–325 of SEQ ID NO:2 (297–306 of SEQ ID NO:7), and 360–377 of SEQ ID NO:2 (341–358 of SEQ ID NO:7). The possible amino acid modifications include replacing an amino acid with A, E, F, P, or S. The modifications replace one or more amino acids in the identified regions, without increasing or decreasing the total number of amino acids in the protein.

Alternatively, the recombinant host cell comprises a structural nucleic acid sequence encoding SEQ ID NO:2 modified by one or more of the following changes or encoding SEQ ID NO:7 modified by one or more of the following changes: the Y corresponding to position 106 of SEQ ID NO:2 or position 87 of SEQ ID NO:7 is replaced with F or A; the I corresponding to position 113 of SEQ ID NO:2 or position 94 of SEQ ID NO:7 is replaced with A; the Y corresponding to position 129 of SEQ ID NO:2 or position 110 of SEQ ID NO:7 is replaced with F or A; the K corresponding to position 137 of SEQ ID NO:2 or position 118 of SEQ ID NO:7 is replaced with A; the S corresponding to position 184 of SEQ ID NO:2 or position 165 of SEQ ID NO:7 is replaced with A; the Y corresponding to position 185 of SEQ ID NO:2 or position 166 of SEQ ID NO:7 is replaced with F or A; the A corresponding to position 188 of SEQ ID NO:2 or position 169 of SEQ ID NO:7 is replaced with S; the T corresponding to position 192 of SEQ ID NO:2 or position 173 of SEQ ID NO:7 is replaced with A or P; the Y corresponding to position 193 of SEQ ID NO:2 or position 174 of SEQ ID NO:7 is replaced with F or A; the K corresponding to position 268 of SEQ ID NO:2 or position 249 of SEQ ID NO:7 is replaced with A or E; the T corresponding to position 269 of SEQ ID NO:2 or position 250 of SEQ ID NO:7 is replaced with A; the Y corresponding to position 270 of SEQ ID NO:2 or position 251 of SEQ ID NO:7 is replaced with F or A; the K corresponding to position 273 of SEQ ID NO:2 or position 254 of SEQ ID NO:7 is replaced with A; the K corresponding to position 313 of SEQ ID NO:2 or position 294 of SEQ ID NO:7 is replaced with E; the N corresponding to position 314 of SEQ ID NO:2 or position 295 of SEQ ID NO:7 is replaced with A; the N corresponding to position 315 of SEQ ID NO:2 or position 296 of SEQ ID NO:7 is replaced with A; the Y corresponding to position 316 of SEQ ID NO:2 or position 297 of SEQ ID NO:7 is replaced with F or A; the Y corresponding to position 362 of SEQ ID NO:2 or position 343 of SEQ ID NO:7 is replaced with F; the K corresponding to position 367 of SEQ ID NO:2 or position 348 of SEQ ID NO:7 is replaced with A; the R corresponding to position 368 of SEQ ID NO:2 or position 349 of SEQ ID NO:7 is replaced with A; the F corresponding to position 369 of SEQ ID NO:2 or position 350 of SEQ ID NO:7 is replaced with A; the K corresponding to position 371 of SEQ ID NO:2 or position 352 of SEQ ID NO:7 is replaced with A; the L corresponding to position 372 of SEQ ID NO:2 or position 353 of SEQ ID NO:7 is replaced with A; and the L corresponding to position 373 of SEQ ID NO:2 or position 354 of SEQ ID NO:7 is replaced with A.

More preferably, the recombinant host cell comprises a structural nucleic acid sequence encoding SEQ ID NO:2 modified by the following changes or SEQ ID NO:7 modified by the following changes: the Y corresponding to position 106 of SEQ ID NO:2 or position 87 of SEQ ID NO:7 is replaced with F; the Y corresponding to position 129 of SEQ ID NO:2 or position 110 of SEQ ID NO:7 is replaced with F; the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Most preferably, the recombinant host cell comprises a structural nucleic acid sequence encoding SEQ ID NO:2 modified by the following changes or SEQ ID NO:7 modified by the following changes: the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

The recombinant host cell can generally be any type of host cell, and preferably is a bacterial, fungal, or plant cell. The bacterial cell is preferably an *Escherichia coli* bacterial cell. The fungal cell is preferably a *Saccharomyces cerevisiae, Schizosaccharomyces pombe*, or *Pichia pastoris* fungal cell. The plant cell can be a monocot, dicot, or conifer plant cell. The plant cell is preferably an alfalfa, banana, canola, corn, cotton, cucumber, peanut, potato, rice, soybean, sunflower, sweet potato, tobacco, tomato, or wheat plant cell. The recombinant host cell preferably further comprises operatively linked to the structural nucleic acid sequence a promoter that directs transcription of the structural nucleic acid sequence. The recombinant host cell preferably further comprises operatively linked to the structural nucleic acid sequence a 3' transcription terminator and a polyadenylation site.

Recombinant Plants

An additional embodiment of the invention is a recombinant plant comprising a structural nucleic acid sequence encoding a deallergenized patatin protein. The recombinant plant preferably produces a deallergenized patatin protein. More preferably, the recombinant plant produces a deallergenized patatin protein in a concentration sufficient to inhibit growth or to kill an insect which ingests plant tissue from the recombinant plant.

The recombinant plant can comprise a structural nucleic acid sequence encoding SEQ ID NO:2 modified in one or more of the following regions, or SEQ ID NO:7 modified in one or more of the following regions. The single or multiple amino acid modifications reduce the binding of the modified protein relative to the binding of the corresponding unmodified protein. The regions for modification include amino acid positions 104–113 of SEQ ID NO:2 (85–94 of SEQ ID NO:7), 128–137 of SEQ ID NO:2 (109–118 of SEQ ID NO:7), 184–197 of SEQ ID NO:2 (165–178 of SEQ ID NO:7), 264–277 of SEQ ID NO:2 (245–258 of SEQ ID NO:7), 316–325 of SEQ ID NO:2 (297–306 of SEQ ID NO:7), and 360–377 of SEQ ID NO:2 (341–358 of SEQ ID NO:7). The possible amino acid modifications include replacing an amino acid with A, E, F, P, or S. The modifications replace one or more amino acids in the identified regions, without increasing or decreasing the total number of amino acids in the protein.

Alternatively, the recombinant plant can comprise a structural nucleic acid sequence encoding SEQ ID NO:2 modified by one or more of the following changes or encoding SEQ ID NO:7 modified by one or more of the following changes: the Y corresponding to position 106 of SEQ ID NO:2 or position 87 of SEQ ID NO:7 is replaced with F or A; the I corresponding to position 113 of SEQ ID NO:2 or position 94 of SEQ ID NO:7 is replaced with A; the Y corresponding to position 129 of SEQ ID NO:2 or position 110 of SEQ ID NO:7 is replaced with F or A; the K corresponding to position 137 of SEQ ID NO:2 or position 118 of SEQ ID NO:7 is replaced with A; the S corresponding to position 184 of SEQ ID NO:2 or position 165 of SEQ ID NO:7 is replaced with A; the Y corresponding to position 185 of SEQ ID NO:2 or position 166 of SEQ ID NO:7 is replaced with F or A; the A corresponding to position 188 of SEQ ID NO:2 or position 169 of SEQ ID NO:7 is replaced with S; the T corresponding to position 192 of SEQ ID NO:2 or position 173 of SEQ ID NO:7 is replaced with A or P; the Y corresponding to position 193 of SEQ ID NO:2 or position 174 of SEQ ID NO:7 is replaced with F or A; the K corresponding to position 268 of SEQ ID NO:2 or position 249 of SEQ ID NO:7 is replaced with A or E; the T corresponding to position 269 of SEQ ID NO:2 or position 250 of SEQ ID NO:7 is replaced with A; the Y corresponding to position 270 of SEQ ID NO:2 or position 251 of SEQ ID NO:7 is replaced with F or A; the K corresponding to position 273 of SEQ ID NO:2 or position 254 of SEQ ID NO:7 is replaced with A; the K corresponding to position 313 of SEQ ID NO:2 or position 294 of SEQ ID NO:7 is replaced with E; the N corresponding to position 314 of SEQ ID NO:2 or position 295 of SEQ ID NO:7 is replaced with A; the N corresponding to position 315 of SEQ ID NO:2 or position 296 of SEQ ID NO:7 is replaced with A; the Y corresponding to position 316 of SEQ ID NO:2 or position 297 of SEQ ID NO:7 is replaced with F or A; the Y corresponding to position 362 of SEQ ID NO:2 or position 343 of SEQ ID NO:7 is replaced with F; the K corresponding to position 367 of SEQ ID NO:2 or position 348 of SEQ ID NO:7 is replaced with A; the R corresponding to position 368 of SEQ ID NO:2 or position 349 of SEQ ID NO:7 is replaced with A; the F corresponding to position 369 of SEQ ID NO:2 or position 350 of SEQ ID NO:7 is replaced with A; the K corresponding to position 371 of SEQ ID NO:2 or position 352 of SEQ ID NO:7 is replaced with A; the L corresponding to position 372 of SEQ ID NO:2 or position 353 of SEQ ID NO:7 is replaced with A; and the L corresponding to position 373 of SEQ ID NO:2 or position 354 of SEQ ID NO:7 is replaced with A.

More preferably, the recombinant plant comprises a structural nucleic acid sequence encoding SEQ ID NO:2 modified by the following changes or SEQ ID NO:7 modified by the following changes: the Y corresponding to position 106 of SEQ ID NO:2 or position 87 of SEQ ID NO:7 is replaced with F; the Y corresponding to position 129 of SEQ ID NO:2 or position 110 of SEQ ID NO:7 is replaced with F; the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Most preferably, the recombinant plant comprises a structural nucleic acid sequence encoding SEQ ID NO:2 modified by the following changes or SEQ ID NO:7 modified by the following changes: the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

The recombinant plant can generally be any type of plant. The plant can be a monocot, dicot, or conifer plant. The plant is preferably an alfalfa, banana, canola, corn, cotton, cucumber, peanut, potato, rice, soybean, sunflower, sweet potato, tobacco, tomato, or wheat plant.

The recombinant plant preferably further comprises operatively linked to the structural nucleic acid sequence a promoter that directs transcription of the structural nucleic acid sequence. The recombinant plant preferably further comprises operatively linked to the structural nucleic acid sequence a 3' transcription terminator and a polyadenylation site.

Methods of Preparation

Embodiments of the invention are further directed towards methods of preparing recombinant host cells and recombinant plants useful for the production of deallergenized patatin proteins.

A method of preparing a recombinant host cell useful for the production of deallergenized patatin proteins can comprise selecting a host cell; transforming the host cell with a recombinant vector; and obtaining recombinant host cells.

The recombinant vector comprises a structural nucleic acid sequence encoding SEQ ID NO:2 modified in one or more of the following regions, or SEQ ID NO:7 modified in one or more of the following regions. The single or multiple amino acid modifications reduce the binding of the modified protein relative to the binding of the corresponding unmodified protein. The regions for modification include amino acid positions 104–113 of SEQ ID NO:2 (85–94 of SEQ ID NO:7), 128–137 of SEQ ID NO:2 (109–118 of SEQ ID NO:7), 184–197 of SEQ ID NO:2 (165–178 of SEQ ID NO:7), 264–277 of SEQ ID NO:2 (245–258 of SEQ ID NO:7), 316–325 of SEQ ID NO:2 (297–306 of SEQ ID NO:7), and 360–377 of SEQ ID NO:2 (341–358 of SEQ ID NO:7). The possible amino acid modifications include replacing an amino acid with A, E, F, P, or S. The modifications replace one or more amino acids in the identified regions, without increasing or decreasing the total number of amino acids in the protein.

Alternatively, the recombinant vector comprises a structural nucleic acid sequence encoding SEQ ID NO:2 modified by one or more of the following changes or encoding SEQ ID NO:7 modified by one or more of the following changes: the Y corresponding to position 106 of SEQ ID NO:2 or position 87 of SEQ ID NO:7 is replaced with F or A; the I corresponding to position 113 of SEQ ID NO:2 or position 94 of SEQ ID NO:7 is replaced with A; the Y corresponding to position 129 of SEQ ID NO:2 or position 110 of SEQ ID NO:7 is replaced with F or A; the K corresponding to position 137 of SEQ ID NO:2 or position 118 of SEQ ID NO:7 is replaced with A; the S corresponding to position 184 of SEQ ID NO:2 or position 165 of SEQ ID NO:7 is replaced with A; the Y corresponding to position 185 of SEQ ID NO:2 or position 166 of SEQ ID NO:7 is replaced with F or A; the A corresponding to position 188 of SEQ ID NO:2 or position 169 of SEQ ID NO:7 is replaced with S; the T corresponding to position 192 of SEQ ID NO:2 or position 173 of SEQ ID NO:7 is replaced with A or P; the Y corresponding to position 193 of SEQ ID NO:2 or position 174 of SEQ ID NO:7 is replaced with F or A; the K corresponding to position 268 of SEQ ID NO:2 or position 249 of SEQ ID NO:7 is replaced with A or E; the T corresponding to position 269 of SEQ ID NO:2 or position 250 of SEQ ID NO:7 is replaced with A; the Y corresponding to position 270 of SEQ ID NO:2 or position 251 of SEQ ID NO:7 is replaced with F or A; the K corresponding to position 273 of SEQ ID NO:2 or position 254 of SEQ ID NO:7 is replaced with A; the K corresponding to position 313 of SEQ ID NO:2 or position 294 of SEQ ID NO:7 is replaced with E; the N corresponding to position 314 of SEQ ID NO:2 or position 295 of SEQ ID NO:7 is replaced with A; the N corresponding to position 315 of SEQ ID NO:2 or position 296 of SEQ ID NO:7 is replaced with A; the Y corresponding to position 316 of SEQ ID NO:2 or position 297 of SEQ ID NO:7 is replaced with F or A; the Y corresponding to position 362 of SEQ ID NO:2 or position 343 of SEQ ID NO:7 is replaced with F; the K corresponding to position 367 of SEQ ID NO:2 or position 348 of SEQ ID NO:7 is replaced with A; the R corresponding to position 368 of SEQ ID NO:2 or position 349 of SEQ ID NO:7 is replaced with A; the F corresponding to position 369 of SEQ ID NO:2 or position 350 of SEQ ID NO:7 is replaced with A; the K corresponding to position 371 of SEQ ID NO:2 or position 352 of SEQ ID NO:7 is replaced with A; the L corresponding to position 372 of SEQ ID NO:2 or position 353 of SEQ ID NO:7 is replaced with A; and the L corresponding to position 373 of SEQ ID NO:2 or position 354 of SEQ ID NO:7 is replaced with A.

More preferably, the vector comprises a structural nucleic acid sequence encoding SEQ ID NO:2 modified by the following changes or SEQ ID NO:7 modified by the following changes: the Y corresponding to position 106 of SEQ ID NO:2 or position 87 of SEQ ID NO:7 is replaced with F; the Y corresponding to position 129 of SEQ ID NO:2 or position 110 of SEQ ID NO:7 is replaced with F; the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Most preferably, the vector comprises a structural nucleic acid sequence encoding SEQ ID NO:2 modified by the following changes or SEQ ID NO:7 modified by the following changes: the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

The method can generally be used to prepare any type of recombinant host cell. Preferably, the method can be used to prepare a recombinant bacterial cell, a recombinant fungal cell, or a recombinant plant cell. The bacterial cell is preferably an *Escherichia coli* bacterial cell. The fungal cell is preferably a *Saccharomyces cerevisiae, Schizosaccharomyces pombe,* or *Pichia pastoris* fungal cell. The plant cell can be a monocot, dicot, or conifer plant cell. The plant cell is preferably an alfalfa, banana, canola, corn, cotton, cucumber, peanut, potato, rice, soybean, sunflower, sweet potato, tobacco, tomato, or wheat plant cell.

An additional embodiment is directed towards methods for the preparation of recombinant plants useful for the production of deallergenized patatin proteins. The method can comprise selecting a host plant cell; transforming the host plant cell with a recombinant vector; obtaining recombinant host cells; and regenerating a recombinant plant from the recombinant host plant cells.

The recombinant vector comprises a structural nucleic acid sequence encoding SEQ ID NO:2 modified in one or more of the following regions, or SEQ ID NO:7 modified in one or more of the following regions. The single or multiple amino acid modifications reduce the binding of the modified protein relative to the binding of the corresponding unmodified protein. The regions for modification include amino acid positions 104–113 of SEQ ID NO:2 (85–94 of SEQ ID NO:7), 128–137 of SEQ ID NO:2 (109–118 of SEQ ID NO:7), 184–197 of SEQ ID NO:2 (165–178 of SEQ ID NO:7), 264–277 of SEQ ID NO:2 (245–258 of SEQ ID NO:7), 316–325 of SEQ ID NO:2 (297–306 of SEQ ID NO:7), and 360–377 of SEQ ID NO:2 (341–358 of SEQ ID NO:7). The possible amino acid modifications include replacing an amino acid with A, E, F, P, or S. The modifications replace one or more amino acids in the identified regions, without increasing or decreasing the total number of amino acids in the protein.

Alternatively, the recombinant vector comprises a structural nucleic acid sequence encoding SEQ ID NO:2 modified by one or more of the following changes or encoding SEQ ID NO:7 modified by one or more of the following changes: the Y corresponding to position 106 of SEQ ID NO:2 or position 87 of SEQ ID NO:7 is replaced with F or A; the I corresponding to position 113 of SEQ ID NO:2 or position 94 of SEQ ID NO:7 is replaced with A; the Y corresponding to position 129 of SEQ ID NO:2 or position 110 of SEQ ID NO:7 is replaced with F or A; the K corresponding to position 137 of SEQ ID NO:2 or position 118 of SEQ ID NO:7 is replaced with A; the S corresponding to position 184 of SEQ ID NO:2 or position 165 of SEQ ID NO:7 is replaced with A; the Y corresponding to position 185 of SEQ ID NO:2 or position 166 of SEQ ID NO:7 is replaced with F or A; the A corresponding to position 188 of SEQ ID NO:2 or position 169 of SEQ ID NO:7 is replaced with S; the T corresponding to position 192 of SEQ ID NO:2 or position 173 of SEQ ID NO:7 is replaced with A or P; the Y corresponding to position 193 of SEQ ID NO:2 or position 174 of SEQ ID NO:7 is replaced with F or A; the K corresponding to position 268 of SEQ ID NO:2 or position 249 of SEQ ID NO:7 is replaced with A or E; the T corresponding to position 269 of SEQ ID NO:2 or position 250 of SEQ ID NO:7 is replaced with A; the Y corresponding to position 270 of SEQ ID NO:2 or position 251 of SEQ ID NO:7 is replaced with F or A; the K corresponding to position 273 of SEQ ID NO:2 or position 254 of SEQ ID NO:7 is replaced with A; the K corresponding to position 313 of SEQ ID NO:2 or position 294 of SEQ ID NO:7 is replaced with E; the N corresponding to position 314 of SEQ ID NO:2 or position 295 of SEQ ID NO:7 is replaced with A; the N corresponding to position 315 of SEQ ID NO:2 or position 296 of SEQ ID NO:7 is replaced with A; the Y corresponding to position 316 of SEQ ID NO:2 or position 297 of SEQ ID NO:7 is replaced with F or A; the Y corresponding to position 362 of SEQ ID NO:2 or position 343 of SEQ ID NO:7 is replaced with F; the K corresponding to position 367 of SEQ ID NO:2 or position 348 of SEQ ID NO:7 is replaced with A; the R corresponding to position 368 of SEQ ID NO:2 or position 349 of SEQ ID NO:7 is replaced with A; the F corresponding to position 369 of SEQ ID NO:2 or position 350 of SEQ ID NO:7 is replaced with A; the K corresponding to position 371 of SEQ ID NO:2 or position 352 of SEQ ID NO:7 is replaced with A; the L corresponding to position 372 of SEQ ID NO:2 or position 353 of SEQ ID NO:7 is replaced with A; and the L corresponding to position 373 of SEQ ID NO:2 or position 354 of SEQ ID NO:7 is replaced with A.

More preferably, the vector comprises a structural nucleic acid sequence encoding SEQ ID NO:2 modified by the following changes or SEQ ID NO:7 modified by the following changes: the Y corresponding to position 106 of SEQ ID NO:2 or position 87 of SEQ ID NO:7 is replaced with F; the Y corresponding to position 129 of SEQ ID NO:2 or position 110 of SEQ ID NO:7 is replaced with F; the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

Most preferably, the vector comprises a structural nucleic acid sequence encoding SEQ ID NO:2 modified by the following changes or SEQ ID NO:7 modified by the following changes: the Y corresponding to position 185 of SEQ ID NO:2 or position 166 of SEQ ID NO:7 is replaced with F; the Y corresponding to position 193 of SEQ ID NO:2 or position 174 of SEQ ID NO:7 is replaced with F; the Y corresponding to position 270 of SEQ ID NO:2 or position 251 of SEQ ID NO:7 is replaced with F; the Y corresponding to position 316 of SEQ ID NO:2 or position 297 of SEQ ID NO:7 is replaced with F; and the Y corresponding to position 362 of SEQ ID NO:2 or position 343 of SEQ ID NO:7 is replaced with F.

The recombinant plant can generally be any type of plant. The plant can be a monocot, dicot, or conifer plant. The plant is preferably an alfalfa, banana, canola, corn, cotton, cucumber, peanut, potato, rice, soybean, sunflower, sweet potato, tobacco, tomato, or wheat plant.

Deallergenized patatin proteins can be prepared by isolating the deallergenized patatin protein from any one of the above described host cells or plants.

Deglycosylation

The examples herein provide evidence that glycosylation of can contribute to the allergenicity of a protein. Accordingly, rational substitution of amino acid residues likely to be the targets of glycosylation within a subject allergen protein may reduce or eliminate the allergenic properties of the protein without adversely affecting the enzymatic, insecticidal, antifungal or other functional properties of the protein.

Glycosylation commonly occurs as either N-linked or O-linked forms. N-linked glycosylation usually occurs at the motif Asn-Xaa-Ser/Thr, where Xaa is any amino acid except Pro (Kasturi, L. et al., *Biochem J.* 323: 415–519, 1997; Melquist, J. L. et al., *Biochemistry* 37: 6833–6837, 1998). O-linked glycosylation occurs between the hydroxyl group of serine or threonine and an amino sugar.

Site directed mutagenesis of selected asparagine, serine, or threonine may be used to reduce or eliminate the glycosylation of patatin proteins. A search of SEQ ID NO:2 for the Asn-Xaa-Ser/Thr motif reveals one occurrence at amino acid positions 202–204. Mutagenization of the nucleic acid sequence encoding this region may result in a reduced allergenicity of the encoded protein.

In order to test this conceptual approach to reducing allergenicity of patatin proteins, two sets of experiments were performed: a) production of patatin proteins in *Escherichia coli*, which do not glycosylate proteins; and b) production of patatin proteins with an N202Q site directed mutation.

Antibodies obtained from patients HS-07 and G15-MON (not potato allergic) did not show specific binding to wild type patatin, patatin produced in *E. coli*, or the N202Q variant. Antibodies obtained from patient HS-01 (potato allergic) bound to wild type patatin, but not to patatin produced in *E. coli* or the N202Q variant. Antibodies obtained from patient HS-02 (potato allergic) bound strongly to wild type patatin, but extremely weakly to patatin produced in *E. coli*, and binding to the N202Q variant resembled vector controls. Antibodies obtained from patient HS-03 (potato allergic) bound to wild type patatin, but not to patatin produced in *E. coli* or the N202Q variant. Antibodies obtained from patient HS-05 (potato allergic) bound to wild type patatin, but very weakly to patatin produced in *E. coli* and the N202Q variant. Antibodies obtained from patient HS-06 (potato allergic) strongly bound wild type patatin, the N202Q variant, and to patatin produced in *E. coli*. These results strongly suggest that glycosylation is at least partially responsible for the antigenic properties of patatin proteins, and that site directed mutagenesis may be used to reduce or eliminate specific antibody binding. Mutagenesis at position 202 of SEQ ID NO:2 may be useful for reducing or eliminating specific antibody binding.

Permuteins

The positions of the internal breakpoints described in the following Examples are found on the protein surface, and are distributed throughout the linear sequence without any obvious bias towards the ends or the middle. Breakpoints occurring below the protein surface can additionally be selected. The rearranged two subunits can be joined by a peptide linker. A preferred embodiment involves the linking of the N-terminal and C-terminal subunits by a three amino acid linker, although linkers of various sizes can be used. Additionally, the N-terminal and C-terminal subunits can be joined lacking a linker sequence. Furthermore, a portion of the C-terminal subunit can be deleted and the connection made from the truncated C-terminal subunit to the original N-terminal subunit and vice versa as previously described (Yang and Schachman, *Proc. Natl. Acad. Sci. U.S.A.*, 90: 11980–11984, 1993; Viguera, et al., *Mol. Biol.*, 247: 670–681, 1995; Protasova, et al., *Prot. Eng.*, 7: 1373–1377, 1994).

The novel insecticidal proteins of the present invention can be represented by the formula:

$$X^1\text{-}(L)_a\text{-}X^2$$

wherein;
a is 0 or 1, and if a is 0, then the permutein does not contain a linker sequence;
$X^1$ is a polypeptide sequence corresponding to amino acids n+1 through J;
$X^2$ is a polypeptide corresponding to amino acids 1 through n;
n is an integer ranging from 1 to J-1;
J is an integer greater than n+1; and
L is a linker.

In the formula above, the constituent amino acid residues of the novel insecticidal protein are numbered sequentially 1 through J from the original amino terminus to the original carboxyl terminus. A pair of adjacent amino acids within this protein can be numbered n and n+1 respectively where n is an integer ranging from 1 to J-1. The residue n+1 becomes the new N-terminus of the novel insecticidal protein and the residue n becomes the new C-terminus of the novel insecticidal protein.

For example, a parent protein sequence consisting of 120 amino acids can be selected as a starting point for designing a permutein (J=120). If the breakpoint is selected as being between position 40 and position 41, then n=40. If a linker is selected to join the two subunits, the resulting permutein will have the formula: (amino acids 41–120)-L-(amino acids 1–40). If a linker was not used, the resulting permutein will have the formula: (amino acids 41–120)-(amino acids 1–40).

The length of the amino acid sequence of the linker can be selected empirically, by using structural information, or by using a combination of the two approaches. When no structural information is available, a small series of linkers can be made whose length can span a range of 0 to 50 Å and whose sequence is chosen in order to be substantially consistent with surface exposure (Hopp and Woods, *Mol. Immunol.*, 20: 483–489, 1983; Kyte and Doolittle, *J. Mol. Biol.*, 157: 105–132, 1982; Lee and Richards, *J. Mol. Biol.*, 55: 379–400, 1971) and the ability to adopt a conformation which does not significantly affect the overall configuration of the protein (Karplus and Schulz, *Naturwissenschaften*, 72: 212–213, 1985). Assuming an average length of 2.0 to 3.8 Å per residue, this would mean the length to test would be between about 0 to about 30 residues, with 0 to about 15 residues being the preferred range. Accordingly, there are many such sequences that vary in length or composition that can serve as linkers with the primary consideration being that they be neither excessively long nor excessively short (Sandhu, et al., *Critical Rev. Biotech.*, 12: 437–467, 1992). If the linker is too long, entropy effects may destabilize the three-dimensional fold and may affect protein folding. If the linker is too short, it may destabilize the molecule due to torsional or steric strain.

Use of the distance between the chain ends, defined as the distance between the C-alpha carbons, can be used to define the length of the sequence to be used, or at least to limit the number of possibilities that can be tested in an empirical selection of linkers. Using the calculated length as a guide, linkers with a range of number of residues (calculated using 2 to 3.8 Å per residue) can be selected. These linkers can be composed of the original sequence, shortened or lengthened as necessary, and when lengthened the additional residues can be chosen to be flexible and hydrophilic as described above; or optionally the original sequence can be substituted for using a series of linkers, one example being Gly-Pro-Gly (SEQ ID NO:277); or optionally a combination of the original sequence and new sequence having the appropriate total length can be used. An alternative short, flexible linker sequence is Gly-Gly-Gly-Ser-Gly-Gly-Gly (SEQ ID NO:276).

Selection of Permutein Breakpoints

Sequences of novel patatin analogs capable of folding to biologically active molecules can be prepared by appropriate selection of the beginning (amino terminus) and ending (carboxyl terminus) positions from within the original polypeptide chain while optionally using a linker sequence as described above. Amino and carboxyl termini can be selected from within a common stretch of sequence, referred to as a breakpoint region, using the guidelines described below. A novel amino acid sequence is thus generated by selecting amino and carboxyl termini from within the same breakpoint region. In many cases, the selection of the new termini will be such that the original position of the carboxyl terminus immediately preceded that of the amino terminus. However, selections of termini anywhere within the region may result in a functional protein, and that these will effectively lead to either deletions or additions to the amino or carboxyl portions of the new sequence.

The primary amino acid sequence of a protein dictates folding to the three-dimensional structure beneficial for expression of its biological function. It is possible to obtain and interpret three-dimensional structural information using x-ray diffraction of single protein crystals or nuclear magnetic resonance spectroscopy of protein solutions. Examples of structural information that are relevant to the identification of breakpoint regions include the location and type of protein secondary structure (alpha and 3–10 helices, parallel and anti-parallel beta sheets, chain reversals and turns, and loops (Kabsch and Sander, *Biopolymers*, 22: 2577–2637, 1983), the degree of solvent exposure of amino acid residues, the extent and type of interactions of residues with one another (Chothia, C., *Ann. Rev. Biochem.*, 53: 537–572, 1984), and the static and dynamic distribution of conformations along the polypeptide chain (Alber and Mathews, *Methods Enzymol.*, 154: 511–533, 1987). In some cases additional information is known about solvent exposure of residues, one example is a site of post-translational attachment of carbohydrate which is necessarily on the surface of the protein. When experimental structural information is not available, or when it is not feasible to obtain the information, methods are available to analyze the primary amino acid sequence in order to make predictions of protein secondary and tertiary structure, solvent accessibility and the occurrence of turns and loops (Fasman, G., Ed. Plenum, New York, 1989; Robson, B. and Garnier, J. *Nature* 361: 506, 1993).

Biochemical methods can be applicable for empirically determining surface exposure when direct structural methods are not feasible; for example, using the identification of sites of chain scission following limited proteolysis in order to infer surface exposure (Gentile, F. and Salvatore, G., *Eur. J. Biochem.*, 218: 603–621, 1993). Thus, using either the experimentally derived structural information or predictive methods (Srinivasan, R. and Rose, G. D. *Proteins*, 22: 81–99, 1995), the parental amino acid sequence can be analyzed to classify regions according to whether or not they are integral to the maintenance of secondary and tertiary structure. The sequences within regions that are known to be involved in periodic secondary structure (alpha and 3–10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. Regions that are known or predicted to be in surface turns or loops, and especially those regions that are known not to be required for biological activity, can be preferred sites for new amino and carboxyl termini. Stretches of amino acid sequence that are preferred based on the above criteria can be selected as breakpoint regions.

An embodiment of the invention is directed towards patatin permutein proteins. The permutein proteins preferably maintain esterase activity and insecticidal properties. The permutein proteins preferably are less allergenic than the wild type patatin protein to individuals or animals allergic to potatoes. This can be assayed by the binding of antibodies to the wild type patatin and patatin permutein proteins.

The permutein proteins can optionally contain a linker sequence. The linker can generally be any amino acid sequence, preferably is Gly-Gly-Gly-Ser-Gly-Gly-Gly (SEQ ID NO:276) or Gly-Pro-Gly (SEQ ID NO:277), and more preferably is Gly-Pro-Gly (SEQ ID NO:277). Specific permutein proteins comprise: (amino acids 247–386 of SEQ ID NO:2)-linker-(amino acids 24–246 of SEQ ID NO:2), (amino acids 269–386 of SEQ ID NO:2)-linker-(amino acids 24–268 of SEQ ID NO:2), SEQ ID NO:247, and SEQ ID NO:259.

Embodiments of the invention also include isolated nucleic acid molecule segments comprising a structural nucleic acid sequence encoding a patatin permutein protein. The encoded permutein protein can generally be any permutein protein, and preferably comprises (amino acids 247–386 of SEQ ID NO:2)-linker-(amino acids 24–246 of SEQ ID NO:2), (amino acids 269–386 of SEQ ID NO:2)-linker-(amino acids 24–268 of SEQ ID NO:2), SEQ ID NO:247, or SEQ ID NO:259. The linker can generally be any amino acid sequence, preferably is Gly-Gly-Gly-Ser-Gly-Gly-Gly (SEQ ID NO:276) or Gly-Pro-Gly (SEQ ID NO:277), and more preferably is Gly-Pro-Gly (SEQ ID NO:277). Alternatively, the encoded patatin permutein protein can lack a linker sequence. The structural nucleic acid sequence is preferably SEQ ID NO:246 or SEQ ID NO:258.

An embodiment of the invention is directed towards recombinant vectors which encode a patatin permutein protein. The vector can comprise operatively linked in the 5' to 3' orientation: a promoter that directs transcription of a structural nucleic acid sequence; a structural nucleic acid sequence encoding a protein selected from the group consisting of: (amino acids 247–386 of SEQ ID NO:2)-linker-(amino acids 24–246 of SEQ ID NO:2); and (amino acids 269–386 of SEQ ID NO:2)-linker-(amino acids 24–268 of SEQ ID NO:2); and a 3' transcription terminator. The linker can comprise Gly-Pro-Gly (SEQ ID NO:277) or Gly-Gly-Gly-Ser-Gly-Gly-Gly (SEQ ID NO:276). Alternatively, the encoded patatin permutein protein can lack a linker sequence. The structural nucleic acid sequence can preferably be SEQ ID NO:246 or SEQ ID NO:258, and preferably encodes SEQ ID NO:247 or SEQ ID NO:259.

An additional embodiment of the invention is directed towards recombinant host cells useful for the production of a patatin permutein protein. The recombinant host cell preferably produces a patatin permutein protein. More preferably, the recombinant host cell produces a patatin permutein protein in a concentration sufficient to inhibit growth or to kill an insect which ingests the recombinant host cell. The recombinant host cell can comprise a structural nucleic acid sequence encoding a protein selected from the group consisting of: (amino acids 247–386 of SEQ ID NO:2)-linker-(amino acids 24–246 of SEQ ID NO:2); and (amino acids 269–386 of SEQ ID NO:2)-linker-(amino acids 24–268 of SEQ ID NO:2). The linker can generally be any amino acid sequence, and preferably is Gly-Pro-Gly (SEQ ID NO:277) or Gly-Gly-Gly-Ser-Gly-Gly-Gly (SEQ ID NO:276). Alternatively, the encoded patatin permutein protein can lack a linker sequence. The structural nucleic acid sequence is preferably SEQ ID NO:246 or SEQ ID NO:258, and preferably encodes SEQ ID NO:247 or SEQ ID NO:259. The structural nucleic acid sequence can be operatively linked to a promoter sequence that directs transcription of the structural nucleic acid sequence, a 3' transcription terminator, and a 3' polyadenylation signal sequence. The recombinant host cell can generally be any type of host cell, and preferably is a bacterial, fungal, or plant host cell. The bacterial cell is preferably an *Escherichia coli* bacterial cell. The fungal cell is preferably a *Saccharomyces cerevisiae*, *Schizosaccharomyces pombe*, or *Pichia pastoris* fungal cell. The plant cell can be a monocot, dicot, or conifer plant cell. The plant cell is preferably an alfalfa, banana, canola, corn, cotton, cucumber, peanut, potato, rice, soybean, sunflower, sweet potato, tobacco, tomato, or wheat plant cell.

An additional embodiment of the invention is directed towards recombinant plants which are useful for the production of patatin permutein proteins. The recombinant plant preferably produces a patatin permutein protein. More preferably, the recombinant plant produces a patatin permutein protein in a concentration sufficient to inhibit growth or to kill an insect which ingests tissue from the recombinant plant. The recombinant plant can comprise a structural nucleic acid sequence encoding a protein selected from the group consisting of: (amino acids 247–386 of SEQ ID NO:2)-linker-(amino acids 24–246 of SEQ ID NO:2); and (amino acids 269–386 of SEQ ID NO:2)-linker-(amino acids 24–268 of SEQ ID NO:2). The linker can comprise Gly-Pro-Gly (SEQ ID NO:277) or Gly-Gly-Gly-Ser-Gly-Gly-Gly (SEQ ID NO:276). Alternatively, the encoded protein can lack a linker sequence. The structural nucleic acid sequence is preferably SEQ ID NO:246 or SEQ ID NO:258, and preferably encodes SEQ ID NO:247 or SEQ ID NO:259. The structural nucleic acid sequence can be operatively linked to a promoter sequence that directs transcription of the structural nucleic acid sequence, a 3' transcription terminator, and a 3' polyadenylation signal sequence. The recombinant plant can generally be any type of plant, and preferably is an alfalfa, banana, canola, corn, cotton, cucumber, peanut, potato, rice, soybean, sunflower, sweet potato, tobacco, tomato, or wheat plant.

Permutein proteins can be prepared by isolating the permutein protein from any one of the above described host cells or plants.

Immunotherapy for Potato Allergy

Immunotherapy for food allergy has been largely unsuccessful due to the lack of appropriate therapeutic reagents (Sampson, H. A., *J. Allergy Clin. Immunol.*, 90(2): 151–152, 1992). Immunotherapy has typically involved the administration (orally or by subcutaneous injections) of increasing doses of crude protein extracts of the offending allergenic entities which usually contain variable mixes of many different proteins (Scheiner, O., *Wien Klin Wochenschr.*, 105(22): 653–658, 1993). While there are reports of highly successful clinical applications of immunotherapy for food allergens (Romano, P. C., et al., *Allergol. Immunopathol. (Madr)*, 12(4): 275–281, 1984), those reports are rare and the clinical literature in general recommends avoidance far more strongly than therapy (Gay, G., *Allerg. Immunol. (Paris)*, 29(6): 169–170, 1997). One of the primary reasons for the failure of many clinical attempts to induce tolerance to allergens in general and food allergens in particular relates to anecdotal comments by numerous allergists, that patients don't tolerate the doses of allergen required to achieve tolerance. Animal studies examining the relationship of antigen dose and the induction of tolerance have demonstrated a strong positive correlation (Chen, Y., et al., *Proc. Natl. Acad. Sci., U.S.A.*, 93: 388–391, 1996; Tokai, T., et al., *Nat. Biotechnol.*, 15(8): 754–758, 1997). Due to the very real possibility of inducing an anaphylactic reaction in patients with native allergen, most clinical therapists are quite hesitant to use high doses therapeutically and are therefore compromising the likelihood of successful therapy.

In recent reports, recombinant technology has been used to reduce the allergenic potential of a major allergen without modifying the T cell epitopes, and allowing higher doses of protein to be used in therapy (Tokai, T., et al., *Nat. Biotechnol.*, 15(8): 754–758, 1997). In addition, a lack of understanding about the appropriate route of administration, the uncertainty of mechanisms responsible for induction of allergy and the uncertainty of mechanisms by which immunotherapy suppresses or blocks the T cell-IgE-eosinophil/mast cell cycle have contributed to the large number of equivocal studies and clinical trials. Recent studies in animal models dealing with mechanisms, routes of administration, adjuvants and vaccine formulations have increased the likelihood that immunotherapy for allergies, including food allergies, will become a reproducibly successful clinical treatment when the appropriate therapeutic reagents are available (Sampson, H. A. and Burks, A. W., *Annu. Rev. Nutr.*, 16: 161–177, 1996; Kaminogawa, S., *Biosci. Biotechnol. Biochem.*, 60(11): 1749–1756, 1996; Chapman, M. D., et al., *Allergy*, 52: 374–379, 1997; Barbeau, W. E., *Adv. Exp. Med. Biol.*, 415: 183–193, 1997; Cao, Y, et al., *Immunology*, 90(1): 46–51, 1997; Garside, P. and Mowat, A. M., *Crit. Rev. Immunol.*, 17(2): 119–137, 1997; Rothe, M. J. and Grant-Kels, J. M., *J. Am. Acad. Dermatol.*, 35(1): 1–13, 1996; Strobel, S., *Allergy*, 50(20): 18–25, 1995; Kruisbeek, A. M. and Amsen, D., *Curr. Opin. Immunol.*, 8(2): 233–244, 1996; Herz, U., et al., *Adv. Exp. Med. Biol.*, 409: 25–32, 1996; Litwin, A., et al., *J. Allergy Clin. Immunol.*, 100: 30–38, 1997; Vandewalker, M. L., *Mo. Med.*, 94(7): 311, 1997; Marshall, G. D., Jr. and Davis, F., *Nat. Biotechnol.*, 15(8): 718–719, 1997; Van Deusen, M. A., et al., *Ann. Allergy Asthma Immunol.*, 78: 573–580, 1997; Jacobsen, L., et al., *Allergy*, 52: 914–920, 1997, Scheiner, O. and Kraft, D., Allergy 50(5): 384–391, 1995).

Relative to immunotherapy, the critical aspects of the modified patatin genes described in this patent are that they can be used to synthesize purified, deallergenized-protein which can be used for patatin (potato) specific immunotherapy, with reduced potential for adverse and potentially fatal anaphylactic reactions in human or veterinary patients who have allergies to patatin or potatoes. Various strategies, including fixing or cross linking allergens, encapsulation of allergen for oral delivery, the use of small, T-cell epitope peptides and most recently, the use of engineered recombinant proteins, or modified gene vaccines are being tested in attempts to decrease the potential for anaphylactic reactions while inducing tolerance (Cao, Y., et al., *Immunology*, 90(1): 46–51, 1997; Chapman, M. D., et al., *Allergy*, 52: 374–379, 1997; Chapman, M. D., et al., *Int. Arch. Allergy Immunol.*, 113(1–3): 102–104, 1997; Collins, S. P., et al., *Clin. Exp. Allergy*, 26(1): 36–42, 1996; Takai, T., et al., *Mol. Immunol.*, 34(3): 255–261, 1997; Takai, T., et al., *Nat. Biotechnol.*, 15(8) 754–758, 1997; Jirapongsananruk, O. and Leung, D. Y. M., *Ann. Allergy Asthma Immunol.*, 79: 5–20, 1997; Litwin, A., et al., *J. Allergy Clin. Immunol.*, 100: 30–38, 1997; Vandewalker, M. L., *Mo. Med.*, 94(7): 311, 1997; Raz, E., et al., *Proc. Natl. Acad. Sci., U.S.A.*, 93: 5141–5145, 1996; Hoyne, G. F., et al., *Clin. Immunol. Immunopathol.*, 80: S23–30, 1996; Hoyne, G. F., et al., *Int. Immunol.*, 9(8): 1165–1173, 1997; Vrtala, S., et al., *J. Clin. Invest.*, 99(7): 1673–1681, 1997; Sato, Y., et al., *Science*, 273: 352–354, 1996; Lee, D. J., et al., *Int. Arch. Allergy Immunol.*, 113(1–3): 227–230, 1997; Tsitoura, D. C., et al., *J. Immunol.*, 157(5): 2160–2165, 1996; Hsu, C. H., et al., *Int. Immunol.*, 8(9):1405–1411, 1996; Hsu, C. H., et al., *Nat. Med.*, 2(5): 540–544, 1996).

The instant invention uses an engineered patatin protein, as expressed in any living cell, with or without post-synthesis modifications, for immunotherapy by the routes of cutaneous or subcutaneous exposure, injection, or by oral, gastro-intestinal, respiratory or nasal application, either with, or without the use of specific carriers, vehicles and adjuvants. The direct application of nucleic acid encoding recombinant patatin as the in vivo (in the patient) expression template (gene) as RNA-, DNA- or gene-vaccines is also the intended use of the engineered genetic materials defined here, coding for patatin, but with modified IgE binding sites. It is also the intent of this patent to cover the use of these modified genes described here including insertion into various DNA vectors including adenovirus, retrovirus, pox virus and replicating or non-replicating eukaryotic expression plasmids (Lee, D. J., et al., *Int. Arch. Allergy Immunol.*, 113(1–3): 227–230, 1997) with various promoters and regulatory sequences, which can be inserted into the patient's somatic cells (dendritic cells, epithelial cells, muscle fiber-cells, fibroblasts, etc.) for the purpose of expressing the recombinant gene product to alter the patient's immune response to the patatin proteins (Lee D. J., et al., *Int. Arch. Allergy Immunol.*, 113(1–3): 227–230, 1997). Potential routes of administration foreseen in this application include previously described methods of encapsulation, emulsion, receptor or membrane fusion mediated uptake and methods of direct permeabilization or insertion of the DNA or corresponding RNA into the host cells.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Identification of Patatin as an Allergen

Since patatin is commonly obtained from an allergenic source (potato), it was hypothesized that patatins in fact encode an important class of offending potato allergens (patatin was reported as allergenic by Seppala, U. et al., *J.*

*Allergy Clin. Immunol.* 103: 165–171, 1999). Assessment of potential allergens preferably include appropriate in vitro testing for IgE binding, in this case with potato allergic sera (Fuchs, R. L. and Astwood, J. D., *Food Technology*, 50: 83–88, 1996; Astwood, J. D., et al., *Monographs in allergy Vol. 32: Highlights in food allergy*, pp. 105–120, 1996, Metcalfe, D. D., et al., *Critical Reviews in Food Science and Nutrition*, 36S: 165–186, 1996). It is the recommendation of a working group organized by the IFBC and the ILSI Allergy and Immunology Institute that proteins encoded by nucleic acid sequences from allergenic sources such as potato (a "less-commonly" allergenic source) should be examined for their ability to react with IgEs of potato-allergic patients using a minimum of five individual patient sera (Metcalfe, D. D., et al., *Critical Reviews in Food Science and Nutrition*, 36S: 165–186, 1996). Patatin-17 protein was tested for IgE binding using standard in vitro testing with serum taken from patients with bona fide well defined clinically displayed potato allergy as described below.

Clinical Characterization of Potato Allergic Subjects (Serum Donors)

Patients who suffer from potato allergy were identified at Johns Hopkins Clinic (Baltimore, Md.) and were evaluated for potato allergy using clinical criteria outlined in Table 2.

Serum was obtained from patients with convincing clinical history of potato allergy. The convincing history was defined as being one or more of the following: a) positive potato allergic as evaluated by double-blind placebo-control food challenge b) anaphylaix and/or hospitalization due to the consumption of potatoes or c) dramatic skin test results.

cessed by standard Western blotting (immunoblotting) techniques and were incubated in potato allergic serum diluted 1:5 in PBS buffer for 1 hour. After washing the blots 3 times with PBS, the blots were incubated in biotinylated anti-IgE (Johns Hopkins Hospital, Baltimore, Md.) for 1 hour, followed by a 30 minute incubation in HRP-linked avidin (Promega, New York, N.Y.). IgE-reactive protein bands were visualized by DAB staining (3,3 diaminobenzidine). The blots were dried and photographed. Individual blots are labeled according to patient serum used. As a control, one blot was incubated in anti-IgE only.

Patatins were shown to be an allergen of potato by examining the reactivity of purified patatin to sera obtained from patients allergic to potato. Sera from five potato allergic subjects were tested by Western blotting techniques. All five sera reacted with purified patatin protein.

Figures 1, 1A, 1B, 1C, 1D, 1E, 1F, 1G, 1H, 1I:
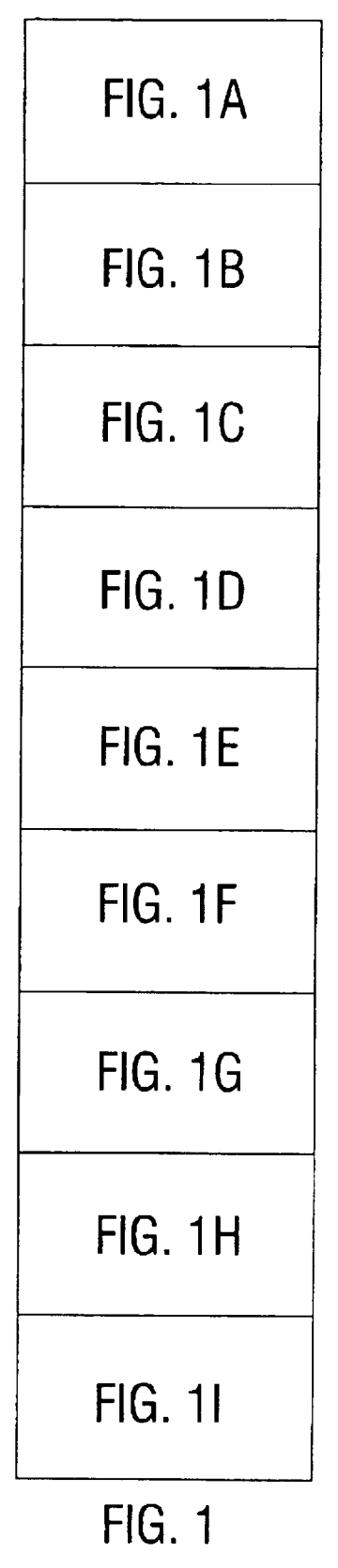

Patatin isozymes (SEQ ID NOS:278–282, FIG. 1) were tested for IgE binding by Western blotting. Isozymes of patatin were cloned into a yeast expression system and purified prior to analysis. The isozymes were subjected to IgE western blotting as described above with the exception that all five patient sera were pooled. The resulting Western blot of the yeast-expressed isozymes showed that all five isozymes bound IgE in a manner similar to patatin 17, and that all isozymes of patatin tested are also allergens.

TABLE 2

Clinical patient data

| Patient | Clinical History | Flare/Wheal (Skin prick test) | DBPCFC (potato) |
|---|---|---|---|
| HS01 | Most recent hospitalization: Oct. 19, 1993 AD, A, AR, FH, MFS, IgE = 1397 KIAUa/L | 7/19, 4/14, 7/17 | Not performed |
| HS02 | Most recent hospitalization: Jun. 1994 AD, FH, Latex (+) RAST, MFS, IgE = 7544 K/L | 20/26 | Not performed |
| HS03 | Most recent hospitalization: Jul. 27, 1995 AD, A, FH, MFS, IgE = N/A | 5/13 | Yes |
| HS05 | Most recent hospitalization May 30, 1995 AD, A, FH, MFS, IgE = 12341 ng/ml | 4/9 | Yes |
| HS06 | Most recent hospitalization Jun. 13, 1995 AD, A FH, MFS IgE = N/A | 5/20, 4/13, 5/12 | Yes |
| HS07 | Not potato allergic, allergic to egg, milk, peanuts, seafood. AD, A, AR, FH, MFS | High IgE control serum, not allergic to potato. | |
| HS08 | Non-atopic (normal) | Low IgE control serum | |

AD = Atopic dermatitis;
FH = Food hypersensitivity;
AR = Allergic rhinitis;
A = Asthma;
MFS = Multiple food sensitivity;
N/A = not available.

Example 2

Western Blotting of Patatin Proteins

Western blotting experiments were performed using patatin protein purified to near homogeneity from corn plants genetically engineered to produce patatin, patatin producing crude genetically engineered corn leaf extracts, crude potato tuber extracts, and non-transgenic corn leaf samples.

Protein samples were electrophoresed by SDS-PAGE (Laemmli, U. K., *Nature* 227: 680–685, 1970) and were electroblotted onto nitrocellulose. Protein blots were pro- Example 3

Western Blotting of Patatin Proteins

Eighty-nine 10-mer peptides were synthesized using the Genosys SPOTs system, each consecutive 10-mer overlapping by 6 amino acids based on the amino acid sequence of patatin 17 (SEQ ID NO:2). The peptides were evaluated for IgE binding with five different potato allergic patient sera using the same incubation procedures as described above. The results are summarized graphically in FIG. 2, showing major and minor allergenic epitopes. Interestingly, many of the immunogenic epitopes contain tyrosine. The peptide numbers, sequences, and immunoreactivity is detailed in Table 3.

TABLE 3

Peptide scan of patatin 17

| Peptide # (SEQ ID NO) | Peptide Sequence | HS01 | HS02 | HS03 | HS05 | HS06 | Cumulative Total |
|---|---|---|---|---|---|---|---|
| 1 (16) | QLGEMVTVLS | 0.47 | 0.33 | 0.02 | 0.05 | 0.06 | 0.93 |
| 2 (17) | MVTVLSIDGG | 0.53 | 0.33 | 0.02 | 0.07 | 0.05 | 1 |
| 3 (18) | LSIDGGGIRG | 0.52 | 0.38 | 0.07 | 0.08 | 0.09 | 1.14 |
| 4 (19) | GGGIRGIIPA | 0.53 | 0.19 | 0.06 | 0.19 | 0.23 | 1.2 |
| 5 (20) | RGIIPATILE | 0.46 | 0.28 | 0.04 | 0.09 | 0.05 | 0.92 |
| 6 (21) | PATILEFLEG | 0.49 | 0.31 | 0.05 | 0.09 | 0.07 | 1.01 |
| 7 (22) | LEFLEGQLQE | 0.36 | 0.24 | 0.04 | 0.1 | 0.06 | 0.8 |
| 8 (23) | EGQLQEMDNN | 0.29 | 0.19 | 0.02 | 0.09 | 0.05 | 0.64 |
| 9 (24) | QEMDNNADAR | 0.22 | 0.13 | 0.01 | 0.05 | 0.04 | 0.45 |
| 10 (25) | NNADARLADY | 0.21 | 0.17 | 0.03 | 0.05 | 0.07 | 0.53 |
| 11 (26) | ARLADYFDVI | 0.54 | 0.31 | 0.16 | 0.15 | 0.25 | 1.41 |
| 12 (27) | DYFDVIGGTS | 0.61 | 0.34 | 0.46 | 0.06 | 0.15 | 1.62 |
| 13 (28) | VIGGTSTGGL | 0.63 | 0.72 | 0.05 | 0.15 | 0.09 | 1.64 |
| 14 (29) | TSTGGLLTAM | 0.3 | 0.17 | 0.03 | 0.06 | 0.09 | 0.65 |
| 15 (30) | GLLTAMISTP | 0.63 | 0.41 | 0.05 | 0.24 | 0.12 | 1.45 |
| 16 (31) | AMISTPNENN | 0.34 | 0.18 | 0.02 | 0.07 | 0.02 | 0.63 |
| 17 (32) | TPNENNRPFA | 0.46 | 0.22 | 0.03 | 0.19 | 0.07 | 0.97 |
| 18 (33) | NNRPFAAAKE | 0.37 | 0.21 | 0.05 | 0.07 | 0.06 | 0.76 |
| 19 (34) | FAAAKEIVPF | 0.52 | 0.29 | 0.08 | 0.11 | 0.08 | 1.08 |
| 20 (35) | KEIVPFYFEH | 0.29 | 0.14 | 0.28 | 0.29 | 0.23 | 1.23 |
| 21 (36) | PFYFEHGPQI | 0.65 | 0.06 | 1.08 | 0.51 | 0.17 | 2.47 |
| 22 (37) | EHGPQIFNPS | 0.34 | 0.15 | 0.03 | 0.05 | 0.06 | 0.63 |
| 23 (38) | QIFNPSGQIL | 0.33 | 0.29 | 0.02 | 0.07 | 0.07 | 0.78 |
| 24 (39) | PSGQILGPKY | 0 | 0 | 0.02 | 0 | 0.05 | 0.07 |
| 25 (40) | ILGPKYDGKY | 0 | 0 | 0.07 | 0 | 0.02 | 0.09 |
| 26 (41) | KYDGKYLMQV | 0.02 | 0 | 0.11 | 0.01 | 0.04 | 0.18 |
| 27 (42) | KYLMQVLQEK | 0.12 | 0.04 | 1.08 | 0.07 | 0.79 | 2.1 |
| 28 (43) | QVLQEKLGET | 0.46 | 0.16 | 0.01 | 0.07 | 0.02 | 0.72 |
| 29 (44) | EKLGETRVHQ | 0.5 | 0.12 | 0.01 | 0.07 | 0.04 | 0.74 |
| 30 (45) | ETRVHQALTE | 0.42 | 0.16 | 0.03 | 0.05 | 0.03 | 0.69 |
| 31 (46) | HQALTEVVIS | 0.43 | 0.21 | 0.04 | 0.1 | 0.05 | 0.83 |
| 32 (47) | TEVVISSFDI | 0.44 | 0.25 | 0.05 | 0.08 | 0.04 | 0.86 |
| 33 (48) | ISSFDlKTNK | 0.1 | 0.02 | 0.04 | 0.06 | 0.13 | 0.35 |
| 34 (49) | DIKTNKPVIF | 0.57 | 0.22 | 0.04 | 0.18 | 0.28 | 1.29 |
| 35 (50) | NKPVIFTKSN | 0 | 0.01 | 0.02 | 0.07 | 0.24 | 0.34 |
| 36 (51) | IFTKSNLANS | 0 | 0 | 0.03 | 0.06 | 0.17 | 0.26 |

TABLE 3-continued

Peptide scan of patatin 17

| Peptide # (SEQ ID NO) | Peptide Sequence | HS01 | HS02 | HS03 | HS05 | HS06 | Cumulative Total |
|---|---|---|---|---|---|---|---|
| 37 (52) | SNLANSPELD | 0.43 | 0.96 | 0.01 | 0.09 | 0.02 | 1.51 |
| 38 (53) | NSPELDAKMY | 0.18 | 0.12 | 0.01 | 0.05 | 0.05 | 0.41 |
| 39 (54) | LDAKMYDISY | 0.54 | 0.26 | 0.19 | 0.15 | 0.23 | 1.37 |
| 40 (55) | MYDISYSTAA | 0.92 | 0.08 | 0.52 | 0.04 | 0.22 | 1.78 |
| 41 (56) | SYSTAAAPTY | 1.15 | 0.25 | 1.04 | 0.33 | 0.55 | 3.32 |
| 42 (57) | AAAPTYFPPH | 1.02 | 0.52 | 1.12 | 0.81 | 0.86 | 4.33 |
| 43 (58) | TYFPPHYFVT | 0.02 | 0.01 | 0.54 | 0.03 | 0.24 | 0.84 |
| 44 (59) | PHYFVTNTSN | 0.03 | 0.01 | 1.17 | 0.13 | 0.44 | 1.78 |
| 45 (60) | VTNTSNGDEY | 0.23 | 0.15 | 0.04 | 0.03 | 0.03 | 0.48 |
| 46 (61) | SNGDEYEFNL | 0.33 | 0.25 | 0.08 | 0.1 | 0.11 | 0.87 |
| 47 (62) | EYEFNLVDGA | 0.34 | 0.25 | 0.07 | 0.1 | 0.2 | 0.96 |
| 48 (63) | NLVDGAVATV | 0.3 | 0.18 | 0.02 | 0.06 | 0.05 | 0.61 |
| 49 (64) | GAVATVADPA | 0.45 | 0.54 | 0.01 | 0.07 | 0.02 | 1.09 |
| 50 (65) | TVADPALLSI | 0.48 | 0.29 | 0.01 | 0.07 | 0.03 | 0.88 |
| 51 (66) | PALLSISVAT | 0.65 | 0.33 | 0.02 | 0.1 | 0.01 | 1.11 |
| 52 (67) | SISVATRLAQ | 0.61 | 0.23 | 0.14 | 0.53 | 0.53 | 2.04 |
| 53 (68) | ATRLAQKDPA | 0.87 | 0.34 | 0.05 | 0.29 | 0.22 | 1.77 |
| 54 (69) | AQKDPAFASI | 0.86 | 0.32 | 0.04 | 0.12 | 0.03 | 1.37 |
| 55 (70) | PAFASIRSLN | 0.81 | 0.15 | 0.05 | 0.51 | 0.59 | 2.11 |
| 56 (71) | SIRSLNYKKM | 0.07 | 0.01 | 0.17 | 0.07 | 0.11 | 0.43 |
| 57 (72) | LNYKKMLLLS | 0.05 | 0.01 | 0.35 | 0.08 | 0.39 | 0.88 |
| 58 (73) | KMLLLSLGTG | 1.15 | 0.15 | 0.04 | 0.38 | 0.71 | 2.43 |
| 59 (74) | LSLGTGTTSE | 0.34 | 0.23 | 0.02 | 0.04 | 0.03 | 0.66 |
| 60 (75) | TGTTSEFDKT | 0.92 | 0.39 | 0.6 | 0.1 | 0.09 | 2.1 |
| 61 (76) | SEFDKTYTAK | 1.33 | 1.35 | 1.41 | 0.12 | 0.28 | 4.49 |
| 62 (77) | KTYTAKEAAT | 1.36 | 0.94 | 1.11 | 0.76 | 0.4 | 4.57 |
| 63 (78) | AKEAATWTAV | 0.45 | 0.15 | 0.01 | 0.2 | 0.04 | 0.85 |
| 64 (79) | ATWTAVHWML | 0.1 | 0.02 | 0.01 | 0.08 | 0.06 | 0.27 |
| 65 (80) | AVHWMLVIQK | 0.69 | 0.05 | 0.03 | 0.43 | 0.62 | 1.82 |
| 66 (81) | MLVIQKMTDA | 0.32 | 0.15 | 0.02 | 0.15 | 0.03 | 0.67 |
| 67 (82) | QKMTDYYLST | 0.26 | 0.125 | 0.03 | 0.21 | 0.05 | 0.675 |
| 68 (83) | DAASSYMTDY | 0.2 | 0.14 | 0.08 | 0.08 | 0.1 | 0.6 |
| 69 (84) | SYMTDYYLST | 0.5 | 0.03 | 0.32 | 0.06 | 0.11 | 1.02 |

TABLE 3-continued

Peptide scan of patatin 17

| Peptide # (SEQ ID NO) | Peptide Sequence | HS01 | HS02 | HS03 | HS05 | HS06 | Cumulative Total |
|---|---|---|---|---|---|---|---|
| 70 (85) | DYYLSTAFQA | 0.14 | 0 | 0.22 | 0.03 | 0.13 | 0.52 |
| 71 (86) | STAFQALDSK | 0.4 | 0.3 | 0.04 | 0.06 | 0.08 | 0.88 |
| 72 (87) | QALDSKNNYL | 0.44 | 0.46 | 0.28 | 0.26 | 0.43 | 1.87 |
| 73 (88) | SKNNYLRVQE | 0.44 | 0.05 | 1.31 | 0.07 | 0.21 | 2.08 |
| 74 (89) | YLRVQENALT | 1.38 | 0.03 | 1.31 | 0.11 | 0.2 | 3.03 |
| 75 (90) | QENALTGTTT | 0.47 | 0.25 | 0 | 0.06 | 0 | 0.78 |
| 76 (91) | LTGTTTEMDD | 0.41 | 0.24 | 0 | 0.06 | 0 | 0.71 |
| 77 (92) | TTEMDDASEA | 0.38 | 0.3 | 0 | 0.05 | 0 | 0.73 |
| 78 (93) | DDASEANMEL | 0.44 | 0.24 | 0 | 0.06 | 0 | 0.74 |
| 79 (94) | EANMELLVQV | 0.42 | 0.27 | 0 | 0.04 | 0 | 0.73 |
| 80 (95) | ELLVQVGENL | 0.4 | 0.25 | 0 | 0.05 | 0 | 0.7 |
| 81 (96) | QVGENLLKKP | 0.44 | 0.14 | 0 | 0.07 | 0 | 0.65 |
| 82 (97) | NLLKKPVSED | 0.47 | 0.2 | 0 | 0.03 | 0 | 0.7 |
| 83 (98) | KPVSEDNPET | 0.27 | 0.21 | 0 | 0.03 | 0 | 0.51 |
| 84 (99) | EDNPETYEEA | 0.13 | 0.11 | 0 | 0.01 | 0 | 0.25 |
| 85 (100) | ETYEEALKRF | 1.26 | 1.2 | 1.36 | 0.53 | 0.71 | 5.06 |
| 86 (101) | EALKRFAKLL | 1.38 | 0.04 | 0 | 1.06 | 1.12 | 3.6 |
| 87 (102) | RFAKLLSDRK | 0.98 | 0.05 | 0 | 0.84 | 0.94 | 2.81 |
| 88 (103) | LLSDRKKLRA | 0.2 | 0.01 | 0 | 0.37 | 0.51 | 1.09 |
| 89 (104) | RKKLRANKAS | 0.28 | 0 | 0 | 0.31 | 0.64 | 1.23 |
| | Patient Cumulative Totals | 41.84 | 20.565 | 18.1 | 14.17 | 16.55 | |

Example 4
Identification of Result Effective Substitutions

For each major and several minor allergenic epitopes of patatin, result effective substitutions were identified by synthesizing peptides that were altered by individually substituting an alanine residue at each non-alanine position in the epitope. Similarly, the reported nucleic acid sequence encoding corn patatin (U.S. Pat. No. 5,882,668; clone 5c9) was evaluated for IgE binding by producing peptides at corresponding positions to the potato patatin protein.

For example, Epitope 41 was analyzed by alanine scanning and rational substitution as follows.

| Epitope 41 | SEFDKTYTAK | (SEQ ID NO:76) |
| Alanine scan | AEFDKTYTAK | (SEQ ID NO:165) |
| | SAFDKTYTAK | (SEQ ID NO:166) |
| | SEADKTYTAK | (SEQ ID NO:167) |
| | SEFAKTYTAK | (SEQ ID NO:168) |
| | SEFDATYTAK | (SEQ ID NO:169) |
| | SEFDKAYTAK | (SEQ ID NO:170) |
| | SEFDKTATAK | (SEQ ID NO:171) |
| | SEFDKTYAAK | (SEQ ID NO:172) |
| | SEFDKTYTAA | (SEQ ID NO:173) |
| Rational substitution | AFFDKTYTAK | (SEQ ID NO:283) |
| | SEFDKTFTAK | (SEQ ID NO:176) |
| Corn homolog | CIFDSTYTAK | (SEQ ID NO:284) |

Selected epitopes were analyzed by alanine scanning and rational substitution. Immunoassay with potato-allergic serum was used as described above. Table 4 summarizes the results of these experiments to identify result effective substitutions for patatin. Blank spaces in the table indicate that binding of the peptide to patient IgE was not detectable.

TABLE 4

Scanning of patatin for result effective substitutions

| Sequence | SEQ ID NO | HS03 | HS06 | HS01 | HS02 |
|---|---|---|---|---|---|
| DYFDVIGGTS | 105 | | 0.12 | 0.16 | 0.36 |
| DYFDVIAGTS | 106 | | 0.14 | 0.17 | 0.4 |
| VIGGTSTGGL | 107 | | | | 0.04 |
| VIAGTSTGAL | 108 | | | | |
| AFYFEHGPQI | 109 | | 0.96 | 0.5 | 0.78 |
| PAYFEHGPQI | 110 | | 0.75 | 0.41 | 0.69 |
| PFAFEHGPQI | 111 | | | | |
| PFYAEHGPQI | 112 | | 0.7 | 0.43 | 0.79 |
| PFYFAHGPQI | 113 | 0.93 | 1.07 | 0.59 | 1.44 |
| PFYFEAGPQI | 114 | 0.08 | 0.93 | 0.65 | 1.34 |
| PFYFEHAPQI | 115 | | 0.75 | 0.54 | 1.11 |
| PFYFEHGAQI | 116 | | 0.63 | 0.29 | 0.6 |
| PFYFEHGPAI | 117 | | 0.63 | 0.25 | 0.56 |
| PFYFEHGPQA | 118 | | 0.27 | 0.16 | 0.33 |
| TFYLENGPKI | 119 | 0.05 | 0.48 | 0.68 | 1.07 |
| PFFFEHGPQI | 120 | | | | |
| AYLMQVLQEK | 121 | | 0.26 | 0.11 | 0.53 |
| KALMQVLQEK | 122 | | | | |
| KYAMQVLQEK | 123 | 0.11 | 0.43 | 0.1 | 1.25 |
| KYLAQVLQEK | 124 | 0.22 | 0.48 | 0.11 | 1.34 |
| KYLMAVLQEK | 125 | 0.22 | 0.83 | 0.16 | 1.33 |
| KYLMQALQEK | 126 | 0.11 | 0.6 | 0.15 | 0.95 |
| KYLMQVAQEK | 127 | | 0.53 | 0.15 | 0.81 |
| KYLMQVLAEK | 128 | 0.06 | 0.69 | 0.11 | 1.34 |
| KYLMQVLQAK | 129 | 0.74 | 0.79 | 0.05 | 0.58 |
| KYLMQVLQEA | 130 | | 0.28 | 0.27 | 0.37 |
| VFLHDKIKSL | 131 | 0.06 | 0.26 | | 0.41 |
| AYSTAAAPTY | 132 | | 0.1 | 0.12 | 0.12 |
| SASTAAAPTY | 133 | | | | |
| SYATAAAPTY | 134 | | 0.16 | 0.13 | 0.37 |
| SYSAAAAPTY | 135 | | 0.13 | 0.12 | 0.32 |
| SYSTAAAATY | 136 | | 0.15 | 0.13 | 0.34 |
| SYSTAAAPAY | 137 | | 0.15 | 0.14 | 0.29 |
| SYSTAAAPTA | 138 | | 0.55 | 0.54 | 1.13 |
| CISTSAAPTY | 139 | 0.4 | | | |
| SYSTAAAPAF | 140 | 0.39 | 1.02 | 0.65 | 1.42 |
| AFAAAAAPTY | 141 | | | 0.07 | |
| SYSTAAAPTF | 142 | 0.15 | 0.97 | 0.48 | 1.09 |
| STSAAPTYFP | 143 | | 0.21 | 0.23 | 0.39 |
| STSAAPTFFP | 144 | | | | 0.23 |
| STSAAPTAFP | 145 | | | | 0.08 |
| STAAAPTFFP | 146 | | | 0.12 | 0.28 |
| AAAATYFPPH | 147 | | 0.13 | 0.1 | 0.05 |
| AAAPAYFPPH | 148 | | | 0.07 | 0.04 |
| AAAPTAFPPH | 149 | | | | |
| AAAPTYAPPH | 150 | | 0.23 | 0.14 | 0.21 |
| AAAPTYFAPH | 151 | | 0.45 | 0.18 | 0.44 |
| AAAPTYFPAH | 152 | | 0.15 | 0.07 | 0.18 |
| AAAPTYFPPA | 153 | | 0.1 | 0.06 | 0.31 |
| SAAPTYFPAH | 154 | | 0.77 | 0.73 | 0.96 |
| AAAPAFFPPH | 155 | | | | |
| AAAPPFFPPH | 156 | | | | |
| AAAPTFFPPH | 157 | | | | |
| SISVATRLAQ | 158 | | | 0.26 | 0.26 |
| AMSMLTKEVH | 159 | | | | |
| PAFASIRSLN | 160 | | | | |
| PNFNAGSPTE | 161 | | | | |
| KMLLLSLGTG | 162 | | | | |
| NYLIISVGTG | 163 | 0.49 | 1.08 | 0.64 | 1.48 |
| KMLLLSLGAG | 164 | | 0.13 | | |
| AEFDKTYTAK | 165 | 0.09 | 0.22 | | 1.34 |
| SAFDKTYTAK | 166 | 0.66 | 0.71 | 0.06 | 1.42 |
| SEADKTYTAK | 167 | | | | 0.99 |
| SEFAKTYTAK | 168 | 0.5 | 0.57 | | 0.91 |
| SEFDATYTAK | 169 | | | | 0.17 |
| SEFDKAYTAK | 170 | 0.1 | 0.24 | | 1.38 |
| SEFDKTATAK | 171 | | | | 0.81 |
| SEFDKTYAAK | 172 | 0.2 | 0.35 | | 1.39 |
| SEFDKTYTAA | 173 | | | 0.1 | 1.18 |

TABLE 4-continued

Scanning of patatin for result effective substitutions

| Sequence | SEQ ID NO | HS03 | HS06 | HS01 | HS02 |
|---|---|---|---|---|---|
| KQAEKYTAEQ | 174 | | | 0.08 | 0.24 |
| SEFDAAFAAA | 175 | | | | |
| SEFDKTFTAK | 176 | 0.09 | 0.16 | 0.07 | 1.45 |
| AEKYTAEQCA | 177 | | | | |
| ATYTAKEAAT | 178 | | 0.24 | | 0.18 |
| KAYTAKEAAT | 179 | | 0.28 | | 0.33 |
| KTATAKEAAT | 180 | | | | |
| KTYAAKEAAT | 181 | 0.1 | 0.32 | | 0.73 |
| KTYTAAEAAT | 182 | | | | 0.35 |
| KTYTAKAAAT | 183 | 0.4 | 0.59 | | 0.82 |
| KTYTAKEAAA | 184 | | | | 0.36 |
| EKYTAEQCAK | 185 | | | | |
| AAFAAAEAAT | 186 | | | | |
| KTFTAKEAAT | 187 | | | | |
| QALHCEKKYL | 188 | | | | |
| QALDSKAAYL | 189 | | | | |
| QALDSKNNFL | 190 | | | | |
| QALHCENNFL | 191 | | | | |
| CEKKYLRIQD | 192 | 1.01 | 0.16 | | |
| SKNNFLRVQE | 193 | | | | |
| SENNYLRVQE | 194 | 0.31 | 0.96 | 0.42 | 1 |
| ALRVQENALT | 195 | | | | |
| YARVQENALT | 196 | 1.06 | 1.02 | 0.05 | 0.54 |
| YLAVQENALT | 197 | 0.37 | 1.04 | 0.11 | 1.06 |
| YLRAQENALT | 198 | 1.1 | 1 | 0.06 | 1.26 |
| YLRVAENALT | 199 | 1.03 | 0.92 | 0.08 | 1.26 |
| YLRVQANALT | 200 | 1.05 | 0.92 | 0.06 | 1.24 |
| YLRVQEAALT | 201 | 0.93 | 0.92 | 0.07 | 1.11 |
| YLRVQENAAT | 202 | 0.94 | 0.93 | 0.04 | 1.24 |
| YLRVQENALA | 203 | 1.05 | 0.96 | 0.43 | 1.16 |
| YLRIQDDTLT | 204 | 1.07 | 0.85 | 0.39 | 1.12 |
| YLTVAAAALT | 205 | 1.05 | 0.86 | 0.28 | 1.33 |
| FLRVQENALT | 206 | | | | |
| NNYLRVQENA | 207 | 0.23 | 0.88 | 0.5 | 1.17 |
| KKYLRIQDDT | 208 | | | 0.26 | 0.09 | 0.37 |
| NNFLRVQENA | 209 | | | | |
| NAYLRVQENA | 210 | 0.17 | 1.02 | 0.53 | 1.06 |
| ATYEEAKLRF | 211 | 0.26 | 1.03 | | 0.65 |
| EAYEEALKRF | 212 | 0.06 | 0.43 | | 0.33 |
| ETAEEALKRF | 213 | | 1.04 | | |
| ETYAEALKRF | 214 | 0.62 | 1.02 | | 1.15 |
| ETYEAALKRF | 215 | 1.06 | 0.38 | | 0.89 |
| ETYEEAAKRF | 216 | 0.08 | 0.1 | | 0.9 |
| ETYEEALARF | 217 | | | | 0.11 |
| ETYEEALKAF | 218 | | | | 0.1 |
| ETYEEALKRA | 219 | | | | 0.1 |
| GTNAQSLADF | 220 | | | | |
| ETYEAALAAF | 221 | 0.07 | 0.78 | 0.33 | 0.77 |
| ETFEEALKRF | 222 | | | | |
| YEEALKTFAK | 223 | 1.08 | 0.85 | 0.14 | 1.46 |
| FEEALKRFAK | 224 | 0.46 | 0.72 | | 0.67 |
| AALKRFAKLL | 225 | 0.15 | 0.17 | | |
| EAAKRFAKLL | 226 | 0.08 | 0.33 | | 0.05 |
| EALARFAKLL | 227 | | 0.09 | | |
| EALKAFAKLL | 228 | | | | |
| EALKRAAKLL | 229 | 0.08 | 0.07 | | |
| EALKRFAALL | 230 | | | | |
| EALKRFAKAL | 231 | 0.06 | 0.09 | | 0.1 |
| EALKRFAKLA | 232 | 0.06 | | | 0.1 |
| QSLADFAKQL | 233 | | | | |
| AALAAFAKLL | 234 | | | | |
| LADFAKQLSD | 235 | | | | |
| DFAKQLSDER | 236 | | | | 0.17 |
| AFAALLSDRK | 237 | | | | |

Result effective substitutions were identified by a reduction in IgE binding ability with respect to the non-substituted peptide sequence. Table 5 shows the identified result effective substitutions. Blank spaces in the table indicate that binding of the peptide to patient IgE was not detectable. Many substitutions of alanine or phenylalanine for the original tyrosine resulted in reduced or eliminated antibody binding.

TABLE 5

Result effective substitutions of patatin

| Location (SEQ ID NO) | Peptide | (SEQ ID NO) | HS03 | HS06 | HS01 | HS02 |
|---|---|---|---|---|---|---|
| Minor Epitope 21 | PFYFEHGPQI | (36) | 1.08 | 0.17 | 0.65 | 0.06 |
|  | ::A::::::: | (111) |  |  |  |  |
|  | ::F::::::: (r) | (120) |  |  |  |  |
|  | :::::::::A | (118) |  | 0.27 | 0.16 | 0.33 |
| Minor Epitope 27 | KYLMQVLQEK | (42) | 1.08 | 0.79 | 0.12 | 0.04 |
|  | :A:::::::: | (122) |  |  |  |  |
|  | :::::::::A | (130) |  | 0.28 | 0.27 | 0.37 |
|  | VFLHDKIKSL (c) | (131) | 0.06 | 0.26 |  | 0.41 |
| Major Epitope 41 | SYSTAAAPTY | (56) | 1.04 | 0.55 | 1.15 | 0.25 |
|  | A::::::::: | (132) |  | 0.1 | 0.12 | 0.12 |
|  | :A:::::::: | (133) |  |  |  |  |
|  | AFAA:::::: (r) | (141) |  |  |  | 0.007 |
|  | CI::S:::::  (c) | (139) | 0.04 |  |  |  |
| Overlap Epitope 41/42 | STAAAPTYFP | (238) |  |  |  |  |
|  | ::S::::A:: (r) | (145) |  |  |  | 0.08 |
| Major Epitope 42 (57) | AAAPTYFPPH | (57) | 1.12 | 0.86 | 1.02 | 0.52 |
|  | ::::A::::: | (148) |  |  | 0.07 | 0.04 |
|  | :::::A:::: | (149) |  |  |  |  |
|  | ::::AF:::: (r) | (155) |  |  |  |  |
|  | ::::PF:::: (r) | (156) |  |  |  |  |
|  | :::::F:::: (r) | (157) |  |  |  |  |
| Major Epitope 61 | SEFDKTYTAK | (76) | 0.12 | 0.28 | 1.33 | 1.35 |
|  | ::::A::::: | (169) |  |  |  | 0.17 |
|  | KQAE:YTAEQ (c) | (174) |  |  | 0.08 | 0.24 |
|  | ::::AAFA:A (r) | (175) |  |  |  |  |
| Major Epitope 62 | KTYTAKEAAT | (77) | 1.11 | 0.04 | 1.36 | 0.94 |
|  | A::::::::: | (178) |  | 0.24 |  | 0.18 |
|  | ::A::::::: | (180) |  |  |  |  |
|  | :::::A:

N-terminus of amino acids 24–386 of SEQ ID NO:2. Position four of SEQ ID NO:7 therefore corresponds to position 23 of SEQ ID NO:2.

The concentration of patatin in the culture was determined using a patatin ELISA assay and the enzyme activity was measured using the method of Hofgen and Willmitzer (*Plant Science*, 66: 221–230, 1990). The variants containing multiple mutations were further purified using Mono Q and hydrophobic interaction chromatography (HIC). Each culture was purified by first sizing on Amicon YM10 membranes (Millipore, Bedford, Mass.) to a >10 kDa fraction, followed by chromatography on the Mono Q HR 10/10 column (Pharmacia, Piscataway, N.J.). For chromatography on the Mono Q column, the samples were loaded on the column in 25 mM Tris pH 7.5 and eluted with a gradient of 1.0 M KCl in 25 mM Tris pH 7.5. Fractions containing patatin protein were determined using SDS-PAGE. For chromatography on the HIC column, the appropriate fractions were pooled and dialyzed into 1 M ammonium sulfate in 25 mM Tris pH 7.5. The dialyzed sample was then loaded on 16/10 phenyl Sepharose column (Pharmacia, Piscataway, N.J.) and eluted with a gradient of 25 mM Tris pH7.5.

The protein concentration was determined using the Bradford method, using BSA as a standard. SDS-PAGE analysis showed that these proteins were essentially pure. The esterase activity of the newly formed variants are shown in Table 6. The activity was determined using p-nitrophenyl caprate substrate as described by Hofgen and Willmitzer (*Plant Science*, 66: 221–230, 1990).

TABLE 6

Esterase activity of patatin mutants

| Variant | Activity (mOD · min$^{-1}\mu$g$^{-1}$) |
|---|---|
| Wild type | 93.2 |
| Y106F | 51.1 |
| Y129F | 74.7 |
| Y185F | 85.6 |
| Y193F | 82.2 |
| Y185F/Y193F | 99.4 |
| Y270F | 163.4 |
| Y316F | 94.88 |
| Y362F | 130.7 |
| Y106F/Y129F/Y185F/Y193F/Y270F/Y316F/Y362F | 57.1 |
| Y185F/Y193F/Y270F/Y316F/Y362F | 161.5 |

Patatin proteins having a phenylalanine substitution at each of the amino acid positions 106, 129, 185, 193, 270, 316 and 362 (numbers correspond to positions in SEQ ID NO:2) of expressed SEQ ID NO:7 exhibit full enzyme activity. Proteins having multiple substitutions also displayed full enzyme activity.

In addition to nucleotide sequences encoding conservative amino acid changes within the fundamental polypeptide sequence, biologically functional equivalent nucleotide sequences include nucleotide sequences containing other base substitutions, additions, or deletions. These include nucleic acids containing the same inherent genetic information as that contained in the cDNA which encode peptides, polypeptides, or proteins conferring pathogen resistance the same as or similar to that of pathogen upon host cells and plants. Such nucleotide sequences can be referred to as "genetically equivalent modified forms" of the cDNA, and can be identified by the methods described herein.

Mutations made in the cDNA, plasmid DNA, genomic DNA, synthetic DNA, or other nucleic acid encoding the deallergenized gene preferably preserve the reading frame of the coding sequence. Furthermore, these mutations preferably do not create complementary regions that could hybridize to produce secondary mRNA structures, such as loops or hairpins, that would adversely affect mRNA translation.

Although mutation sites can be predetermined, it is not necessary that the nature of the mutations per se be predetermined. For example, in order to select for optimum characteristics of mutants at a given site, random mutagenesis can be conducted at the target codon.

Alternatively, mutations can be introduced at particular loci by synthesizing oligonucleotides containing a mutant sequence, flanked by restriction sites enabling ligation to fragments of the native cDNA sequence. Following ligation, the resulting reconstructed nucleotide sequence encodes a derivative form having the desired amino acid insertion, substitution, or deletion.

Example 6

Construction of Permutein Sequences

Figure 3:
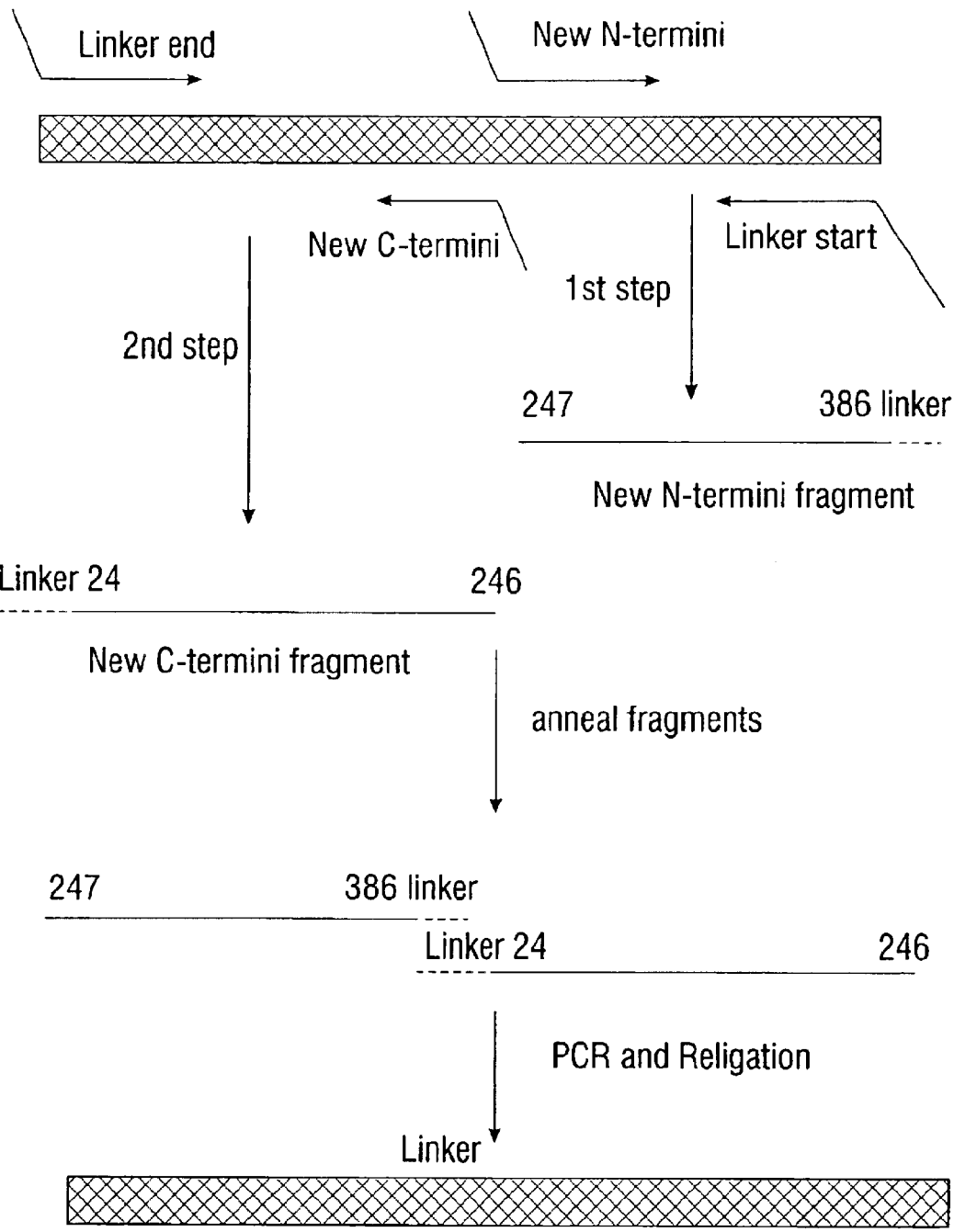
FIG. 3 illustrates construction of nucleic acid sequences encoding patatin permutein proteins, and in this figure for illustrative purposes a breakpoint at position 247 is shown.

Nucleic acid sequences encoding permutein proteins having rearranged N-terminus/C-terminus protein sequences can be made by following the general method described by Mullins et al. (*J. Am. Chem. Soc.* 116: 5529–5533, 1994). The steps are shown in FIG. 3. The Figure and the following Examples involve the design and use of a linker region separating the original C-terminus and N-terminus, but the use of a linker is not a critical or required element of permutein design.

Two sets of oligonucleotide primers are used in the construction of a nucleic acid sequence encoding a permutein protein. In the first step, oligonucleotide primers "new N-termini" and "linker start" are used in a PCR reaction to create amplified nucleic acid molecule "new N-termini fragment" that contains the nucleic acid sequence encoding the new N-terminal portion of the permutein protein, followed by the polypeptide linker that connects the C-terminal and N-terminal ends of the original protein. In the second step, oligonucleotide primers "new C-termini" and "linker end" are used in a PCR reaction to create amplified nucleic acid molecule "new C-termini fragment" that contains the nucleic acid sequence encoding the same linker as used above, followed by the new C-termini portion of the permutein protein. The "new N-termini" and "new C-termini" oligonucleotide primers are designed to include appropriate restriction enzyme recognition sites which assist in the cloning of the nucleic acid sequence encoding the permutein protein into plasmids.

Any suitable PCR conditions and polymerase can be used. It is desirable to use a thermostable DNA polymerase with high fidelity to reduce or eliminate the introduction of sequence errors. Typical PCR conditions are 25 cycles 94° C. denaturation for 1 minute, 45° C. annealing for one minute and 72° C. extension for 2 minutes; plus one cycle 72° C. extension for 10 minutes. A 50 μL reaction contains 30 pmol of each primer and 1 μg of template DNA; and 1×PCR buffer with MgCl$_2$, 200 μM dGTP, 200 μM dATP, 200 μM dTTP, 200 μM dCTP, 2.5 units of Pwo DNA polymerase. PCR reactions are performed in RoboCycler Gradient 96 Temperature Cycler (Stratagene, La Jolla, Calif.).

The amplified "new N-termini fragment" and "new C-termini fragment" are annealed to form a template in a third PCR reaction to amplify the full-length nucleic acid sequence encoding the permutein protein. The DNA fragments "new N-termini fragment" and "new C-termini fragment" are resolved on a 1% TAE gel, stained with ethidium bromide, and isolated using the QIAquick Gel Extraction Kit (Qiagen, Valencia, Calif.). These fragments are combined in equimolar quantities with oligonucleotide primers "new N-termini" and "new C-termini" in the third PCR reaction. The conditions for the PCR are the same as used previously. PCR reaction products can be purified using the QIAquick PCR purification kit (Qiagen, Valencia, Calif.).

Alternatively, a linker sequence can be designed containing a restriction site, allowing direct ligation of the two amplified PCR products.

Example 7
Construction of Plasmid pMON 37402

The patatin protein contains a trypsin protease sensitive site at the arginine amino acid at position 246, as determined by electrophoresis of a trypsin digest reaction. In order to determine if the exposed protease site is an antigenic epitope, a permutein was constructed using positions 246–247 as a breakpoint.

The nucleic acid sequence encoding the permutein protein in plasmid pMON 37402 was created using the method illustrated in FIG. 3 and described in Example 6. Nucleic acid molecule "new N-termini fragment" was created and amplified from the sequence encoding patatin in plasmid pMON26820 using oligonucleotide primers 27 (SEQ ID NO:242) and 48 (SEQ ID NO:243). Nucleic acid molecule "new C-termini fragment" was created and amplified from the sequence encoding patatin in plasmid pMON26820 using oligonucleotide primers 47 (SEQ ID NO:244) and 36 (SEQ ID NO:245). The full-length nucleic acid molecule encoding the permutein protein was created and amplified from annealed fragments "new N-termini fragment" and "new C-termini fragment" using oligonucleotide primers 27 (SEQ ID NO:242) and 36 (SEQ ID NO:245).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform *E. coli* strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON 37402 (containing SEQ ID NO:246, encoding protein sequence SEQ ID NO:247).

Example 8
Construction of Plasmid pMON 37405

Amino acids 201–202, near tyrosine 193, were chosen as a breakpoint for the construction of a permutein protein.

The nucleic acid sequence encoding the permutein protein in plasmid pMON 37405 was created using the method illustrated in FIG. 3 and described in Example 6. Nucleic acid molecule "New N-termini fragment" was created and amplified from the sequence encoding patatin in plasmid pMON26820 using oligonucleotide primers 48 (SEQ ID NO:243) and 58 (SEQ ID NO:249). Nucleic acid molecule "New C-termini fragment" was created and amplified from the sequence encoding patatin in plasmid pMON26820 using oligonucleotide primers 47 (SEQ ID NO:244) and 59 (SEQ ID NO:249). The full-length nucleic acid molecule encoding the permutein protein was created and amplified from annealed fragments "New N-termini fragment" and "New C-termini fragment" using oligonucleotide primers 58 (SEQ ID NO:248) and 59 (SEQ ID NO:249).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform *E. coli* strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON 37405 (containing SEQ ID NO:250, encoding protein sequence SEQ ID NO:251).

Example 9
Construction of Plasmid pMON 37406

Amino acids 183–184, adjacent to tyrosine 185, were chosen as a breakpoint for the construction of a permutein protein.

The nucleic acid sequence encoding the permutein protein in plasmid pMON 37406 was created using the method illustrated in FIG. 3 and described in Example 6. Nucleic acid molecule "New N-termini fragment" was created and amplified from the sequence encoding patatin in plasmid pMON26820 using oligonucleotide primers 48 (SEQ ID NO:243) and 60 (SEQ ID NO:252). Nucleic acid molecule "New C-termini fragment" was created and amplified from the sequence encoding patatin in plasmid pMON26820 using oligonucleotide primers 47 (SEQ ID NO:244) and 61 (SEQ ID NO:253). The full-length nucleic acid molecule encoding the permutein protein was created and amplified from annealed fragments "New N-termini fragment" and "New C-termini fragment" using oligonucleotide primers 60 (SEQ ID NO:252) and 61 (SEQ ID NO:253).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform *E. coli* strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON37406 (containing SEQ ID NO:254, encoding protein sequence SEQ ID NO:255).

Example 10
Construction of Plasmid pMON 37407

Amino acids 268–269, adjacent to tyrosine 270, were chosen as a breakpoint for the construction of a permutein protein.

The nucleic acid sequence encoding the permutein protein in plasmid pMON 37407 was created using the method illustrated in FIG. 3 and described in Example 6. Nucleic acid molecule "New N-termini fragment" was created and amplified from the sequence encoding patatin in plasmid pMON26820 using oligonucleotide primers 48 (SEQ ID NO:243) and 62 (SEQ ID NO:256). Nucleic acid molecule "New C-termini fragment" was created and amplified from the sequence encoding patatin in plasmid pMON26820 using oligonucleotide primers 47 (SEQ ID NO:244) and 63 (SEQ ID NO:257). The full-length nucleic acid molecule encoding the permutein protein was created and amplified from annealed fragments "New N-termini fragment" and "New C-termini fragment" using oligonucleotide primers 62 (SEQ ID NO:256) and 63 (SEQ ID NO:257).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform *E. coli* strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON37407 (containing SEQ ID NO:258, encoding protein sequence SEQ ID NO:259).

Example 11
Construction of Plasmid pMON 37408

Amino acids 321–322, near tyrosine 216, were chosen as a breakpoint for the construction of a permutein protein.

The nucleic acid sequence encoding the permutein protein in plasmid pMON 37408 was created using the method illustrated in FIG. 3 and described in Example 6. Nucleic acid molecule "New N-termini fragment" was created and amplified from the sequence encoding patatin in plasmid pMON26820 using oligonucleotide primers 48 (SEQ ID NO:243) and 64 (SEQ ID NO:260). Nucleic acid molecule "New C-termini fragment" was created and amplified from the sequence encoding patatin in plasmid pMON26820 using oligonucleotide primers 47 (SEQ ID NO:244) and 65 (SEQ ID NO:261). The full-length nucleic acid molecule encoding the permutein protein was created and amplified from annealed fragments "New N-termini fragment" and "New C-termini fragment" using oligonucleotide primers 64 (SEQ ID NO:260) and 65 (SEQ ID NO:261).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform *E. coli* strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON37408 (containing SEQ ID NO:262, encoding protein sequence SEQ ID NO:263).

Example 12
Production of Permutein Proteins in *Pichia pastoris*

Plasmids pMON37402, pMON37405, pMON37406, pMON37407, and pMON37408 were individually used to electroporate KM71 cells from *Pichia pastoris* according to the procedure supplied by the manufacturer (Invitrogen, Carlsbad, Calif.). The resulting transformed cells were used to produce protein in *Pichia pastoris* following the procedure supplied by the manufacturer (Invitrogen, Carlsbad, Calif.).

The concentration of patatin in the culture was determined using a patatin ELISA assay and the enzyme activity was measured using the method of Hofgen and Willmitzer (*Plant Science*, 66: 221–230, 1990). The variants containing multiple mutations were further purified using Mono Q and hydrophobic interaction chromatography (HIC). Each culture was purified by first sizing on YM10 membranes (Amicon, Mass.) to a [>10 kDa] fraction, followed by chromatography on the Mono Q HR 10/10 column (Pharmacia, N.J.). For chromatography on the Mono Q column, the samples were loaded on the column in 25 mM Tris pH 7.5 and eluted with a gradient of 1.0 M KCl in 25 mM Tris pH 7.5. Fractions containing patatin protein were determined using SDS-PAGE. For chromatography on the HIC column, the appropriate fractions were pooled and dialyzed into 1 M ammonium sulfate in 25 mM Tris pH 7.5. The dialyzed sample was then loaded on 16/10 phenyl Sepharose column (Pharmacia, N.J.) and eluted with a gradient of 25 mM Tris pH7.5.

The protein concentration was determined using the Bradford method, using BSA as a standard. SDS-PAGE analysis showed that these proteins were essentially pure. The esterase activity of the variants are shown in Table 7.

TABLE 7

| | Activity of permuteins | |
|---|---|---|
| pMON | Breakpoint | Activity ($\Delta$OD min$^{-1}\mu$g$^{-1}$) |
| Native enzyme | | 83.21 |
| pMON37402 | 246/247 | 66.7 |
| pMON37405 | 201/202 | No expression |
| pMON37406 | 183/184 | No expression |
| pMON37407 | 268/269 | 12.1 |
| pMON37408 | 321/322 | No expression |

The activity was determined using p-nitrophenyl caprate substrate as described by Hofgen and Willmitzer (*Plant Science*, 66: 221–230, 1990).

Example 13
Insect Bioefficacy Assays

Assays for activity against larvae of SCRW are carried out by overlaying the test sample on an agar diet similar to that described by Marrone (*J. Econ. Entom*. 78: 290–293, 1985). Test samples were prepared in 25 mM Tris, pH 7.5 buffer. Neonate larvae are allowed to feed on the treated diet at 26° C., and mortality and growth stunting were evaluated after 5 or 6 days. The results of this assay are shown in Table 8.

TABLE 8

Insect bioefficacy assay

| Protein (200 ppm) | Mean Survival Weight | % Weight Reduction |
|---|---|---|
| Tris buffer (control) | 1.26 ± 0.3 | — |
| Wild Type | 0.21 ± 0.02 | 83 |
| pMON37402 | 0.21 ± 0.03 | 83 |
| pMON37407 | 0.32 ± 0.04 | 75 |

These data demonstrate that the growth of the SCRW larvae is similarly reduced upon ingestion of the proteins encoded by pMON37402 and pMON37407 as compared to the wild type patatin protein.

Example 14

Permutein Sequences Improved for Monocot Expression

Modification of coding sequences has been demonstrated above to improve expression of insecticidal proteins. A modified coding sequence was thus designed to improve expression in plants, especially corn (SEQ ID NO:264).

Example 15
Construction of pMON40701 for Monocot Expression

Plasmid pMON19767 was digested with restriction endonucleases NcoI and EcoRI and the 1100 bp gene fragment was purified using the QIAquick PCR purification kit (Qiagen, Valencia, Calif.). Plasmid pMON33719 was digested with restriction endonucleases NcoI and EcoRI, and gel purified, resulting in an approximately 3900 base pair vector fragment. The two purified restriction fragments were combined and ligated using T4 DNA ligase.

The ligation reaction mixture was used to transform E. coli strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON40700. Plasmid pMON40700 was digested with restriction endonuclease NotI and the resulting 2200 bp DNA fragment was purified using the QIAquick PCR purification kit (Qiagen, Valencia, Calif.). Plasmid pMON30460 was digested with restriction endonuclease NotI, and gel purified, resulting in an approximately 4200 base pair vector fragment. The two purified restriction fragments were combined and ligated using T4 DNA ligase.

The ligation reaction mixture was used to transform E. coli strain DH5α cells (Life Technologies, Gaithersburg, Md.). Transformant bacteria were selected on kanamycin-containing plates. The resulting plasmid was designated pMON40701 (containing SEQ ID NO:264, encoding protein sequence SEQ ID NO:265).

Example 16
Construction of pMON40703 for Monocot Expression

The nucleic acid sequence encoding the permutein protein in plasmid pMON40703 was created using the method illustrated in FIG. 3 and described in Example 6. Nucleic acid molecule "New N-termini fragment" was created and amplified from the sequence encoding patatin in plasmid pMON19767 using oligonucleotide primers Syn1 (SEQ ID NO:266) and Syn2 (SEQ ID NO:267). Nucleic acid molecule "New C-termini fragment" was created and amplified from the sequence encoding patatin in plasmid pMON19767 using oligonucleotide primers Syn3 (SEQ ID NO:268) and Syn4 (SEQ ID NO:269). The full-length nucleic acid molecule encoding the permutein protein was created and amplified from annealed fragments "New N-termini fragment" and "New C-termini fragment" using oligonucleotide primers Syn1 (SEQ ID NO:266) and Syn4 (SEQ ID NO:269).

The resulting amplified nucleic acid molecule was digested with restriction endonucleases NcoI and EcoRI, and purified using the QIAquick PCR purification kit (Qiagen, Valencia, Calif.). Plasmid pMON33719 was digested with restriction endonucleases NcoI and EcoRI, and gel purified, resulting in an approximately 3900 base pair vector fragment. The purified restriction fragments were combined and ligated using T4 DNA ligase.

The ligation reaction mixture was used to transform E. coli strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON40702. Plasmid pMON40702 was digested with NotI, and the resulting 2200 bp DNA fragment was purified using the QIAquick PCR purification kit (Qiagen, Valencia, Calif.). Plasmid pMON30460 was digested with restriction endonuclease NotI, and gel purified, resulting in an approximately 4200 base pair vector fragment. The purified restriction fragments were combined and ligated using T4 DNA ligase.

The ligation reaction mixture was used to transform E. coli strain DH5α cells (Life Technologies, Gaithersburg, Md.). Transformant bacteria were selected on kanamycin-containing plates. The resulting plasmid was designated pMON40703 (containing SEQ ID NO:270, encoding protein sequence SEQ ID NO:271). Plasmid pMON40703 encodes a permutein protein with a "breakpoint" at positions 246/247 of the wild type patatin protein sequence (SEQ ID NO:2). The first 23 amino acids of SEQ ID NO:2 are a signal peptide sequence which is cleaved in the mature protein.

Example 17
Construction of pMON40705 for Monocot Expression

The nucleic acid sequence encoding the permutein protein in plasmid pMON40705 was created using the method illustrated in FIG. 3 and described in Example 6. Nucleic acid molecule "New N-termini fragment" was created and amplified from the sequence encoding patatin in plasmid pMON19767 using oligonucleotide primers Syn10 (SEQ ID NO:272) and Syn2 (SEQ ID NO:267). Nucleic acid molecule "New C-termini fragment" was created and amplified from the sequence encoding patatin in plasmid pMON19767 using oligonucleotide primers Syn3 (SEQ ID NO:268) and Syn11 (SEQ ID NO:273). The full-length nucleic acid molecule encoding the permutein protein was created and amplified from annealed fragments "New N-termini fragment" and "New C-termini fragment" using oligonucleotide primers Syn10 (SEQ ID NO:272) and Syn11 (SEQ ID NO:273).

The resulting amplified nucleic acid molecule was digested with restriction endonucleases NcoI and EcoRI, and purified using the QIAquick PCR purification kit (Qiagen, Valencia, Calif.). Plasmid pMON33719 was digested with restriction endonucleases NcoI and EcoRI, and gel purified, resulting in an approximately 3900 base pair vector fragment. The purified restriction fragments were combined and ligated using T4 DNA ligase.

The ligation reaction mixture was used to transform E. coli strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON40704. Plasmid pMON40704 was digested with restriction endonuclease NotI, and the resulting 2200 bp DNA fragment was purified using the QIAquick PCR purification kit (Qiagen, Valencia, Calif.). Plasmid pMON30460 was digested with restriction endonuclease NotI, and gel purified, resulting in an approximately 4200 base pair vector fragment. The purified restriction fragments were combined and ligated using T4 DNA ligase.

The ligation reaction mixture was used to transform E. coli strain DH5α cells (Life Technologies, Gaithersburg, Md.). Transformant bacteria were selected on plates containing kanamycin. The resulting plasmid was designated pMON40705 (containing SEQ ID NO:274, encoding protein sequence SEQ ID NO:275). Plasmid pMON40705 encodes a permutein protein with a "breakpoint" at positions 268/269 of the wild type patatin protein sequence (SEQ ID NO:2). The first 23 amino acids of SEQ ID NO:2 are a signal peptide sequence which is cleaved in the mature protein.

Example 18
Transient Expression of Protein in Corn Leaf Protoplasts

Plasmids pMON40701, pMON40703, and pMON40705 (all containing the native signal sequence for vacuolar targeting) were separately electroporated into corn leaf protoplasts as described by Sheen (*Plant Cell* 3: 225–245, 1991). Protein was extracted with glass beads and the supernatant was assayed for protein expression using ELISA for patatin and NPTII. Expression of protein by the transformed corn protoplasts was confirmed by Western blot analysis. Expression results are shown in Table 9.

TABLE 9

ELISA data

| Sample | Patatin ELISA (μg/mL) | NPTII ELISA (μg/mL) | Normalized Expression (Patatin ELISA/ NPTII ELISA) |
|---|---|---|---|
| pMON40701 | 1.1 | 0.6 | 1.8 |
| pMON40703 | 2.1 | 0.3 | 7.0 |
| pMON40705 | 1.3 | 0.6 | 2.2 |

The results indicate that the permutein encoded by plasmid pMON40703 surprisingly shows approximately 4-fold higher expression compared to the wild type enzyme.

Example 19
Deglycosylation of Protein Sequences

This example provides evidence that glycosylation of can contribute to the allergenicity of a protein. Accordingly, rational substitution of amino acid residues likely to be the targets of glycosylation within a subject allergen protein may reduce or eliminate the allergenic properties of the protein without adversely affecting the enzymatic, insecticidal, antifungal or other functional properties of the protein.

Glycosylation commonly occurs as either N-linked or O-linked forms. N-linked glycosylation usually occurs at the motif Asn-Xaa-Ser/Thr, where Xaa is any amino acid except Pro (Kasturi, L. et al., *Biochem J.* 323: 415–519, 1997; Melquist, J. L. et al., *Biochemistry* 37: 6833–6837, 1998). O-linked glycosylation occurs between the hydroxyl group of serine or threonine and an amino sugar.

Site directed mutagenesis of selected asparagine, serine, or threonine may be used to reduce or eliminate the glycosylation of patatin proteins. A search of SEQ ID NO:2 for the Asn-Xaa-Ser/Thr motif reveals one occurrence at amino acid positions 202–204. Mutagenization of the nucleic acid sequence encoding this region results in a reduced allergenicity of the encoded protein.

In order to test this approach to reducing allergenicity of patatin proteins, two sets of experiments were performed: a) production of patatin proteins in *Escherichia coli*, which do not glycosylate proteins; and b) production of patatin proteins with an N202Q site directed mutation.

Antibodies obtained from patients HS-07 and G15-MON (not potato allergic) did not show specific binding to wild type patatin, patatin produced in *E. coli*, or the N202Q variant. Antibodies obtained from patient HS-01 (potato allergic) bound to wild type patatin, but not to patatin produced in *E. coli* or the N202Q variant. Antibodies obtained from patient HS-02 (potato allergic) bound strongly to wild type patatin, but extremely weakly to patatin produced in *E. coli*, and binding to the N202Q variant resembled vector controls. Antibodies obtained from patient HS-03 (potato allergic) bound to wild type patatin, but not to patatin produced in *E. coli* or the N202Q variant. Antibodies obtained from patient HS-05 (potato allergic) bound to wild type patatin, but very weakly to patatin produced in *E. coli* and the N202Q variant. Antibodies obtained from patient HS-06 (potato allergic) strongly bound wild type patatin, the N202Q variant, and to patatin produced in *E. coli*. These results strongly suggest that glycosylation is at least partially responsible for the antigenic properties of patatin proteins, and that site directed mutagenesis may be used to reduce or eliminate specific antibody binding. Mutagenesis at position 202 of SEQ ID NO:2 may be useful for reducing or eliminating specific antibody binding.

The deglycosylation approach was also tested using a patatin homolog, Pat17. As demonstrated above, patatin epitopes exhibiting IgE binding were identified, and each contained a Tyr residue. Substitution of these Tyr residues within each epitope led to loss of IgE binding. Site-directed mutagenesis was used to produce variants with individual and multiple Tyr substitutions in the protein, which was expressed in *Pichia pastoris* and assessed for enzyme activity. All the variants were found to have enzymatic activity no less than the wild type protein. A single variant with all 5 tyrosine residues substituted with phenylalinine was found to have insecticidal activity no less than the unsubstituted protein and was expressed in *E. coli* to produce the non-glycosylated version. The *E. coli* 5-"Tyr to Phe" variant was assessed for IgE binding. An isozyme of patatin, designated Pat17, was also expressed in corn to produce a plant glycoprotein and in *E. coli* to produce a nonglycosylated protein. Sera of seven patients (five exhibiting potato allergy and one exhibiting other allergies but no allergy to potatoes) were were used to assay Pat17 or Pat17 variant binding by immunoblot assay. Four of the five sera from patients exhibiting potato allergy showed either very weak or no binding to wild type patatin expressed in *E. coli* but did bind to the 5-Tyr variant. Serum from one patient exhibiting potato allergy showed strong binding to recombinant wild type patatin protein expressed in *E. coli* but weak binding to the 5-Tyr variant. Sera from all five patients exhibiting potato allergy bound strongly to patatin expressed in corn and native patatin present in potatoes. Serum from a control patient allergic to eggs, milk, peanuts and seafood, but exhibiting no allergy to potatoes showed no binding to patatin expressed in *E. coli* but did bind to patatin expressed in corn. Immunoblot results suggested that the sugar moiety in patatin is a non-specific IgE binding epitope and the polypeptide portion of patatin also contains immunogenic IgE epitopes.

Patients who suffer from potato allergy were identified at Johns Hopkins Clinic (Baltimore, Md.) and were evaluated for potato allergy using clinical criteria outlined in Table 2.

Serum was obtained from patients with convincing clinical history of potato allergy. The convincing history was defined as being one or more of the following: a) positive potato allergic reaction as evaluated by double-blind placebo-control food challenge b) anaphylaix and/or hospitalization due to the consumption of potatoes or c) dramatic skin test results.

Peptide Synthesis

Peptides were synthesized on cellulose membranes using the SPOTS system (Genosys Biotechnologies, TX). Membranes were stored at −20° C. until use.

Site Directed Mutagenesis

Site specific mutations were introduced into patatin by first incorporating part of the a-factor signal sequence (*Pichia* expression manual, Invitrogen, Carlsbad, Calif.) to the patatin gene using PCR. Primers used for the PCR were GGAGCTCGAGAAAAGAGAGGCTGAAGCT-CAGTTGGGAGAAATGGTGACTGTTCT (SEQ ID NO: 3) (XhoI site in italics) and GGTCTAGAG GAATTCTCAT-TAATAAGAAG (SEQ ID NO: 4) (EcoRI site in italics). The primers contained restriction sites to facilitate cloning into Pichia pastoris yeast secretion vector pPIC9 (GenBank accession number Z46233; Invitrogen, Carlsbad, Calif.). Typical PCR conditions are 25 cycles 94° C. denaturation for 1 minute, 45° C. annealing for one minute and 72° C. extension for 2 minutes; plus one cycle 72° C. extension for 10 minutes. A 50 mL reaction contained 30 pmol of each primer and 1 mg of template DNA; and 1×PCR buffer with MgCl$_2$, 200 mM dGTP, 200 mM dATP, 200 mM dTTP, 200 mM dCTP, 2.5 units of Pwo DNA polymerase. PCR reactions are performed in RoboCycler Gradient 96 Temperature Cycler (Stratagene, La Jolla, Calif.).

The amplified patatin gene was digested with restriction enzymes XhoI and EcoRI and cloned into the pBluescript vector (Stratagene, La Jolla, Calif.), digested with the same two restriction enzymes. The template plasmid DNA used for the PCR was pMON26820. The resulting plasmid (pMON 26869) was used for oligonucleotide-directed mutagenesis using the Bio-Rad mutagenesis kit based on the method of Kunkel et al., *Proc Natl Acad Sci USA* 82, 477–92 (1985). Briefly, single-stranded pMON26869 was used as template for mutagenesis and was prepared by superinfection of plasmid containing cells with M13K07 (Gorman et al., *DNA and Protein Engineering techniques* 2, 3–10 (1990)). DNA purified from transformed DH5a *E. coli* colonies was used for sequence determination. Sequencing was performed using the ABI PRISM sequencing kit (Perkin Elmer Biosystems, Foster City, Calif.).

Protein Expression in *Pichia pastoris*

Plasmids containing the mutations in the patatin gene were digested with restriction enzymes XhoI and EcoRI. The patatin nucleic acid fragment was then ligated into the pPIC9 vector (Invitrogen, Carlsbad, Calif.), digested with the same two restriction enzymes to afford plasmid pMON37401. *Pichia pastoris* KM71 cells were electroporated with pMON37401 containing the appropriate mutation. The resulting transformed cells were used to produce protein in *Pichia pastoris* using the procedure supplied by the manufacturer (Invitrogen, Carlsbad, Calif.). The proteins were purified in the same way as the proteins expressed in *E. coli* (see below).

Western Blotting of Proteins

Protein samples were electrophoresed by SDS-PAGE and electroblotted onto PVDF membrane (Millipore, Bedford Mass.). Protein blots were processed by standard Western blotting (immunoblotting) techniques and were incubated in potato allergic serum diluted 1:5 in PBS buffer for 1 hour. After washing the blots 3 times with PBS, the blots were incubated in biotinylated anti-IgE (Johns Hopkins Hospital, Baltimore Md.) for 1 hour, followed by a 30 minute incubation in HRP-linked avidin (Promega, New York, N.Y.). IgE-reactive protein bands were visualized by using the ECL system (Amersham Pharmacia Biotech, N.J.). As a control, one blot was incubated in anti-IgE only. His-tagged glyphosate oxidase and potato extracts was prepared and provided for this study by Regulatory Sciences, Monsanto Company. The peptides were evaluated using the same incubation procedures as described above.

Expression and Purification of Patatin in Corn

An isozyme of patatin, Pat17, was generated for expression in corn using a modified plant optimized gene sequence as described by Brown et al (U.S. Pat. No. 5,689,052). All the constructs contained the native 23 amino acid signal peptide for vacuolar targeting. Corn was transformed by microprojectile bombardment (Morrish et al., in *Transgenic plants. Fundamentals and Applications* (ed. Hiatt, A.) 133–171 (Marcel Dekker, New York, 1993); Songstad et al., *In Vitro Cell Dev Biol—Plant* 32, 179–183 (1996)). Protein from the transformed corn plants was purified by first grinding the leaves in liquid nitrogen and extracting the protein using 25 mM Tris/HCl. The plant extract was further dialyzed against 25 mM Tris/HCl pH 7.5. The plant extract was then loaded onto Mono Q HR 10/10 anion-exchange column (Amersham Pharmacia, N.J.) equilibrated with 25 mM Tris/HCl pH 7.5 (buffer A). The protein was eluted with 25 mM Tris/HCl pH 7.5, 1 M KCl (buffer B) using a linear gradient of 0–100% buffer B using an HPLC system (Shimadzu). Fractions containing protein were assayed for esterase activity and dialyzed against 25 mM Tris/HCl pH 7.5, 1 M Ammonium Sulfate (buffer C). The protein was purified to homogeneity by loading onto a phenyl-Sepharose 16/10 column (Amersham Pharmacia, N.J.) equilibrated with buffer C. Esterase active fractions were pooled and dialyzed against 25 mM Tris/HCl pH 7.5.

Expression and Purification of Patatin in *E. coli*

Pat17 was expressed in *E. coli* using the pET expression system (Novagen, Wis.). The coding region of the mature Pat17 gene (without its signal peptide) was amplified by PCR using the primers 5'-GGGCCATGGCGCAGTTGGGAGAAATGGTG-3' (SEQ ID NO: 294) (NcoI site in italics) and 5'-AACAAAGCTTCTTATTGAGGTGCGGCCGCTTG CATGC-3' (SEQ ID NO: 295) (NotI site in italics) using standard PCR reaction conditions as described in the Gene Amp kit (Perkin-Elmer Cetus, Conn.) and an annealing temperature of 40° C. The template was plasmid pMON26820. The resulting DNA was digested with NcoI and NotI and cloned into a modified pET24d plasmid, designed to add an N-terminal hexa-histidine tag to the protein. The correct sequence of the PCR product was verified by sequencing, and the plasmid was transformed into *E.coli* BL21 (DE3), and transformants selected on LB containing 25 mg/mL kanamycin. The expression strain was grown in LB containing 25 mg/mL kanamycin and induced for 8 hrs at 28° C. with 1 mM IPTG. Cells were harvested and washed in 50 mM Tris/HCl pH 8.5, 150 mM NaCl, and lysed by French Press at 20,000 psi. His-tagged protein was recovered in the soluble fraction of lysed cells and subsequently purified using Ni—NTA resin as described in the QIAexpressionist manual (Qiagen Calif.). The partially purified protein was then dialyzed against 25 mM Tris/HCl pH 7.5 (buffer A) and loaded onto Mono Q HR 10/10 anion-exchange column (Amershani Pharmacia, N.J.) equilibrated with buffer A. The protein was eluted with 25 mM Tris/HCl pH 7.5, 1 M KCl (buffer B) using a linear gradient of 0–100% buffer B run over 30 min at a flow rate of 4 mL/min using an HPLC system (Shimadzu). Fractions containing protein were assayed for esterase activity. Esterase active fractions were pooled, concentrated and dialyzed against 25 mM Tris/HCl pH 7.5 and stored at 4° C.

Enzyme Activity Assays

Enzyme activity was measured as described previously using p-nitrophenyl caprate (Sigma, MO) as a substrate, dissolved in dimethylsulfoxide (5 mM stock solution) and diluted in 4% Triton X-100, 1% SDS to a final concentration of 1 mM. For the assay, 20 mL of protein solution was added to a mixture of 25 mL of the 1 mM substrate solution and 80 mL of 50 mM Tris pH 8.5. The enzyme activity was monitored at 405 nm in 6 sec interval for a period of 10 min.

Esterase activity was expressed as DOD min$^{-1}$ mg$^{-1}$ protein.

Insect Bioassay

The protein was also assayed for activity against larvae of *Diabrotica virigifera* (Western corn rootworm) by overlaying the test sample on an agar diet similar to that described previously (Marrone et al., *J. Econ. Entom.* 78, 290–3 (1985)). Proteins to be tested were diluted in 25 mM Tris/HCl pH 7.5 and overlayed on the diet surface. Neonate larvae were allowed to feed on the diet and mortality and growth stunting were evaluated after 6 days.

IgE Binding Epitopes on Patatin

A panel of eighty-nine overlapping peptides representing the amino acid sequence of patatin were synthesized to determine the regions responsible for IgE binding. Each peptide was 10 amino acids long and consisted of 6 amino acid overlap between the consecutive peptides. The peptides were evaluated for IgE binding with five different potato allergic patient sera. Patatin has 3 major epitopes. These major IgE binding regions represent amino acids 184–193, 188–197, 269–278 and 360–369. Other minor IgE binding regions represent amino acids 104–113, 138–147 and 316–325. The amino acids essential for IgE binding in each major and minor epitopes were determined by synthesizing peptides with single amino acid changes at each position by individually substituting an alanine residue at each non-alanine position in the epitopes. The resulting alanine substituted peptides were evaluated for IgE binding. Result effective substitutions were identified by a reduction in IgE binding with respect to the non-substituted peptide sequence. It was very interesting to note that all the epitopes contained a Tyr residue and substitution of this Tyr for Ala or Phe eliminated IgE binding.

Enzyme and Bioactivity

The Tyr residues identified to be critical for IgE binding in each of the epitopes were substituted with Phe either individually or in concert using site-directed mutagenesis. All the variants were expressed in *Pichia pastoris* and assessed for enzyme activity and insecticidal activity. The variants included Y106F, Y129F, Y185F, Y193F, Y270F, Y316F, Y362F, Y185F/Y193F, Y185F/Y193F/Y270F/Y316F/Y362F (5-Tyr) and Y106F/Y129F/Y185F/Y193F/Y270F/Y316F/Y362F (7-Tyr). All the variants maintained enzyme activity. The 5-Tyr and 7-Tyr variants were then assessed for insecticidal activity by overlaying protein (200 ppm final concentration). The proteins caused significant stunting of the larval growth as measured by the weight of the larvae after 6 days with the 5-Tyr variant showing higher insecticidal activity compared to the 7-Tyr and wild type proteins. The 7-Tyr variant was unstable upon long term storage at 4° C. and thus was not pursued further.

Immunoblotting

In order to test if the glycan moiety on patatin was important for binding of IgE, Pat17 was expressed in *E. coli* to produce a nonglycosylated protein and in corn to produce a plant glycosylated protein. The 5-Tyr variant was also expressed in *E. coli* to assess the individual contribution of the linear epitopes without the glycan moiety on the protein. The proteins were tested for binding to IgE using sera from five patients with allergy to potatoes and sera from one patient with allergies to many things but no allergy to potatoes. Proteins from both corn and *E. coli* were purified to homogeneity. These proteins were transferred to PVDF membrane (Millipore, Mass.) and subsequently probed with sera from patients with and without allergy to potatoes. A His-tagged glyphosate oxidase control was included in all the studies to verify that the His-tag did not affect the binding of IgE. Serum obtained from patient HS-07 (no allergy to potatoes) did not bind Pat17 expressed in *E. coli* but showed good binding to Pat17 from corn and also a protein at the same molecular weight in potato extract. It is interesting to note that this sera also showed strong binding to another protein (>46 kDa) in the potato. Sera from patients HS-01, HS-02, HS-03, HS-05 (allergy to potatoes) shows strong binding to Pat17 expressed in corn, but very weak to no binding to Pat17 produced in *E. coli*. Also, the sera from patients HS-01, HS-2, HS-03 and HS-05 bound to a protein of similar molecular weight in the potato extract. Sera from patients HS-01, HS-02 and HS-03 also showed binding to another protein in potato extract of a lower molecular weight (<30 kDa). Serum obtained from patient HS-06 (allergic to potatoes) showed very strong binding to wild type patatin expressed in both corn and *E. coli* but weaker binding to the 5-Tyr variant expressed in *E. coli*. Sera from HS-06 also showed very strong binding to a protein in potato extract with similar molecular weight as patatin. The sera from all the patients showed no binding to His-tagged glyphosate oxidase indicating that the His-tag does not bind IgE. These results strongly suggest that the glycan moiety on Pat17 is responsible for IgE binding in some potato allergic patients and linear epitopes also contribute to the antigenicity of patatin.

Example 20

Alternative Nucleic Acid and Protein Sequences

For future variations of the patatin protein, sequences showing high similarity to the sequences disclosed herein could be used in producing deallergenized patatin proteins and permuteins. For example, a BLAST search (Altschul, S. F. et al., *J. Mol. Biol.* 215: 403–410, 1990) can be performed to identify additional patatin sequences. Sources other than those disclosed herein can be used to obtain a patatin nucleic acid sequence, and the encoded patatin protein. Furthermore, subunit sequences from different organisms can be combined to create a novel patatin sequence incorporating structural, regulatory, and enzymatic properties from different sources.

Example 21

Nucleic Acid Mutation and Hybridization

Variations in the nucleic acid sequence encoding a patatin protein may lead to mutant patatin protein sequences that display equivalent or superior enzymatic characteristics when compared to the sequences disclosed herein. This invention accordingly encompasses nucleic acid sequences which are similar to the sequences disclosed herein, protein sequences which are similar to the sequences disclosed herein, and the nucleic acid sequences that encode them. Mutations can include deletions, insertions, truncations, substitutions, fusions, shuffling of subunit sequences, and the like.

Mutations to a nucleic acid sequence can be introduced in either a specific or random manner, both of which are well known to those of skill in the art of molecular biology. A myriad of site-directed mutagenesis techniques exist, typically using oligonucleotides to introduce mutations at specific locations in a nucleic acid sequence. Examples include single strand rescue (Kunkel, T. *Proc. Natl. Acad. Sci. U.S.A.*, 82: 488–492, 1985), unique site elimination (Deng and Nickloff, *Anal. Biochem.* 200: 81, 1992), nick protection (Vandeyar, et al. *Gene* 65: 129–133, 1988), and PCR (Costa, et al. *Methods Mol. Biol.* 57: 31–44, 1996). Random or non-specific mutations can be generated by chemical agents (for a general review, see Singer and Kusmierek, *Ann. Rev. Biochem.* 52: 655–693, 1982) such as nitrosoguanidine (Cerda-Olmedo et al., *J. Mol. Biol.* 33: 705–719, 1968;

Guerola, et al. *Nature New Biol.* 230: 122–125, 1971) and 2-aminopurine (Rogan and Bessman, *J. Bacteriol.* 103: 622–633, 1970), or by biological methods such as passage through mutator strains (Greener et al. *Mol. Biotechnol.* 7: 189–195, 1997).

Nucleic acid hybridization is a technique well known to those of skill in the art of DNA manipulation. The hybridization properties of a given pair of nucleic acids is an indication of their similarity or identity. Mutated nucleic acid sequences can be selected for their similarity to the disclosed patatin nucleic acid sequences on the basis of their hybridization to the disclosed sequences. Low stringency conditions can be used to select sequences with multiple mutations. One may wish to employ conditions such as about 0.15 M to about 0.9 M sodium chloride, at temperatures ranging from about 20° C. to about 55° C. High stringency conditions can be used to select for nucleic acid sequences with higher degrees of identity to the disclosed sequences. Conditions employed may include about 0.02 M to about 0.15 M sodium chloride, about 0.5% to about 5% casein, about 0.02% SDS and/or about 0.1% N-laurylsarcosine, about 0.001 M to about 0.03 M sodium citrate, at temperatures between about 50° C. and about 70° C. More preferably, high stringency conditions are 0.02 M sodium chloride, 0.5% casein, 0.02% SDS, 0.001 M sodium citrate, at a temperature of 50° C.

Example 22
Determination of Homologous and Degenerate Nucleic Acid Sequences

Modification and changes can be made in the sequence of the proteins of the present invention and the nucleic acid segments which encode them and still obtain a functional molecule that encodes a protein with desirable properties. The following is a discussion based upon changing the amino acid sequence of a protein to create an equivalent, or possibly an improved, second-generation molecule. The amino acid changes can be achieved by changing the codons of the nucleic acid sequence, according to the codons given in Table 10.

TABLE 10

Codon degeneracies of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GAG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

Certain amino acids can be substituted for other amino acids in a protein sequence without appreciable loss of enzymatic activity. It is thus contemplated that various changes can be made in the peptide sequences of the disclosed protein sequences, or their corresponding nucleic acid sequences without appreciable loss of the biological activity.

In making such changes, the hydropathic index of amino acids can be considered. The importance of the hydropathic amino acid index in conferring interactive biological function on a protein is generally understood in the art (Kyte and Doolittle, *J. Mol. Biol.*, 157: 105–132, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics. These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids can be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids can be made effectively on the basis of hydrophilicity. U.S. Pat. No. 4,554,101 (Hopp, T. P., issued Nov. 19, 1985) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid can be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantageous may also be used if these resulted in functional patatin proteins.

Example 23
Production of Patatin Proteins and Permuteins in Plants

Plant Vectors

In plants, transformation vectors capable of introducing nucleic acid sequences encoding patatin proteins and permuteins are easily designed, and generally contain one or more nucleic acid coding sequences of interest under the transcriptional control of 5' and 3' regulatory sequences. Such vectors generally comprise, operatively linked in sequence in the 5' to 3' direction, a promoter sequence that directs the transcription of a downstream heterologous structural nucleic acid sequence in a plant; optionally, a 5' non-translated leader sequence; a nucleic acid sequence that encodes a protein of interest; and a 3' non-translated region that encodes a polyadenylation signal which functions in plant cells to cause the termination of transcription and the addition of polyadenylate nucleotides to the 3' end of the mRNA encoding the protein. Plant transformation vectors also generally contain a selectable marker. Typical 5'-3' regulatory sequences include a transcription initiation start site, a ribosome binding site, an RNA processing signal, a transcription termination site, and/or a polyadenylation signal. Vectors for plant transformation have been reviewed in Rodriguez et al. (Vectors: A Survey of Molecular Cloning Vectors and Their Uses, Butterworths, Boston., 1988), Glick et al. (Methods in Plant Molecular Biology and Biotechnology, CRC Press, Boca Raton, Fla., 1993), and Croy (Plant Molecular Biology Labfax, Hames and Rickwood (Eds.), BIOS Scientific Publishers Limited, Oxford, UK., 1993).

Plant Promoters

Plant promoter sequences can be constitutive or inducible, environmentally- or developmentally-regulated, or cell- or tissue-specific. Often-used constitutive promoters include the CaMV 35S promoter (Odell, J. T. et al., *Nature* 313: 810–812, 1985), the enhanced CaMV 35S promoter, the Figwort Mosaic Virus (FMV) promoter (Richins et al., *Nucleic Acids Res.* 20: 8451–8466, 1987), the mannopine synthase (mas) promoter, the nopaline synthase (nos) promoter, and the octopine synthase (ocs) promoter. Useful inducible promoters include promoters induced by salicylic acid or polyacrylic acids (PR-1, Williams, S. W. et al, *Biotechnology* 10: 540–543, 1992), induced by application of safeners (substituted benzenesulfonamide herbicides, Hershey, H. P. and Stoner, T. D., *Plant Mol. Biol.* 17: 679–690, 1991), heat-shock promoters (Ou-Lee et al., *Proc. Natl. Acad. Sci. USA*. 83: 6815–6819, 1986; Ainley et al., *Plant Mol. Biol.* 14: 949–967, 1990), a nitrate-inducible promoter derived from the spinach nitrite reductase gene (Back et al., *Plant Mol. Biol.* 17: 9–18, 1991), hormone-inducible promoters (Yamaguchi-Shinozaki, K. et al., *Plant Mol. Biol.* 15: 905–912, 1990; Kares et al., *Plant Mol. Biol.* 15: 225–236, 1990), and light-inducible promoters associated with the small subunit of RuBP carboxylase and LHCP gene families (Kuhlemeier et al., *Plant Cell* 1: 471, 1989; Feinbaum, R. L. et al., *Mol. Gen. Genet.* 226: 449–456, 1991; Weisshaar, B. et al., *EMBO J.* 10: 1777–1786, 1991; Lam, E. and Chua, N. H., *J. Biol. Chem.* 266: 17131–17135, 1990; Castresana, C. et al., *EMBO J.* 7: 1929–1936, 1988; Schulze-Lefert et al., *EMBO J.* 8: 651, 1989). Examples of useful tissue-specific, developmentally-regulated promoters include the β-conglycinin 7S promoter (Doyle, J. J. et al., *J. Biol. Chem.* 261: 9228–9238, 1986; Slighton and Beachy, *Planta* 172: 356–363, 1987), and seed-specific promoters (Knutzon, D. S. et al., *Proc. Natl. Acad. Sci. U.S.A.* 89: 2624–2628, 1992; Bustos, M. M. et al., *EMBO J.* 10: 1469–1479, 1991; Lam and Chua, *Science* 248: 471, 1991; Stayton et al., *Aust. J Plant. Physiol.* 18: 507, 1991). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al., *Seed Sci. Res.* 1: 209–219, 1991), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Comai, L. and Moran, P. M., U.S. Pat. No. 5,106,739, issued Apr. 21, 1992), or to combine desired transcriptional activity and tissue specificity.

Plant Transformation and Regeneration

A variety of different methods can be employed to introduce such vectors into plant protoplasts, cells, callus tissue, leaf discs, meristems, etcetera, to generate transgenic plants, including *Agrobacterium*-mediated transformation, particle gun delivery, microinjection, electroporation, polyethylene glycol mediated protoplast transformation, liposome-mediated transformation, etcetera (reviewed in Potrykus, I. *Ann. Rev. Plant Physiol. Plant Mol. Biol.* 42: 205–225, 1991). In general, transgenic plants comprising cells containing and expressing DNAs encoding patatin proteins and permuteins can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the protein-encoding nucleotide sequence.

Specific methods for transforming a wide variety of dicots and obtaining transgenic plants are well documented in the literature (Gasser and Fraley, *Science* 244: 1293–1299, 1989; Fisk and Dandekar, *Scientia Horticulturae* 55: 5–36, 1993; Christou, *Agro Food Industry Hi Tech*, p. 17, 1994; and the references cited therein).

Successful transformation and plant regeneration have been reported in the monocots as follows: asparagus (*Asparagus officinalis*; Bytebier et al., *Proc. Natl. Acad. Sci. U.S.A.* 84: 5345–5349, 1987); barley (*Hordeum vulgarae*; Wan and Lemaux, *Plant Physiol.* 104: 37–48, 1994); maize (*Zea mays*; Rhodes, C. A. et al., *Science* 240: 204–207, 1988; Gordon-Kamm et al., *Plant Cell* 2: 603–618, 1990; Fromm, M. E. et al., *Bio/Technology* 8: 833–839, 1990; Koziel et al., *Bio/Technology* 11: 194–200, 1993); oats (*Avena sativa*; Somers et al., *Bio/Technology* 10: 1589–1594, 1992); orchardgrass (*Dactylis glomerata*; Horn et al., *Plant Cell Rep.* 7: 469–472, 1988); rice (*Oryza sativa*, including indica and japonica varieties; Toriyama et al., *Bio/Technology* 6: 10, 1988; Zhang et al., *Plant Cell Rep.* 7: 379–384, 1988; Luo and Wu, *Plant Mol. Biol. Rep.* 6: 165–174, 1988; Zhang and Wu, *Theor. Appl. Genet.* 76: 835–840, 1988; Christou et al., *Bio/Technology* 9: 957–962, 1991); rye (*Secale cereale*; De la Pena et al., *Nature* 325: 274–276, 1987); sorghum (*Sorghum bicolor*; Casas, A. M. et al., *Proc. Natl. Acad. Sci. U.S.A.* 90: 11212–11216, 1993); sugar cane (*Saccharum* spp.; Bower and Birch, *Plant J*. 2: 409–416, 1992); tall fescue (*Festuca arundinacea*; Wang, Z. Y. et al., *Bio/Technology* 10: 691–696, 1992); turfgrass (*Agrostis palustris*; Zhong et al., *Plant Cell Rep.* 13: 1–6, 1993); wheat (*Triticum aestivum*; Vasil et al., *Bio/Technology* 10: 667–674, 1992; Weeks, T. et al., *Plant Physiol.* 102: 1077–1084, 1993; Becker et al., *Plant J.* 5: 299–307, 1994), and alfalfa (Masoud, S. A. et al., *Transgen. Res.* 5: 313, 1996); *Brassica* (canola/oilseed rape) (Fry, J. *Plant Cell Rep.* 6: 321–325, 1987); and soybean (Hinchee, M. *Bio/Technol.* 6: 915–922, 1988).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the methods described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention.

What is claimed is:

1. An isolated nucleic acid sequence encoding the protein of SEQ ID NO: 247.

2. The isolated nucleic acid sequence of claim 1, comprising SEQ ID NO: 246.

3. A recombinant vector operatively linked in the 5' to 3' orientation, comprising:

a) a promoter that directs transcription of a structural nucleic acid sequence;

b) a nucleic acid sequence encoding the protein of SEQ ID NO: 247; and c) a 3' transcription terminator.

4. The recombinant vector of claim 3, wherein the vector expresses a protein exhibiting corn rootworm insect inhibitory activity and acyl lipid hydrolase activity.

5. A recombinant host cell comprising a nucleic acid sequence encoding the protein of SEQ ID NO: 247.

6. The recombinant host cell of claim 5, wherein the protein of SEQ ID NO: 247 exhibits corn rootworm insect inhibitory activity and acyl lipid hydrolase activity.

7. A recombinant plant comprising a nucleic acid sequence encoding the protein of SEQ ID NO: 247.

8. The recombinant plant of claim 7, wherein the protein of SEQ ID NO: 247 exhibits corn rootworm insect inhibitory activity and acyl lipid hydrolase activity.

* * * * *